United States Patent [19]
Dolganov

[11] Patent Number: 5,821,091
[45] Date of Patent: Oct. 13, 1998

[54] METHOD OF IDENTIFYING ACTIVATED T-CELLS

[75] Inventor: Gregory Dolganov, Menlo Park, Calif.

[73] Assignee: Genelabs Technologies, Inc., Redwood City, Calif.

[21] Appl. No.: 592,126

[22] Filed: Jan. 26, 1996

[51] Int. Cl.[6] .............................. C12P 19/34; C12Q 1/68
[52] U.S. Cl. ........................ 435/91.2; 435/6; 536/24.33
[58] Field of Search ................................. 435/5, 6, 91.2; 536/23.1, 24.33, 24.3

[56] References Cited

PUBLICATIONS

Kofler (1992) Mol. Immunol. 29:161–66.
Goring (1992) Exp. Eye Res. 54:785–95.
Takahashi (1993) FEBS Lett. 319:45–8.
Kwan et al. (1994) Cytogenet. Cell Genet. 67:341 abstract.
Boultwood, J., et al., "The 5q¯Syndrome," *Blood* 84(10) :3253–3260 (1994).
Dolganov, G., et al., "Coexpression of the Interleukin–13 and Interleukin–4 Genes Correlates with Their Physical Linkage in the Cytokine Gene Cluster on Human Chromosome 5q23–32," *Blood* 87(8):3316–3326 (1996).
Hays, S.L., et al., "Complex Formation in Yeast Double–Strand Break Repair: Participation of Rad51, Rad52, Rad55, and Rad57 Proteins," *Proc. Natl. Acad. Sci. USA* 92:6925–6929 (1995).
Kinzler, K.W., et al., "Identification of a Gene Located at Chromosome 5q21 That is Mutated in Colorectal Cancers," *Science 251*: 1366–1370 (1991).
Kinzler, K.W., et al., "Identification of FAP Locus Genes from Chromosome 5q21," *Science 253*:661–664 (1991).
LeBeau, M.M., et al., "Cytogenetic and Molecular Delineation of the Smallest Commonly Deleted Region of Chromosome 5 in Malignant Myeloid Diseases," *Proc. Natl. Acad. Sci. USA 90*:5484–5488 (1993).
Lengyel, P., "Tumor–Suppressor Genes: News About the Interferon Connection," *Proc. Natl. Acad. Sci. USA* 90:5893–5895 (1993).
Morgan, J.G., et al., "The Selective Isolation of Novel cDNAs Encoded by the Regions Surrounding the Human Interleukin 4 and 5 Genes," *Nuc. Acids Res.* 20(19) :5173–5179 (1992).
Nagarajan, L., et al., "Consistent Loss of the D4S89 Locus Mapping Telomeric to the Interleukin Gene Cluster and Centromeric to EGR–1 in Patients with 5q Chromosome," *Blood 83*(1) :1994).
Neuman, W.L., et al., "Chromosomal Loss and Deletion are the Most Common Mechanisms for Loss of Heterozygosity from Chromosomes 5 and 7 in Malignant Myeloid Disorders," *Blood 79*(6) :1501–1510 (1992).
Solomon, E., et al., "Chromosome Aberrations and Cancer," *Science 254*:1153–1160 (1991).
Weinberg, R.A., "Tumor Suppressor Genes," *Science* 254:1138–1146 (1991).

*Primary Examiner*—W. Gary Jones
*Assistant Examiner*—Amy Atzel
*Attorney, Agent, or Firm*—Charles K. Sholtz; Vincent M. Powers

[57] ABSTRACT

A method of identifying the presence of activated T-cells in a sample containing a plurality of different cell types is disclosed. The method includes the detection of polynucleotide sequences selectively expressed in activated T-cells.

3 Claims, 2 Drawing Sheets

GCCACTCACACAGCATCTCCAAGATCAGGGACCAGTACTTCCTGAGCTTGACAGAGAATGA

ATGTGTCAGACTGACCTCTGCCCATTTTGTAGTTTTCTCATCATTTTCTCACTCAGTCTTC

CCTTTTCAAGGGCCCACACTCTTCCCGAGGGCTGGGCCTAGTGAGCGGGGTCACAGTACAT

ATGGTTTCTGGGACTGAGAAGGTGGAAGATGTGTCCATAGAGCTTTTGTTTCCTAAGCAAC

GTATTACTGCCATGATTCCATTCCCTAGATGATGCTGGTGATGCAAGCTGGCTTCTCTTGG

CCAGCCTACCCTACTGCTGGGTAGTGTTTATGCCCCATGGCCAGACACTGAAGAGGGAGAC

AGGAAAAGCACATATCCACACCTTCCACCCTCAGACATTCCTGTAACTTGAGCTTATCTAA

GGGGGCATTGTCATATGTCAGGGGTTCCCAAACTACGGTCTTCAGAAACACTGTTTACCCT

CCATAGAGGTTGTGTGCATCAGCCCAGGCAGAATCCTGCTTCATGAAGGTGTTTTCCTAAT

GCATGTGTGCATGGACCTGTCTCATGCTACACTGCAGGGCTGGTATTCAGCACCAATAGTT

ATTGTTGGCTGCTAAAATAGCAAACTAGCCAAAATGGCAG

Fig. 1

METHOD OF IDENTIFYING ACTIVATED T-CELLS

FIELD OF THE INVENTION

The present invention relates to immunomodulatory compositions and methods.

REFERENCES

Alani, E., et al., *Genetics* 122:47–57 (1989).
Ausubel, F. M., et al., in *CURRENT PROTOCOLS IN MOLECULAR BIOLOGY*, John Wiley and Sons, Inc., Media, Pa. (1988).
Balasubramanian, M. K., et al., *J. Cell. Biol.* 125:1289 (1994).
Beames, et al., *Biotechniques* 11:378 (1991).
Bellanne-Chantelot, C., et al., *Cell* 70:1059–1068 (1992).
Boyum, A., *Scan J. Lab Invest* 21:77 (1968).
Burke, D. T., et al., *Science* 236:806–812 (1987).
Chenchik, A., et al., *Clontechniques* X(1):5–8 (1995).
Chomczynski, P., and Sacchi, N., *Anal. Biochem.* 162:156 (1987).
Chumakov, I., et al., *Nature* 359:380–387 (1992).
Fujino, T. and Yamamoto, T., *J. Biochem.* 111:197–203 (1992).
Glisin, V., et al., *Biochemistry* 13:2633 (1974).
Georgopoulos, K., et al. *EMBO J.* 9:109–115 (1990).
Harlow, E., et al., in *ANTIBODIES: A LABORATORY MANUAL*, Cold Spring Harbor Laboratory Press (1988).
Innis, M. A., et al., in *PCR PROTOCOLS*, Academic Press (1990).
Jakobsen, K. S., et al., *Nucleic Acids Res.* 18:3669 (1990).
Jakobsen, K. S., et al., "Direct mRNA Isolation Using Magnetic Oligo(dT) Beads: A Protocol for All Types of Cell Cultures, Animal and Plant Tissues" in *ADVANCES IN BIOMAGNETIC SEPARATION*, M. Uhlen, et al., Eds., Eaton Publishing (1994).
Lewis, D. B., et al., *Proc. Natl. Acad. Sci. USA* 85:9743 (1988).
Longmire, J. L., et al., *GATA* 10:69–76 (1993).
Morgan, J. G., et al., *Nucleic Acids Res.* 20:5173–5179 (1992).
Mullis, K. B., U.S. Pat. No. 4,683,202, issued 28 Jul. 1987.
Mullis, K. B., et al., U.S. Pat. No. 4,683,195, issued 28 Jul. 1987.
Piatak, M., et al., *AIDS* 7 (supp 2):S65–71 (1993).
Raymond, W. E. and Kleckner, N., *Mol. Gen. Genet.* 238:390–400 (1993).
Reilly, P. R., et al., *BACULOVIRUS EXPRESSION VECTORS: A LABORATORY MANUAL*, 1992.
Sambrook, J., et al., in *MOLECULAR CLONING: A LABORATORY MANUAL*, Second Edition, Cold Spring Harbor Laboratory, Cold Spring Harbor, N.Y. (1989).
Siebert, P. D., et al., *Nuc. Acids Res.* 23(6):1087–1088 (1995).
Thorpe, R., et al., *Blood Rev.* 6:133–148 (1992).
Vandevyver, C., et al., *Genome Res.* 5:195–201 (1995).
Wadhwa, M., et al., in *CYTOKINES: A PRACTICAL APPROACH*, Balkwill, F. R., Ed., IRL Press, Oxford, 309–330 (1992).
Warrington, J. A., et al., *Genomics* 13:803–808 (1992).

BACKGROUND OF THE INVENTION

Cytokines and related immunomodulatory compounds play an important role in the regulation and function of the immune system, making them suitable targets for therapeutic intervention in diseases involving immune system dysfunction. It would therefore be desirable to identify heretofore undiscovered genes encoding cytokines and other immunomodulatory compounds, which may be useful as a basis for treatment of diseases affecting or influenced by the immune system. Present methods for the identification of such genes have met with limited success. These methods include (i) screening for DNAse I hypersensitive sites and HTF islands as potential markers for transcription units, (ii) cross-species hybridization analysis of genomic sequences, (iii) hybridization of radiolabelled cDNAs to arrayed genomic clones, (iv) screening of cDNA libraries with complex genomic probes, (v) exon trapping, (vi) random sequencing and assignment of tissue-specific cDNAs, (vii) "software trapping" of the genes in extensive genomic sequencing projects, and (viii) cDNA normalization, subtraction or/and hybridization selection using extensive genomic fragments.

Most of the above approaches have proven either unreliable, or have required a substantial effort to find the genes of interest. For instance, a conventional "functional" gene cloning route includes purifying the protein factor with a particular biological activity, microsequencing the protein to design a redundant oligoprobe, raising antibodies to the protein, expression cloning of the candidate gene or conventional screening of cDNA libraries with the redundant probe.

En masse cDNA sequencing efforts have contributed substantially to novel gene discovery by identifying a large number of novel sequences and tissue expression "profiles". However, because these efforts typically had no defined targets and depended on screening conventional cDNA libraries, they resulted in the preferential identification of common, abundant cDNAs, and were thus biased against the identification of novel cytokine genes, which tend to be selectively expressed at relatively low levels.

Exon trapping can be efficiently used to screen complex genomic DNA. This method is widely-used due to its independence of the gene expression in any particular cell line or tissue, but it requires substantial further efforts for isolation and identification of the genes in question.

Many of the difficulties in cytokine gene identification mentioned above have been overcome by employing methods detailed in the present specification. These methods were used to isolate a number of human cDNA fragments which may encode immunomodulatory molecules.

SUMMARY OF THE INVENTION

In one aspect, the present invention includes a substantially-isolated polynucleotide having a sequence encoding a human polypeptide having immunomodulatory activity. In one embodiment, the polynucleotide has the sequence represented as SEQ ID NO:65. In another embodiment, the polynucleotide has the sequence represented as SEQ ID NO:66. In another embodiment, the polynucleotide has the sequence represented as SEQ ID NO:67. In another embodiment, the polynucleotide has the sequence represented as SEQ ID NO:68. In another embodiment, the polynucleotide has the sequence represented as SEQ ID NO:70. In another embodiment, the polynucleotide has the sequence represented as SEQ ID NO:71. In another embodiment, the polynucleotide has the sequence represented as SEQ ID NO:72. In another embodiment, the polynucleotide has the sequence represented as SEQ ID NO:73. In another embodiment, the polynucleotide has the sequence represented as SEQ ID NO:74. In another embodiment, the polynucleotide has the sequence represented as SEQ ID NO:76. In another embodiment, the polynucleotide has the sequence represented as SEQ ID NO:78. In another embodiment, the polynucleotide has the sequence represented as SEQ ID NO:79. In another embodiment, the polynucleotide has the sequence represented as SEQ ID NO:82. In another embodiment, the polynucleotide has the sequence represented as SEQ ID NO:83. In another embodiment, the polynucleotide has the sequence represented as SEQ ID NO:85. In another embodiment, the polynucleotide has the sequence represented as SEQ ID NO:86. In another embodiment, the polynucleotide has the sequence represented as SEQ ID NO:88. In another embodiment, the polynucleotide has the sequence represented as SEQ ID NO:92. In another embodiment, the polynucleotide has the sequence represented as SEQ ID NO:95. In another embodiment, the polynucleotide has the sequence represented as SEQ ID NO:98. In another embodiment, the polynucleotide has the sequence represented as SEQ ID NO:99. In another embodiment, the polynucleotide has the sequence represented as SEQ ID NO:100. In another embodiment, the polynucleotide has the sequence represented as SEQ ID NO:104. In another embodiment, the polynucleotide has the sequence represented as SEQ ID NO:105. In another embodiment, the polynucleotide has the sequence represented as SEQ ID NO:106. In another embodiment, the polynucleotide has the sequence represented as SEQ ID NO:107. In another embodiment, the polynucleotide has the sequence represented as SEQ ID NO:108. In another embodiment, the polynucleotide has the sequence represented as SEQ ID NO:109. In another embodiment, the polynucleotide has the sequence represented as SEQ ID NO:112. In another embodiment, the polynucleotide has the sequence represented as SEQ ID NO:113. In another embodiment, the polynucleotide has the sequence represented as SEQ ID NO:114. In another embodiment, the polynucleotide has the sequence represented as SEQ ID NO:115. In another embodiment, the polynucleotide has the sequence represented as SEQ ID NO:124. In another embodiment, the polynucleotide has the sequence represented as SEQ ID NO:130. In another embodiment, the polynucleotide has the sequence represented as SEQ ID NO:132. In another embodiment, the polynucleotide has the sequence represented as SEQ ID NO:133. In another embodiment, the polynucleotide has the sequence represented as SEQ ID NO:134. In another embodiment, the polynucleotide has the sequence represented as SEQ ID NO:135. In another embodiment, the polynucleotide has the sequence represented as SEQ ID NO:136. In another embodiment, the polynucleotide has the sequence represented as SEQ ID NO:137. In yet another embodiment, the polynucleotide has the sequence represented as SEQ ID NO:138.

In a preferred embodiment, the polynucleotide contains a sequence selected from the group represented by SEQ ID NO:65, SEQ ID NO:66, SEQ ID NO:67, SEQ ID NO:68, SEQ ID NO:70, SEQ ID NO:71, SEQ ID NO:72, SEQ ID NO:73, SEQ ID NO:74, SEQ ID NO:76, SEQ ID NO:85, SEQ ID NO:86, SEQ ID NO:92, SEQ ID NO:95, SEQ ID NO:99, SEQ ID NO:105, SEQ ID NO:106, SEQ ID NO:107, SEQ ID NO:124, SEQ ID NO:130, SEQ ID NO:135, SEQ ID NO:136, SEQ ID NO:137 and SEQ ID NO:138. In another preferred embodiment, the polynucleotide contains a sequence selected from the group represented by SEQ ID NO:65, SEQ ID NO:66, SEQ ID NO:67, SEQ ID NO:70, SEQ ID NO:71, SEQ ID NO:72, SEQ ID NO:73, SEQ ID NO:74, SEQ ID NO:75, SEQ ID NO:76, SEQ ID NO:78 and SEQ ID NO:79.

In another aspect, the present invention includes a substantially-isolated human polypeptide having immunomodulatory activity, where the polypeptide has a sequence encoded by a polynucleotide having a sequence represented by SEQ ID NO:65. In another embodiment, the polypeptide has a sequence encoded by a polynucleotide having a sequence represented by SEQ ID NO:66. In another embodiment, the polypeptide has a sequence encoded by a polynucleotide having a sequence represented by SEQ ID NO:67. In another embodiment, the polypeptide has a sequence encoded by a polynucleotide having a sequence represented by SEQ ID NO:68. In another embodiment, the polypeptide has a sequence encoded by a polynucleotide having a sequence represented by SEQ ID NO:70. In another embodiment, the polypeptide has a sequence encoded by a polynucleotide having a sequence represented by SEQ ID NO:71. In another embodiment, the polypeptide has a sequence encoded by a polynucleotide having a sequence represented by SEQ ID NO:72. In another embodiment, the polypeptide has a sequence encoded by a polynucleotide having a sequence represented by SEQ ID NO:73. In another embodiment, the polypeptide has a sequence encoded by a polynucleotide having a sequence represented by SEQ ID NO:74. In another embodiment, the polypeptide has a sequence encoded by a polynucleotide having a sequence represented by SEQ ID NO:76. In another embodiment, the polypeptide has a sequence encoded by a polynucleotide having a sequence represented by SEQ ID NO:78. In another embodiment, the polypeptide has a sequence encoded by a polynucleotide having a sequence represented by SEQ ID NO:79. In another embodiment, the polypeptide has a sequence encoded by a polynucleotide having a sequence represented by SEQ ID NO:82. In another embodiment, the polypeptide has a sequence encoded by a polynucleotide having a sequence represented by SEQ ID NO:83. In another embodiment, the polypeptide has a sequence encoded by a polynucleotide having a sequence represented by SEQ ID NO:85. In another embodiment, the polypeptide has a sequence encoded by a polynucleotide having a sequence represented by SEQ ID NO:86. In another embodiment, the polypeptide has a sequence encoded by a polynucleotide having a sequence represented by SEQ ID NO:88. In another embodiment, the polypeptide has a sequence encoded by a polynucleotide having a sequence represented by SEQ ID NO:92. In another embodiment, the polypeptide has a sequence encoded by a polynucleotide having a sequence represented by SEQ ID NO:95. In another embodiment, the polypeptide has a sequence encoded by a polynucleotide having a sequence represented by SEQ ID NO:98. In another embodiment, the polypeptide has a sequence encoded by a polynucleotide having a sequence represented by SEQ ID NO:99. In another embodiment, the polypeptide has a sequence encoded by a polynucleotide having a sequence represented by SEQ ID NO:100. In another embodiment, the polypeptide has a sequence encoded by a polynucleotide having a sequence represented by SEQ ID NO:104. In another embodiment, the polypeptide has a sequence encoded by a polynucleotide having a sequence represented by SEQ ID NO:105. In another embodiment, the polypeptide has a sequence encoded by a polynucleotide having a sequence represented by SEQ ID NO:106. In another embodiment, the polypeptide has a sequence encoded by a polynucleotide having a sequence represented by SEQ ID NO:107. In another embodiment, the polypeptide has a sequence encoded by a polynucleotide having a sequence represented by SEQ ID NO:108. In another embodiment, the polypeptide has a sequence encoded by a polynucleotide having a sequence represented by SEQ ID NO:109. In another embodiment, the polypeptide has a sequence encoded by a polynucleotide having a sequence represented by SEQ ID NO:112. In another embodiment, the polypeptide has a sequence encoded by a polynucleotide having a sequence represented by SEQ ID NO:113. In another embodiment, the polypeptide has a sequence encoded by a polynucleotide having a sequence represented by SEQ ID NO:114. In another embodiment, the polypeptide has a sequence encoded by a polynucleotide having a sequence represented by SEQ ID NO:115. In another embodiment, the polypeptide has a sequence encoded by a polynucleotide having a sequence represented by SEQ ID NO:124. In another embodiment, the polypeptide has a sequence encoded by a polynucleotide having a sequence represented by SEQ ID NO:130. In another embodiment, the polypeptide has a sequence encoded by a polynucleotide having a sequence represented by SEQ ID NO:132. In another embodiment, the polypeptide has a sequence encoded by a polynucleotide having a sequence represented by SEQ ID NO:133. In another embodiment, the polypeptide has a sequence encoded by a polynucleotide having a sequence represented by SEQ ID NO:134. In another embodiment, the polypeptide has a sequence encoded by a polynucleotide having a sequence represented by SEQ ID NO:135. In another embodiment, the polypeptide has a sequence encoded by a polynucleotide having a sequence represented by SEQ ID NO:136. In another embodiment, the polypeptide has a sequence encoded by a polynucleotide having a sequence represented by SEQ ID NO:137. In yet another embodiment, the polypeptide has a sequence encoded by a polynucleotide having a sequence represented by SEQ ID NO:138.

In a preferred embodiment, the polypeptide has a sequence encoded by a polynucleotide selected from the group consisting of SEQ ID NO:65, SEQ ID NO:66, SEQ ID NO:67, SEQ ID NO:68, SEQ ID NO:70, SEQ ID NO:71, SEQ ID NO:72, SEQ ID NO:73, SEQ ID NO:74, SEQ ID NO:76, SEQ ID NO:85, SEQ ID NO:86, SEQ ID NO:92, SEQ ID NO:95, SEQ ID NO:99, SEQ ID NO:105, SEQ ID NO:106, SEQ ID NO:107, SEQ ID NO:124, SEQ ID NO:130, SEQ ID NO:135, SEQ ID NO:136, SEQ ID NO:137 and SEQ ID NO:138. In another preferred embodiment, the polypeptide has a sequence encoded by a polynucleotide selected from the group consisting of SEQ ID NO:65, SEQ ID NO:66, SEQ ID NO:67, SEQ ID NO:70, SEQ ID NO:71, SEQ ID NO:72, SEQ ID NO:73, SEQ ID NO:74, SEQ ID NO:75, SEQ ID NO:76, SEQ ID NO:78 and SEQ ID NO:79.

In another aspect, the present invention includes a substantially-isolated polynucleotide having a sequence encoding a human homologue of yeast RAD50. In one embodiment, the polypeptide contains a polypeptide sequence encoded by a polynucleotide sequence selected from the group consisting of SEQ ID NO:54 and SEQ ID NO:55.

In a related aspect, the invention includes a substantially-isolated human homolog of yeast RAD50 polypeptide. In one embodiment, the homolog polypeptide contains a polypeptide sequence encoded by a polynucleotide sequence selected from the group consisting of SEQ ID NO:54 and SEQ ID NO:55.

Yet another aspect of the present invention includes a substantially-isolated polynucleotide having a sequence encoding a human homologue of *Drosophila melanogaster* Septin-2. In one embodiment, the polypeptide contains a polypeptide sequence encoded by the polynucleotide sequence represented by SEQ ID NO:97.

In a related aspect, the invention includes a substantially-isolated human Septin-2 homolog polypeptide. In one embodiment, the homolog polypeptide contains a polypeptide sequence encoded by the polynucleotide sequence represented by SEQ ID NO:97.

Still another aspect of the present invention includes a method of identifying the presence of activated T-cells in a sample containing a plurality of different cell types. The method includes performing a polymerase chain reaction amplification, where an aliquot of the sample (or homogenate/fraction thereof) serves as an amplification target and where the amplification is done using an oligonucleotide primer pair capable of selective amplification of a polynucleotide fragment having the sequence represented as SEQ ID NO:151. The amplification reaction generates an amplification product having a specific size, and the size of the amplification product is determined. The presence of amplification product of an expected size is indicative of the presence of activated T cells in the sample. In one embodiment, the oligonucleotide primer pair consists of primers having sequences represented as SEQ ID NO:149 and SEQ ID NO:150. In another embodiment, the sample is derived from adult tissue.

The invention also encompasses a method of identifying sequences encoding polypeptides having immunomodulatory activity. The method includes (i) selecting, by direct selection using sequences specific for region 5q23-31 of human chromosome 5, cDNA fragments isolated from tissues or cells expressing cytokines, (ii) grouping the fragments into "bins", where each bin represents cDNA fragments corresponding to a single gene or genetic locus, the grouping performed by sequencing the fragments and/or mapping the fragments to longer sequences derived from region 5q23-31 of human chromosome 5, and (iii) analyzing the tissue specificity of expression of transcripts corresponding to the fragments (transcripts from the gene or locus which the fragments represent). In one embodiment, the first step (step (i)) is performed using cDNAs obtained from cell lines and/or tissues expressing cytokines, such as activated T-cells. In another embodiment, the first step is performed using cDNAs obtained from a chromosome 5-specific activated T-cell cDNA library in lambda gt10, which was constructed using a kit from Life Technologies, Inc. and is deposited at Genelabs Technologies, Inc., Redwood City. In another general embodiment, the analyzing of tissue-specific expression is carried out using sequence-specific primers in a polymerase chain reaction amplification reaction containing target nucleic acids derived from tissues or cell lines of interest. Examples of tissues which may be used in determining the tissue specificity of expression include total embryo, fetal liver, fetal brain, fetal muscle, placenta, adult heart, adult muscle, adult liver, adult brain, adult pancreas, adult kidney, adult aorta, adult spleen, adult testis, adult bone marrow, resting T-cells and activated T-cells.

The present invention also includes a method of obtaining full-length sequences of genes or loci identified as having immunomodulatory activity. The method includes selecting a desired sequence identified in Table 1 and using the sequence to isolate overlapping clones. In one embodiment, such overlapping clones are isolated using rapid amplification of cDNA ends (RACE) PCR with cDNA obtained from tissues or cell lines of interest or from a cDNA or genomic DNA library. In another embodiment, the overlapping clones are isolated by direct hybridization screening of a cDNA or genomic DNA library made from, for example, T-cells, a lymphoma or a leukemia.

Also included in the invention is a method of identifying proteins having immunomodulatory activity. The method includes obtaining a full-length coding sequence of a gene represented by a sequence presented in Table 1 (e.g., as described above) and cloning the sequence into a recombinant expression vector. The resulting vector is then used to express recombinant polypeptides in selected host cells, such as *E. coli*.

The invention also includes a method of identifying small molecules that affect alter and/or modulate the activity of immunomodulatory proteins such as described above. The method includes assaying the effects of a polypeptide having immunomodulatory activity in the presence and absence of a test small molecule compound, and identifying the test compound as effective if the test compound is effective to significantly alter the effects of the polypeptide. In one embodiment, the small molecule compound is one of a plurality of such compounds present in a combinatorial library, such as one of a plurality of small molecules in a small molecule combinatorial library, or one of a plurality of peptides in a peptide combinatorial library.

These and other objects and features of the invention will be more fully appreciated when the following detailed description of the invention is read in conjunction with the accompanying drawings.

BRIEF DESCRIPTION OF THE FIGURES

FIG. 1 shows the location of primers SEQ ID NO:149 and SEQ ID NO:150 relative to sequence SEQ ID NO:151.

DETAILED DESCRIPTION OF THE INVENTION

I. Definitions

Figure 2:
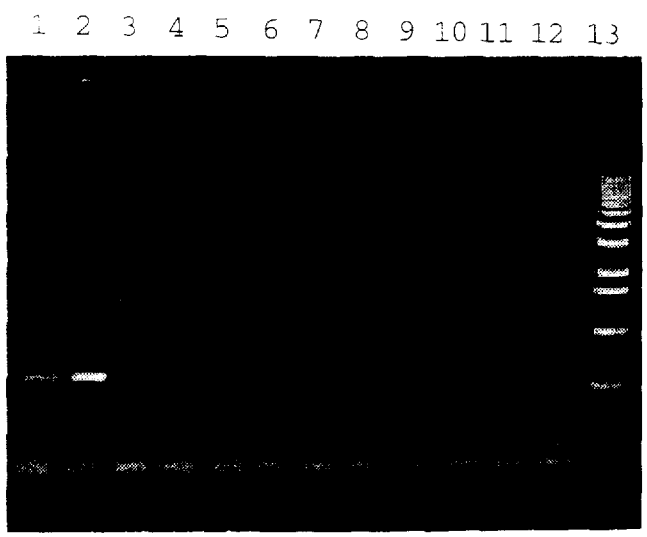
FIG. 2 shows a computer-generated image of an ethidium bromide-stained agarose gel, showing the expression pattern of SEQ ID NO:151.

"Substantially isolated" when used with respect to polynucleotide or polypeptides refers to the at least partial purification of such polynucleotides or polypeptides away from unrelated or contaminating components (e.g., cellular components other than the specified polynucleotide or polypeptide, and polypeptides or polynucleotides having a sequence different from that of the selected polypeptide or polynucleotide. Methods and procedures for the isolation or purification of compounds or components of interest are described below (e.g., recombinant production of polypeptides having immunomodulatory activity).

Compounds or polypeptides having "immunomodulatory activity" are compounds or polypeptides that affect the regulation or function of the immune system. Examples of compounds or polypeptides having immunomodulatory activity include but are not limited to cytokines, which include growth factors, colony- stimulating factors, interleukins, lymphokines, monokines, interferons, chemokines and the like. Such polypeptides are typically secretory regulatory proteins that control the survival, growth, differentiation and effector function of tissues or cells. Polypeptides having immunomodulatory activity also include receptors for immunomodulatory compounds or polypeptides, including but not limited to, cytokine receptors, which include interleukin receptors, growth factor receptors, interferon receptors and receptors for other factors. Other examples of immunomodulatory compounds or polypeptides include transcription regulatory factors and signal transduction transmitters, such as NF-kB, interleukin regulatory factor 1 (IRFL), interleukin regulatory factor 2 (IRF2), G-proteins, signal transducers and activators of transcription (STATs), cell division control proteins, proteins involved in DNA repair and recombination, etc. that are expressed in human stromal or immune cells or tissues. "Adult tissue" refers to tissue isolated from individuals older than about 1 year of age.

II. Cytokine Gene Cluster on Chromosome 5

Gene families tend to evolve by a process of tandemization, divergence, and in some cases, transposition. Linked families of genes are usually assumed to be together because they evolved from a common ancestor rather than being locked into a functional unit within a chromosomal region. There are numerous examples of linked genes that show strong homology to each other (e.g. HLA) but their are also many examples of genes that are strongly homologous but are scattered throughout the genome (e.g. tubulin genes).

Cytokine genes differ from these cases because they typically do not show strong homology at the nucleic acid sequence level, and should not necessarily be clustered in chromosomal regions. It is has been recognized herein, however, that there exist at least nine cytokine genes and at least ten receptor genes on the long arm of human chromosome 5 (e.g., Warrington, et al., 1992), suggesting that functionally-related molecules having little or no sequence homology may be situated together in a defined region of a chromosome.

III. Direct Selection and Analysis of Chromosome 5—Specific cDNA Sequences

Experiments performed in support of the present invention detail the generation of cDNA samples enriched for sequences from the 5q23-31 region of human chromosome 5. This region has been identified as containing a cluster of cytokine genes, including IL13, IL4, IL5, IRF1, IL3 and GM-CSF. Such immunomodulatory molecules may be involved in the development of certain cancers and immunodeficiencies, making them suitable targets for anti-cancer and immunotherapeutic drug candidates. The cDNA samples were derived from a variety of tissues, including human fetal brain and liver, adult bone marrow, leukemias, lymphomas, activated lymphocytes and cytokine-producing clones, as detailed in Example 1A. The samples were assayed for the presence of known cytokines as detailed in Example 1B using primers shown in Table 2. Results of these assays are shown in Table 3. Those samples showing increased expression of cytokines were combined to create "cDNA pools". The composition of the different pools is detailed in Example 1.

A similar approach may be employed to obtain cDNA samples enriched for various other selected sequences. For example, cDNA sequences upregulated during periods of increased synaptic transmission may be isolated from hippocampal slices following electrical stimulation of the slices. Such cDNA samples may be assayed for, e.g., cDNAs encoding other classes of selected molecules, such as protein kinases, phosphatases, neurotransmitters, hormones, and the like.

Pools containing relatively high levels of cDNAs encoding different cytokines (see Example 1, Table 3) were further processed using genomic "direct selection", as detailed in Examples 2 and 3. Here, yeast artificial chromosome (YAC) clones containing the 5q23-31 region of chromosome 5 were used to select cDNA that hybridized to sequences in that region. Analysis of approximately 3,000 cDNAs selected with the genomic region spanning 1.3 Mb of 5q23-31 revealed several hundred cDNA clones ranging from about 500 to about 800 bp in length. The sequences were further analyzed by mapping them to YAC clones containing fragments of the 5q23-31 region. About 790% of these clones were mapped to human chromosome 5 and starting YACs either by RT-PCR or Southern blot hybridization.

The data obtained from the physical mapping of the cDNAs to the starting YACs and chromosome 5-specific cosmids were used to group the cDNAs according to their location and partial overlap with one another, resulting in over 50 groups, or "bins", of cDNAs comprised of overlapping clones. Some of the selected cDNAs were also sequenced as described in Example 4 to facilitate placement into the bins. The results of these analyses are presented in Table 1, below.

| Bin # | Consensus sequence | SEQ NO. | Type | Sequence length | Best BlastX homology score | Expression profile |
|---|---|---|---|---|---|---|
| 1 | Rad50.seq | 54 | con1 | ~5.7 kb | ~35% overall homology to *S.cerevisiae* Rad50: Score = 390, P = 3.8e-89 | Activated T-cells, testis, fetal liver, heart |
|  | 18.seq | 55 | con2 |  |  |  |
| 2 | Tc1.seq | 56 | alt | multiple isoforms: ~2.5-0.6 kb | ~90% overall homology to the Rat Brain Long Chain Acyl-CoA Synthetase | Activated T-cells, testis, fetal liver |
|  | Tc2.seq | 57 | alt |  |  |  |
|  | Tc3.seq | 58 | alt |  |  |  |
|  | TcA.seq | 59 | alt |  |  |  |
|  | TcB.seq | 60 | alt |  |  |  |
|  | TS.seq | 61 | alt |  |  |  |
|  | TS2.seq | 62 | alt |  |  |  |
|  | FL.seq | 63 | alt |  |  |  |
|  | FL2.seq | 64 | alt |  |  |  |
| 3 | G205a.seq | 65 | con1 | ~1.0 kb | homology to 1-PI 3-kinase: Score = 66, P = 0.024, (14/29). | Activated T-cells*, fetal liver |
|  | G205b.seq | 66 | con2 |  |  |  |
|  | G205c.seq | 67 | con3 |  |  |  |
| 4 | G221.seq | 68 | con | ~1.70 kb | homology to *S.cerevisiae* ZMS1 gene: Score = 75, P = 0.038, (19/44); homology to FGF: Score = 62, P = 0.74, (14/52) | Activated T-cells*, testis, fetal thymus |
| 5 | G238con.seq | 69 | con | ~1.4 kb | homology to drosophila Notch 2 gene: Score = 56, P = 0.00058, (12/29) | Activated T-cells, testis, fetal thymus |
| 6 | G229con.seq | 70 | con | ~2.76 kb | NSM | Activated T-cells** |
| 7 | G248.seq | 71 | con1 |  | NSM | Activated T-cells |
|  | G248a.seq | 72 | con2 |  |  |  |
|  | G248b.seq | 73 | con3 |  |  |  |
|  | G248c.seq | 74 | con4 |  |  |  |
|  | G220a.seq | 75 | con5 |  |  |  |
|  | G255.seq | 76 | con6 |  |  |  |
| 8 | G306.seq | 77 | con | ~0.65 kb | homology to *M.musculus* Modifier 3: Score = 67, P = 0.21 (12/17) |  |
| 9 | G256.seq | 78 | con | ~0.90 kb | homology to mouse formin 4 gene: Score = 71, P = 1.8e-09 | Activated T-cells** |
| 10 | G181.seq | 79 | con | ~1.40 kb | homology to *P.Aeroginosa* hypothetical 62.8 K protein: Score = 73, P = 0.33 (13/26) | Activated T-cells** |
| 11 | G257.seq | 80 | con | ~0.70 kb | homology to *M.Sativa* NADH-glutamate synthase: Score = 69, P = 0.33 (13/26) | Lung, activated T-cells, brain, liver and heart |
| 12 | E2.seq | 81 | con1 | ~0.7 kb; E9: ~1.0 kb; ~0.32 kb | NSM | E2: kidney, activated T-cells, fetal liver and muscle, bone marrow; E9: activated T-cells, fetal liver, testis, brain, kidney, small intestine |
|  | E9f.seq | 82 | con2 |  |  |  |
|  | E9r.seq | 83 | con3 |  |  |  |
|  | G123con.seq | 84 | con4 |  |  |  |
| 13 | A116con.seq | 85 | con | ~3.1 kb | NSM | Activated T-cells, placenta, fetal liver |

-continued

| Bin # | Consensus sequence | SEQ NO. | Type | Sequence length | Best BlastX homology score | Expression profile |
|---|---|---|---|---|---|---|
| | | | | | | and muscle, kidney, heart, bone marrow |
| 14 | A25con.seq | 86 | con | ~1.9 kb | NSM | Activated T-cells, fetal liver and muscle, placenta, kidney, bone marrow |
| 15 | A46.seq | 87 | con | ~0.85 kb | NSM | fetal liver, kidney and muscle, placenta, activated T-cells, heart, bone marrow |
| 16 | A66.seq | 88 | con | ~0.68 kb | NSM | activated T-cells, fetal liver, placenta, heart, bone marrow |
| 17 | A42.seq | 89 | con | ~0.57 kb | homology to rabbit T-cell receptor, beta chain: Score = 59, P = 7.9-0.6 (21/60) | Activated T-cells, fetal muscle, placenta, heart, kidney |
| 18 | A76con.seq | 90 | con | ~1.044 bp | homology to ATP synthase: Score = 67, P = 5.4-0.6 (21/60) and ubiquinone: Score = 63, P = 8.8-0.6 (11/28) | Activated T-cells, placenta, heart |
| 19 | E105con.seq | 91 | con | ~1.7 kb | homology to 3 ESTs | |
| 20 | G180con.seq | 92 | con | ~0.93 kb | | |
| 21 | G310con.seq G326con.seq G164con.seq | 93 94 95 | con1 con2 con3 | ~2.10 kb ~1.38 kb ~1.10 kb | NSM | G310: lung, liver, brain, small intestine, testis, activated T-cells; G326: lung, liver, brain, thymus, activated T-cells; G164: lung, liver, brain, thymus, ovary, activated T-cells; |
| 22 | G65.seq | 96 | con | ~2.1 kb | ~60%, aa homology to human and chick propyl 4-hydroxylase, procollagen-proline dioxygenase, gamma-butyrobetaine, 2-oxoglutarate dioxygenase: Score = 797, P = 5.1e-164 | |
| 23 | CDC3.seq | 97 | con | ~1.2 kb (partial sequence) | homology to Drosophila Septin-2; ~50% aa homology to human and yeast cell division control proteins, such as CDC3 and CDC10: Score = 196, P = 2.9e-63 | |
| 24 | G42con.seq | 98 | con | ~0.5 kb | NSM | |
| 25 | G105con.seq | 99 | con | ~0.64 kb | NSM | Activated T-cells, fetal |

-continued

| Bin # | Consensus sequence | SEQ NO. | Type | Sequence length | Best BlastX homology score | Expression profile |
|---|---|---|---|---|---|---|
| | | | | | | liver, kidney, lung, small intestine, heart, brain, spleen and testis |
| 26 | G98con.seq | 100 | con | ~0.41 kb | NSM | |
| 27 | G73con.seq | 101 | con | ~0.4 kb | ~76% homology to human ubiquinol cytochrome C reductase: Score = 338, P = 6.3e-45 | Ubiquitous |
| 28 | G89con.seq | 102 | con | ~2.2 kb (partial sequence) | homology to *X.laevis* apical plasma membrane protein: Score = 149, P = 2.7e-35 | Prostate, brain, kidney, liver, small intestine, placenta |
| 29 | G102.seq | 103 | con | ~0.4 kb | homology to human ataxin-1 gene: Score = 67, P = 0.2 (13/24) | |
| 30 | G57.seq | 104 | con | ~0.4 kb | NSM | |
| 31 | G108.seq | 105 | con | ~0.25 kb | NSM | Activated T-cells, small intestine |
| 32 | G127.seq | 106 | con | ~0.42 kb | NSM | Activated T-cells, fetal liver, heart, kidney, brain, spleen, placenta, testis, small intestine |
| 33 | G86.seq | 107 | con | ~0.28 kb | NSM | Activated T-cells, brain |
| 34 | G78.seq H993.seq | 108 109 | con1 con2 | ~0.5 kb | NSM | |
| 35 | G38a.seq | 110 | con | ~0.5 kb | NSM | |
| 36 | G90.seq | 111 | con | | NSM | |
| 37 | G66.seq H973.seq | 112 113 | con1 con2 | | NSM | |
| 38 | H505.seq H989.seq | 114 115 | con1 con2 | | NSM | |
| 39 | E118con.seq | 116 | con | ~0.82 kb | ~95% homology to several ESTs in Genbank | Activated T-cells, fetal muscle and liver, heart, kidney, brain, muscle, aorta, placenta |
| 40 | E69f.seq E69r.seq | 117 118 | con1 con2 | ~0.9 kb | 100% homology to human eF-1 alpha gene | |
| 41 | E36.seq | 119 | con | | NSM | |
| 42 | A104f.seq A104r.seq | 120 121 | con1 con2 | ~0.8 kb | 100% homology to human serine protease B gene | |
| 43 | H622.seq | 122 | con | ~0.59 kb | homology to human gamma-G globin gene: Score 348, P = 7.2-45, (67/70) | |
| 44 | G61con.seq | 123 | con | ~0.7 kb | NSM | |
| 45 | G45.seq | 124 | con | ~0.29 kb | | Lung, kidney, brain, thymus, fetal liver and brain, activated T-cells |
| 46 | G3con.seq | 125 | con | ~1.26 kb | NSM | |
| 1a | G30.seq | 126 | con | ~0.32 kb | NSM | Lung, brain, |

-continued

| Bin # | Consensus sequence | SEQ NO. | Type | Sequence length | Best BlastX homology score | Expression profile |
|---|---|---|---|---|---|---|
| | | | | | | kidney, heart, muscle, liver, placenta, small intestine, activated T-cells |
| 2a | G32.seq | 127 | con | ~0.38 kb | NSM | Ubiquitous |
| 3a | G37.seq | 128 | con | ~0.4 kb | NSM | |
| 4a | G39.seq | 129 | con | ~0.43 kb | NSM | Kidney, fetal liver, activated T-cells |
| 5a | G75.seq | 130 | con | ~0.4 kb | NSM | Kidney, fetal liver, small intestine, activated T-cells |
| 6a | H100.seq | 131 | con | ~0.37 kb | 100% to known human H19 gene | |
| 7a | H414f.seq | 132 | con | ~0.8 kb | NSM | |
| 8a | H631.seq | 133 | con | ~0.5 kb | NSM | |
| 9a | G93.seq | 134 | con | ~0.4 kb | NSM | |
| 10a | G115a G115b G115c.seq | 135 136 137 | con1 con2 con3 | ~2.0 kb (partial sequence) | homology to drosophila homeotic Cad gene: Score = 69, P = 0.12 (12/19) | Kidney, lung, liver, brain, heart, placenta, spleen, small intestine, testis, muscle, activated T-cells, fetal liver |
| 11a | G122.seq | 138 | con | ~0.25 kb | homology to human heparin-binding growth factor: Score = 57, P = 0.26, (11/26) | Activated T-cells, spleen, fetal liver |
| 12a | G329f.seq | 139 | con | ~1.00 kb | 100% homology to human HSP70 gene | |
| 13a | E67.seq | 140 | con | ~2.57 kb | ~90% homology to the human ubiquitin gene: Score = 460, P = 1.8e-119 | |
| 14a | E94.seq | 141 | con | ~0.63 kb | homology to lilium longiformium HSP70 gene: Score = 62, P = 0.48 (12/28) | |

*expression in tissue at least 10x stronger that other tissues listed
**expression profile tested using only samples containing activated T-cells (no other tissues tested)

The bin number, name, type, SEQ ID NO: and approximate size of each sequence are provided in the first set of columns. The "type" of sequence is either (i) a single contiguous consensus sequence derived from the overlapping cDNA clones that comprise that bin ("con"), (ii) two or more non-overlapping consensus sequences within a bin (e.g., "con", "con2", . . . ), representing consensus sequences covering, e.g., a 3' and a 5' portion of a region that has not been completely sequenced, or (iii) alternatively-spliced variants ("alt") derived from the same "parent" sequence.

All sequences identified in Table 1 were analyzed by subjecting them to a "BLASTX" homology search against a protein sequence database (PIR+SWISS-PROT). The results of these analyses are also presented in Table 1. In cases where the BLASTX search did not yield a significant match, the cell in the Table is labeled "NSM" (no significant matches).

The last column of Table 1 presents a summary of experiments performed to address the expression patterns of the various cDNAs. Most of these experiments were performed using RT-PCR with primers specific for the consensus sequence representing each bin. The details of the experimental methods are presented in Example 6B. Primers specific for the sequences to be amplified were constructed using standard methods. The primers were selected such that the expected amplification products were typically between 200 and 1000 bp in length. The following tissues were used for the RT-PCR reactions: total embryo (6, 8, 12 weeks of gestation), fetal liver, fetal brain, fetal muscle, placenta, adult heart, adult muscle, adult liver, adult brain, adult pancreas, adult kidney, adult aorta, adult spleen, adult testis, adult bone marrow, JY B-cell line, resting T-cells and activated T-cells. The RT-PCR expression analyses revealed that many of the novel, previously uncharacterized cDNAs, were expressed in activated T-cells, suggesting that they may encode novel immunomodulatory molecules.

Many of the consensus sequences presented above were arrived at by analysis of a number of overlapping clones. In some cases, the clones overlapped only near their ends and the sequence between the overlaps was derived from a single cDNA. In such cases and some others, the consensus sequence may contain alternatively-spliced sequences from the same gene, even though different alternatively-spliced transcripts derived from the same region of the gene were not detected. Such alternatively-spliced sequences in the consensus sequences may have different tissue specificities, and thus give rise to different patterns of expression, depending on which portion of the cDNA is being amplified. In cases where different patterns of expression for cDNAs that were part of the same consensus sequence were detected, the "expression profile" in Table 1 above lists all the tissues in which expression of any of the cDNAs constituting the bin or consensus sequence was detected, unless indicated otherwise.

One such difference in expression profiles was observed with the cDNAs comprising bin 13 (A6con.seq; SEQ ID NO:85). A series of experiments designed to detect expression profiles of various cDNAs which comprised SEQ ID NO:85 yielded the results shown in Table 1. However, as described in Example 9 and illustrated in FIG. 2, experiments using primers SEQ ID NO:149 and SEQ ID NO:150, designed to amplify the indicated portion of the sequence shown in FIG. 1 (SEQ ID NO:151), consistently detected this transcript only in activated T-cells. Accordingly, amplification of this DNA fragment may be used as a sensitive method to detect the presence of activated T-cells.

The cDNAs identified as described above may also be used to identify the chromosome region from which they are derived, using standard mapping techniques, as detailed, for instance, in Example 5. Such mapping information may be used, for example, to identify clones which map to regions implicated in genetic diseases or disorders.

Physical mapping of selected cDNAs can be done by a variety of means. A particularly rapid method is PCR mapping to the YAC clones and natural or radiation hybrid panels that carry whole human chromosome 5 or its portions. Such experiments preferably include appropriate controls, such as no genomic DNA, total genomic DNA, rodent genomic DNA that is present in radiation hybrids, etc. Another approach employs Southern blot hybridization of the YAC clones or genomic DNA, and isolation of chromosome 5-specific cosmids or any other genomic clones, such as bacteriophage 1 (P) or bacterial artificial chromosomes (BACs), with cDNA as a probe.

Some of the nucleotide sequences presented in Table 1 do not include the entire coding region of the gene to which they correspond. In such cases, the remaining sequences may be obtained by one of skill in the art using the sequence information and teachings contained in the present specification combined with standard molecular techniques. For example, the cDNA clones described herein, or fragments thereof, may be used to screen a cDNA library constructed from, e.g., human T-cells using standard methods (e.g., Ausubel, et al., 1988). Such libraries are commercially available, for example, from Clontech (Palo Alto, Calif.). Full length clones may also be obtained by similar screening of cDNA pools generated as described herein.

Using the sequence information disclosed herein, one of skill in the art employing standard techniques may derive near full length cDNAs, express and purify protein products of such cDNAs, and confirm function using, e.g., gene knock-out experiments. This information may then be used to develop specific assay systems to test for biological activities and to screen for therapeutic compounds that modulate those activities.

IV. Characterization of Exemplary cDNA Sequences

Expression of specific sequences was assessed using Northern blot analyses, as detailed in Example 6A. The Northern analyses were performed with cDNA fragments representing bins 1, 2, 3, 13, 16, 18, 22, 23, and 28, on blots generated essentially as described in Example 6A or obtained commercially, typically from Clontech (Palo Alto, Calif.).

A. Human Acyl-CoA Synthetase

Fragments derived from the Human Acyl-CoA synthetase gene (SEQ ID NO:59) were used to assess the expression pattern of this gene using Northern blot in the following adult human tissues: spleen, thymus, prostate, testis, ovary, small intestine, colon and leukocytes. The experiments were also performed using fetal brain, fetal lung, fetal liver and fetal kidney. A prominent band was seen in all tissues at approximately 1.8 kb. In addition, a 2.8 kB form was detected in testis, prostate, fetal liver and activated T-cells.

The expression pattern of human Acyl-CoA synthetase is different from that of the rat brain Acyl-CoA synthetase, where two predominant transcripts of 2.9 and 6.3 kb are observed predominantly in brain and heart, and to some extent, in adrenal tissue (Fujino and Yamamoto, 1992). Based on these data, it is suggested that the human Long-chain acyl-CoA synthetase (LACS) gene described herein may be transcribed from two different promoters and that it's alternative processing represents a ubiquitous mechanism for generation of multiple protein isoforms or tissue-specific regulation. LACS from different species have been isolated and shown to play a critical role in fatty acid metabolism, acylation of many membrane proteins, and signal transduction.

The above results suggest that sequences derived from the human Acyl-CoA Synthetase gene may be used as a marker for testis tissue. Further, the promoters from the human LACS gene, which may be isolated using standard methods (e.g., Ausubel, et al., 1988), may be used to target expression of heterologous genes in testis tissue. Such expression may desirable, for example, in gene therapy approaches to testicular cancer.

B. Human RAD50 Homolog

Northern experiments were also performed using probes derived from sequences (SEQ ID NO:54 and SEQ ID NO:55) from the human homologue of yeast Rad50. A non-coding 3'-flanking fragment of the gene corresponding to nucleotides 4333–5567 of SEQ ID NO:54 was used to probe a Northern Blot containing RNA derived from the same set of adult tissues as described above. mRNA species of 1.9 and 0.85 kb were detected in all tissues tested, with the strongest expression in testis, ovary and small intestine. Uniformity of RNA loading was confirmed using a beta-actin probe.

Similar experiments employing a probe corresponding to nucleotides 417–4353 of SEQ ID NO:54 revealed two mRNA species. A stronger signal was observed at about 5.8 kb and much lower signal was detected at about 6.5 kb in all tissues, with strongest expression in testis. The results of RT-PCR and Northern blot analyses taken together confirmed expression of the human gene in activated T-cells, B-cells, placenta and multiple fetal tissues, including fetal liver. Genomic equivalent of this gene is about 100 kb.

In yeast, Rad50encodes major and minor transcripts of 4.2 and 4.6 kb in length, respectively (Raymond and Kleckner, 1993). Steady-state levels of both transcripts increase during meiosis, reaching maximal levels midway during meiotic prophase. Yeast RAD50 appears to be involved in DNA repair. It is required during vegetative growth for recombinational repair of double strand breaks and for efficient mating type switching, a direct recombination event promoted by a site-specific double strand break. Most *S. cerevisiae* mutants of rad50 are deficient in repair of damage induced by X rays and in meiotic recombination.

The polypeptide predicted for *S. cerevisiae* Rad50 protein is 153 kDa (1312 aa) (Alani, et al., 1989). The protein contains an amino-terminal ATP-binding domain. Inactivation of this site by point mutations results in a null phenotype, and primary defects in meiosis. The remainder of the protein includes two long segments of heptad repeat sequence diagnostic of regions capable of forming alpha-helical coiled coils, one of which is similar to the S-2 domain of the myosin heavy chain. Since some mutations in the protein affect meiotic recombination but not the repair, it is likely that the protein has domains with different roles.

It is contemplated that the human homologue of Rad50 described herein (e.g, as represented by SEQ ID NO:144) plays a role in human DNA repair and may be a target for cancer related therapeutics. For example, since attenuating the function of Rad50 gene products may sensitize cells to DNA damage, they may be targets for therapeutic interventions that rely on DNA damage to differentially inhibit tumor survival.

C. Human Septin-2 Homolog

A fragment corresponding to nucleotides 203–1464 of SEQ ID NO:97 was used to probe a Northern blot containing RNA from the same adult tissues listed above. The probe identified a faint band at ~4.6 kb in lymph node, thymus, appendix, bone marrow and fetal liver. A near full-length cDNA containing ~4.6 kb of the human gene was isolated using Marathon RACE using primer designed based on sequence SEQ ID NO:97. The cDNA encodes a protein that has higher homology to Septin-2 than to CDC3 and that is 40 aa longer than Drosophila Septin-2.

In yeast, mutants of cell division cycle (cdc) gene 3 (cdc3) are incapable of forming an F-actin contractile ring. It is now believed that cdc3 encodes a profilin that plays essential in cytokinesis, by catalyzing the formation of the F-actin contractile ring (Balasubramanian, et al., 1994).

In Drosophila, Septin-2 is present at the bud neck during cell division, and is required for cytokinesis: in pnut mutants, imaginal tissues fail to proliferate and instead develop clusters of large, multinucleate cells. Pnut interacts with a gene required for neuronal fate determination in the compound eye.

Computer analysis of the human septin protein described herein has identified several important motifs, such as NTP-binding site (ATP/GTP-binding loop) at N-terminus, a coiled-coil region and a bipartite nuclear targeting site at C-terminus. These data suggest that its role in signal transduction to the nucleus may be associated with cell division. The coiled-coil region may be involved in the formation of protein complexes and in chromosome condensation and disjunction in the cell cycle.

In view of septin-2's involvement in cell proliferation, it is contemplated that the human Septin-2 homolog, peptide represented by SEQ ID NO:143, may be a target for anticancer therapies and methods. Further, monitoring septin-2 expression by quantitative RT-PCR can be used as a diagnostic tool for measuring proliferative potential of selected cell types.

D. Other Genes and Methods

It will be understood that human cDNA sequences isolated as described herein may be characterized using any of a number of assays known to those of skill in the art, in addition to the expression assays detailed above. For example, functional assays particularly advantageous for the characterization of immunomodulatory molecules (i.e., assays which may be used to further characterize the immunomodulatory activity of polypeptide compositions detailed herein) include proliferation assays (e.g., as described in Example 8), as well as assays based on the stimulation of expression of specific proteins in cell lines responsive to the immunomodulatory molecules (e.g., cytokines) under study (e.g., Thorpe, et al., 1992; Wadhwa, et al., 1992). Specifically, compounds or polypeptides which inhibit, e.g., T-cell proliferation, may be characterized as immunosuppressants, whereas compounds or polypeptides which stimulate, e.g., T-cell proliferation, may be identified as immunostimulants.

In the case of polypeptides comprising receptors for, e.g., other immunomodulatory compounds, such as cytokines, standard methods may be employed to express the receptors in a suitable host cell suitable for additional experiments, such as binding assays or physiological experiments.

Other methods of assaying expression may also be employed in the characterization of novel cDNA sequences isolated as described herein. For example, in situ hybridization may be used to perform cellular localization in tissues having comprised of distinct cell types. The cDNA sequences presented herein may also be used to produce proteins (e.g., by cloning the sequences into an expression vector; Ausubel, et al., 1988). Such proteins may in turn may be employed to generate antibodies using standard methods (e.g., Harlow, et al., 1988) to localize the gene products at the cellular and sub-cellular levels.

V. Utility

Methods and compositions of the present invention are useful in a number of applications. For example, they may be employed in cell typing applications. In this aspect, the invention includes a method of identifying the presence of activated T-cells in a sample containing a plurality of different cell types. Experiments performed in support of the present invention The method includes performing a polymerase chain reaction amplification which employs an aliquot of the sample or an extract thereof as the amplification target. The reaction is conducted using standards PCR conditions (Mullis, 1987; Mullis, et al., 1987) with oligonucleotide primers capable of selective amplification of a polynucleotide fragment having the sequence SEQ ID NO:151, to generate an amplification product having a specific size.

The selection of regions of a sequence suitable for serving as templates for PCR primer design is well known in the art (e.g., Innis, et al., 1990). In fact computer programs designed specifically for this purpose are commercially-available (e.g., "OLIGO" primer analysis software, NCBI, Inc., Plymouth, Minn.). An exemplary primer pair for such an amplification consists of primers having sequences SEQ ID NO:149 and SEQ ID NO:150.

The size of the amplification is then determined using, for example, agarose or polyacrylamide gel electrophoresis (see, e.g., Ausubel, et al., 1988), and the observed size is compared with the expected size. The detection of amplification product corresponds to the existence of activated T-cells in the sample. The amount of amplification product may be correlated with the number of activated T-cells using a quantitative PCR approach (e.g., Piatak, et al., 1993; Vandevyver, et al., 1995).

The identification of activated T-cells in a sample is useful in, e.g., the diagnosis of diseases affecting activated T-cells or T-cell activation, such as AIDS, rheumatoid arthritis, asthma, cystic fibrosis, atherosclerosis, ulcerative colitis, asthma and severe allergies.

Another utility enabled by the present disclosure is a method of identifying sequences encoding polypeptides having immunomodulatory activity. The method includes (i) selecting, by direct selection using sequences specific for region 5q23-31 of human chromosome 5, cDNA fragments isolated from tissues or cells expressing cytokines, (ii) grouping the fragments into bins, where each bin represents cDNA fragments corresponding to a single gene or genetic locus, the grouping performed by sequencing the fragments and/or mapping the fragments to longer sequences derived from region 5q23-31 of human chromosome 5, and (iii) analyzing the tissue specificity of expression of transcripts corresponding to the fragments (transcripts from the gene or locus which the fragments represent). In one embodiment, the first step is performed using cDNAs obtained from cell lines and/or tissues expressing cytokines, such as activated T-cells. In another embodiment, the first step is performed using cDNAs obtained from a chromosome 5-specific activated T-cell cDNA library in lambda gt10, which was constructed using a kit from Life Technologies, Inc. and is deposited at Genelabs Technologies, Inc., Redwood City. In another embodiment, the analyzing of tissue-specific expression is carried out using sequence-specific primers in a polymerase chain reaction amplification reaction containing target nucleic acids derived from tissues or cell lines of interest. Tissues which may be used in determining the tissue specificity of expression include total embryo, fetal liver, fetal brain, fetal muscle, placenta, adult heart, adult muscle, adult liver, adult brain, adult pancreas, adult kidney, adult aorta, adult spleen, adult testis, adult bone marrow, resting T-cells and activated T-cells.

The teachings of the present disclosure may also be employed in a method of obtaining full-length sequences of genes or loci identified as having immunomodulatory activity. The method includes selecting a desired sequence identified in Table 1 and using the sequence to isolate overlapping clones. In one embodiment, such overlapping clones are isolated using rapid amplification of cDNA ends (RACE) PCR with cDNA obtained from tissues or cell lines of interest or from a cDNA or genomic DNA library. In another embodiment, the overlapping clones are isolated by direct hybridization screening of a cDNA or genomic DNA library made from, for example, T-cells, a lymphoma or a leukemia.

As another example of a utility, the present invention includes a method of identifying proteins having immunomodulatory activity. The method includes obtaining a full-length coding sequence of a gene represented by a sequence presented in Table 1 (e.g., as described above) and cloning the sequence into a recombinant expression vector. The resulting vector is then used to express recombinant polypeptides in selected host cells, such as $E.\ coli$. Expression vectors such as described above typically contain control sequences, such as sequences containing promoter regions, enhancer elements, and the like, which are compatible with the selected host cell. These control sequences are operably linked to the insert sequence such that the insert sequence can be expressed in the selected host cell.

One example of an expression vector for recombinant production of latency-associated polypeptides is the plasmid pGEX (Smith, et al., 1985, 1988) and its derivatives (e.g., the pGEX series from Pharmacia Biotech, Piscataway, N.J.). These vectors express the polypeptide sequences of a cloned insert fused in-frame with glutathione-S-transferase. Recombinant PGEX plasmids can be transformed into appropriate strains of $E.\ coli$ and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al., 1988).

Alternatively, affinity chromatography may also be employed for isolating β-galactosidase fusion proteins, such as those produced by cloning latency-associated polypeptide sequences in lambda gt11. The fused protein is isolated by passing cell lysis material over a solid support having surface-bound anti-β-galactosidase antibody.

Other suitable expression systems include a number of bacterial expression vectors, such as lambda gt11 (Promega, Madison Wis.), pGEX (Smith, et al.), and pBS (Stratagene, La Jolla Calif.) vectors; yeast expression systems, such as the Pichia expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ionexchange chromatography, isoelectric focusing, gel electrophoresis and affinity chromatography. Protein preparations can also be concentrated by, for example, filtration (Amicon, Danvers, Mass.).

In addition to recombinant methods, latency-associated proteins or polypeptides may be chemically synthesized using methods known to those skilled in the art.

Polypeptides obtained as described above may be further evaluated by methods known in the art of cytokines and interleukins. For example, the polypeptides may be tested in functional assays, such as cell proliferation assays and assays designed to monitor the activation of gene expression in response to cytokine stimulation as described above.

It is further contemplated that polypeptides identified as having immunomodulatory activity may be employed in therapeutic applications to augment, affect and/or correct the functioning of the immune system in a subject in need of such treatment.

In another example of the utility of the present invention, the teachings herein may applied in a method of identifying small molecules that affect alter and/or modulate the activity of immunomodulatory proteins such as described above. The method includes assaying the effects of a polypeptide having immunomodulatory activity in the presence and absence of a test small molecule compound, and identifying the test compound as effective if the test compound is effective to significantly alter the effects of the polypeptide. In one embodiment, the small molecule compound is one of a plurality of such compounds present in a combinatorial library, such as one of a plurality of small molecules in a small molecule combinatorial library, or one of a plurality of peptides in a peptide combinatorial library. Small molecule compounds include, but are not limited to, peptides, macromolecules, small molecules, chemical and/or biological mixtures, and fungal, bacterial, or algal extracts. Such compounds, or molecules, may be either biological, synthetic organic, or even inorganic compounds, and may be obtained from a number of sources, including pharmaceutical companies and specialty suppliers of libraries (e.g., combinatorial libraries) of compounds.

The following examples illustrate but in no way are intended to limit the present invention.

MATERIALS AND METHODS

Unless otherwise indicated, restriction enzymes and DNA modifying enzymes were obtained from New England Biolabs (Beverly, Mass.) or Boehringer Mannheim (Indianapolis, Ind.). Nitrocellulose paper was obtained from Schleicher and Schuell (Keene, N.H.). Materials for SDS-polyacrylamide gel electrophoresis (SDS-PAGE) were obtained from Bio-Rad Laboratories (Hercules, Calif.). Other chemicals were purchased from Sigma (St. Louis, Mo.) or United States Biochemical (Cleveland, Ohio).

A. Buffers and Media

Phosphate-buffered saline (PBS)

10×stock solution, 1 liter:

80 g NaCl 2 g KCl 11.5 g $Na_2HPO4-7H_2O$ 2 g $KH_2PO_4$

Working solution, pH 7.3:

137 mM NaCl 2.7 mM KCl 4.3 mM $Na_2HPO_4-7H_2O$ 1.4 mM $KH_2PO_4$

SSC (sodium chloride/sodium citrate), 20×

3M NaCl (175 g/liter)

0.3M $Na_3$citrate-$2H_2O$(88 g/liter)

Adjust pH to 7.0 with 1M HCl

SSPE (sodium chloride/sodium phosphate/edta), 20×

3.0M NaCl 0.20M $NaH_2PO_4$ 20 mM EDTA, pH 7.4

Tris/EDTA Buffer (TE)

10 mM Tris-Cl, pH as indicated 1 mM EDTA, pH 8.0

AHC Medium and Plates (ura$^-$, trp$^-$)

1.7 g yeast nitrogen base without amino acids and without ammonium sulfate (Difco Laboratories, Detroit, Mich.).

5 g ammonium sulfate.

10 g casein hydrolysate-acid, salt-free and vitamin-free (United States Biochemical, Cat. #12852, Cleveland, Ohio).

50 ml (for medium) or 10 ml (for plates) of 2 mg/ml adenine hemisulfate (Sigma Chemical, Cat. #A-9126, St. Louis, Mo.).

Dissolve in a final volume of 900 ml $H_2O$, adjust pH to 5.8.

Autoclave 30 min, then add 100 ml sterile 20% (w/v) glucose. For AHC plates, add 20 g agar prior to autoclaving. Store at 4° C. for ≦6 weeks.

Denhardt solution, 100×

10 g Ficoll 400

10 g polyvinylpyrrolidone 10 g bovine serum albumin (Pentex Fraction V, Miles Laboratories, Kankakee, Ill.)

$H_2O$ to 500 ml

Filter sterilize and store at −20° C. in 25-ml aliquots

EXAMPLE 1

Construction of cDNA Pools for Use in Direct Selection

Complementary DNA (cDNA) was prepared using standard methods from tissues and cell lines that expressed or were likely to express sufficient amounts of messenger RNA (mRNA) encoding proteins of interest. cDNA samples from several sources were sometimes grouped into "cDNA pools". For example, ionomycin-stimulated T cells, T cell clones, and T-lineage lymphomas were found be the best mRNA source for construction of a polymerase chain reaction (PCR) -amplifiable cDNA pool for direct selection due to high levels of corresponding cytokines expressed (first eight samples in Table 3, below). Similarly, a hybrid cDNA pool, termed pool #1, was constructed using mRNA isolated from a mixture of several activated T-cell clones and lymphomas (obtained from David Lewis, University of Washington, Seattle; Lewis, et al., 1988).

A complex primary cDNA pool, termed pool #2, was constructed from human fetal and adult tissues, including fetal brain and liver, adult bone marrow, and activated lymphocytes, as well as the following cytokine-producing cell lines, which, unless otherwise indicated, were obtained form the American Type Culture Collection (ATCC), Rockville Md.: A-10 cells (T cell clone), Jurkat cells (ATCC TIB-152), CEM cells (ATCC CCL-119), HUT-78 cells (ATCC TIB-161), JM cells (ATCC CRL-8294), Molt-4 cells (ATCC accession number CRL1582) and NG-1 cells.

Prior to isolating mRNA from "activated" T-cell samples, the cells were grown at $5\times10^6$ cells/ml in RPMI medium (GIBCO/BRL Life Technologies) supplemented with 5% human AB serum as previously described (Georgopoulos, et al., 1990) and activated using 50 ng/ml phorbol myristate acetate (PMA; Sigma, St. Louis, Mo.) in combination with either 25 µg/ml concanavalin A (Con A) (Pharmacia, Piscataway, N.J.) or 0.5 µM ionomycin (Calbiochem-Behring, San Diego, Calif.).

A. Cell Isolation and Synthesis of cDNA

1. Isolation of Primary T Cells and Thymocytes. Circulating adult T cells and thymocytes were isolated as previously described (Georgopoulos, et al., 1990) by Ficoll-Hypaque density gradient centrifugation and treated with CD4 Lymphokwik (One Lambda, Los Angeles, Calif.), a mixture of complement and monoclonal antibodies (mAb) directed against non-T-lineage markers and the CD8 surface antigen, following the manufacturer's instructions. The final purity of each T-lineage cell population was consistently >95% based on flow cytometric analysis after staining with appropriate mAbs.

2. Cell Activation. Cells were activated at $5\times10^6$/ml in RPMI medium supplemented with 5% human AB serum as previously described (Georgopoulos, et al., 1990) using 50 ng/ml phorbol myristate acetate (PMA; Sigma, St. Louis, Mo.) in combination with either 25 µg/ml concanavalin A (ConA) (Pharmacia, Piscataway, N.J.), 0.5 µM ionomycin (Calbiochem-Behring, San Diego, Calif.), or 2.5 µg/ml PHA (Sigma, St. Louis, Mo.).

3. RNA Isolation. Cell or tissue homogenates were prepared using a Polytron homogenizer as described (Chomczynski and Sacchi, 1987). Total RNA was isolated by the guanidinium isothiocyanate/CsCl method (Glizin, et al., 1974) or by the acid guanidinium isothiocyanate-phenol-chloroform extraction method (Chomczynski and Sacchi, 1987) using a commercial kit ("TRIZOL", Life Technologies, Inc., Gaithersburg, Md.). mRNA was isolated from the total RNA using oligo(dT)$_{25}$ "DYNABEADS" (Dynal Inc., Lake Success, N.Y.) following manufacturer's instructions ("mRNA Isolation Using "DYNABEADS" OLIGO(dT)$_{25}$", pp 35–60 in *BIOMAGNETIC TECHNIQUES IN MOLECULAR BIOLOGY*—TECHNICAL HANDBOOK, Second Edition, Dynal, A. S. (Oslo, Norway) (1995). Briefly, Poly-A+ mRNA was selected using "MAG- NETIC DYNABEADS OLIGO (dT)$_{25}$" (Dyndal A. S., Oslo, Norway) according to protocol 2.3.1 (Jakobsen, et al., 1990, 1994) as recommended by the manufacturer.

4. cDNA Synthesis. Cell or tissue Double-stranded (ds) cDNA was synthesized using the "SUPERSCRIPT" "CHOICE SYSTEM" kit for cDNA synthesis (GIBCO/BRL Life Technologies, Gaithersburg, Md.) according to the manufacturer's instructions, except that custom adapters (Adapter #3 and adapter #5, described below) were used in place of the EcoR1 adapters supplied with the kit. Approximately 5 μg of poly(A$^+$) mRNA were used with oligo dT15 or random hexamers to synthesize ds cDNA. The cDNA was purified from the primers and the low molecular weight products (<250 bp) on "WIZARD" PCR Preps DNA Purification System columns (Promega, Madison, Wis.) according to the manufacturer's protocol, and ligated to dephosphorylated adapters #3 (SEQ ID NO:1, SEQ ID NO:2) or #5 (SEQ ID NO:3, SEQ ID NO:4) using standard methods (Sambrook, et al., 1989). Typically, cDNA pools designed for direct selection contained adapter #3 at their ends to allow single primer PCR amplification (e.g., using primer #A32 (SEQ ID NO:5) or primer #AD3-CUA (SEQ ID NO:6; see below).

5'-biotinylated primer #A5-2b (SEQ ID NO:7) was designed to synthesize biotinylated subtraction probes (e.g., ribosomal, mitochondrial, Alu-, etc.) from cDNA fragments containing Adapter #5 using PCR. Primer #A3-2 (SEQ ID NO:5) was designed to synthesize similar probes from cDNA fragments containing Adapter #3. CUA-containing primer #AD3-CUA (SEQ ID NO:6) was designed to PCR amplify cDNAs that subcloned into the pAMP10 vector (GIBCO/BRL Life Technologies, Inc).

B. Screening of cDNA Samples with Cytokine PCR Primers

The presence of specific cytokine cDNAs in the different cDNA samples/pools was determined using PCR to provide an estimate of the degree to which such cytokine transcripts were present, i.e., to "validate" the cDNA samples/pools as sources for cytokine cDNAs. The PCR reactions were carried out using standard methods (Mullis, 1987; Mullis, et al., 1987) with the primer pairs presented in Table 2, below.

TABLE 2

| Primers | SEQ ID NO: | T$_{ann}$ | Sequence | Product Size |
|---------|------------|-----------|----------|--------------|
| GM-CSF-2 | 8 | 60° C. | CCTTGACCATGATGGCCAGCC | 187 bp |
| GM-CSF-1 | 9 | | CCCGGCTTGGCCAGCCTCATC | |
| IL3-1 | 10 | 55° C. | CTCTGTGGTGAGAAGGCCCA | 287 bp |
| IL3-2 | 11 | | CTTCGAAGGCCAAACCTGGA | |
| IL4-3 | 12 | 55° C. | GGTTTCCTTCTCAGTTGTGTT | 210 bp |
| IL4-4 | 13 | | CTCACCTCCCAACTGCTTCCC | |
| IL5-1 | 14 | 55° C. | CACCAACTGTGCACTGAAGAAATC | 213 bp |
| IL4-2 | 15 | | CCACTCGGTGTTCATTACACC | |
| IL9-1 | 16 | 60° C. | AGCTTCTGGCCATGGTCCTTAC | 360 bp |
| IL9-6 | 17 | | TCAGCGCGTTGCCTGCCGTGGT | |
| IL13-1 | 18 | 55° C. | ATGGCGCTTTTGTTGACCAC | 1013 bp |
| IL13-5 | 19 | | CCTGCCTCGGATGAGGCTCC | |
| IRF1-7 | 20 | 55° C. | GAAGGCCAACTTTCGCTGTG | 367 bp |
| IRF1-8 | 21 | | CACTGGGATGTGCCAGTCGG | |
| TCF7-3 | 22 | 55° C. | CCGTTCCTTCCGATGACAGTGCT | 898 bp |
| TCF7-4 | 23 | | GACATCAGCCAGAAGCAAGT | |
| EGRI1-6 | 24 | 60° C. | CCACCTCCTCTCTCTCTTCCTA | 750 bp |
| EGRI1-7 | 25 | | TCCATGGCACAGATGCTGTAC | |
| CD14-5 | 26 | 65° C. | CCGCTGGTGCACGTCTCTGCGACC | 1022 bp |
| CD14-6 | 27 | | CACGCCGGAGTTCATTGAGCC | |
| CDC25-3 | 28 | 65° C. | GAGAGGAAGGAAGCTCTGGCTC | 282 bp |
| CDC25-5 | 29 | | GTCCTGAAGAATCCAGGTGACC | |

The adapters were made by combining oligonucleotides #4665 (SEQ ID NO:1) and #4666 (SEQ ID NO:2) (Adapter #3), or oligonucleotides #A5-1 (SEQ ID NO:3) and #A5-2 (SEQ ID NO:4) (Adapter #5), heating the mixtures to 95° C. for 5 minutes, and allowing the mixtures to gradually cool to room temperature over about 30 minutes. This caused the oligonucleotides in the mixtures to hybridize and form double stranded adapters with 3' overhangs as illustrated below. The adapters were then dephosphorylated with calf intestine phosphatase (CIP) using a standard protocol (Ausubel, et al., 1988), and the phosphatase inactivated by incubating at 70° C. for 10 min.

All cDNA samples and cDNA pools #1 and #2 were screened using PCR with the above primers, and the relative amount of specific amplification product determined. Prior to amplification, the samples were diluted such that the concentration of cDNA was the same in each sample (about 200 μg/ml). The results for individual cDNA samples are presented in the Table 3, below. Three pluses (+++) indicate a relatively high level of expression, (++) an intermediate level, (+) a relatively low level, (±) a very low but consistent level, (∓) a very low and inconsistent level, and (−) no detectable expression.

TABLE 3

| cDNA | IL13 | IL4 | IRF1 | IL5 | IL3 | GM-CSF | TCF7 | IL9 | EGR1 | CD14 | CDC25 |
|------|------|-----|------|-----|-----|--------|------|-----|------|------|-------|
| T-cells | ++ | +++ | +++ | +++ | +++ | ++++ | +++ | +++ | − | ± | − |
| A-10 | +++ | ++++ | +++ | ++++ | +++ | ++++ | ± | +++ | ++ | ± | ∓ |

TABLE 3-continued

| cDNA | IL13 | IL4 | IRF1 | IL5 | IL3 | GM-CSF | TCF7 | IL9 | EGR1 | CD14 | CDC25 |
|---|---|---|---|---|---|---|---|---|---|---|---|
| Jurkat | + | + | +++ | − | +++ | +++ | +++ | − | − | ± | + |
| CEM | ++ | ++ | +++ | ∓ | +++ | +++ | +++ | − | ++ | ± | ++ |
| HUT78 | ++ | ++ | +++ | + | +++ | ++++ | +++ | − | +++ | ± | ++ |
| JM | + | − | +++ | ∓ | +++ | ++++ | +++ | − | − | ± | +++ |
| Molt4 | + | ++ | +++ | − | − | − | +++ | − | − | ± | ++ |
| HNG-1 | ++ | − | ++= | − | − | ++++ | +++ | − | +++ | ± | ++ |
| Daudi | − | − | + | − | − | − | ± | − | − | ∓ | + |
| 816 | − | +++ | +++ | ± | − | − | ± | +++ | − | − | ∓ |
| Mono | − | − | +++ | − | − | +++ | − | − | − | +++ | − |

Daudi B-lineage cell lymphoma (Daudi); Monocytes stimulated with LPS for 6 hrs (Mono); Adult T cells stimulated with Con A and PMA for 6 hrs (T-cells); EBV-transformed B-cell line 816 (816); HNG-1 T-cell lineage lymphoma (HNG-1); Molt-4 T-cell lineage lymphoma (Molt4); JM T-cell lineage lymphoma (JM); HUT-78 T-cell lineage lymphoma (HUT78); CEM T-cell lineage lymphoma stimulated with ionomycin and PMA for 6 hrs (CEM); Jurkat T-cell lineage lymphoma (Jurkat); and Clone A-10 of T-cell origin, producing high levels of IL4 and IL5 and stimulated with Con A for 6 hrs (A-10).

The data in Table 3, above, suggest that a cDNA pool formed of cDNA samples in the first 6 rows of the table, along with the monocyte cDNA, may be particularly effective as a source of cytokine cDNAs. Accordingly, cDNA pool #3 was formed by combining equal fractions of these seven cDNA samples. cDNA pool #4 was formed by combining equal fractions of all eleven cDNA samples listed in Table 3, above, along with cDNA from adult bone marrow.

Eight additional cDNA pools, termed cDNA pools #5–12, were constructed by combining, at a 1:1 vol/vol ratio, cDNA pool #3 with cDNA samples of similar concentrations isolated from human tissues, including total embryo (6, 8, 12 weeks of gestation; pools #5, 6 and 7, respectively), fetal liver (pool #8), fetal brain (pool #9), adult bone marrow (pool #10), adult thymus (pool #11), and adult spleen (pool #12).

EXAMPLE 2

Preparation of Genomic DNA for Direct Selection

A. Mapping of Genomic Clones used for Direct Selection

Yeast artificial chromosome (YAC) clones containing sequences from the cytokine gene cluster area of chromosome 5 (5q23-31) were isolated and physically mapped to provide a template for the direct selection of the cDNA samples and pools described in Example 1. YAC clone A94G6 (~425 kb) was obtained from the YAC Washington University library (St. Louis, Mo.) (Burke, et al., 1987; Morgan, et al., 1992). Clones 259E7 (~490 kb) and 854G6 (~1.3 mb) were isolated from CEPH regular and mega YAC libraries (Bellanne-Chantelot, et al., 1992).

To construct a physical map of the YAC clones, the clones were digested with NotI and run on a clamped homogeneous electrical fields (CHEF) mapper system ("CHEF-DR III" Variable Angle Pulsed Field Electrophoresis System, Bio-Rad Laboratories, Hercules, Calif.). The yeast clones were grown in liquid AHC medium (Bellanne-Chantelot, et al., 1992) for 48 hrs at 30° C. Cells were harvested, washed and embedded in 0.5% low melting temperature agarose (LMT) as described (Chumakov, et al., 1992). After the zymolase treatment and lysis, YACs were separated in 1% LMT agarose pulsed field gels in 0.5×TBE at 14° C. as described below.

All the separations were carried out in "CHEF-DR III" pulsed-field electrophoresis system (Bio-Rad) with following parameters: 1) small YACs (400–500 kb)—power 06 V/cm; run time 24 hrs 4 min; initial switch time 21.41; final switch time 39.48; 2) mega YACs (1–1.5 mb)— power 0.6V/cm; run time$^1$ 22 hrs 30 min; switch time$^1$ 60.00; run time$^2$ 12 hrs 30 min; switch time$^2$ 90.00.

The CHEF gels were blotted and hybridized by standard Southern hybridization (Sambrook, et al., 1989) to probes for IL13, IL4, IL5, IRF1, IL3, GM-CSF, all of which are located in 5q23-31. The hybridization conditions, unless specified, were: 5×SSPE, 0.1% SDS, 5×Denhardt's, $^{32}$P-labelled probe, 65° C. overnight. The blots were washed first with 1×SSC+0.1% SDS at room temperature, and then with 0.1×SSC+0.1% SDS at 65° C. several times, 15 min each.

The results from the hybridizations were used to construct a physical map of the 1.3 megabase (Mb) region encompassed by YACs A94G6, 259E7 and 854G6, which is presented in FIG. 1. This map was confirmed and further refined by physically mapping a panel of chromosome 5-specific cosmids, as described in Example 5, below.

B. Direct Selection Protocol

DNA from the genomic clones was isolated as described in part C, below. The isolated DNA was labeled with biotin either by PCR using biotinylated primers SEQ ID NO:34 and SEQ ID NO:35, or by conventional labelling technique. For PCR labelling 5'-biotinylated primers were used that had been synthesized at Genosys Biotechnologies, Inc. (Woodlands, Tex.). For conventional labelling either photoactivatable biotin (PAB) or Biotin-21-dUTP nick translation labelling kits from Clontech (Palo Alto, Calif.) were used.

Biotinylated genomic DNA was hybridized in solution with complex representative cDNA pools #4–12. In selection with YACs A94G6 and 259E7, cDNA pool #4 was used. In selection with the mega YAC 854G6, a mixture of equal amounts of cDNA pools #4–12 was used. Hybridization was done at 65° C. in 20 μl of 5×SSPE, 1×Denhardt, 0.1% SDS to Cot=500. cDNAs that was close to saturation was efficiently-captured under these conditions. Specifically-bound cDNAs were captured with Dynal streptavidin beads and washed with 400 μl of 2×SSC, 0.5% SDS twice at RT, 10 min each and 4 times with 400 μl of 0.2×SSC +0.1% SDS at 65° C., 5 min each time.

Biotinylated genomic DNA-cDNA hybrids and free YAC DNA fragments were captured with streptavidin coated magnetic beads (Dynal A. S., Oslo, Norway) for 30 min at RT with occasional tapping. Two hundred μg of the beads (40 μl, 5 μg/μl) were added per each 5 pMoles of biotinylated PCR product (up to 4 kb in length). About 4 μg of the biotinylated PCR products within the range of 1–4 kb could be captured by this amount of beads. Dynabeads were washed twice with buffer containing 1M NaCl in preblocking buffer (TE pH 7.5 +200 μg/ml Herring sperm DNA +0.1% BSA) and resuspended to 5 µg/µl in the same buffer without DNA or RNA. The suspension was incubated at room temperature (RT) for 30 min, and the beads were captured and isolated with the aid of a magnet. The isolated beads were then washed with 400 µl of 2×SSC, 0.5% SDS twice at RT, 10 min each and 4 times with 400 µl of 0.2×SSC+0.1% SDS at 65° C., 5 min each time.

After washing, specifically bound cDNAs were eluted from the hybrids of the biotinylated DNA-cDNA either by incubating the beads with 40 µl of 2.5 mM EDTA at 80° C. or with 100 mM NaOH at RT. The latter was followed by neutralization with 20 µl of 0.2M HCl and 10 µl of 1M Tris-HCl pH 8.0.

Eluted cDNAs were PCR amplified by single primer amplification (SISPA) using either primer #AD3-2 (SEQ ID NO:5) or #AD3-CUA (SEQ ID NO:6). Primer #AD3-CUA was used when PCR products were to be cloned in pAMP10. This cloning system substantially reduced the background of "0"-insert and chimeric clones.

A second round of direct selection was usually performed following completion of the first round. The first round typically resulted in a several hundred to a thousand fold enrichment. The second round of selection enabled enrichment up to about a hundred-thousand-fold (Morgan, et al., 1992).

To determine whether a second round of selection was necessary, cDNA aliquots were SISPA-propagated the #AD3-2 primer (SEQ ID NO:5), cleaned up by "WIZARD" PCR column chromatography, quantitated, and run a on 1% agarose gel (about 1 µg/lane) both before and after selection. The gels were visualized, blotted, and hybridized with the probes known to reside within given genomic DNA. Alternatively, PCR was used to assess the enrichment by direct selection (Morgan, et al., 1992). If the degree of enrichment was less than about ten thousand-fold, a second round was performed.

C. Preparation of YAC DNA for Direct Selection

YAC clones A94G6, 259E7 and 854G6 were grown overnight in AHC medium at 30° C. Agarose blocks were prepared according to the protocol of LePaslier (Chumakov, et al., 1992). Briefly, yeast cells harboring the YACs were harvested, washed, counted and embedded in 0.5% Sea-Plaque GTG agarose (FMC, Rockland, Me.) as described in CHEF-DR$^R$III instruction manual and application guide. YAC DNAs or their restriction fragments were separated in 1% LMT agarose (FMC) pulsed field gels in 0.5×TBE at 14° C. according to the Bio-Rad protocols. For smaller YACs (400–500 kb), the following parameters were applied: power 0.6 V/cm; run time 24 hrs 4 min; initial switch time 21.41; final switch time 39.48. For mega YACs (1–1.5 mb), the following parameters were applied: power 0.6V/cm; run time$^1$ 22 hrs 30 min; switch time$^1$ 60.00; run time$^2$ 12 hrs 30 min; switch time$^2$ 90.00.

YAC DNA-containing bands (containing ~250 ng DNA) were excised, placed into tubes with 2 vol of 1×Sau3AI buffer (New England Biolabs (NEB), Beverly, Mass.), and treated with 12 U of Sau3AI (NEB) at 37° C. for 5 hrs.

The agarose containing the digested YAC DNA was then melted in 1 volume of TE at 68° C., and the DNA isolated using the "WIZARD" PCR Preps DNA Purification System (Promega, Madison, Wis.) at 37° C. following the manufacturer's instructions. DNA was eluted with TE (pH 8.0).

Due to steric hindrance of the incorporated biotin, one of the following adapters was ligated to the eluted YAC DNA to allow more efficient SISPA amplification and PCR controlled labelling with biotin: (i) Sau3AI semiadapter #1, made of primers having sequences SEQ ID NO:52 and SEQ ID NO:53, (ii) Sau3A1 semiadapter #2, made of primers having sequences SEQ ID NO:30 and SEQ ID NO:31, or (iii) Sau3Al adapter #S-1/S-2, made of primers having sequences SEQ ID NO:32 and SEQ ID NO:33. Sau3Al semiadapter #2 provided better yields and specificity in ligations and subsequent PCRs.

Ligation of the linkers was typically carried overnight at +14° C. in 20 µl of the reaction mix, containing 100 ng of Sau3AI-digested YAC DNA, 100 pmoles of adapter, and 6 U of T4 DNA Ligase (New England Biolabs).

EXAMPLE 3

Direct Selection with the Genomic DNA Fragments Encompassing Cytokine Gene Cluster in 5q23-31

YAC clone DNA was PCR-amplified for 30 cycles using biotinylated primers SEQ ID NO:34 and SEQ ID NO:35. The amplified YAC DNA was then preblocked with Cot1 DNA (GIBCO/BRL Life Technologies, Inc.) and used for direct selection with cDNA samples as follows.

One hundred ng of the amplified biotinylated YAC DNA were mixed with 5 µg Cot1 DNA and 5 µg yeast host strain AB1380 in 8 µl of water and denatured for 15 min under mineral oil at 98° C. in a heating block. The mixture was then supplemented with 2 µl of 25×SSPE +5×Denhardt+ 0.5% SDS to a final concentration of 5×SSPE, 1×Denhardt solution and 0.1% sodium dodecyl sulfate (SDS) in 10 µl, and hybridized for 2.0 hrs at 60° C. to Cot=20. In parallel, 10 µg of cDNAs were denatured in 8 µl of water for 15 min under mineral oil and treated as described above.

Ten µg of cDNAs from selected samples were denatured in 8 µl of water for 15 min under mineral oil as described above and supplemented to a final concentration of 5×SSPE, 1×Denhardt and 0.1% SDS. Direct selection was initiated by mixing 10 µl of the amplified cDNAs with 10 µl of the amplified and preblocked biotinylated YAC DNA (100 ng), and hybridization was conducted to a Cot=500 (about 40 hrs) at 65° C. under mineral oil. A Cot value of 1 is equivalent to 83 µg/ml of DNA×1 hour at 60° C. in 5×SSPE.

A. Isolation of cDNA/DNA Hybrids with Magnetic Beads

The hybridization mixture was then incubated with streptavidin coated magnetic beads (Dynal, Inc., Lake Success, N.Y.) in a buffer containing 1M NaCl in TE pH 7.5 +0.1% BSA for 30 min at room temperature with occasional tapping to immobilize the biotinylated genomic DNA fragments, some of which contained hybridized cDNA species. Two hundred µg of the beads (40 µl, 5 µg/µl), effective to capture about 4 µg of the biotinylated PCR products (1–4 kb), were added per each 5 pMoles of biotinylated YAC DNA PCR product.

Following the incubation, the "DYNABEADS" were collected using a magnetic stand (Dynal, Inc.). The beads were then washed with 400 µl of 2×SSC, 0.5% SDS twice at RT, 10 min each, and 4 times with 400 µl of 0.2×SSC +0.1% SDS at 65° C., 5 min each. Specifically bound biotinylated DNA-cDNAs were incubated either with 40 µl of 2.5 mM EDTA at 80° C., or with 100 mM NaOH at RT with occasional tapping of the tube, eluted and neutralized with 20 µl of 0.2M HCl and 10 µl of 1M Tris-HCl pH 8.0.

Specifically bound biotinylated DNA-cDNAs were eluted either with 40 µl of 2.5 mM EDTA at 80° C. or with 100 mM NaOH at RT with occasional tapping of the tube. In cases where NaOH was used, the eluted beads were neutralized with 20 µl of 0.2M HCl and 10 µl of 1M Tris-HCl pH 8.0.

B. Subcloning of Selected cDNAs

The eluted material (~2 µl) was PCR-amplified for approximately 30 cycles in 100 µl tubes using approximately 50 pmoles each of primers SEQ ID NO:5 and SEQ ID NO:6, typically for 30 cycles using 2 μl of the eluate per 100 μl reaction. Primer SEQ ID NO:6 was used only when the PCR products were to be subcloned into the pAM10 vector. The PCR cycle parameters were as follows: 30 sec at 94° C., 30 sec at $T_{ann}$–5° C., and 2 min at 72° C. After the last cycle, the reactions were incubated for 7 min at 72° C., and then kept at 4° C. until further processing.

The PCR-amplified material was typically used for a second round of direct selection as described above, selected products were PCR amplified with primer SEQ ID NO:6, and ~1–5 μg of the selected cDNAs were subcloned into the pAMP10 vector ("CLONEAMP" directional PCR cloning system, GIBCO/BRL Life Technologies, Inc), which is adapted for uracil DNA glycosilase (UDG) cloning. This approach does not require restriction endonuclease digestion, end-polishing, purification or ligation. With this system, PCR products should contain specified 12-base 5' sequence that contains dUMP residues instead of dTMP.

Treatment with UDG renders dUMP residues abasic, disrupting base-pairing which results in 3'-protruding termini. pAMP10 plasmid contains a modified multiple cloning site and 3' ends that are complementary to the 3' protruding termini of the UDG-treated PCR amplification products obtained with the primer SEQ ID NO:6. Linear vector and UDG both go to the selected amplified cDNAs, without ligase, and are complete in less than 30 min, producing recombinant molecules ready for transformation.

1 μl of 20 μl UDG-reaction mixture was typically used to electroporate 50 μl of electrocompetent JS5 E.coli cells (Bio-Rad) according to manufacture's protocol in a "GENE PULSER" apparatus (Bio-Rad), in 0.1 cm electrode gap cuvettes. After 1 hr incubation of electroporated cells in 1 ml of Luria Broth (LB), 100 μl of the culture was plated onto LB plates containing 100 μg/ml Ampicillin.

The quality of a direct selection was monitored by Southern blot hybridization using a probe known to reside on the YAC, when similar quantities of the PCR amplified cDNA were loaded on the gel before and after the selection. Usually up to 100,000 —fold enrichment was observed in two rounds of selection. Before and after the selection cDNA aliquots were SISPA-propagated with the primer SEQ ID NO:5, cleaned up by Wizard PCR column chromatography, quantitated, and run in 1% agarose gel (about 1 μg/lane). The gels were visualized, blotted, and hybridized with the probes known to reside within given genomic DNA. Alternatively, quantitative PCR was used to assess the enrichment by direct selection. The enrichment ratios of direct selection were also monitored by plating cDNA aliquots before and after the selection, and counting the ratio of several marker clones to overall colonies. For example, if there was one IL3 positive clone in $10^6$ colonies before and one in 10 after the selection, the enrichment was considered to be around $10^5$ fold on this step. The selection process was controlled such that there was at least a 10 thousand-fold enrichment for at least one marker. Alternatively, negative selection was controlled for the markers known not to be on the YACs. In this case, the data were examined for a decrease in the ratio of this gene during selection.

EXAMPLE 4

Hybridization and Sequence Analysis of the Arrayed Region-Specific cDNAs
A. Analysis and Subcloning of the PCR Products Individual colonies of PCR pAMP10 clones generated as described above were used to inoculate wells containing LB broth in 96 well plates. The cultures were incubated overnight at 37° C. and an aliquot from each well was transferred to an Immobilon-N membrane (Millipore, Bedford, Mass.), forming a grid corresponding to the locations of the samples in the plate.

The DNA was immobilized on the membranes using UV-crosslinking, and the membranes were then screened with $^{32}$P-labelled YAC, Cot1, mitochondrial, ribosomal and single copy probes known to reside on a starting genomic clone, in order to eliminate nonspecific or already known cDNAs from further analysis, as follows.

Membranes with the arrayed cDNAs were hybridized with different $^{32}$P-labelled probes: highly repetitive, high molecular weight human COT1 DNA (Life Technologies, Inc.), human mitochondrial and ribosomal probes, starting YAC probe, single copy marker genes, known to reside within the genomic region in question. Because starting total cellular RNA contained certain amount of heteronuclear, ribosomal and mitochondrial species, final cDNA pools still contained these species, and it was much easier to prescreen the arrayed libraries for them rather than to introduce additional steps into the selection protocol.

About 55% of the clones in arrayed selected cDNA libraries were eliminated in such a prescreening procedure. Single copy known genes from the genomic region in question were monitored as well, and were used to evaluate the quality of the selected material and the depth of the libraries. These statistics also aided in determining how many novel cDNAs might be expected. For instance, 18% of the clones in the A94G6 YAC selection library belonged to IRF1, IL13, IL3 and IL5.

Negative clones were subject to sequencing. Sequencing data confirmed that there were at least 7 novel gene candidates, one of which was assembled into a full-length clone of a human homolog of S.cerevisiae RAD50. After computer analysis of the sequencing data, PCR primers were designed for prospective novel gene cDNAs and were used both to evaluate the tissue-specificity of expression of the gene candidates and for physical mapping of cDNAs to human chromosome 5 and the starting YAC, as described below.
B. Sequence Analysis Unique and presumably novel cDNA clones were sequenced and screened for similarity of their nucleotide and amino acid sequences using Fasta, BlastN, BlastX, tBlastN programs in known protein and nucleic acid databases. For efficient and quick identification of non-overlapping cDNAs, redundant cDNAs were eliminated by subsequent hybridization of the arrayed libraries with already identified individual cDNAs as probes and unique sequences were further analyzed as described below.

After two rounds of selection, ~66% of all clones mapped back to the starting genomic region, i.e., YAC or any other genomic DNA used to select these particular cDNAs. Each cDNA species comprised >1% of the selected material. The complexity of the selected cDNAs (i.e., the number of distinct species of DNAs) was dependent on the gene density in the region with respect to which the cDNAs were selected, and on the complexity of the starting cDNA sources.

EXAMPLE 5

Mapping Selected Clones to Chromosome 5:
Physical Mapping of cDNAs to Cosmids

A human chromosome 5-specific cosmid library was obtained from L. Deaven (Los Alamos National laboratories, N.M.) as arrayed individual clones in 96 well-plates that represented 8×genome equivalents subcloned in the sCos1 vector (Longmire, et al., 1993). The E. coli DH5 clones contained about 81% human inserts, 8% rodent inserts and 3% nonrecombinants. About 25,000 individual cosmid clones were microgridded onto "HYBOND-N" nylon membrane (Amersham Life Sciences, UK) using a "BIOMEK 1" (Beckman, Palo Alto, Calif.) robotic station. The filters with spotted clones were grown overnight on 96-well plate lids (Cat.#76-205-05, ICN Flow, Costa Mesa, Calif.) filled with 1.5% LB SeaKem GTG agarose (FMC Bioproducts, Rockland, Me.) supplemented with 20 µg/ml kanamycin (Sigma).

After treating the filters on Whatman 3 mm paper saturated with 2×SSC/0.5% SDS for 2 min, the filters were microwaved for 2.5 min at ~750 W until dry. Then they were submerged in a buffer containing 50 mM Tris-HCl pH 8.0, 50 mM EDTA, 100 mM NaCl, 1% Na-lauryl-sarcosine, and 250 mg/ml Proteinase K (Boehringer). After incubation for 20 min at 37° C. the filters were UV-crosslinked on Fotodyne crosslinker for 35 sec. After washing, the microgrids were hybridized with different $^{32}$P-oligolabelled YAC, cDNA or terminal cosmid walking probes as described below. Many cDNAs selected with the above specified YACs were mapped to the clones on the microgrids. Other libraries may be similarly used for mapping purposes, including YAC, BAC, and P1 genomic libraries.

EXAMPLE 6

Determining Tissue Specific Expression Tissue specificity of expression was performed using Northern blot analyses and PCR detection.

A. Northern Blot Analyses

Total RNA was isolated by the guanidinium isothiocyanate/CsCl method (Glisin, et al., 1974) or by the acid guanidinium isothiocyanate-phenol-chloroform extraction method using a commercial kit (Tri-reagent, Molecular Research Center, Cincinnati, Ohio), and was resolved on formaldehyde gels using standard methods (Sambrook, et al., 1989). The gels were blotted onto "HYBOND N" membranes (Amersham Life Sciences, UK), fixed by UV-crosslinking, and the membranes probed with radiolabeled probes corresponding to the clones. Conditions: Hybridization buffer, containing 5×SSPE, 2×Denhardt, 100 µg/ml sonicated salmon sperm DNA, 0.5% SDS; Hybridization temperature=65° C.

All probes consisted of DNA labeled by the random hexamer priming method using a commercial kit (Pharmacia, Piscataway, N.J.), with the exception of the IL4 probe, for which a single-stranded RNA probe was employed.

B. RT-PCR Analysis

About 1 µg of total RNA from different sources was reverse transcribed (RT) by random priming with "SUPERSCRIPT II" (GIBCO/BRL Life Technologies, Gaithersburg, Md.) in 20 µl of reaction mix as specified by the manufacturer. After heat inactivation, 1 µl of the RT-reaction was used in a 30 µl PCR of 30 cycles of conventional PCR with the primers and $T_{ann}$ specified below. Each PCR reaction contained 20 mM Tris-HCl pH 8.9 (at 25° C.), 16.7 mM $(NH_4)_2SO_4$, 1.5 mM $MgCl_2$, 200 µM dNTPs, 1 µM primers, and 0.8 U AmpliTaq (Cetus).

PCR-based detection of tissue-specific expression was performed using the following PCR-amplifiable primary cDNA pools: Total Embryo (6, 8, 12 weeks of gestation), Fetal Liver, Fetal Brain, Fetal Muscle, Placenta, Adult Heart, Adult Muscle, Adult Liver, Adult Brain, Adult Pancreas, Adult Kidney, Adult Aorta, Adult Spleen, Adult Testis, Adult Bone Marrow, JY B-cell line, Resting T-cells and Activated T-cells.

These cDNAs were either used directly as targets or PCR amplified for 30 cycles using primer SEQ ID NO:5. Amplified cDNAs were purified on a "WIZARD-PCR" column (Promega, Madison, Wis.), quantitated, and used in PCR reactions with different specifically-designed primers. The primer used were as indicated in Table 1.

Each PCR reaction contained 50 ng of one cDNA sample or pool (amplified or unamplified) as the target. After 30 cycles of PCR the products were separated on agarose gels and the intensity of the signals recorded and represented in Table 1, above.

EXAMPLE 7

Identification of Gene Function by Homology and Motif Identification

A. Identification of the Human Homolog of the Yeast Gene RAD50

Three cDNA clones A106, G157, G170, selected with the YACs A94G6 and 854G6 as described in Example 3, were mapped to chromosome 5-specific cosmid 256E1 about 10 kb upstream of the IL13 gene. Clone A106, when used as a probe, detected a predominant and ubiquitous mRNA species of 1.9 kb on a Northern blot of various mRNA species, including T-cells, B-cells, testis, small intestine, and brain. The primers A106-1 and A106-2 (SEQ ID NO:36 and SEQ ID NO:37, respectively) were used in RT PCR to evaluate the tissue distribution and to extend the cDNA to its full length.

RT PCR analysis confirmed that this message was expressed in activated adult T-cells, total embryo, fetal muscle, fetal liver, placenta, adult heart, and adult bone marrow. The extension of the A106 cDNA clone confirmed that it is a human homolog of the yeast gene RAD50. Northern blot hybridizations with the C-terminal coding portion of the gene used as a probe revealed two mRNA species: a strong signal of about 5.8 kb and a weaker signal at 6.5 kb.

A near full-length cDNA, termed G10 (also referred to as "rad50.seq"; SEQ ID NO:54), was obtained using marathon RACE (rapid amplification of cDNA ends; Chenchik, et al., 1995) techniques with activated T-cell and testis cDNA marathon pools. A marathon cDNA pool in contrast to a regular cDNA pool has a special adapter at the ends of cDNAs. Such cDNAs can not be SISPA amplified, because the adapter design suppresses PCR with a single adapter-specific primer (Siebert, et al., 1995). Exponential PCR will be observed only if a gene-specific primer is employed along with the adapter-specific primer. Such cDNA pools allow both 5'- and 3'-RACE amplifications, and finally isolation of intact genes via combination PCR (Chenchik, et al., 1995).

cDNA clone G10 is about 5,800 bp long and encodes a protein of 1312 aa with two highly-conserved domains with respect yeast RAD50: an N-terminal ATP-binding domain and a conserved C-terminal domain. A non-coding 3'-flanking portion of the gene, when used as a probe, detected mRNA species of 1.9 and 0.85 kb in multiple tissues. This may indicate either unusual alternative splicing of the RAD50 gene or an overlap with another gene. RT-PCR and Northern blot analyses have confirmed that G10 is expressed in activated T-cells, B-cells, placenta and multiple fetal tissues, including fetal liver.

Clones G18 and H230 have a 31 bp stretch at their 3'-end homologous to RAD50. RT-PCR analysis on different cDNA pools and genomic DNA with primers G18-1/2 (SEQ ID NO:50 and SEQ ID NO:51), respectively suggested alternative splicing of the RAD50. The RAD50 had been first mapped by PCR using the primers A106 1/2 (SEQ ID NO:36 and SEQ ID NO:37) and then by YAC Southern blot hybridization. Several chromosome 5-specific cosmids had been isolated that span the RAD50 gene. The genomic equivalent of G10 was found to be between about 80 and 150 kb in length. RAD50 appears to be a large gene with at least six exons. The C-terminal 2b fragment (~6 kb) of RAD50 was sequenced, enabling the positioning of four C-terminal exons.

C. Isolation and Mapping of cdc3 Human Homolog

Seventeen cDNAs encoding a novel cell division control gene were identified using direct selection with YAC clone 854G6. These cDNAs represent bin 23 in Table 1. The consensus sequence of these cDNAs was extended using the marathon RACE technique and is presented herein as SEQ ID NO:97.

EXAMPLE 8

Assays to Evaluate Immunomodulatory Activity of Compounds or Polypeptides

A. Peripheral Blood Lymphocyte (PBL) Proliferation Assay

Human peripheral blood lymphocytes are prepared using an established method (e.g., Boyum, 1968). Human blood buffy coat samples are resuspended in a calcium and magnesium-free Hank's balanced salt solution (HBSS, Gibco/BRL Life Technologies) at ~24° C. Approximately 25 ml of the cell suspension is then layered onto ~15 ml of Ficoll-Paque (Pharmacia LKB Biotechnology, Inc.), and is centrifuged at ~400×g for ~30 minutes at 15° C.

Following centrifugation, the PBL suspension at the interface is transferred to new centrifuge tubes, resuspended in a total volume of ~45 ml HBSS and centrifuged at ~350×g for ~10 minutes at 15° C. The supernatants are discarded and the PBL's are resuspended in 10 ml HBSS, combined, and centrifuged at ~260×g for ~10 minutes at 15° C. The cell pellets are suspended in 10 ml of X-Vivo tissue culture medium (Bio Whittaker, Walkersville, Md.) and counted using a hemocytometer. Tissue culture medium is then added to achieve a final cell concentration of ~1×10$^6$ cells/ml.

Proliferation assays are carried out in 96 well sterile tissue culture plates (e.g., Costar 3790 or Costar 3595). A volume of 100 μl PBL suspension is added to each well and the plates are incubated under an atmosphere of 93% air/7% $CO_2$ in a tissue culture incubator at 37° C. Compounds or polypeptides whose immunomodulatory activity is to be evaluated are then added to the wells. Different wells may have different compounds or polypeptides, or they may have different concentrations of the same compound or polypeptide. The plates may also have several wells with the same immunomodulatory compound or polypeptide at the same concentration, with other types of immunomodulatory compounds (e.g., small molecules) present in some wells.

After a selected period of time (e.g., 48 hours), ~50 μl of X-Vivo tissue culture medium containing ~8 μCi/ml [$^3$H] Thymidine (Amersham, ~50 Ci/mmol) are added to each tissue culture well. Following four hours additional incubation at 37° C., the cells are removed from the tissue culture wells and applied to filter paper using, e.g., a cell harvester. The filter paper is dried and cut into small (e.g., 1 cm) discs, which are placed in a scintillation vial containing ~2 ml of scintillation fluid (Biosafe, Research Products International Corp.). Samples are then counted in a scintillation counter (e.g., the Beckman LS 6000SC).

B. Spleen Cell Proliferation Assay

C3H mice are sacrificed by $CO_2$ inhalation and the spleens removed and cleaned of any fat or connective tissue. A nick is made in the tip of each spleen, and cells are collected by gentle aspiration through the tissue with Hank's balanced salt solution (HBSS) using a syringe and 18-gauge needle. The resultant spleen cell solution is filtered through Nytex sterile nylon mesh (Tetco), centrifuged at 200×g for 10 minutes, resuspended in HBSS, and centrifuged as above.

The pelleted cells are resuspended in a small amount of HBSS, counted using a hemocytometer and then resuspended in RPMI 1640 medium (Gibco/BRL Life Technologies, catalog #430-1800GL), containing 2-mercaptoethanol (50 μM), glutamine (2 mM), penicillin (100 U/ml), streptomycin (100 mg/ml and 5% (v/v) fetal calf serum (Hyclone or Sigma) to a concentration of 2.5×10$^6$ cells/ml.

A 100 μl volume of spleen cell solution is added to each well of a 96-well plate. Compounds or polypeptides having immunomodulatory activity or medium alone are added in a volume of 50 μl. The cultures are incubated for 2 days (37° C., 5% $CO_2$), and tritiated thymidine incorporation is assayed as described above.

EXAMPLE 9

PCR-Based Detection of Activated T-Cells

Polymerase chain reaction amplifications were performed as described above using cDNA derived from the following sources. Unless otherwise indicated, the tissues samples were obtained from adult individuals. (1) cDNA pool #3, (2) activated T-cells, (3) bone marrow, (4) fetal liver, (5) testis, (6) thymus, (7) peripheral leukocytes, (8) lymph node, (9) brain, (10) fetal thymus, (11) fetal brain, (12) spleen, (13) placenta, (14) muscle, (15) kidney and (16) heart.

Each 100 μl PCR reaction contained 50 ng of cDNA target, 50 pmols each of primers A116-1 (SEQ ID NO:150) and A116-2 (SEQ ID NO:149), 200 μM dNTPs, 2 mM MgCl2, 1×magnesium-free amplification buffer (Perkin-Elmer) and 2.5 U Taq DNA Polymerase. The primers were designed based on the sequence shown in FIG. 1 (SEQ ID NO:151), which is a portion of the A116 sequence (SEQ ID NO:85). The locations of the primers relative to the sequence are underlined.

The samples were cycled using a Perkin Elmer DNA Thermal Cycler 480 (Norwalk, Conn.) thermal cycler for 30 times through the following steps: 30 s at 94° C., 30 s at 55° C. and 2 minutes at 72° C. The amplification products were then separated on agarose gels, stained with ethidium bromide, and visualized to determine their size. An exemplary image of such a gel is shown in FIG. 2. The lanes in the gel correspond to cDNA from tissues (1) through (12), above. Amplification products of the appropriate size were consistently detected only in samples containing activated T-cells (1 and 2). Such amplification products were not detected in any of the other samples (3–16), with the exception of fetal liver (4), where a much fainter signal was occasionally observed.

These results indicate that PCR-based amplification of a DNA fragment having the sequence SEQ ID NO:151 may be used as a sensitive diagnostic for the presence of activated T-cells in a sample of cells. An exemplary primer pair suitable for use with such an amplification reaction consists of primers having sequences SEQ ID NO:149 and SEQ ID NO:150.

While the invention has been described with reference to specific methods and embodiments, it is appreciated that various modifications and changes may be made without departing from the invention.

It is claimed:

1. A method of identifying the presence of activated T-cells in a sample of human cells comprising, providing an mRNA or cDNA sample from said cells, and performing polymerase chain reaction amplification with primers that selectively amplify a portion of SEQ ID NO:151, wherein the presence of an amplified product of expected size indicates presence of activated T-cells.

2. The method of claim 1, wherein the primers are SEQ ID NO:149 and SEQ ID NO:150.

3. The method of claim 1, wherein said sample is from adult tissue.

* * * * *

SEQUENCE LISTING ( 1 ) GENERAL INFORMATION:

( i i i ) NUMBER OF SEQUENCES: 151

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: oligonucleotide #4665 for adapter #3

( x i ) SEQUENCE DESCRIPTION: SEQ ID NO:1:

GAGGATCCAG AATTCTCGAG TT                                          22

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: oligonucleotide #4666 for adapter #3

( x i ) SEQUENCE DESCRIPTION: SEQ ID NO:2:

CTCCTAGGTC TTAAGAGCTC                                             20

( 2 ) INFORMATION FOR SEQ ID NO:3:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: oligonucleotide #A5-1 for adapter #5

( x i ) SEQUENCE DESCRIPTION: SEQ ID NO:3:

TGGATCCTCT AGAGAGTGTG GTT                                         23

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: oligonucleotide #A5-2 for adapter #5

( x i ) SEQUENCE DESCRIPTION: SEQ ID NO:4:

ACCTAGGAGA TCTCTCACAC C  21

( 2 ) INFORMATION FOR SEQ ID NO:5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: oligo #AD3-2 for PCR amp of cDNAs ( x i ) SEQUENCE DESCRIPTION: SEQ ID NO:5:

ACTCGAGAAT TCTGGATCCT C  21

( 2 ) INFORMATION FOR SEQ ID NO:6:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: oligo #AD3-CUA for PCR amp of cDNAs ( x i ) SEQUENCE DESCRIPTION: SEQ ID NO:6:

CUACUACUAC UAACTCGAGA ATTCTGGATC CTC  33

( 2 ) INFORMATION FOR SEQ ID NO:7:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: oligo #A5-2b for PCR amp of cDNAs ( x i ) SEQUENCE DESCRIPTION: SEQ ID NO:7:

CCACACTCTC TAGAGGATCC A  21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GM-CSF-2

( x i ) SEQUENCE DESCRIPTION: SEQ ID NO:8:

CCTTGACCAT GATGGCCAGC C        21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer GM-CSF-1

( x i ) SEQUENCE DESCRIPTION: SEQ ID NO:9:

CCCGGCTTGG CCAGCCTCAT C        21

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer IL3-1

( x i ) SEQUENCE DESCRIPTION: SEQ ID NO:10:

CTCTGTGGTG AGAAGGCCCA        20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO (i v) ANTI-SENSE: NO (v i) ORIGINAL SOURCE:
    (C) INDIVIDUAL ISOLATE: Primer IL3- 2

(x i) SEQUENCE DESCRIPTION: SEQ ID NO:11:

CTTCGAAGGC CAAACCTGGA                                                           20

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: Primer IL4- 3

(x i) SEQUENCE DESCRIPTION: SEQ ID NO:12:

GGTTTCCTTC TCAGTTGTGT TCT                                                 23

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: Primer IL4- 4

(x i) SEQUENCE DESCRIPTION: SEQ ID NO:13:

CTCACCTCCC AACTGCTTCC C                                                     21

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: Primer IL5- 1

(x i) SEQUENCE DESCRIPTION: SEQ ID NO:14:

CACCAACTGT GCACTGAAGA AATC                                               24

(2) INFORMATION FOR SEQ ID NO:15:

(i) SEQUENCE CHARACTERISTICS:
        (A) LENGTH: 21 base pairs (B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer IL4-2

(xi) SEQUENCE DESCRIPTION: SEQ ID NO:15:

CCACTCGGTG TTCATTACAC C 21

(2) INFORMATION FOR SEQ ID NO:16:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer IL9-1

(xi) SEQUENCE DESCRIPTION: SEQ ID NO:16:

AGCTTCTGGC CATGGTCCTT AC 22

(2) INFORMATION FOR SEQ ID NO:17:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer IL9-6

(xi) SEQUENCE DESCRIPTION: SEQ ID NO:17:

TCAGCGCGTT GCCTGCCGTG GT 22

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Primer IL13-1

(xi) SEQUENCE DESCRIPTION: SEQ ID NO:18:

ATGGCGCTTT TGTTGACCAC 20

(2) INFORMATION FOR SEQ ID NO:19:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (vi) ORIGINAL SOURCE:
  (C) INDIVIDUAL ISOLATE: Primer IL13-5

(xi) SEQUENCE DESCRIPTION: SEQ ID NO:19:

CCTGCCTCGG ATGAGGCTCC 20

(2) INFORMATION FOR SEQ ID NO:20:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (vi) ORIGINAL SOURCE:
  (C) INDIVIDUAL ISOLATE: Primer IRF1-7

(xi) SEQUENCE DESCRIPTION: SEQ ID NO:20:

GAAGGCCAAC TTTCGCTGTG 20

(2) INFORMATION FOR SEQ ID NO:21:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: NO (vi) ORIGINAL SOURCE:
  (C) INDIVIDUAL ISOLATE: Primer IRF1-8

(xi) SEQUENCE DESCRIPTION: SEQ ID NO:21:

CACTGGGATG TGCCAGTCGG 20

(2) INFORMATION FOR SEQ ID NO:22:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: DNA (i i i) HYPOTHETICAL: NO (i v) ANTI-SENSE: NO (v i) ORIGINAL SOURCE:
(C) INDIVIDUAL ISOLATE: Primer TCF7- 3

(x i) SEQUENCE DESCRIPTION: SEQ ID NO:22:

CCGTTCCTTC CGATGACAGT GCT 23

(2) INFORMATION FOR SEQ ID NO:23:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Primer TCF7- 4

(x i) SEQUENCE DESCRIPTION: SEQ ID NO:23:

GACATCAGCC AGAAGCAAGT 20

(2) INFORMATION FOR SEQ ID NO:24:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Primer EGRI1- 6

(x i) SEQUENCE DESCRIPTION: SEQ ID NO:24:

CCACCTCCTC TCTCTCTTCC TA 22

(2) INFORMATION FOR SEQ ID NO:25:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Primer EGRI1- 7

(x i) SEQUENCE DESCRIPTION: SEQ ID NO:25:

TCCATGGCAC AGATGCTGTA C 21

(2) INFORMATION FOR SEQ ID NO:26:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: Primer CD14- 5

( x i ) SEQUENCE DESCRIPTION: SEQ ID NO:26:

CCGCTGGTGC ACGTCTCTGC GACC 24

( 2 ) INFORMATION FOR SEQ ID NO:27:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: Primer CD14- 6

( x i ) SEQUENCE DESCRIPTION: SEQ ID NO:27:

CACGCCGGAG TTCATTGAGC C 21

( 2 ) INFORMATION FOR SEQ ID NO:28:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: Primer CDC25- 3

( x i ) SEQUENCE DESCRIPTION: SEQ ID NO:28:

GAGAGGAAGG AAGCTCTGGC TC 22

( 2 ) INFORMATION FOR SEQ ID NO:29:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: Primer CDC25- 5

( x i ) SEQUENCE DESCRIPTION: SEQ ID NO:29:

GTCCTGAAGA ATCCAGGTGA CC                                                    2 2

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Sau3AI-2 for semiadapter #2

( x i ) SEQUENCE DESCRIPTION: SEQ ID NO:30:

TCGCGGCCGA ATTCTAGAGC TCGCT                                                 2 5

( 2 ) INFORMATION FOR SEQ ID NO:31:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Sau3AI-3

( x i ) SEQUENCE DESCRIPTION: SEQ ID NO:31:

CGCCGGCTTA AGATCTCGAG C                                                     2 1

( 2 ) INFORMATION FOR SEQ ID NO:32:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer Sau3AI S-1

( x i ) SEQUENCE DESCRIPTION: SEQ ID NO:32:

GATCTCGAGG ATCCTCAGAG AGTAGTAG                                              2 8

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer Sau3AI S-2 for adapter #S-1/2

( x i ) SEQUENCE DESCRIPTION: SEQ ID NO:33:

AGCTCCTAGG AGTCTCTCAT CATC      24

( 2 ) INFORMATION FOR SEQ ID NO:34:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 5'Biotin- YAC primer #1: PCR amp of YACs ( x i ) SEQUENCE DESCRIPTION: SEQ ID NO:34:

AGCGAGCTCT AGAATTCGGC CGC      23

( 2 ) INFORMATION FOR SEQ ID NO:35:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 5'Biotin- YAC primer #2: PCR amp of YACs ( x i ) SEQUENCE DESCRIPTION: SEQ ID NO:35:

CTACTACTCT CTGAGGATCC TCGAGA      26

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer A106- 1 for RAD50

( x i ) SEQUENCE DESCRIPTION: SEQ ID NO:36:

GTCATCCAGA CTCAGAGCTC      20

( 2 ) INFORMATION FOR SEQ ID NO:37:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Primer A106- 2 for RAD50

( x i ) SEQUENCE DESCRIPTION: SEQ ID NO:37:

CTGTCTAGGC AAACATGCTC                                                                                                      20

( 2 ) INFORMATION FOR SEQ ID NO:38:

( i ) SEQUENCE CHARACTERISTICS:
                ( A ) LENGTH: 38 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Primer G10-C for RAD50

( x i ) SEQUENCE DESCRIPTION: SEQ ID NO:38:

GAGAGGAATT CTTTTAATGA ACATTGAATC CCAGGGAG                                           38

( 2 ) INFORMATION FOR SEQ ID NO:39:

( i ) SEQUENCE CHARACTERISTICS:
                ( A ) LENGTH: 39 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
                ( C ) INDIVIDUAL ISOLATE: Primer G10-N for RAD50

( x i ) SEQUENCE DESCRIPTION: SEQ ID NO:39:

GAGAGGATCC TTTGTGGACT CCAGGTCCCT GGTGAGATT                                           39

( 2 ) INFORMATION FOR SEQ ID NO:40:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
   ( C ) INDIVIDUAL ISOLATE: Primer G34- 2

( x i ) SEQUENCE DESCRIPTION: SEQ ID NO:40:

CCACACTGAT GAACACACTC T                                    21

( 2 ) INFORMATION FOR SEQ ID NO:41:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
   ( C ) INDIVIDUAL ISOLATE: Primer G34- 3

( x i ) SEQUENCE DESCRIPTION: SEQ ID NO:41:

AGCTCGCTCT TGGAGATGGT G                                    21

( 2 ) INFORMATION FOR SEQ ID NO:42:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
   ( C ) INDIVIDUAL ISOLATE: Primer G34- 4

( x i ) SEQUENCE DESCRIPTION: SEQ ID NO:42:

TGGCTTCCTC AGTCTCGAAG G                                    21

( 2 ) INFORMATION FOR SEQ ID NO:43:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
   ( C ) INDIVIDUAL ISOLATE: Primer G34- 5

( x i ) SEQUENCE DESCRIPTION: SEQ ID NO:43:

CACCATCTCC AAGAGCGAGC T                                    21

( 2 ) INFORMATION FOR SEQ ID NO:44:

( i ) SEQUENCE CHARACTERISTICS:
   ( A ) LENGTH: 24 base pairs ( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer G34-6

( x i ) SEQUENCE DESCRIPTION: SEQ ID NO:44:

CACCATGAGG CATGCGTGCG CCTG 24

( 2 ) INFORMATION FOR SEQ ID NO:45:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer G34-7

( x i ) SEQUENCE DESCRIPTION: SEQ ID NO:45:

CAGGCGCACG CATGCCTCAT GGTG 24

( 2 ) INFORMATION FOR SEQ ID NO:46:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer G34-8

( x i ) SEQUENCE DESCRIPTION: SEQ ID NO:46:

GTAGATCTGG ACCCGTTGC TGAC 24

( 2 ) INFORMATION FOR SEQ ID NO:47:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Primer G34-9

( x i ) SEQUENCE DESCRIPTION: SEQ ID NO:47:

GTCAGCAACG GGGTCCAGAT CTAC    24

( 2 ) INFORMATION FOR SEQ ID NO:48:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer G34- 10

( x i ) SEQUENCE DESCRIPTION: SEQ ID NO:48:

ACCAGTTCCC CACGGATGAT GAGGCTG    27

( 2 ) INFORMATION FOR SEQ ID NO:49:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer G34- 11

( x i ) SEQUENCE DESCRIPTION: SEQ ID NO:49:

CCTCCGCGAG CAGACCCACA GCCGGCA    27

( 2 ) INFORMATION FOR SEQ ID NO:50:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer G18- 1

( x i ) SEQUENCE DESCRIPTION: SEQ ID NO:50:

ATCAGACCAG GGACAGACTT GCC    23

( 2 ) INFORMATION FOR SEQ ID NO:51:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (  i i i ) HYPOTHETICAL: NO ( i v ) ANTI-SENSE: NO ( v i ) ORIGINAL SOURCE:
    ( C ) INDIVIDUAL ISOLATE: Primer G18- 2

( x i ) SEQUENCE DESCRIPTION: SEQ ID NO:51:

CATCTTCTTC ATGCCCTAAC TG    22

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide #4578

( x i ) SEQUENCE DESCRIPTION: SEQ ID NO:52:

TAGGAGATCT CTTAAGAGCT    20

( 2 ) INFORMATION FOR SEQ ID NO:53:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide #4579

( x i ) SEQUENCE DESCRIPTION: SEQ ID NO:53:

TCTCGAGAAT TCTCTAGAGG ATCC    24

( 2 ) INFORMATION FOR SEQ ID NO:54:

( i ) SEQUENCE CHARACTERISTICS:
        ( A ) LENGTH: 5893 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Rad50.seq ( i x ) FEATURE:
        ( A ) NAME/KEY: CDS
        ( B ) LOCATION: 389..4324

( x i ) SEQUENCE DESCRIPTION: SEQ ID NO:54:

CCAGGAGAGC GGCGTGGACG CGTGCGGGCC TAGAGGCCCA CGTGATCCGC AGGGCGGCCG    60

| | | | | | |
|---|---|---|---|---|---|
| AGGCAGGAAG | CTTGTGAGTG | CGCGGTTGCG | GGGTCGCATT | GTGGCTACGG | CTTTGCGTCC | 120 |
| CCGGCGGGCA | GCCCCAGGCT | GGTCCCCGCC | TCCGCTCTCC | CCACCGGCGG | GGAAAGCAGC | 180 |
| TGGTGTGGGA | GGAAAGGCTC | CATCCCCCGC | CCCCTCTCTC | CCGCTGTTGG | CTGGCAGGAT | 240 |
| CTTTTGGCAG | TCCTGTGGCC | TCGCTCCCCG | CCCGGATCCT | CCTGACCCTG | AGATTCGCGG | 300 |
| GTCTCACGTC | CCGTGCACGC | CTTGCTTCGG | CCTCAGTTAA | GCCTTTGTGG | ACTCCAGGTC | 360 |
| CCTGGTGAGA | TTAGAAACGT | TTGCAAACAT | GTCCCGGATC | GAAAAGATGA | GCATTCTGGG | 420 |
| CGTGCGGAGT | TTTGAATAG | AGGACAAAGA | TAAGCAAATT | ATCACTTTCT | TCAGCCCCCT | 480 |
| TACAATTTTG | GTTGGACCCA | ATGGGGCGGG | AAAGACGACC | ATCATTGAAT | GTCTAAAATA | 540 |
| TATTTGTACT | GGAGATTTCC | CTCCTGGAAC | CAAAGGAAAT | ACATTTGTAC | ACGATCCAA | 600 |
| GGTTGCTCAA | GAAACAGATG | TGAGAGCCCA | GATTCGTCTG | CAATTTCGTG | ATGTCAATGG | 660 |
| AGAACTTATA | GCTGTGCAAA | GATCTATGGT | GTGTACTCAG | AAAAGCAAAA | AGACAGAATT | 720 |
| TAAAACTCTG | GAAGGAGTCA | TTACTAGAAC | AAAGCATGGT | GAAAAGGTCA | GTCTGAGCTC | 780 |
| TAAGTGTGCA | GAAATTGACC | GAGAAATGAT | CAGTTCTCTT | GGGGTTTCCA | AGGCTGTGCT | 840 |
| AAATAATGTC | ATTTTCTGTC | ATCAAGAAGA | TTCTAATTGG | CCTTTAAGTG | AAGGAAAGGC | 900 |
| TTTGAAGCAA | AAGTTTGATG | AGATTTTTTC | AGCAACAAGA | TACATTAAAG | CCTTAGAAAC | 960 |
| ACTTCGGCAG | GTACGTCAGA | CACAAGGTCA | GAAAGTAAAA | GAATATCAAA | TGGAACTAAA | 1020 |
| ATATCTGAAG | CAATATAAGG | AAAAAGCTTG | TGAGATTCGT | GATCAGATTA | CAAGTAAGGA | 1080 |
| AGCCCAGTTA | ACATCTTCAA | AGGAAATTGT | CAAATCCTAT | GAGAATGAAC | TTGATCCATT | 1140 |
| GAAGAATCGT | CTAAAAGAAA | TTGAACATAA | TCTCTCTAAA | ATAATGAAAC | TTGACAATGA | 1200 |
| AATTAAAGCC | TTGGATAGCC | GAAAGAAGCA | AATGGAGAAA | GATAATAGTG | AACTGGAAGA | 1260 |
| GAAAATGGAA | AAGGTTTTTC | AAGGGACTGA | TGAGCAACTA | AATGACTTAT | ATCACAATCA | 1320 |
| CCAGAGAACA | GTAAGGGAGA | AAGAAAGGAA | ATTGGTAGAC | TGTCATCGTG | AACTGGAAAA | 1380 |
| ACTAAATAAA | GAATCTAGGC | TTCTCAATCA | GGAAAAATCA | GAACTGCTTG | TTAACAGGG | 1440 |
| TCGTCTACAG | CTGCAAGCAG | ATCGCCATCA | AGAACATATC | CGAGCTAGAG | ATTCATTAAT | 1500 |
| TCAGTCTTTG | GCAACACAGC | TAGAATTGGA | TGGCTTTGAG | CGTGGGCCAT | TCAGTGAAAG | 1560 |
| ACAGATTAAA | AATTTTCACA | AACTTGTGAG | AGAGAGACAA | GAAGGGGAAG | CAAAAACTGC | 1620 |
| CAACCAACTG | ATGAATGACT | TTGCAGAAAA | AGAGACTCTG | AAACAAAAAC | AGATAGATGA | 1680 |
| GATAAGAGAT | AAGAAAACTG | GACTGGGAAG | AATAATTGAG | TTAAAATCAG | AAATCCTAAG | 1740 |
| TAAGAAGCAG | AATGAGCTGA | AAAATGTGAA | GTATGAATTA | CAGCAGTTGG | AAGGATCTTC | 1800 |
| AGACAGGATT | CTTGAACTGG | ACCAGGAGCT | CATAAAAGCT | GAACGTGAGT | TAAGCAAGGC | 1860 |
| TGAGAAAAAC | AGCAATGTAG | AAACCTTAAA | AATGGAAGTA | ATAAGTCTCC | AAAATGAAA | 1920 |
| AGCAGACTTA | GACAGGACCC | TGCGTAAACT | TGACCAGGAG | ATGGAGCAGT | TAAACCATCA | 1980 |
| TACAACAACA | CGTACCCAAA | TGGAGATGCT | GACCAAAGAC | AAAGCTGACA | AGATGAACA | 2040 |
| AATCAGAAAA | ATAAAATCTA | GGCACAGTGA | TGAATTAACC | TCACTGTTGG | GATATTTTCC | 2100 |
| CAACAAAAAA | CAGCTTGAAG | ACTGGCTACA | TAGTAAATCA | AAAGAAATTA | ATCAGACCAG | 2160 |
| GGACAGACTT | GCCAAATTGA | ACAAGGAACT | AGCTTCATCT | GAGCAGAATA | AAAATCATAT | 2220 |
| AAATAATGAA | CTAAAAAGAA | GGGAAGAGCA | GTTGTCCAGT | TACGAAGACA | AGCTGTTTGA | 2280 |
| TGTTTGTGGT | AGCCAGGATT | TTGAAAGTGA | TTTAGACAGG | CTTAAAGAGG | AAATTGAAAA | 2340 |
| ATCATCAAAA | CAGCGAGCCA | TGCTGGCTGG | AGCCACAGCA | GTTACTCCC | AGTTCATTAC | 2400 |
| TCAGCTAACA | GACGAAAACC | AGTCATGTTG | CCCCGTTTGT | CAGAGAGTTT | TTCAGACAGA | 2460 |

```
GGCTGAGTTA   CAAGAAGTCA   TCAGTGATTT   GCAGTCTAAA   CTGCGACTTG   CTCCAGATAA    2520
ACTCAAGTCA   ACAGAATCAG   AGCTAAAAAA   AAAGGAAAAG   CGGCGTGATG   AAATGCTGGG    2580
ACTTGTGCCC   ATGAGGCAAA   GCATAATTGA   TTTGAAGGAG   AAGGAAATAC   CAGAATTAAG    2640
AAACAAACTG   CAGAATGTCA   ATAGAGACAT   ACAGCGCCTA   AGAACGACA    TAGAAGAACA    2700
AGAAACACTC   TTGGGTACAA   TAATGCCTGA   AGAAGAAAGT   GCCAAAGTAT   GCCTGACAGA    2760
TGTTACAATT   ATGGAGAGGT   TCCAGATGGA   ACTAAAGAT    GTTGAAAGAA   AAATTGCACA    2820
ACAAGCAGCT   AAGCTACAAG   GAATAGACTT   AGATCGAACT   GTCCAACAAG   TCAACCAGGA    2880
GAAACAAGAG   AAACAGCACA   AGTTAGACAC   AGTTTCTAGT   AAGATTGAAT   TGAATCGTAA    2940
GCTTATACAG   GACCAGCAGG   AACAGATTCA   ACATCTAAAA   AGTACAACAA   ATGAGCTAAA    3000
ATCTGAGAAA   CTTCAGATAT   CCACTAATTT   GCAACGTCGT   CAGCAACTGG   AGGAGCAGAC    3060
TGTGGAATTA   TCCACTGAAG   TTCAGTCTTT   GTACAGAGAG   ATAAAGGATG   CTAAAGAGCA    3120
GGTAAGCCCT   TTGGAAACAA   CATTGGAAAA   GTTCCAGCAA   GAAAAGAAG    AATTAATCAA    3180
CAAAAAAAT    ACAAGCAACA   AAATAGCACA   GGATAAACTG   AATGATATTA   AGAGAAGGT     3240
TAAAAATATT   CATGGCTATA   TGAAAGACAT   TGAGAATTAT   ATTCAAGATG   GAAAGACGA     3300
CTATAAGAAG   CAAAAAGAAA   CTGAACTTAA   TAAAGTAATA   GCTCAACTAA   GTGAATGCGA    3360
GAAACACAAA   GAAAAGATAA   ATGAAGATAT   GAGACTCATG   AGACAAGATA   TTGATACACA    3420
GAAGATACAA   GAAAGGTGGC   TACAAGATAA   CCTTACTTTA   AGAAAAAGAA   ATGAGGAACT    3480
AAAAGAAGTT   GAAGAAGAAA   GAAACAACA    TTTGAAGGAA   ATGGGTCAAA   TGCAGGTTTT    3540
GCAAATGAAA   AGTGAACATC   AGAAGTTGGA   AGAGAACATA   GACAATATAA   AAGAAATCA     3600
TAATTTGGCA   TTAGGGCGAC   AGAAAGGTTA   TGAAGAAGAA   ATTATTCATT   TTAAGAAAGA    3660
ACTTCGAGAA   CCACAATTTC   GGGATGCTGA   GGAAAAGTAT   AGAGAAATGA   TGATTGTTAT    3720
GAGGACAACA   GAACTTGTGA   ACAAGGATCT   GGATATTTAT   TATAAGACTC   TTGACCAAGC    3780
AATAATGAAA   TTTCACAGTA   TGAAAATGGA   AGAAATCAAT   AAAATTATAC   GTGACCTGTG    3840
GCGAAGTACC   TATCGTGGAC   AAGATATTGA   ATACATAGAA   ATACGGTCTG   ATGCCGATGA    3900
AAATGTATCA   GCTTCTGATA   AAAGGCGGAA   TTATAACTAC   CGAGTGGTGA   TGCTGAAGGG    3960
AGACACAGCC   TTGGATATGC   GAGGACGATG   CAGTGCTGGA   CAAAAGGTAT   TAGCCTCACT    4020
CATCATTCGC   CTGGCCCTGG   CTGAAACGTT   CTGCCTCAAC   TGTGGCATCA   TTGCCTTGGA    4080
TGAGCCAACA   ACAAATCTTG   ACCGAGAAAA   CATTGAATCT   CTTGCACATG   CTCTGGTTGA    4140
GATAATAAAA   AGTCGCTCAC   AGCAGCGTAA   CTTCCAGCTT   CTGGTAATCA   CTCATGATGA    4200
AGATTTTGTG   GAGCTTTTAG   GACGTTCTGA   ATATGTGGAG   AAATTCTACA   GGATTAAAAA    4260
GAACATCGAT   CAGTGCTCAG   AGATTGTGAA   ATGCAGTGTT   AGCTCCCTGG   GATTCAATGT    4320
TCATTAAAAA   TATCCAAGAT   TTAAATGCCA   TAGAAATGTA   GGTCCTCAGA   AAGTGTATAA    4380
TAAGAAACTT   ATTTCTCATA   TCAACTTAGT   CAATAAGAAA   ATATATTCTT   TCAAAGGAAC    4440
ATTGTGTCTA   GGATTTTGGA   TGTTGAGAGG   TTCTAAAATC   ATGAAACTTG   TTTCACTGAA    4500
AATTGGACAG   ATTGCCTGTT   TCTGATTTGC   TGCTCTTCAT   CCCATTCCAG   GCAGCCTCTG    4560
TCAGGCCTTC   AGGGTTCAGC   AGTACAGCCG   AGACTCGACT   CTGTGCCTCC   CTCCCCAGTG    4620
CAAATGCATG   CTTCTTCTCA   AAGCACTGTT   GAGAAGGAGA   TAATTACTGC   CTTGAAAATT    4680
TATGGTTTTG   GTATTTTTTT   AAATCATAGT   TAAATGTTAC   CTCTGAATTT   ACTTCCTTGA    4740
CATGTGGTTT   GAAAAACTGA   GTATTAATAT   CTGAGGATGA   CCAGAAATGG   TGAGATGTAT    4800
GTTTGGCTCT   GCTTTTAACT   TTATAAATCC   AGTGACCTCT   CTCTCTGGGA   CTTGGTTTCC    4860
```

```
CCAACTAAAA  TTTGAAGTAG  TTGAATGGGG  TCTCAAAGTT  TGACAGGAAC  CTTAAGTAAT    4920

CATCTAAGTC  AGTACCCACC  ACCTTCTTCT  CCTACATATC  CCTTCCAGAT  GGTCATCCAG    4980

ACTCAGAGCT  CTCTCTACAG  AGAGGAAATT  CTCCACTGTG  CACACCCACC  TTTGGAAAGC    5040

TCTGACCACT  TGAGGCCTGA  TCTGCCCATC  GTGAAGAAGC  CTGTAACACT  CCTCTGCGTC    5100

TATCCTGTGT  AGCATACTGG  CTTCACCATC  AATCCTGATT  CCTCTCTAAG  TGGGCATTGC    5160

CATGTGGAAG  GCAAGCCAGG  CTCACTCACA  GAGTCAAGGC  CTGCTCCCTG  TAGGGTCCAA    5220

CCAGACCTGG  AAGAACAGGC  CTCTCCATTT  GCTCTTCAGA  TGCCACTTCT  AAGAAAGCC     5280

TAATCACAGT  TTTTCCTGGA  ATTGCCAGCT  GACATCTTGA  ATCCTTCCAT  TCCACACAGA    5340

ATGCAACCAA  GTCACACGCT  TTGAATTAT   GCTTTGTAGA  GTTTTGTCAT  TCAGAGTCAG    5400

CCAGGACCAT  ACCGGGTCTT  GATTCAGTCA  CATGGCATGG  TTTTGTGCCA  TCTGTAGCTA    5460

TAATGAGCAT  GTTTGCCTAG  ACAGCTTTTC  TCAACTGGGT  CCAGAAGAGA  ATTAAGCCCT    5520

AAGGTCCTAA  GGCATCTATC  TGTGCTAGGT  TAAATGGTTG  GCCCCCAAAG  ATAGACAGGT    5580

CCTGATTTCT  AGAACCCGTG  ACTGTTACTT  TATACAGCAA  AGGAAACTTT  GCAGATGTGA    5640

TTAAAGCTAA  GGACCTTAAG  ACAGAGTATC  CTGGGGGTGG  TGGTGGGGTG  GGGGGGGGTC    5700

CTAAATGTAA  TCACGAGTAA  GATTAAGAGC  CAATCAATTC  TAGTCATATA  TTAAACATCC    5760

ACAATAACCA  AGATATTTTT  ATCCCAAGAA  TGCAAGATTT  CAGAAAATGA  AAAATCTGTT    5820

GATAAATCCA  TCACTATAAT  AAAACCGAAG  GTGAAAAAAA  TTCTGAAAAA  AAAAAAAAA     5880

AAAAAAAAA   AAA                                                           5893
```

( 2 ) INFORMATION FOR SEQ ID NO:55:

( i ) SEQUENCE CHARACTERISTICS:
        ( A ) LENGTH: 472 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G18.seq ( x i ) SEQUENCE DESCRIPTION: SEQ ID NO:55:

```
GTGGAAGAAT  GGTGAAATCA  TTGATACTTT  ACAACAAGTT  TATGAGATCA  ATGCCCCAAA      60

CAAATCAGCA  GTTTACAAAT  GGATAACTCA  GTTAAGAAG   GGATGAGACG  ATATTAAAGA     120

TGAAGCCCAC  AGTGACAGAC  TGTTCACATC  AATTTGTGAG  GAAAAAAATC  ATCTTCTTCA     180

TGCCCTAACT  GAAGAAGATC  AATGATTAAC  AGCAGAAACA  ATAGCCAACA  CCATAGACAC     240

CTCAATTGAT  TCAGGTTACA  CAATTCTGAC  TGAAAAATTA  AAGTTGAGTA  AACGTTCTAC     300

TTGATGGATG  CCCAAATCAC  TGCTTCCAGA  TCAGCTGCAG  ACAACAGCAG  AACTTCCTCA     360

ATAAGTGGGA  TCAAGTTCCT  AAAGCATTTC  TTCAAAGAAT  TGTAACAGGA  GGTGATGGAA     420

TGTGGCTTTA  CCAGTACAAT  CTTCAATTTG  GCAAGTCTGT  CCCTGGTCTG  AT              472
```

( 2 ) INFORMATION FOR SEQ ID NO:56:

( i ) SEQUENCE CHARACTERISTICS:
        ( A ) LENGTH: 1189 base pairs
        ( B ) TYPE: nucleic acid
        ( C ) STRANDEDNESS: double (D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: Tc1.seq (xi) SEQUENCE DESCRIPTION: SEQ ID NO:56:

| | | | | | | |
|---|---|---|---|---|---|---|
| CCTGTGAACA | TTGACAATAT | ATTACTTTTA | GTGGTACACA | GTTCTTGAGA | AAATGTCTTG | 60 |
| ATTTTTACAT | TGCCATTTGT | GATATTTTTA | GCAGTCCACC | ACAATATCAT | TTTTATAATA | 120 |
| AAAATAAAAT | ATACTCATTG | ATGATAGAGA | AAATATTGTT | AAAGACCTCT | TGGGACAGGA | 180 |
| AAAGGCTCAG | TCATAAAATC | AGATGCTTAT | TCATTTTCAG | CTGTGTCATT | TTGACTCATT | 240 |
| ACTTTCAAGA | ATAACTATAA | TATTGCTAGA | CAGTTCATTA | CACTGAGAAG | AACTTTCCTT | 300 |
| GAACTTCACA | TGGAGATTGA | GTAAAGCTCT | TCTATTTGTT | TTTTGAAGTA | CTCTCTCAGC | 360 |
| TCAGGTCTCT | TAGCTTTTAG | TGTTGGTGTC | AGCAAGCCAT | TTTGAACTGA | GAACATGTCA | 420 |
| GAATGGATGT | GAATGGCTTT | AACCTGCTCA | AAAGAATGGA | GTCCACTTTC | TTTTCCTAAC | 480 |
| CTCACCATAT | CTTCCAAAAT | GGCTTTCTTC | AGATCCTTAT | TTGTGCAGAG | ATCTGCATAT | 540 |
| GTTCCTTCAA | TTCCTCTCTT | CTGGGCCCAG | GAGGGCATAA | CTTCAGGGTC | AGGCACAACA | 600 |
| ATGCCTACCA | AAAAGGCCTT | TAAGCTGTCC | CCATGGACAT | AGATTTGCGC | CACAGGTTGG | 660 |
| CTCCGGATGT | AGATGTTCTC | AATCTTCTCG | GGTGCAACAT | ATTCTCCCTG | AGCAAGTTTA | 720 |
| AATATATGCT | TTTTCCGATC | AATAATTTTA | AGAGTTCCTG | CCGGCAGCCA | TTTTCCGATG | 780 |
| TCTCCAGTGT | GAAGCCAGCC | ATCGCTGTCC | AGGGCCTCCT | TCGTCCTGTC | TGGATCTTTC | 840 |
| AAGTAGCCTC | TGAACACATT | TGGTCCTCTC | ACACATATCT | CTCCCTCTCC | TTTGCAGGCC | 900 |
| CAGTAGTTCA | GTTCCTCAAC | ATCAACGAGC | TTGATATGAT | TGCAGGGAAG | TGGCGCCCCT | 960 |
| ACGTGCCCTG | AGGTCCAGTC | GCCAGGAGTG | GTGAAGGTAC | ATCCAGCTGT | GCACTCAGTT | 1020 |
| TGGCCATAAC | CTTCATAAAC | CTGGCACCCT | AGAGCTGCCC | GGAGAAATCC | CAGAACTGTT | 1080 |
| GGTGATGCTG | GGGCTGCTCC | AGTAACAATC | ATCCGCACAA | GTCACCTAGC | TCAGGCAGTC | 1140 |
| GCAGTATCCT | CAGGATCTCC | TGTGTCTGCA | TCTTCTCAGA | AGTGAGAGG | | 1189 |

(2) INFORMATION FOR SEQ ID NO:57:

(i) SEQUENCE CHARACTERISTICS:
(A) LENGTH: 987 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: Tc2.seq (xi) SEQUENCE DESCRIPTION: SEQ ID NO:57:

| | | | | | | |
|---|---|---|---|---|---|---|
| CCTCTCACTT | CTGAGAAGAT | GCAGACACAG | GAGATCCTGA | GGATACTGCG | ACTGCCTGAG | 60 |
| CTAGGTGGCT | TGGGACAGTT | TTTCCGCAGC | CTCTCGGCCA | CCACCCTCGT | GAGTATGGGT | 120 |
| GCCCTGGCTG | CCATCCTTGC | CTACTGGTTC | ACTCACCGGC | CAAAGGCCTT | GCAGCCGCCA | 180 |
| TGCAACCTCC | TGATGCAGTC | AGAAGAAGTA | GAGGACAGTG | GCGGGGCACG | GCGATCTGTG | 240 |

| | | | | | | |
|---|---|---|---|---|---|---|
| ATTGGGTCTG | GCCCTCAGCT | ACTTACCCAC | TACTATGATG | ATGCCCGGAT | CATGTACCTG | 300 |
| GTGTCCCGCC | GTGGGCTTAG | CATCTCAGGG | AATGGGCCCT | GTCTTGGTTT | CAGGAAGCCT | 360 |
| AAGCAGCCTT | ACCAGTGGCT | GTCCTACCAG | GAGGTGGCCG | ACAGGGCTGA | ATTTCTGGGG | 420 |
| TCCGGACTTC | TCCAGCACAA | TTGTAAAGCA | TGCACTGTCA | GTTTATTGGT | GTTTTTGCAC | 480 |
| AAAATCGGCC | AGAGTGGATC | ATTGTGGAGC | TGGCCTGCTA | CACATATTCC | ATTCTTTTGA | 540 |
| GCAGGTTAAG | GCCATTTACA | TCCATTCTGA | CATGTTCTCA | GTTCAAAATG | GCTTGCTGAC | 600 |
| ACCAACACTA | AAAGCTAAGA | GACCTGAGCT | GAGAGAGTAC | TTCAAAAAAC | AAATAGAAGA | 660 |
| GCTTTACTCA | ATCTCCATGT | GAAGTTCAAG | GAAAGTTCTT | CTCAGTGTAA | TAAACTGTCT | 720 |
| AGCAATATTA | TAGTTATTCT | TGAAAGTAAT | GAGTCAAAAT | GACACAACTG | AAAATGAATA | 780 |
| AGCATCTGAT | TTTATGACTG | AGCCTTTTCC | TGTCCCATGA | GGTCTTTAAC | AATATTTTCT | 840 |
| CTATCATCAA | TGAGTATATT | TTATTTTTAT | TATAAAAATG | ATATTGTGGT | GGACTGCTAA | 900 |
| AAATATCACA | AGTGGCAATG | TAAAAATCAA | GACATTTTCT | CAAGAACTGT | GTACCACTAA | 960 |
| AAGTAATATA | TTGTCAATGT | TCACAGG | | | | 987 |

( 2 ) INFORMATION FOR SEQ ID NO:58:

( i ) SEQUENCE CHARACTERISTICS:
        ( A ) LENGTH: 691 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Tc3.seq ( x i ) SEQUENCE DESCRIPTION: SEQ ID NO:58:

| | | | | | | |
|---|---|---|---|---|---|---|
| CCTGTGAACA | TTGACAATAT | ATTACTTTTA | GTGGTACACA | GTTCTTGAGA | AAATGTCTTG | 60 |
| ATTTTTACAT | TGCCATTTGT | GATATTTTTA | GCAGTCCACC | ACAATATCAT | TTTTATAATA | 120 |
| AAAATAAAAT | ATACTCATTG | ATGATAGAGA | AAATATTGGA | GGATCCAGAA | TTCTCGAGTT | 180 |
| GCCTCCTTTT | TTGGCAGACT | TCATCTTCTC | ATCTCCCAAA | CCCCCTGAGC | CCGTAGGGTT | 240 |
| TTCATAGTGG | ACAAAGAACT | TGTGGTCTTT | TAAAACTGGG | ACTGATACTT | TTTTGAGAGA | 300 |
| GTATCGTGTC | GAAAGTGTGA | TGTTCTACCA | CTTACCAAT | AACTAATTTT | AAATACACAT | 360 |
| TGTCCTCTCG | ATTTTTGGAC | CAAACAGACG | CTCACAGTGG | AGGCTTATCA | AGGGTTGCAT | 420 |
| TGGGGAAGAA | GCCTCTCCCT | CTCTGTCAGC | ACCAGCTGGT | AAAGGTGACT | GTACAGATGT | 480 |
| GCATTTTCCT | TTTGGTATAA | ATGGTCCACA | GCACTAACTG | GTAAGGCTTA | TTGTGCAGTA | 540 |
| TATTGTCAGT | ATTCTTCTGG | TTCAGCATGC | CTTATAGTTC | ANATATAACC | TGTATTAANT | 600 |
| GTATAGATTG | TGCAGTAAAA | GCTGTTACCA | AGTTGTCAGA | ACATAAGAGC | GAAAACAAGG | 660 |
| TCATATGTAA | TATATTGTCA | ATGTTCACAG | G | | | 691 |

( 2 ) INFORMATION FOR SEQ ID NO:59:

( i ) SEQUENCE CHARACTERISTICS:
        ( A ) LENGTH: 2511 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
 ( C ) INDIVIDUAL ISOLATE: TcA.seq ( x i ) SEQUENCE DESCRIPTION: SEQ ID NO:59:

| | | | | | | |
|---|---|---|---|---|---|---|
| CCTCTCACTT | CTGGAGAAGA | TGCAGACACA | GGAGATCCTG | AGGATACTGC | GACTGCCTGA | 60 |
| GCTAGGTGAC | TTGGGACAGT | TTTTCCGCAG | CCTCTCGGCC | ACCACCCTCG | TGAGTATGGG | 120 |
| TGCCCTGGCT | GCCATCCTTG | CCTACTGGTT | CACTCACCGG | CCAAAGGCCT | GCAGCCGCC | 180 |
| ATGCAACCTC | CTGATGCAGT | CAGAAGAAGT | AGAGGACAGT | GGCGGGGCAC | GGCGATCTGT | 240 |
| GATTGGGTCT | GGCCCTCAGC | TACTTACCCA | CTACTATGAT | GATGCCCGGA | CCATGTACCA | 300 |
| GGTGTTCCGC | CGTGGGCTTA | GCATCTCAGG | GAATGGGCCC | TGTCTTGGTT | TCAGGAAGCC | 360 |
| TAAGCAGCCT | TACCAGTGGC | TGTCCTACCA | GGAGGTGGCC | GACAGGGCTG | AATTTCTGGG | 420 |
| GTCCGGACTT | CTCCAGCACA | ATTGTAAAGC | ATGCACTGAT | CAGTTTATTG | GTGTTTTTGC | 480 |
| ACAAAATCGG | CCAGAGTGGA | TCATTGTGGA | GCTGGCCTGC | TACACATATT | CCATGGTGGT | 540 |
| GGTCCCGCTC | TATGACACCC | TGGGCCCTGG | GGCTATCCGC | TACATCATCA | ATACAGGGCT | 600 |
| CAGCTGCCAA | GAAGGAGCCT | CTGCAACAGC | CTCCACACAG | GGTACAGCCC | TCTGAAGTTC | 660 |
| ATGACAGCTT | GGCACAGATG | CAGGGGGTGC | GGACATCAGC | ACCGTGATTG | TGGACAAACC | 720 |
| TCAGAAGGCT | GTGCTTCTGC | TAGAGCATGT | GGAGAGGAAG | GAGACTCCAG | GCCTCAAGCT | 780 |
| GATCATCCTC | ATGGACCCAT | TCGAAGAAGC | CCTGAAAGAG | AGAGGGCAGA | AGTGCGGGT | 840 |
| GGTCATTAAG | TCCATGCAGG | CCGTGGAGGA | CTGTGGCCAA | GAGAATCACC | AGGCTCCTGT | 900 |
| GCCCCGCAG | CCTGATGACC | TCTCCATTGT | GTGTTTCACA | AGCGGCACGA | CAGGGAACCC | 960 |
| AAAAGGTGCG | ATGCTCACCC | ATGGGAACGT | GGTGGCTGAT | TTCTCAGGCT | TTCTGAAAGT | 1020 |
| GACAGAGAGT | CAGTGGGCTC | CCACTTGTGC | GGATGTGCAC | ATTTCCTAGT | TGCCTTTAGC | 1080 |
| ACACATGTTT | GAGCGAATGG | TGCAGTCTGT | CGTCTATTGC | CACGGAGGGC | GTGTTGGCTT | 1140 |
| CTTCCAGGGA | GATATCCGCC | TTCTCTCAGA | TGACATGAAG | GCTCTATGCC | CCACCATCTT | 1200 |
| CCCTGTGGTC | CCACGACTGC | TGAACCGGAT | GTACGACAAG | ATCTTCAGCC | AGGCAAACAC | 1260 |
| ACCATTAAAG | CGCTGGCTCC | TGGAGTTTGC | AGCAAAACGT | AAGCAAGCCG | AGGTCCGGAG | 1320 |
| TGGAATCATC | AGGAATGATA | GTATCTGGGA | TGAACTCTTC | TTTAATAAGA | TTCAGGCCAG | 1380 |
| TCTTGGTGGG | TGTGTGCGGA | TGATTGTTAC | TGGAGCAGCC | CCAGCATCAC | CAACAGTTCT | 1440 |
| GGGATTTCTC | CGGGCAGCTC | TAGGGTGCCA | GGTTTATGAA | GGTTATGGCC | AAACTGAGTG | 1500 |
| CACAGCTGGA | TGTACCTTCA | CCACTCCTGG | CGACTGGACC | TCAGGGCACG | TAGGGGCGCC | 1560 |
| ACTTCCCTGC | AATCATATCA | AGCTCGTTGA | TGTTGAGGAA | CTGAACTACT | GGGCCTGCAA | 1620 |
| AGGAGAGGGA | GAGATATGTG | TGAGAGGACC | AAATGTGTTC | AAAGGCTACT | TGAAAGATCC | 1680 |
| AGACAGGACG | AAGGAGGCCC | TGGACAGCGA | TGGCTGGCTT | CACACTGGAG | ACATCGGAAA | 1740 |
| ATGGCTGCCG | GCAGGAACTC | TTAAAATTAT | TGATCGGAAA | AAGCATATAT | TTAAACTTGC | 1800 |
| TCAGGGAGAA | TATGTTGCAC | CCGAGAAGAT | TGAGAACATC | TACATCCGGA | GCCAACCTGT | 1860 |
| GGCGCAAATC | TATGTCCATG | GGGACAGCTT | AAAGGCCTTT | TTGGTAGGCA | TTGTTGTGCC | 1920 |
| TGACCCTGAA | GTTATGCCCT | CCTGGGCCCA | GAAGAGAGGA | ATTGAAGGAA | CATATGCAGA | 1980 |
| TCTCTGCACA | AATAAGGATC | TGAAGAAAGC | CATTTTGGAA | GATATGGTGA | GGTTAGGAAA | 2040 |
| AGAAAGTGGA | CTCCATTCTT | TTGAGCAGGT | TAAAGCCATT | CACATCCATT | CTGACATGTT | 2100 |

```
CTCAGTTCAA AATGGCTTGC TGACACCAAC ACTAAAAGCT AAGAGACCTG AGCTGAGAGA      2160

GTACTTCAAA AAACAAATAG AAGAGCTTTA CTCAATCTCC ATGTGAAGTT CAAGGAAAGT      2220

TCTTCTCAGT GTAATGAACT GTCTAGCAAT ATTATAGTTA TTCTTGAAAG TAATGAGTCA      2280

AAATGACACA GCTGAAAATG AATAAGCATC TGATTTTATG ACTGAGCCTT TTCCTGTCCC      2340

AAGAGGTCTT TAACAATATT TTCTCTATCA TCAATGAGTA TATTTTATTT TTATTATAAA      2400

AATGATATTG TGGTGGACTG CTAAAAATAT CACAAATGGC AATGTAAAAA TCAAGACATT      2460

TTCTCAAGAA CTGTGTACCA CTAAAAGTAA TATATTGTCA ATGTTCACAG G               2511
```

( 2 ) INFORMATION FOR SEQ ID NO:60:

( i ) SEQUENCE CHARACTERISTICS:
        ( A ) LENGTH: 2416 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: TcB.seq ( x i ) SEQUENCE DESCRIPTION: SEQ ID NO:60:

```
CCTCTCACTT CTGGAGAAGA TGCAGACACA GGAGATCCTG AGGATACTGC GACAGCCTGA        60

GCTAGGTGAC TTGGGACAGT TTTTCCGCAG CCTCTCGGCC ACCACCCTCG TGAGTATGGG       120

TGCCCTGGCT GCCATCCTTG CCTACTGGTT CACTCACCGG CCAAAGGCCT TGCAGCCGCC       180

ATGCAACCTC CTGATGCAGT CAGAAGAGGT AGAGGACAGT GGCGGGGCAC GGCGATCTGT       240

GATTGGGTCT GGCCCTCAGC TACTTACCCA CTACTATGAT GATGCCCGGA CCATGTACCA       300

GGTGTTCCGC CGTGGGCTTA GCATCTCAGG GAATGGGCCC TGTCTTGGTT TCAGGAAGCC       360

TAAGCAGCCT TACCAGTGGC TGTCCTACCA GGAGGTGGCC GACAGGCTG AATTTCTGGG        420

GTCCGGACTT CTCCAGCACA ATTGTAAAGC ATGCACTGAT CAGTTTATTG GTGTTTTTGC       480

ACAAAATCGG CCAGAGTGGA TCATTGTGGA GCTGGCCTGC TACACATATT CCATGGTGGT       540

GGTCCCGCTC TATGACACCC TGGGCCCTGG GGCTATCCGC TACATCATCA ATACAGCGGA       600

CATCAGCACC GTGATTGTGG ACAAACCTCA GAAGGCTGTG CTTCTGCTAG AGCATGTGGA       660

GAGGAAGGAG ACTCCAGGCC TCAAGCTGAT CATCCTCATG GACCCATTCG AAGAAGCCCT       720

GAAAGAGAGA GGGCAGAAGT GCGGGGTGGT CATTAAGTCC ATGCAGGCCG TGGAGGACTG       780

TGGCCAAGAG AATCACCAGG CTCCTGTGCC CCCGCAGCCT GATGACCTCT CCATTGTGTG       840

TTTCACAAGC GGCACGACAG GGAACCCAAA AGGTGCGATG CTCACCCATG GAACGTGGT        900

GGCTGATTTC TCAGGCTTTC TGAAAGTGAC AGAGAGTCAG TGGGCTCCCA CTTGTGCGGA       960

TGTGCACACT TCCTATTTGC CTTTAGCACA CATGTTTGAG CGAATGGTGC AGTCTGTCGT      1020

CTATTGCCAC GGAGGGCGTG TTGGCTTCTT CCAGGGAGAT ATCCGCCTTC TCTCAGATGA      1080

CATGAAGGCT CTATGCCCCA CCATCTTCCC TGTGGTCCCA CGACTGCTGA ACCGGATGTA      1140

CGACAAGATC TTCAGCCAGG CAAACACACC ATTAAAGCGC TGGCTCCTGG AGTTTGCAGC      1200

AAAGCGTAAG CAAGCCGAGG TCCGGAGTGG AATCATCAGG AATGATAGTA TCTGGGATGA      1260

ACTCTTCTTT AATAAGATTC AGGCCAGTCT TGGTGGGTGT GTGCGGATGA TTGTTACTGG      1320

AGCAGCCCCA GCATCACCAA CGGTTCTGGG ATTTCTCCGG GCAGCTCTAG GGTGCCAGGT      1380
```

| | | | | | |
|---|---|---|---|---|---|
| TTATGAAGGT | TATGGCCAAA | CTGAGTGCAC | AGCTGGATGT | ACCTTCACCA | CTCCTGGCGA | 1440
| CTGGACCTCA | GGGCACGTAG | GGGCGCCACT | TCCCTGCAAT | CATATCAAGC | TCGTTGATGT | 1500
| TGAGGAACTG | AACTACTGGG | CCTGCAAAGG | AGAGGGAGAG | ATATGTGAGA | GGACCAAATG | 1560
| TGTTCAAAGG | CTACTTGAAA | GATCCAGACA | GGACGAAGGA | GGCCCTGTAC | GGCGATGGCT | 1620
| GGCTTCACAC | TGGAGACATC | GGTAAATGGC | TGCCGGCAGG | AACTCTTAAA | ATTATTGATC | 1680
| GGAAAAAGCA | TATATTTAAA | CTTGCTCAGG | GAGTATATGT | TGCACCCGAG | AAGATTGAGA | 1740
| ACATCTACAT | CCGGAGCCAA | CCTGTGGCGC | AAATCTATGT | CCATGGGGAC | AGCTTAAAGG | 1800
| CCTTTTTGGT | AGGCATTGTT | GTGCCTGACC | CTGAAGTTAT | GCCCTCCTGG | GCCCAGAAGA | 1860
| GAGGAATTGA | AGGAACATAT | GCAGATCTCT | GCACAAATAA | GGATCTGAAG | AAAGCCATTT | 1920
| TGGAAGATAT | GGTGAGGTTA | GGAAAAGAAA | GTGGACTCCA | TTCTTTTGAG | CAGGTTAAAG | 1980
| CCATTCACAT | CCATTCTGAC | ATGTTCTCAG | TTCAAAATGG | CTTGCTGACA | CCAACACTAA | 2040
| AAGCTAAGAG | ACCTGAGCTG | AGAGAGTACT | TCAAAAAACA | AATAGAAGAG | CTTTACTCAA | 2100
| TCTCCATGTG | AAGTTCAAGG | AAAGTTCTTC | TCAGTGTAAT | GAACTGTCTA | GCAATATTAT | 2160
| AGTTATTCTT | GAAAGTAATG | AGTCAAAATG | ACACAGCTGA | AAATGAATAA | GCATCTGATT | 2220
| TTATGACTGA | GCCTTTTCCT | GTCCCAAGAG | GTCTTTAACA | ATATTTCTC | TATCATCAAT | 2280
| GAGTATATTT | TATTTTTATT | ATAAAAATGA | TATTGTGGTG | GACTGCTAAA | AATATCACAA | 2340
| ATGGCAATGT | AAAAATCAAG | ACATTTCTC | AAGAACTGTG | TACCACTAAA | AGTAATATAT | 2400
| TGTCAATGTT | CACAGG | | | | | 2416

( 2 ) INFORMATION FOR SEQ ID NO:61:

( i ) SEQUENCE CHARACTERISTICS:
        ( A ) LENGTH: 2416 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: TS.seq ( x i ) SEQUENCE DESCRIPTION: SEQ ID NO:61:

| | | | | | |
|---|---|---|---|---|---|
| CCTGTGAACA | TTGACAATAT | ATTACTTTTA | GTGGTACGCA | GTTCTTGAGA | AAATGTCTTG | 60
| ATTTTTACAT | TGCCATTTGT | GATATTTTA | GCAGTCCACC | ACAATATCAT | TTTTATAATA | 120
| AAATAAAATA | TACTCATTGA | TGATAGAGAA | AATATTGTTA | AAGACCTCTT | GGGACAGGAA | 180
| AAGGCTCAGT | CATAAAATCA | GATGCTTATT | CATTTTCAGC | TGTGTCATTT | TGACTCATTA | 240
| CTTTCAAGAA | TAACTATAAT | ATTGCTAGAC | AGTTCATTAC | ACTGAGAAGA | ACTTTCCTTG | 300
| AACTTCACAT | GGAGATTGAG | TAAAGCTCTT | CTATTTGTTT | TTTGAAGTAC | TCTCTCAGCT | 360
| CAGGTCTCTT | AGCTTTTAGT | GTTGGTGTCA | GCAAGCCATT | TTGAACTGAG | AACATGTCAG | 420
| AATGGATGTG | AATGGCTTTA | ACCTGCTCAA | AAGAATGGAG | TCCACTTTCT | TTTCCTAACC | 480
| TCACCATATC | TTCCAAAATG | GCTTTCTTCA | GATCCTTATT | TGTGCAGAGA | TCTGCATATG | 540
| TTCCTTCAAT | TCCTCTCTTC | TGGGCCCAGG | AGGGCATAAC | TTCAGGGTCA | GGCACAACAA | 600
| TGCCTACCAA | AAAGGCCTTT | AAGCTGTCCC | CATGGACATA | GATTTGCGCC | ACAGGTTGGC | 660
| TCCGGATGTA | GATGTTCTCA | ATCTTCTCGG | GTGCAACATA | TTCTCCCTGA | GCAAGTTTAA | 720

-continued

| | | | | | |
|---|---|---|---|---|---|
|ATATATGCTT|TTTCCGATCA|ATAATTTTAA|GAGTTCCTGC|CGGCAGCCAT|TTTCCGATGT|780|
|CTCCAGTGTG|AAGCCAGCCA|TCGCTGTCCA|GGGCCTCCTT|CGTCCTGTCT|GGATCTTTCA|840|
|AGTAGCCTTT|GAACACATTT|GGTCCTCTCA|CACATATCTC|TCCCTCTCCT|TTGCAGGCCC|900|
|AGTAGTTCAG|TTCCTCAACA|TCAACGAGCT|TGATATGATT|GCAGGGAAGT|GGCGCCCTA|960|
|CGTGCCCTGA|GGTCCAGTCG|CCAGGAGTGG|TGAAGGTACA|TCCAGCTGTG|CACTCAGTTT|1020|
|GGCCATAACC|TTCATAAACC|TGGCACCCTA|GAGCTGCCCG|GAGAAATCCC|AGAACTGTTG|1080|
|GTGATGCTGG|GGCTGCTCCA|GTAACAATCA|TCCGCACACA|CCCACCAAGA|CTGGCCTGAA|1140|
|TCTTATTAAA|GAAGAGTTCA|TCCCAGATAC|TATCATTCCT|GATGATTCCA|CTCCGGACCT|1200|
|CGGCTTGCTT|ACGCTTTGCT|GCAAACTCCA|GGAGCCAGCG|CTTTAATGGT|GTGTTTGCCT|1260|
|GGCTGAAGAT|CTTGTCGTAC|ATCCGGTTCA|GCAGTCGTGG|GACCACAGGG|AAGATGGTGG|1320|
|GGCATAGAGC|CTTCATGTCA|TCTGAGAGAA|GGCGGATATC|TCCCTGGAAG|AAGCCAACAC|1380|
|GCCCTCCGTG|GCAATAGACG|ACAGACTGGA|TTACTCTCTC|AAACATGTGA|GCCAGAGGCA|1440|
|GGGAGGAGAT|GAGCACATCG|TCCTGTCTCG|GAAAGATCAC|TTTCTCTGTC|ACTTTCAGAA|1500|
|AGCCTGAGAA|ATCGGCCACC|ACGTTCCCAT|GGGTAAGCAT|CGCACCTTTT|GGGTTCCCTG|1560|
|TCGTGCCGCT|TGTGAAACAC|ACAATGGAGA|GGTCATCAGG|CTGCGGGGGC|ACAGGAGCCT|1620|
|GGTGATTCTC|TTGGCCACAG|TCCTCCACGG|CCTGCATGGA|CTTAATGACC|ACCCCGCACT|1680|
|TCTGCCCTCT|CTCTTTCAGG|GCTTCTTCGA|ATGGGTCCAT|GAGGATGATC|AGCTTGAGGC|1740|
|CTGGAGTCTC|CTTCCTCTCC|ACATGCTCTA|GCAGAAGCAC|AGCCTTCTGA|GGTTTGTCCA|1800|
|CAATCACGGT|GCTGATGTCC|GCTGTATTGA|TGATGTGGCG|GATAGCCCCA|GGGCCCAGGG|1860|
|TGTCATAGAG|CGGGACCACC|ACCATGGAAT|ATGTGTAGCA|GGCCAGCTCC|ACGATGATCC|1920|
|ACTCTGGCCG|ATTTTGTGCA|AAAACACCAA|TAAACTGATC|AGTGCATGCT|TTACAATTGT|1980|
|GCTGGAGAAG|TCCGGACCCC|AGAAATTCAG|CCCTGTCGGC|CACCTCCTGG|TAGGACAGCC|2040|
|ACTGGTAAGG|CTGCTTAGGC|TTCCTGAAAC|CAAGACAGGG|CCCATTCCCT|GAGATGCTAA|2100|
|GCCCACGGCG|GAACACCTGG|TACATGGTCC|GGGCATCATC|ATAGTAGTGG|GTAAGTAGCT|2160|
|GAGGGCCAGA|CCCAATCACA|GATCGCCGTG|CCCCGCCACT|GTCCTCTACT|TCTTCTGACT|2220|
|GCATCAGGAG|GTTGCATGGC|GGCTGCAAGG|CCTTTGGCCG|GTGAGTGAAC|CAGTAGGCAA|2280|
|GGATGGCAGC|CAGGGCACCC|ATACTCACGA|GGGTGGTGGC|CGAGAGGCTG|CGGAAAAACT|2340|
|GTCCCAAGTC|ACCTAGCTCA|GGCAGTCGCA|GTATCCTCAG|GATCTCCTGT|GTCTGCATCT|2400|
|TCTCAGAAGT|GAGAGG| | | | |2416|

( 2 ) INFORMATION FOR SEQ ID NO:62:

( i ) SEQUENCE CHARACTERISTICS:
        ( A ) LENGTH: 1698 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v ) ORIGINAL SOURCE:
        ( C ) INDIVIDUAL ISOLATE: TS2.seq ( x i ) SEQUENCE DESCRIPTION: SEQ ID NO:62:

| | | | | | |
|---|---|---|---|---|---|
|CCTGTGAACA|TTGACAATAT|ATTACTTTTA|GTGGTACACA|GTTCTTGAGA|AAATGTCTTG|60|

| | | | | | | |
|---|---|---|---|---|---|---|
| ATTTTTACAT | TGCCATTTGT | GATATTTTTA | GCAGTCCACC | ACAATATCAT | TTTTATAATA | 120 |
| AAAATAAAAT | ATACTCATTG | ATGATAGAGA | AAATATTGTT | AAAGACCTCT | TGGGACAGGA | 180 |
| AAAGGCTCAG | TCATAAAATC | AGATGCTTAT | TCATTTTCAG | CTGTGTCATT | TTGACTCATT | 240 |
| ACTTTCAAGA | ATAACTATAA | TATTGCTAGA | CAGTTCATTA | CACTGAGAAG | AACTTTCCTT | 300 |
| GAACTTCACA | TGGAGATTGA | GTAAAGCTCT | TCTATTTGTT | TTTTGAAGTA | CTCTCTCAGC | 360 |
| TCAGGTCTCT | TAGCTTTTAG | TGTTGGTGTC | AGCAAGCCAT | TTTGAACTGA | GAACATGTCA | 420 |
| GAATGGATGT | GAATGGCTTT | AACCTGCTCA | AAAGAATGGA | GTCCACTTTC | TTTTCCTAAC | 480 |
| CTCACCATAT | CTTCCAAAAT | GGCTTTCTTC | AGATCCTTAT | TTGTGCAGAG | ATCTGCATAT | 540 |
| GTTCCTTCAA | TTCCTCTCTT | CTGGGCCCAG | GAAGGCATAA | CTTCAGGGTC | AGGCACAACA | 600 |
| ATGCCTACCA | AAAAGGCCTT | TAAGCTGTCC | CCATGGACAT | AGATTTGCGC | CACAGGTTGG | 660 |
| CTCCGGATGT | AGATGTTCTC | AATCTTCTCG | GGTGCAACAT | ATTCTCCCTG | AGCAAGTTTA | 720 |
| AATATATGCT | TTTTCCGATC | AATAATTTTA | AGAGTTCCTG | CCGGCAGCCA | TTTTCCGATG | 780 |
| TCTCCAGTGT | GAAGCCAGCC | ATCGCTGTCC | AGGGCCTCCT | TCGTCCTGTC | TGGATCTTTC | 840 |
| AAGTAGCCTT | TGAACACATT | TGGTCCTCTC | ACACATATCT | CTCCCTCTCC | TTTGCAGGCC | 900 |
| CAGTAGTTCA | GTTCCTCAAC | ATCAACGAGC | TTAATATGAT | TGCAGGGAAG | TGGCGCCCCT | 960 |
| ACGTGCACTG | AGGTCCAGTC | GCCAGGAGTG | GTGAAGGTAC | ATCCAGCTGT | GCACTCAGTT | 1020 |
| TGGCCATAAC | CTTCATAAAC | CTGGCACCCT | AGAGCTGCCC | GGAGAAATCC | CAGAACTGTT | 1080 |
| GGTGATGCTG | GGGCTGCTCC | AGTAACAATC | ATCCGCACAC | ACCCACCAAG | ACTGGCCTGA | 1140 |
| ATCTTATTAA | AGAAGAGTTC | ATCCCAGATA | CTATCATTCC | TGATGATTCC | ACTCCGGACC | 1200 |
| TCGGCTTGCT | TACGCTTTGC | TGCAAACTCC | AGGAGCCAGC | GCTTTAATGG | TGTGTTTGCC | 1260 |
| TGGCTGAAGA | TCCTGTCGTA | CATCCGGTTC | AGCAGTCGTG | GGACCACAGG | GAAGATGGTG | 1320 |
| GGGCATAGAG | CCTTCATGTC | ATCTGAGAGA | AGGCGGATAT | CTCCCTGGAA | GAAGCCAACA | 1380 |
| CGCCCTCCGT | GGCAATAGAC | GACAGACTGG | ATTACTCTCT | CAAACATGTG | AGCCAGAGGC | 1440 |
| AGGAAGGAGA | TGAGCACATC | GTCCTGTCTC | GGAAAGATCA | CTTTCTCTAC | TTCTTCTGAC | 1500 |
| TGCATCAGGA | GGTTGCATGG | CGGCTGCAAG | GCCTTTGGCC | GGTGAGTGAA | CCAGTAGGCA | 1560 |
| AGGATGGCAG | CCAGGGCACC | CATACTCACG | AGGGTGGTGG | CCGAGAGGCT | GCGGAAAAAC | 1620 |
| TGTCCCAAGT | CACCTAGCTC | AGGCAGTCGC | AGTATCCTCA | GGATCTCCTG | TGTCTGCATC | 1680 |
| TTCTCCAGAA | GTGAGAGG | | | | | 1698 |

(2) INFORMATION FOR SEQ ID NO:63:

(i) SEQUENCE CHARACTERISTICS:
        (A) LENGTH: 2416 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: FL.seq (xi) SEQUENCE DESCRIPTION: SEQ ID NO:63:

| | | | | | | |
|---|---|---|---|---|---|---|
| CCTGTGAACA | TTGACAATAT | ATTACTTTTA | GTGGTACACA | GTTCTTGAGA | AAATGTCTTG | 60 |
| ATTTTTACAT | TGCCATCTGT | GATATTTTTA | GCAGTCCACC | ACAATATCAT | TTTTATAATA | 120 |

```
AAAATAAAAT  ATACTCATTG  ATGATAGAGA  AAATATTGTT  AAAGACCTCT  TGGGACAGGA    180

AAAGGCTCAG  TCATAAAATC  AGATGCTTAT  TCATTTTCAG  CCGTGTCATT  TTGACTCATT    240

ACTTTCAAGA  ATAACTATAA  TATTGCTAGA  CAGTTCATTA  CACTGAGAAG  AACTTTCCTT    300

GAACTTCACA  TGGAGATTGA  GTAAAGCTCT  TCTATTTGTT  TTTTGAAGTA  CTCTCTCAGC    360

TCAGGTCTCT  TAGCTTTTAG  TGTTGGTGTC  AGCAAGCCAT  TTTGAACTGA  GAACATGTCA    420

GAATGGATGT  GAATGGCTTT  AACCTGCTCA  AGAATGGAG   TCCACTTTCT  TTTCCTAACC    480

TCACCATATC  TTCCAAAATG  GCTTTCTTCA  GATCCTTATT  TGTGCAGAGA  TCTGCATATG    540

TTCCTTCAAT  TCCTCTCTTC  TGGGCCCAGG  AGGGCATAAC  TTCAGGGTCA  GGCACAACAA    600

TGCCTACCAA  AAAGGCCTTT  AAGCTGTCCC  CATGGACATA  GATTTGCGCC  ACAGGTTGGC    660

TCCGGATGTA  GATGTTCTCA  ATCTTCTCGG  GTGCAACATA  TTCTCCCTGA  GCAAGTTTGA    720

ATATATGCTT  TTTCCGATCA  ATAATTTAA   GAGTTCCTGC  CGGCAGCCAT  TTTCCGATGT    780

CTCCAGTGTG  AAGCCAGCCA  TCGCTGTCCA  GGGCCTCCTT  CGTCCTGTCT  GGATCTTTCA    840

AGTAGCCTTT  GAACACATTT  GGTCCTCTCA  CACATATCTC  TCCCTCTCCT  TTGCAGGCCC    900

AGTAGTTCAG  TTCCTCAACA  TCAACGAGCT  TGATATGATT  GCAGGGAAGT  GGCGCCCCTA    960

CGTGCCCTGA  GGTCCAGTCG  CCAGGAGTGG  TGAAGGTACA  TCCAGCTGTG  CACTCAGTTT   1020

GGCCATAACC  TTCATAAACC  TGGCACCCTA  GAGCTGCCCG  GAGAAATCCC  AGAACTGTTG   1080

GTGATGCTGG  GGCTGCTCCA  GTAACAATCA  TCCGCACACA  CCCACCAAGA  CTGGCCTGAA   1140

TCTTATTAAA  GAAGAGTTCA  TCCCAGATAC  TATCATTCCT  GATGATTCCA  CTCCGGACCT   1200

CGGCTTGCTT  ACGCTTTGCT  GCAAACTCCA  GGAGCCAGCG  CTTTAATGGT  GTGTTTGCCT   1260

GGCTGAAGAT  CTTGTCGTAC  ATCCGGTTCA  GCAGTCGTGG  GACCACAGGG  AAGATGGTGG   1320

GGCATAGAGC  CTTCATGTCA  TCTGAGAGAA  GGCGGATATC  TCCCTGGAAG  AAGCCAACAC   1380

GCCCTCCGTG  GCAATAGACG  ACAGACTGCA  CCATACGCTC  AAACATGTGT  GCTAAAGGCA   1440

AATAGGAAAT  GTGCACATCC  GCACAAGTGG  GAGCCCACTG  ACTCTCTGTC  ACTTTCAGAA   1500

AGCCTGAGAA  ATCAGCCACC  ACGTTCCCAT  GGGTGAGCAT  CGCACCCTTT  GGGTTCCCTG   1560

TCGTGCCGCT  TGTGAAACAC  ACAATGGAGA  GGTCATCAGG  CTGCGGGGC   ACAGGAGCCT   1620

GGTGATTCTC  TTGGCCACAG  TCCTCCACGG  CCTGCATGGA  CTTGATGACC  ACCCCGCACT   1680

TCTGCCCTCT  CTCTTTCAGG  GCTTCTTCGA  ATGGGTCCAT  GAGGATGATC  AGCTTGAGGC   1740

CTGGAGTCTC  CTCCCTCTCC  ACATGCTCTA  GCAGAAGCAC  AGCCTTCTGA  GGTTTGTCCA   1800

CAATCACGGT  GCTGATGTCC  GCTGTATTGA  TGATGTAGCG  GATAGCCCCA  GGGCCCAGGG   1860

TGTCATAGAG  CGGGACCACC  ACTATGGAAT  ATGTGTAGCA  GGCCAGCTCC  ACAATGATCC   1920

ACTCTGGCCG  ATTTTGTGCA  AAAACACCAA  TAAACTGATC  AGTGCATGCT  TTACAATTGT   1980

GCTGGAGAAG  TCCGGACCCC  AGAAATTCGG  CCCTGTCGGC  CACCTCCTGG  TAGGACAGCC   2040

ACTGGTAAGG  CTGCTTAGGC  TTCCTGAAAC  CAAGACAGGG  CCCATTCCCT  GAGATGCTAA   2100

GCCCACGGCG  GAACACCTGG  TACATGGTCC  GGGCATCATC  ATAGTAGTGG  GTAAGTAGCT   2160

GAGGGCCAGA  CCCAATCACA  GATCGCCGTG  CCCCGCCACT  GTCCTCTACT  TCTTCTGACT   2220

GCATCGGGAG  GTTGCATGGC  GGCTGCAAGG  CCTTTGGCCG  GTGGGTGAGC  CAGTAGGCAA   2280

GGATGGCAGC  CAGGGCACCC  ATACTCACGA  GGGTGGTGGC  CGAGAGGCTG  CGGAAAAACT   2340

GTCCCAAGTC  ACCTAGCTCA  GGCAGTCGCA  GTATCCTCAG  GATCTCCTGT  GTCTGCATCT   2400

TCTCAGAAGT  GAGAGG                                                      2416
```

(2) INFORMATION FOR SEQ ID NO:64:

(i) SEQUENCE CHARACTERISTICS:
        (A) LENGTH: 406 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: FL2.seq (xi) SEQUENCE DESCRIPTION: SEQ ID NO:64:

```
TGGTGTCAGG  GGNCAACAGA  GGCCGAAGGC  GCCCTCTTGA  AAAAAAATAA  GCTACAAGAT    60
GAGTAGAGTG  GTTTACACAG  AGGACTGTGG  AGGTGGTGGG  TAATAAACTT  AAGCACCAGT   120
TTTAATCAAG  TACGGGCTGG  ATAATTAGAC  AAGATATNGG  NNNCTGAGCC  TCGCGTCAAC   180
TGAATCGGCA  GCTCGGCCGC  CTGTTGCCAC  AGGCTCCTTT  CTCCACGGCG  TCCTTGCGGG   240
ACCGCCAGAG  TGTGCTTGGC  TTCCGCGTAT  CCGTGTGTCT  GCGCGTCGCC  GGCGACTGTC   300
CCGTGTTTCC  CTGTGAGGCT  GCCACGCCCA  GGCGTGCATG  TGCGTCTCGA  GACCTGTGGA   360
CCTGGGCGGC  AGAAAGGCTT  CCCGTGGCTG  TTGCCCGCTG  ACACCA                   406
```

(2) INFORMATION FOR SEQ ID NO:65:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G205a.seq (xi) SEQUENCE DESCRIPTION: SEQ ID NO:65:

```
CAGGCTCATG  GTGTGGAAGT  CAGACCGGGA  GTCTCCTGGA  GCAGACTCAC  AGTGTAGGGG    60
GTCAGCAGAG  GCAGCAGCTT  TGGGAATCCC  GGCACTGCAG  CCTCAGGGGT  NGGCTCGCTG   120
AGTGGGTCAA  GGTCTTTAGG  GTTCTTGGGC  CCAGCCTTGG  AGCCTGCCCT  CCCAGCCCTC   180
CTGACATTCT  TAGAAGCACC  TACTTTCCTG  CCTGAAATCC  TTTCCTGATT  TAAA         234
```

(2) INFORMATION FOR SEQ ID NO:66:

(i) SEQUENCE CHARACTERISTICS:
        (A) LENGTH: 161 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G205b.seq (xi) SEQUENCE DESCRIPTION: SEQ ID NO:66:

| | | | | | |
|---|---|---|---|---|---|
| GCTGTATAGT | ATTCCACTGT | GTATATATAG | TTTTGGATCT | TATCGCAGTG | CCTCAAGTTC | 60 |
| TGTGAAGGAG | AGAATCTGGA | TAATTGTATC | AGGAGGTCCT | TAGACCATAT | TTAGGATCCT | 120 |
| TCCATTGGGA | CTTGGGCAGC | AAGGTTACCA | AAACTTAAAT | G | | 161 |

( 2 ) INFORMATION FOR SEQ ID NO:67:

( i ) SEQUENCE CHARACTERISTICS:
        ( A ) LENGTH: 445 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G205c.seq ( x i ) SEQUENCE DESCRIPTION: SEQ ID NO:67:

| | | | | | |
|---|---|---|---|---|---|
| CTCTCCTTCT | GCATCCCCGA | CTCTCCTTGA | GAACCTATTT | GGCAGAAGCT | CTCCACCCAG | 60 |
| CAAGTCCGCA | GCTTGATGAG | CTCCCTCCTG | TGTTAACTGG | AACCCCTGCT | GTACTTCATT | 120 |
| CCACATAATA | GTTCATCGGA | TCCAAAGTCC | CCACCTGCTT | TGGAAGCAAC | CACCTGCTCT | 180 |
| TCTCATAACT | CTCCTCCAGT | TTGTGCAGTG | AAGAATCAAC | CTTTATCCAA | GAAGTCTGGC | 240 |
| CTTTGCCCTG | GCTCTTGGGA | GGTCCTACCA | GCTACAAACC | CTTGGAGTAA | ACAACGTGGC | 300 |
| TAGTCCTTGT | CACCAGTTCC | CAGGAGGTAG | CCCCAAATTC | CTAGGGATTT | CCCAAGTGAT | 360 |
| AGGAGTATCT | TATTACTCAT | GGTGGTCTCT | GAGAGTTTAT | GTGAGTGAAG | TGGCTCATGG | 420 |
| TGGGCCCTAG | GTAGTTTTTG | CTGAC | | | | 445 |

( 2 ) INFORMATION FOR SEQ ID NO:68:

( i ) SEQUENCE CHARACTERISTICS:
        ( A ) LENGTH: 1661 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G221.seq ( x i ) SEQUENCE DESCRIPTION: SEQ ID NO:68:

| | | | | | |
|---|---|---|---|---|---|
| TCCAGGTCAG | CTACACACTG | TATGCCTGAG | CCCATGTTAA | TCTGTTGTAG | TGAAGACACA | 60 |
| TTTGGCAAGC | ACAGTGGCTG | CAAATGGGGC | TACTGTTGAA | TTGGTAGTAG | CCTGCTGTCA | 120 |
| TCTTTCAGGA | TTTAACTGGG | TTTTGCTGGT | AAATTAAATG | AAGATATGAC | GGACTCCCTT | 180 |
| TTAGGTCTAT | AATGGTGGCA | ATAATTTCTG | CCATTAACCC | TGGAATGTGA | TATTGTTCTT | 240 |
| GATTTACTAT | TTTGCCTGGA | ATGGGAAGGT | TTTGAAGGCT | TCCACTTGGC | TTTCTTCACT | 300 |
| ATGATCACTC | TCACCATGCA | GGCCAAGGAC | CCAATGTAGG | GGCTGTGCTA | ATTATCAAGT | 360 |
| GTGTTGATCT | GATTATATCA | CTGTGGGTCT | GTGGACCCAG | AGGACCTGCT | ATTAGCAGAA | 420 |
| CTCAGGACAG | GAATCTATCA | CCTGGCCCAC | ATATACCCCT | CATTCTAATG | AGAGGATTGT | 480 |
| GGCGCCACTT | CAGGTACCTA | GGTAACAATG | TCAATTCTAA | TCCCGGGTTC | AATAGTCTTT | 540 |

| | | | | | | |
|---|---|---|---|---|---|---|
| CACATGTTAG | GATATTCTCT | TTCCTAGTAT | GTAGCTATCC | AAGTTAAGTG | CCCACAGGTC | 600 |
| CCCCTGGGAA | AGGGCTGGGG | AAATCATTAT | CATGCACACT | TGCTGTGGTG | GTGTGGGACT | 660 |
| CTTCCTTCTG | GGAGATCTGG | CATCTTCTTC | AATCAGTAGG | TTCTAAGTCT | GAAAACTGGT | 720 |
| TCAGATCTGG | AAACTCGGCA | GGTTACTTTT | TATTGGGGTG | ACTGGACTCA | TTATCCATGA | 780 |
| TTGATTTCTT | TTTCTTGCAC | AGAATAACCC | GCAGCACTGT | TGGCTGGCCA | TCTATTGTGA | 840 |
| CCCTCCAGAT | GCTATGTTTT | ATTAACCATG | TCCATAACTC | CCCGGGAGCC | AGGCCCTCTT | 900 |
| AACAGCCATT | CCAATCTTGC | CACCCAGACA | ACTGGGCCAA | GTGCTATGAC | TTGGCCTCTA | 960 |
| TTATCTCAGA | GTCCTATCAC | CCCTACTGCT | ATCAGTGAGC | CCAGTTCTGT | GACATTTCCT | 1020 |
| ATCAATGCTG | GCCTATTTTA | GCCACCATTT | TAGTTCTTGG | TGATACTGGT | GCCCTTCTTT | 1080 |
| CCAATACATT | TCTTGTTTTG | GTATCTTCTT | GGCCCTCAGG | CGAGTATTCT | GAATTTGCTT | 1140 |
| AGTATATTTA | TTCCTGCACA | CCCACGTCCT | TCATAGTCTG | CCATAGCCAT | TCTGGCTACC | 1200 |
| CTCACTTAAT | ATGGGCCATC | CTCTTTCCAT | GCTTCTAGGA | GCCATCCAAA | CGATGTATTT | 1260 |
| GCACCATCTC | TTGGGGCTTT | GCCACAGTTT | TAAATACTTT | ATCCTGGAAG | AATGTTCCCA | 1320 |
| TATCCATAAA | CTCTTTTGTT | CAAATTTCTG | TTCCACCCCC | TTGGTCCAGA | ATCCAGTCCT | 1380 |
| GTGCATACTC | TCCAAGCTCC | TGCTAGTACT | CTCTGGATAT | GACCAGAATT | TCCTTTGAGG | 1440 |
| TATAGTCCTT | TTCTACACTA | GCAAGTTCAG | CATGTCTGGC | CAGGTTAGGT | TTTGACTTAA | 1500 |
| CCCTAGTTAT | TGGCCTAGCA | CAAAGAGGTA | ACATGGAATG | AGAGCATGTC | TTGCAGGACA | 1560 |
| GAAGCCTCCG | CATTTTCTTT | TTAAAGTAAG | AAGCAAGTTC | TAGCTTTTAA | CAGAGATGAG | 1620 |
| TAGGTCACTT | CTGCAGGTCC | AGAGTGTTTA | GTGAAATCTG | A | | 1661 |

( 2 ) INFORMATION FOR SEQ ID NO:69:

( i ) SEQUENCE CHARACTERISTICS:
        ( A ) LENGTH: 1379 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G238con.seq ( x i ) SEQUENCE DESCRIPTION: SEQ ID NO:69:

| | | | | | | |
|---|---|---|---|---|---|---|
| CTCTGTGCAC | TGTAGNGTCT | TCTTGTGTAC | CAGCACTTTT | TTCTTCCCAT | TTCTTTCTCC | 60 |
| ATGTTTACCA | TCAACACTGT | GAGAATAACT | GAAGTTTCCT | TATCCAAAAA | AAGGGTGCTA | 120 |
| CTCCAGATTC | CGCCACTACT | GTTTTCGAAA | AGCACAAAAC | CAACAGAGCC | TCAGGGGGGG | 180 |
| CTGACCCTCT | TTCTGGATCC | CACCTCCATC | CCCCCGAACT | TACGTTGTGC | TTTCCTCAGC | 240 |
| AGCCACCGAG | GCCTCCAGTT | CCGTCTCCAA | AGATGATGGG | TTCCTTCCAG | TGGGTGCAAA | 300 |
| GTGAGAGCCC | CAGTGATTGG | TGTTCATAGT | GGGTCAGTGT | GAACAACGCC | CAATGGCCTG | 360 |
| CCTGGGCCAG | CTGGGGCCTC | GTTTTGCTTT | GGTCTGAAAG | ACATTTTTGT | TTTCTGGTGA | 420 |
| GAACAGCCCC | AGCCTGGCCA | GGAGCCGGCC | AGCGGCAGGA | ATACAAACCC | TTTCATGTGA | 480 |
| CAGACCCAAG | TGGAGTGATG | CCCTCCTGCC | AACAGCAGGC | CCTCCCTGC | CGCTCCTGGG | 540 |
| AGGCGGCCAT | TTGCATATTT | CCCATTCATC | CTGGCCTTGA | AAAGGAGGCC | TGAGTTCCCA | 600 |
| GTGCTCCTGC | CCGCTGAGGG | CTGGGCCGCT | CCAGTCTAGT | GTTAACTCTG | TGGACACTGT | 660 |

| | | | | | |
|---|---|---|---|---|---|
| AGGCTCTCAC | AGGCCAACAG | CAGAACTTGA | CCGCTTGCTG | CCGGAGGGAG | AGCAGCTTAA 720 |
| GGCTGCAGCT | GCTGTGCCGC | CTGACCTCCA | GAGGGGGGAT | TCAGGAGGTG | GCAGATTCCC 780 |
| GTTGACCAGC | ACAGCCTTTT | GCTAAACTGG | AGGAAATTCA | GATTTGTTTC | TTCTTGAGGC 840 |
| ATTCAGAAGA | GGAATTTTGT | CAGACTATGG | GGATGCCAGA | ATATTCAGCT | ATTTACCAAA 900 |
| TTTGCCAGAA | AATGTGCCCT | TAACCAAGGG | CCAAACTCTT | TTTGTCTTGC | TCACTTTCTA 960 |
| GTCTACAAAA | AAATTCAGTG | ACTCTGGAAT | GGTAGGTGAA | GGAGCCATGC | CGGATCCTGG 1020 |
| CTGCAGCAGC | AATCCCTTTG | CCAAGGATGT | AGGAGCACAG | CTTGCCTGGG | GCACTTTTGC 1080 |
| ATCCCCAGGG | CTGAGTGCCA | TTAGCTTGTG | GGCTGTGACT | CTGAAGGCAT | GAGGCAGATA 1140 |
| TACAGTACCC | ATCACCATCT | TTTTCCTTTC | TCCCATAGCT | AAGTGCCATC | CTGCCAGCCT 1200 |
| CAGCTTCCTG | CCCCAGTCCT | CAGTGCAGAC | AGGCCTCTGC | CTCCTTCCCG | CCACTGTGTG 1260 |
| AGGGCTCCTG | CCAGGGGCCC | CAACATCTTA | CAGGCTCTTC | CTGTGACTTA | CCAACCCACT 1320 |
| TCTGTCCCTC | TTCGATAGCC | CTGTTCTCTA | CCCTTTCCCA | CCCAGCTCGG | ATCCTCTCC 1379 |

( 2 ) INFORMATION FOR SEQ ID NO:70:

( i ) SEQUENCE CHARACTERISTICS:
    ( A ) LENGTH: 2661 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: G229con.seq ( x i ) SEQUENCE DESCRIPTION: SEQ ID NO:70:

| | | | | | |
|---|---|---|---|---|---|
| TCTCTAGACC | CTTCCTGCTT | CTCTCCCCAC | AGCAGCCACC | CATTAATTCA | TTACATAAAT 60 |
| ATGTACTGAG | CACCTACAAA | GTGTCAGGAA | CTGTGCCAGG | CTCTGAAAGG | AAACCAACCC 120 |
| TTGAGGAGCT | TACACTTTAG | GGGTTAGTCT | GGCTGTGTGT | CATAAGGGTT | ACCTGCCAGC 180 |
| TCAGCATGAA | CTCCAAGCCC | TTTGGTCTGA | CCTAAGACCC | TCCCTTACTG | CCCTGGCCCC 240 |
| GACAGCCCCT | GCAGATACCT | CTAGCCTCAT | TGCTCACCAT | CCATCTCCTT | CATATCAGCC 300 |
| CTGGACCCCA | GTAACACGAC | CCAGACCACA | GCACTCCCAC | CATCACCTGC | TACCCCTGCC 360 |
| TGGAATGCAC | CCCAGACCAA | ATGGTTGACA | TCTGTCTCCA | CAATGGGGTA | AGACTAATGT 420 |
| CCAGCGGGAG | GTGGAGAGGT | CCTGCACTGG | GGCCTCCTCT | TCCTCAACAC | CTACTCTGAG 480 |
| GCTTGCCTGC | CCACCTCTTA | CGCCACAGGG | GTGGACTGTT | ATCTGTTCCT | CAGGGGACTG 540 |
| TGAGGGTCTC | TGCTCTGAAC | TACTGCTTTA | TCCCCAGCT | CGGAGGAGGG | CCCCTCATGG 600 |
| CATCAAGTGC | CAGCAGTGAC | TATGTTCCAG | AGTCTGATGA | AAGTGAGCCT | CTTTTCACCT 660 |
| TTGAATAAAA | GAAATGCACA | CAGCTTTTAC | AGAAGTCCGG | ATGGAAAGGC | AACATCCAAT 720 |
| TTTCCAAAGT | TTAGAAAATG | TTCTTGGGAC | CAAGATCAGC | AACAGGCTAT | AAGCAGGTAC 780 |
| TAAGTACACA | GCCAGGGCTG | TTGTTTTCAT | TATTCTTATC | AAAAATAGCA | TCTGTGAGGG 840 |
| AGCCAAGAGG | AGGCCCTTGG | GGCCATCCAG | GAGCCAGGGG | AACTGGGAGC | CAACACCAG 900 |
| CACAGCTGCC | AGCTCTTTTT | CCCACTTAAC | GGATTCGGGA | ACCATCTCAA | AGGAAGCTGC 960 |
| AGGAGGGAGG | GAAGCCCAGC | TCTCTGGGAA | TGTGTCACAC | TTCCTCCAGT | TAGGCCTGGG 1020 |
| GCAGCCCCAA | GCTCTCCTGA | TGGAGGCCCT | GGCTCCTATC | CAGGCCTCTT | CCTCTACCAG 1080 |

| | | | | | | |
|---|---|---|---|---|---|---|
| ACTGGATAAG | GGTGAGGTCA | TGTGCTGGGG | AAGGGAGGCC | AGGGAAGCAG | CAACTGGGTT | 1140 |
| GGAGCCAGTC | AGAAACAACA | CAATAACAGG | ATAACTCATA | GTCTCCCTC | TCCCCTTACA | 1200 |
| CTCCAGGAAG | CTGTCCCTGA | GTGAACTCCA | TACCCCTCAG | GTCCCTTCTC | CCACTGGGAC | 1260 |
| CTCTCTGGGG | CAGATTCTGT | GGGTGCCTCT | TAGTCCTCAA | CTGAAATGGA | AGCTCTCTCT | 1320 |
| CTTCTCAGGG | CTAGGGGCAG | CACTGTGAAT | CAGACAGACC | CTAATGCCTC | CTCTCACCAA | 1380 |
| TCCAGTCCTG | GACATGGGCA | GCAACCAGTG | TTGGAACCCA | GGTGGAAATA | AGAGGAAGCT | 1440 |
| GCCAGAGCCT | CGAGCCATAC | CCTGGGCCAT | GGTCACACCA | AAGGTTCTTG | TGCCTATGGG | 1500 |
| GCTGAGGGAC | AGAGATATGC | AGCCTTGGGC | TCTGAGATCA | AACAAAATG | GGTGTGGGCC | 1560 |
| TGGGTCCCCA | AGTTACAATG | AACCCCCCTG | TTAGGAAGGT | GCATCTGACC | TTAGACTCTG | 1620 |
| TCAGGCTGAA | GGACCAGGTC | CCCAAGTTAC | AATGAACCCC | CCTGTTAGGA | AGGAGCATCT | 1680 |
| GACCTTAGAC | TCTGTCAGGC | TGAAGGACCA | GGAGTCACAA | GCAGACAGAC | AGACACAGCA | 1740 |
| GGACCATGAC | AGGGGCAGAC | AAACAGATAG | GCATAGCTCA | GGCTCCTGGC | AGTGATGAGT | 1800 |
| AAACGGACAG | ACACTGATAG | ACAGTTAGAC | TCAGCGAGAG | CCTGGAAAGG | ACAGATGGAG | 1860 |
| AGACAAGAGG | GAACGCTGGC | AGTGAAAGAC | TGACAGACAT | AGAGGAGATG | GCGGACTTGG | 1920 |
| CAAGAGCCCC | TGGCAGGGAC | AGACAGAGAC | GCAGTTGCAA | GCTGTGGTCA | GGTTAAAATG | 1980 |
| TGGCCATTCT | GTCTCTGAGC | TCAGCCCCTG | ACTGCAGATC | CCGATTCTCT | TGGAGGTTCC | 2040 |
| TCCTCTTGGC | ACTGTGATCA | GAGACTTTGT | GGGACTCTTG | GGACCCATTT | CTCCAGGACT | 2100 |
| ACAATGCCCT | CAACCCCACA | AGTCCAGGA | AGGTAGTAGG | CTGTGGCCCT | CACTGTCCCT | 2160 |
| GGAGTCAGAC | TCAAGAATCA | ATCCATTCTC | CTGGTTTTTT | CCTCCCCTTC | CTGGCCTGTG | 2220 |
| GGGCAGAGAA | AGCCTCCTCG | ACATCTCTCC | TGGGGCCACC | TACTCCCAGC | ATGGTGGCTG | 2280 |
| TGCTTGTCGT | GGAAAAGGTC | CTTTTAGGAA | CCACTATGAG | TCCAGACTCT | GTTGGCACAG | 2340 |
| GGGGCGGTGC | CCAGAAGAGG | CTATAGTCCG | GCATTGCAC | GACTATCCGA | GGATGTTGAG | 2400 |
| CTCCACCTGG | CCGCCTTCTC | TTCTCACCAC | CCCTCATGAC | CTCCAGGCCC | CAGAGGCCTG | 2460 |
| AGGGCCTAAA | AGGTTTTGAC | CCAGGGGAGC | AATTCCAGGC | CAGGTGAGGA | TGGGGTGATT | 2520 |
| AGTCCCCTTC | ATAGCTGCAG | AGACTGAAGC | TGACTTGAAC | ACACTCTGCT | CTGAGGCTGT | 2580 |
| AGGGTCCAAG | AACCCCCCTG | GGGTGAGCTG | AGGTTTTCT | ACTTTCAGGG | GACCGTTGTG | 2640 |
| CTGAAAGCAT | GACGAGGCTG | C | | | | 2661 |

( 2 ) INFORMATION FOR SEQ ID NO:71:

( i ) SEQUENCE CHARACTERISTICS:
      ( A ) LENGTH: 863 base pairs
      ( B ) TYPE: nucleic acid
      ( C ) STRANDEDNESS: double
      ( D ) TOPOLOGY: linear ( i i ) MOLECULE TYPE: cDNA to mRNA ( i i i ) HYPOTHETICAL: NO ( i v ) ANTI-SENSE: NO ( v ) ORIGINAL SOURCE:
      ( C ) INDIVIDUAL ISOLATE: G248.seq ( x i ) SEQUENCE DESCRIPTION: SEQ ID NO:71:

| | | | | | | |
|---|---|---|---|---|---|---|
| CTATGCTAGA | GAAAAGGGA | GGTAGTGGTT | TCATCCGCCA | CTACTACCTA | TGGATGTGAA | 60 |
| CAGAACCTCT | GCTCCTGATG | CAGACCCCTG | GCCCTTTCCC | AGTCCTATT | CTGTTTTGAC | 120 |
| TTCTGCACAC | CCCTTTTTCT | GACCCTGATA | CTATCCCAGA | TCATTATTCT | TCCTCTAGTC | 180 |

| | | | | | |
|---|---|---|---|---|---|
| CTACCCTTGT | TCTAGCCAGT | GCCCCAGACC | CAAGGTGAGC | TAAGGGACAG | TCTCTCAAAG | 240 |
| TCTGGGCAGA | GAGCCTCAGG | AAGTTGGGGT | ATGGCTGAGA | GAAGAGGGGA | GTGCAGGGGG | 300 |
| ATAGGCATAC | AGACTCTGAA | TGCTTGACCT | TCCTTATTTT | CTGTCTTTGA | ACTTATTTCA | 360 |
| ACAGAGGAAC | CCTTATCATC | TAGCCCTGTG | GCTCTCTAGT | ACCTTGTACC | TGCTTCCTGT | 420 |
| CCCATAATTG | TGAGCGTTTA | GCTGTGGTGC | AGGTGAGAGA | CCCATTCTCC | CACCCTCAGG | 480 |
| AGCCAGGAAG | GCCCACCAGT | ATGGCAGGGA | GGCCTAGGCA | GAGATATACA | GGAGAGCAGA | 540 |
| GACGTCTGGA | GCTAGGTCAC | CGGTGGTCAG | CAGGGCCTCC | TGCAGAGGGA | GCAGCCTCCT | 600 |
| TTGGCCTTTG | CTTGTCTGAC | TTCTAATGAT | CCTGTAAAAA | TTAGTTTTGT | TTTTAAGCA | 660 |
| CCCCAATGAT | GCATGAATAC | ACTCTTTTGT | CAAATCTTAA | AAAGAGAAAA | TCCTTTTTTT | 720 |
| TTTAAATAAA | AAAGAAAGTT | ATTTAGTCTT | AAGATTGTAA | AACTGTAAAG | TTAAATAAAG | 780 |
| TGGCCGCCCT | TTGGCTGCCC | TGATCCCCAT | CCCCTACTCC | AGCTTCTGCA | AGTAACCACA | 840 |
| ATTCTCAGCT | AGGTGTATAT | CCT | | | | 863 |

( 2 ) INFORMATION FOR SEQ ID NO:72:

( i ) SEQUENCE CHARACTERISTICS:
        ( A ) LENGTH: 1378 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G248a.seq ( x i ) SEQUENCE DESCRIPTION: SEQ ID NO:72:

| | | | | | |
|---|---|---|---|---|---|
| GCCGCCCGGG | CAGGTTGCTG | AGTCTCTGAA | GGTAGGAGTG | GGAAGTCTCG | CATTGGAAAG | 60 |
| GCCTTCTTAG | GTGCAGTAGT | ATTTGTTATT | TTACACCTTA | ACCTCAAAGG | AAGTCCTTCT | 120 |
| TTTTCTTGGG | ATGGAGCACT | TTAGTTCTCA | TAACTCTTCT | CTGAAGTCAT | TGCAGAGTGG | 180 |
| GTGGAGGAAG | GTGAGGGTGA | TGCTTGGGTC | TGAATTTTCT | TGGTAAACTT | ACAAGTGGAT | 240 |
| CTATCAAAAA | CCAGAGGGTT | TTTTCTTAAC | CACAACACCC | CCCAGAATTC | CATTTCCTGC | 300 |
| AGATGTAGCA | GCAGCACGTC | TAGCCATCTT | GGCCCAGGCC | TCTGGACCAT | GCCTTGGGAG | 360 |
| GGCTCTGCCC | TCTGCCTTGA | GTTCCATTAG | AACTTCTCCA | GTGGAAAGAG | TGAGTTACTT | 420 |
| TGCCCTGGCC | TGGTGGGCAG | GCTTTTCCT | CTCTGACTTG | GCTAAATGAA | ATGGGATTTA | 480 |
| AGGTAGCTCT | CCCTGTGGGT | AAAAGACATT | TTGCTCTATG | CTAGAGAAAA | AGGGAGGTAG | 540 |
| TGGTTTCATC | TGCCACTACT | ACCTATGGAT | GTGAACAGAA | CCTCTGCTCC | TGATGCAGAC | 600 |
| CCCTGGCCCT | TTCCCAGCTC | CTATTCTGTT | TTGACTTCTG | CACACCCCTT | TTTCTGACCC | 660 |
| TGATACTATC | CCAGATCATT | ATTCTTCCTC | TAGTCCTACC | CTTGTTCTAG | CCAGTGCCCC | 720 |
| AGACCCAAGG | TGAGCTAAGG | GACAGTCTCT | CAAAGTCTGG | GCAGAGAGCC | TCAGGAAGTT | 780 |
| GGGGTATGGC | TGAGAGAAGA | GGGGAGTGCA | GGGGATAGG | CATACAGACT | CTGAATGCTT | 840 |
| GACCTTCCTT | ATTTTCTGTC | TTTGAACTTA | TTTCAACAGA | GGAACCCTTA | TCATCTAGCC | 900 |
| CTGTGGCTCT | CTAGTACCTT | GTACCTGCTT | CCTGTCCCAT | AATTGTGAGC | GTTTAGCTGT | 960 |
| GGTGCAGGTG | AGAGACCCAT | TCTCCCACCC | TCAGGAGCCA | GGAAGGCCCA | CCAGTATGGC | 1020 |
| AGGGAGGCCT | AGGCAGAGAT | ATACAGGAGA | GCAGAGACGT | CTGGAGCTAG | GTCACCGGTG | 1080 |

| | | | | | |
|---|---|---|---|---|---|
| GTCAGCAGGG | CCTCCTGCAG | AGGGAGCAGC | CTCCTTTGGC | CTTTGCTTGT | CTGACTTCTA | 1140
| ATGATCCTGT | AAAAATTAGT | TTTGTTTTTT | AAGCACCCCA | ATGATGCATG | AATACACTCT | 1200
| TTTGTCAAAT | CTTAAAAAGA | GAAAATCCTT | TTTTTTTTAA | ATAAAAAGA | AAGTTATTTA | 1260
| GTCTTAAGAT | TGTAAAACTG | TAAAGTTAAA | TAAAGTGGCC | GCCCTTTGGC | TGCCCTGATC | 1320
| CCCATCCCCT | ACTCCAGCTT | CTGCAAGTAA | CCACAATTCT | CAGCTAGGTG | TATATCCT | 1378

(2) INFORMATION FOR SEQ ID NO:73:

(i) SEQUENCE CHARACTERISTICS:
    (A) LENGTH: 797 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: G248b.seq (xi) SEQUENCE DESCRIPTION: SEQ ID NO:73:

| | | | | | |
|---|---|---|---|---|---|
| GTGTATATCC | TTCCAGACGT | CTTTCTATAC | ATTTACTTTT | CCTTATTGTT | TAAACCAATG | 60
| GTGAGTTGTC | TTTTCTCTTA | CTTAAATCTG | AAAGTGTTCC | TAACCAATTT | AATAACAATT | 120
| GCCTCAGTGC | TGTTTATTGA | AAGGTTCTTC | GTTTCATACT | GACATAAAAC | GCCAGTTGTG | 180
| TTAGACCCTG | GCCAGGCCTG | CTTCCTCAAA | GACCCAGAGT | AAACATGAAC | TGTAAACTCC | 240
| AAAACTGTAC | AACTAGTTTT | TAAAGAAAGA | TTGCCCAAGA | TACTGGCACA | AGACTTTTA | 300
| AGGCCTAGGA | TTTGCATATT | AGACCTATGT | AATGTGGCTT | ACTGAAGAGC | AGAGTTCTTG | 360
| CTTTCTTTGG | TAGTGTAAGC | TCTTTCTGGT | GCTCACACAG | GAAGGACTGT | AAAGGGCAGT | 420
| GAGGGCTCGA | ATCTGGACTC | TTCTGACATG | AGGGACATCT | CATTTTATGC | AGGCTGCCAA | 480
| GACCATTGAA | CTTGGAGGAT | GCCTTTGTGA | GAAAGCAAGA | AAGGCAGTGG | GGAGCTGCAG | 540
| CCCCCACATG | CACCTTCATC | TCAGGAACAT | CCTTTGTACT | TTTTTTTTA | ATATTGTACA | 600
| GAGCTGTTTT | TTTTTATTAT | ACTTTAAGTT | TTAGGGTACA | TGTGCACAAC | ATGCAGGTTA | 660
| GTTACATATG | TATACATGTG | CCATGTTGGT | GTGCTGCACC | CATTAACTCG | TCATTTAACA | 720
| TTAGGTATAT | CTCCTAATCC | TGCCCGGGCG | GCCGCTCGAG | CCCTATAGTG | AGTCGTATTA | 780
| GGATGGAAGC | CGAATTC | | | | | 797

(2) INFORMATION FOR SEQ ID NO:74:

(i) SEQUENCE CHARACTERISTICS:
    (A) LENGTH: 403 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: G248c.seq (xi) SEQUENCE DESCRIPTION: SEQ ID NO:74:

| | | | | | |
|---|---|---|---|---|---|
| CATTGATGGA | ACCAATACAG | AAAAAGGATT | TTCATCATCC | AGGCCTTCTT | CTACAGCTGA | 60

| | | | | | |
|---|---|---|---|---|---|
|AAGACTGGCA|GCTGGTATAC|AACTGTTCCC|TGCAAGGATT|GGGAGTTAGC|AGCTTTATGG|120
|ATAAGGGCAA|TGCTAGTGCT|TGCTTCTGTT|CCTTACTAAT|AAATATCGTT|TGTGACACTT|180
|TTTTTCAGAA|TAGGGCATTT|TTGTCTGTAT|TAAAAACCTG|TTGAGGCAGG|TATCCTTTGT|240
|CCTCAATTAT|TTTCTTAATG|ATACCTGGGA|ACCTATCTCC|TGCCTTTGGT|CAGCAGAAAC|300
|TGCTTCTCCT|ATTACCTGGA|TATTTTTAAG|GCCAAACCTC|TTGCTAAAAT|TATCAAACCA|360
|TCCTTTGGTG|GCATTAATTT|TCAAGTTTAG|CTCCTTCAAC|CTC| |403

( 2 ) INFORMATION FOR SEQ ID NO:75:

( i ) SEQUENCE CHARACTERISTICS:
        ( A ) LENGTH: 1083 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G220a.seq ( x i ) SEQUENCE DESCRIPTION: SEQ ID NO:75:

| | | | | | |
|---|---|---|---|---|---|
|GGAAGACACT|GATCATCTGT|CACAAACTTG|GTGAGTCATA|AATAGTGCCA|CCTAAACCAT|60
|GAGATAAACT|GGGGGTGCAC|CTGGAAACCA|GGTAGCCCCC|CTCAAGGGCA|GGGGCTTTTG|120
|TATTATAGGT|CTGCTGCTAT|TCTCCCAGTA|CCCTCAATGG|CACATGTCAT|GTAGAAGAGT|180
|CTCAGTAAAT|ACCTGGTGGG|TGACAGAATG|GAGGTGGGTG|ATTCTGTTGA|TGAGCAGGCT|240
|GGCACCGATG|AGCATGGAGT|ATCTGCCAGC|CCTAGGATGG|TGCTGTGTCT|GTGTCCATCC|300
|ACTGTATGGT|TACAAGAACT|CAAGGTACCT|GGGATCCCTC|AGTCCTCACA|GACCAGCTCC|360
|CAAGCTGGGC|ACAAAAGACA|ATGTATGTTG|AGTGTTGTTT|CTGACATGAG|ACTACTGGGA|420
|CAGTAGGTGT|CTGCCTGCTC|CAGTATGAAG|GATCCCACTA|CTTTGTCACT|GGATGGCTTT|480
|GGGTTGCAGT|GGTTTTCTTA|CCAAAGCACA|ATGACCCTTC|AGTGGGGTCA|GCTTCAGCAA|540
|GATAAAGGCC|TGGCCTGAAA|CAGGTGTCTT|CTATAAGAAA|GACAGAGTTG|TGTCCATTAT|600
|GCCTCTCTCG|CTGCTTCCTG|GTAAAGGGAC|CTAGGCATCC|CTGGGTGACT|GGAGTGCCTG|660
|GTGACCACTT|CCATCCACCC|CCATTATCTG|CTGCTAAGGT|ACACATGAAG|TATCTTAGTT|720
|CCCAGAAAGA|GAACCCCTGT|TGAACAGTAA|CAAGCCCCAG|CATAGGGTGC|TAATGATTTA|780
|TCTGCTTTCA|CATTTGAGCG|TGCTTTCTTG|GAAGTGATGG|AGAATCTTCG|GCCTGAAGAT|840
|GTGGAGGCGC|ATGCAGAGTC|CTGAGCTCCC|CACAGGCAGC|TTAGGTGTAA|CTGAGAAGGA|900
|GCTGTGAGCA|TATCTGGCTC|TCCAGCTCCC|ACAGCAAGCG|GGGTCCACCA|GTATTGACAT|960
|GGCTCTTGTC|TGCATGATAA|GCTGGACCAA|CAAGGCCAGG|GCTCTGCCCA|CAAAGCTAAA|1020
|CTAGTATGGG|GACTTGGCAC|TTGTCCCTGT|CAGGGGAATG|GTAAGCATTT|TCGCACAGAC|1080
|TAG| | | | | |1083

( 2 ) INFORMATION FOR SEQ ID NO:76:

( i ) SEQUENCE CHARACTERISTICS:
        ( A ) LENGTH: 854 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
  ( C ) INDIVIDUAL ISOLATE: G255.seq ( x i ) SEQUENCE DESCRIPTION: SEQ ID NO:76:

| | | | | | | |
|---|---|---|---|---|---|---|
| CTCAGTTTGG | GCTCTGGGCT | AATCATCTGT | CCTGTCCTAC | TTGTCTTCCA | CAAGGGACCG | 60 |
| ACTGGTCATG | AAGGCCATGA | AGGCTGTCTG | CTGTGTGTCC | CTGGAAATGT | CTGTCGACAG | 120 |
| CCTCTCTAGG | CAGAAGTGTT | TCTTCTTGTG | TACCAACCAA | GACCTATAGG | CCTCGCCTCA | 180 |
| TCTCCCAAGC | TATACCTTAC | CACAAAGCAG | AACAAGGGTG | GACTAAGAAC | TGGCAGAGAT | 240 |
| TTATACTTGG | CTTTCCAGAG | GTCCCAGGTT | TGTGGTAGGG | GTTCATGAGG | CTGGCTGCTA | 300 |
| TCTAGATGAG | ATATGCAGAG | TGAGCTCCTT | TCCCTGAATG | CTGGGCATCC | CATCGGTAGT | 360 |
| ATGGGACAGG | GTAAGCTCCT | GGCCTGGCTG | GCTCCAATGC | TGCCTGAGTG | AAGCTATGTA | 420 |
| ACCCTGGGAC | ATCTCTCTTA | GCATGCTGAT | ATTTGGCTGC | TTCTCTGATA | ATGGGAGCAG | 480 |
| CATTCTCTGG | TACGGGGTGC | TGTGGAAGAC | CTAGGGAATG | GGACAACAGA | TTAAAATGGG | 540 |
| CTTTGAAGAC | CCTTGGAGAG | GTGACCAGGG | AGGCCCAACC | TTCTATTTCC | TGTGCTCAGG | 600 |
| CCTTGGGAGA | GACAGAAACC | ACGAGGGTCC | AAGGTCCCCA | ACCAGTGGGA | CCCCGACACC | 660 |
| AGGAGGACAG | GACTCTCAGA | GTTCTGTGCC | TACTCCTCAG | TTTCTTTTGT | GTCTGCTGCT | 720 |
| ATCAGGAGTC | CCAATCTACA | GGGCTCAATC | AGGATGGGAT | CCTTAGTGTG | GCACCTGGGT | 780 |
| CAGAAAACCG | CCCCTGCTAA | GAGGCTCAGG | ACAGGCTAA | CTGGGAGAAG | AGGCCCCACC | 840 |
| TAAGTGTCTG | CCAC | | | | | 854 |

( 2 ) INFORMATION FOR SEQ ID NO:77:

( i ) SEQUENCE CHARACTERISTICS:
    ( A ) LENGTH: 605 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: G306.seq ( x i ) SEQUENCE DESCRIPTION: SEQ ID NO:77:

| | | | | | | |
|---|---|---|---|---|---|---|
| CCCGCACTGG | AACAGAAGCT | TCGTGAGAAC | AGGGACTTTG | TCTTGTGTGT | TCGCTCCTCT | 60 |
| CTTCCCAGGT | CCTAGAACAG | TGTCTCGTCC | ATAACAAACA | CTCAATGAAT | ATTTAGGGAA | 120 |
| TGAATGTCTG | CAAGATGCTG | AGAATCTCTC | ATAGAGTTTT | CATATGTGAC | CCCTCTTTGA | 180 |
| AATTGGGTAT | TATCAAGTTA | TTCATTTAA | TGATTCAACC | TAATTCAGTA | ATCAAGCAAA | 240 |
| TTGGCAGAGA | CCTAAAATAT | TTACCCGTTG | TTGTGAGGAT | GAAATAAGTA | AACAAGTGTA | 300 |
| AGTTATTTAG | AGCAGTGTCT | GGTAACCACA | GCCCTGTGTA | AGAGTTTGCT | GCTGTTGTTA | 360 |
| AGAAATGCTT | GACTTCTTGA | TATCTTAAAG | TTTTGCTGA | CTCTGCTGCC | TGTGTTGGGA | 420 |
| TCCCAAGCAG | AAACTGTTTG | TGGCCCAGCA | GGTGTTGGCA | CTGGGTGAGT | GCTTCTGGCT | 480 |
| CTTGTCCCAC | GACGGACATC | CAGGTCTTCC | AGCGGCCTGA | GGATATAGGA | GGGGCTTCAG | 540 |
| GCGGATGATT | GTGGCCGTTG | CTTATGTTTT | TTCCTTGTTT | GGCCTACAGG | CACATGTCAC | 600 |

| | | | | | | |
|---|---|---|---|---|---|---|
| CACAC | | | | | | 605 |

( 2 ) INFORMATION FOR SEQ ID NO:78:

( i ) SEQUENCE CHARACTERISTICS:
        ( A ) LENGTH: 890 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G256.seq ( x i ) SEQUENCE DESCRIPTION: SEQ ID NO:78:

| | | | | | | |
|---|---|---|---|---|---|---|
| GGGGCCAGTC | ATCTTGAAGA | AGTCTTCCAC | ATGCCCTGT | CACACTCATC | CCTTTACCAA | 60 |
| AAGCCCCTAC | CCATGGGGTG | GGTCAGGCAG | GCCCCAAGAC | AGGCCCGTAT | CAGGAGGACC | 120 |
| CCTCTTCTCT | CAGGGGCTGC | CCTCTGGGAT | AACCACCCCC | GCCCTTCTGG | GTTTCCTGCT | 180 |
| TCCTATCTGG | CTGCAGTTTC | TCAGGTCCCT | TGTGGATTTC | CCCATGGTCT | GTCCCACTC | 240 |
| ACATCCCCTC | TCTGCAAACC | TTGCCTACTG | GGCCTGCACC | TGGCAAATCC | ATGCTCAGCA | 300 |
| CAGACGGGGA | TCAAGACCTC | TCAATACAAC | TGTCTCCTGC | CAATCCCTGC | CCCAGCAGCC | 360 |
| TGAGGCCCAG | TCTGAAACCA | GGGAGTTGCT | CTCCTTTCTC | CTCCCTTGAC | CTCACCCCTC | 420 |
| AGACCATGCC | AATTCTGCCT | CCTAAACCTC | CCAGGCCAGC | CCCTCCCCCA | GCTCCAGTG | 480 |
| ACAGTGTCCT | CAGGTACCTG | AGCTCAGCTC | TCGGTGCTAC | CAGAGGGACT | GCCAGGGCT | 540 |
| GCAGCCGGGC | CTCCTGCAGA | GGCTGAGTCC | CACACGCAGG | GAACAGCCAT | GCCACTGCTA | 600 |
| GCAGACCAGT | AAGAGAATGG | CCACCTGGGG | CCTGAGCGCC | CTCGGCCATC | CACCAGAAAC | 660 |
| AAAGTGTCAA | GGAGAAGCTG | CCCGAAGCCC | ATGGGACAAA | CCACTGGGGA | CTGGAACACC | 720 |
| AGTAATTCTG | TATTGGGAAG | CGGCACCAAG | AGATGTGCTT | CTCAGAGCCT | GAGGCTGAAC | 780 |
| GTGGATGTTT | AGCAGCGTGA | CCGGCTACCA | GACAAACTCT | CATCTGTTCC | AGTGGCCTCC | 840 |
| TGGCCACCCA | CCAGGACCAA | GCAGGGCGGG | CAGCAGAGGG | CCAGGGTAGT | | 890 |

( 2 ) INFORMATION FOR SEQ ID NO:79:

( i ) SEQUENCE CHARACTERISTICS:
        ( A ) LENGTH: 1370 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G181.seq ( x i ) SEQUENCE DESCRIPTION: SEQ ID NO:79:

| | | | | | | |
|---|---|---|---|---|---|---|
| GCAGAGGAGC | CATGTCCTGC | TGCTTCTGCA | AAAAACTCAG | AGTGGGGTGG | GGAGCATGCT | 60 |
| CATTTGTATC | TCGAGTTTTA | AACTGGTTCC | TAGGGATGTG | TGAGAATAAA | CTAGACTCTG | 120 |
| AACAACTGCT | TTGTTACCAG | TGTCTCAATT | TGACTTGGGA | CTTAGTGACC | ATTTTAAGGG | 180 |
| AGACTGGTGC | GCCACAAATC | CTGGGTGGCT | TGATCCTGCC | ACGTGGATGC | TGTCTGGGTG | 240 |

| | | | | | | |
|---|---|---|---|---|---|---|
| AGCTTGTTCT | CACACTGCCC | TCCTGCCACC | CCCATTTCCA | GAAAGGTGAT | GATAACCCTA | 300 |
| GCAATCTTGG | AAAATCCACA | GGAACTGCTA | CCAGGTACCA | GGAGCCGTTC | TGAGCATTTT | 360 |
| ACCTATGCTA | TCTAACTTAT | TCCTCACCCC | AACCAAGAGT | ATGTTTCTC | CGTTTCATGG | 420 |
| GAAACTGAAG | TTCGGCCTGG | TTGAGCAACT | GTCTAAGCTG | ATAGTGGCCC | AGCTGGGGCT | 480 |
| TGAATTCAGG | TCCCTGTGGT | CTGGAGCATG | CTAATCCTGT | GGCATGTCTC | CCCCTAGTGG | 540 |
| TCCTTCCAGA | AACTGCAGCC | GCCGCCCCTG | CTCCTCCCAG | GGCCAACATC | AGGGATCAAC | 600 |
| ATCCCCTGAC | CCCCTCAAGG | CAGCAGGTTC | TGCTGACACA | AGCCACCCAA | TTCTTCATTC | 660 |
| CATTCCTTTA | AAACCCTCCA | AGCCTGGAGT | CTCCACCCCT | GCCTAAGCCC | CCAGCCTCTC | 720 |
| CTGCCTGATG | ATTTAGCAGC | CACCCTGTAG | GCCTCCCGGC | CAGCCCTGGA | ACCCACACCC | 780 |
| TGACGATCTG | TGCTCTACTG | GGGAGCCAGA | TGGAGTTTTA | GAAAATGCAA | ATCTGACCAT | 840 |
| GTGGATCTAT | ACTGAATCCC | CCAGTCCTCG | GGGTCTTCTG | GACCTTGTCC | ATATCCTTAG | 900 |
| GACAACGTAT | AAGGCTCACC | TCCATCTGTT | GCTTCTGTTT | CCCCCATGGC | TACCACCCTA | 960 |
| ATCAATGCTC | CAGCCAACAG | GAGTGCTGGG | ACTTCCTAGA | CAGCCTTCCA | TGAAGCCTCT | 1020 |
| CTTCATGCCC | TGGAGCTTCT | ATCCACATTG | TCACCTCAGT | CTGGCATGCC | CTTACTTGGC | 1080 |
| TTGATGAGTT | CCTATTCCAT | GGACCAACTC | AAACTCTGCC | CACCTCTGGA | CTGTCCACAC | 1140 |
| CATCCCAGGA | TGGGGCCCTC | CTCCGAAATA | GGTGGGTACA | CAGGGACCCA | CTGGAGGGAC | 1200 |
| AGCCACTGTG | GCACGGAGGT | GGTGCAGACC | AGCCTGGAGG | CAGAAGGCAG | GAGGCTGGGA | 1260 |
| CATCCCGAGT | GTGGCTTCAG | TCTACCACCT | GGCCCTTTAG | CCCTGAGTGC | CCCCCTCTAA | 1320 |
| CTCCCCTGCA | CACCACCCTG | TGGCCCTACT | CAGTCTGCCA | GTGGAAGGAG | | 1370 |

( 2 ) INFORMATION FOR SEQ ID NO:80:

( i ) SEQUENCE CHARACTERISTICS:
        ( A ) LENGTH: 695 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G257.seq ( x i ) SEQUENCE DESCRIPTION: SEQ ID NO:80:

| | | | | | | |
|---|---|---|---|---|---|---|
| GGACATGCAG | CGAGCTGTGC | CTGCCCAAAC | AGGGCCTCAG | GGAAAGTCTG | AGGGACCCGT | 60 |
| GAGGGATCCA | GAAGAGTCTT | GGAGGAGGCT | CATTCCAGAA | CCACTCGTCC | TGCTGAGAGC | 120 |
| AGAAAGCCCA | CATCTGCCAC | CTCAATTCTG | ACCCATCAGT | TCCAGGGGA | TGCAGGTGCG | 180 |
| CGAGCCGGGC | AAGGGCCTGG | GACTTCCACC | TGGCATCTTG | ACCCAGACTC | TAGCTCCAGA | 240 |
| CATAGAGGGC | AGGAACGGAT | GCCTGCAGGA | CTTCAGAAAT | TAAACAGGCT | TCTGGTCTCA | 300 |
| TGATTTCTCC | TGCTTTTGAT | TTTTAATGCA | CCTCCCGATG | GCTCTTCCCA | AGAGGGCACA | 360 |
| CATAGGCTGT | GGCCCCTCTG | GGTGCCTGAT | GATCCTCCCA | GCCAGAGATG | AGGCTCAGAG | 420 |
| CAGAGACTCA | GGAGCAGGGG | ATGCATTTCT | GGCCCTAGAG | GGAGTACACC | AGGCGAGTAG | 480 |
| TAGACACAGG | TCAGGGAGGG | CACTGTGGTG | GGAAGGCCTG | GCACACCCAT | TGGGCGTTTG | 540 |
| TGTCCACAAG | GACCCTCTGC | CTGAGTGATG | TGCATGGTGG | AGTTGCCAGA | TCCTGAGGGA | 600 |
| AAAAGGAAG | CCCCAAGAAC | AAAGAAGCAA | ACAAGGAGGT | CTCATTGTCC | TTGGCCATCC | 660 |

TCAAAAGTTG ACACCCCGCC ACTACTTTCT GCCTG 695

(2) INFORMATION FOR SEQ ID NO:81:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (v) ORIGINAL SOURCE:
        (C) INDIVIDUAL ISOLATE: E2.seq (xi) SEQUENCE DESCRIPTION: SEQ ID NO:81:

| | | | | | | |
|---|---|---|---|---|---|---|
| CAAACCCACT | CCACCTTACT | ACCAGACAAC | CTTAGCCAAA | CCATTTACCC | AAATAAAGTA | 60 |
| TAGGCGATAG | AAATTGAAAC | CTGGCGCAAT | AGATATAGTA | CCGCAAGGGA | AAGATGAAAA | 120 |
| ATTATAACCA | CGCATAATAT | AGCAAGGACT | AACCCCTATA | CCTTCTGCAT | AATGAATTAA | 180 |
| CTAGAAATAA | CTTTGCAAGG | AGAACCAAAG | CTAAGACCCC | CGAAACCAGA | CGAGCTACCT | 240 |
| AAGGAACAGC | TAAAAGAGCA | CACCCGTCTA | TGTAGCAAAA | TAGTGGGAAG | ATTTATAGGT | 300 |
| AGAGGCGACA | AACCTACCGA | GCCTGGTGAT | AGCTGGTTGG | CCAAGATTAG | GAATCTTAGT | 360 |
| TCAACTTTAA | AATTTGCCCA | CAGGAACCCT | CTAAATCCCC | TTGGTAAATT | TAACTGTTAG | 420 |
| TCCAAAGAGG | AACAGCTCTT | TGGACACTAG | GGAAAAACCT | TGTAGAGAGA | GTAAAAAATT | 480 |
| TAACACCCAT | AGTAGGCCTA | AAAGCAGCCA | CCAATTAAGA | AAGCGTTCAA | GCTCNACACC | 540 |
| CGCTACCTAA | AAAATCCCCA | CATATNTGTG | GACTCCTCAC | ACCCTANTGG | GCCAATCTAT | 600 |
| CACCCTATAG | AAGAACTAAT | GTTAGTATAG | GTAACATGAA | AACATTCTCC | TCCGCATAAG | 660 |
| CCTGCGTCAG | ATTAAAACAC | TGAACTGACA | ATTAACAGCC | | | 700 |

(2) INFORMATION FOR SEQ ID NO:82:

(i) SEQUENCE CHARACTERISTICS:
        (A) LENGTH: 254 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (v) ORIGINAL SOURCE:
        (C) INDIVIDUAL ISOLATE: E9f.seq (xi) SEQUENCE DESCRIPTION: SEQ ID NO:82:

| | | | | | | |
|---|---|---|---|---|---|---|
| CCCTGAGTTA | AGGATCAGTT | GGNTGTGGTG | TTAGCTAAGA | AGGCTGCCAC | CCATCATTCA | 60 |
| CATAATGAAG | TGACTCAGNG | GACTGTGCTG | ATGGTTCTGT | CCCAGGCACA | GAAGACTAGG | 120 |
| AGGCTATGGA | GGGAGGACAG | ACTGAATTAT | GTTTCANGTG | CAATGGGGGA | GGAGAGGCAG | 180 |
| GCAGCAAGTT | CCTGGGCCCA | AAGTGGCACG | GGTGCAGAGT | GGGAAGGTGG | CAAACCCCTC | 240 |
| TGTGCTGGTG | ATAG | | | | | 254 |

(2) INFORMATION FOR SEQ ID NO:83:

(i) SEQUENCE CHARACTERISTICS:
  (A) LENGTH: 391 base pairs
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO (vi) ORIGINAL SOURCE:
  (C) INDIVIDUAL ISOLATE: E9r.seq (xi) SEQUENCE DESCRIPTION: SEQ ID NO:83:

| | | | | | | |
|---|---|---|---|---|---|---|
| TGCANCTGTG | CCTCCTGTCG | GTGTATTTGC | ATNTGGTGCT | GCCTATGTAG | GGTTGCTATT | 60 |
| CCCTCCTCCT | CACTCTGTCC | GGAGAACCCC | CATCCATCCT | TCGAAGTCCA | GCTTGGTAGN | 120 |
| TGATCGATAA | CACACATGCC | CAGAGAGGAG | CTTCTTCTGT | CCCTGGAATA | CAGNCTCTCC | 180 |
| TNGTACCATA | TCTGTCGCCC | AAGTGCAAGT | GGNTCTGATT | GGATGTGTCC | CAGCTTCTCT | 240 |
| TGCAGGTCTT | AGGTGGGCTT | GGTCCTTGAA | AGCACTGGCC | AATCAGAACT | TGCCACTCGA | 300 |
| AAACAGTCGA | GAGCTGCCTG | TGGGGTTGGA | GTTCGGATGC | TNGATTTCTG | GTTCTCACAG | 360 |
| ATGTNAANAA | TCCTTAGACC | TGCTGTTCCA | A | | | 391 |

(2) INFORMATION FOR SEQ ID NO:84:

(i) SEQUENCE CHARACTERISTICS:
  (A) LENGTH: 302 base pairs
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO (vi) ORIGINAL SOURCE:
  (C) INDIVIDUAL ISOLATE: G123con.seq (xi) SEQUENCE DESCRIPTION: SEQ ID NO:84:

| | | | | | | |
|---|---|---|---|---|---|---|
| CAAGCATGAT | ACCAGGGCCA | TGGCAGGTGA | GCTATCCCCA | GGTTCAGTGG | AGAGAAGCTA | 60 |
| CTCCTGGCCT | TTCTCCCACC | AGTCAGAGAA | GCAGCTGCAT | TATATGGCTA | AAGGGCTGAC | 120 |
| CTCAGCTTTG | TTCCAGCCCT | TGGGGCAGCT | TGACCTTAGG | CCATCACTTG | GCCCACACTC | 180 |
| TATACTCTTG | GGGAGCCTTG | AACTGCCAGG | CCACTGGCTG | GCATGGTTCT | GAACCTGAAC | 240 |
| CTCTGAGATG | TCTGGGTGCT | CTCAGGGTAA | GAGGCAAAGA | GAGGCAGCCT | ACCACCTCCC | 300 |
| AC | | | | | | 302 |

(2) INFORMATION FOR SEQ ID NO:85:

(i) SEQUENCE CHARACTERISTICS:
  (A) LENGTH: 2995 base pairs
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO (vi) ORIGINAL SOURCE:
  (C) INDIVIDUAL ISOLATE: A116con.seq ( x i ) SEQUENCE DESCRIPTION: SEQ ID NO:85:

```
CCGCAAATGT  CTGTAAACTT  GGCCCAACAT  GAGAAATCTA  GCTGGTGTGG  CTGAGCACCA    60
CTTTTGTCAG  TTTACCCCAG  TGGAAAGTGG  TCCTTGATGA  CAGTTATCTC  ATCACAACCC   120
CAGCAAAACA  GATCTTTCAA  CAACCTCCTA  GCTCCCTCAA  CCTAGAACTT  CCACCATTAG   180
TGCTTATACT  GAAACTCTTG  AGAATGACCC  ACAGAAGCAC  TGTCAGGTCC  TTAGAATGAT   240
CTAATTATTA  AGCACAAACT  TGGTTCAGAT  CTTACTAATA  CTGCTCCGTT  TCAGGCACTG   300
TTTGGCTAAT  GACTCGGTAG  TGTCAGCTGC  CATCACCTTT  AGGTGAGCTG  TCAGACCTTA   360
TTTAGTTTCT  TTTCCTAGGA  AAAGGCTGAA  GTCTTGGTAG  GATGTGATGG  GACAGCTCTC   420
CATCCTGAAA  GGTCTGGCTC  TATCCCACAC  TACTCCAGGC  TTGGTCCCTA  GGACCCAGCT   480
CCATTGTGAT  GGGGGCCAGG  GGAGAGTTTT  GAGGTCCCTC  CCTGGAGATT  CCAAGCAATT   540
GCTACCAATC  ATTTAGGACT  CCTGGGATCA  GAGGGGATGG  GGAAATTGAG  GACTCCATCT   600
TGGTTGTGGA  GATTGGAAGC  TGATGGACAT  AATTCCTCTC  TCTTTTGGT   AATTTACAAG   660
CAATTAACTT  TGCTTTTAGA  ACTTGAGAGA  TTTCCACAGC  TGCCTAAGAC  TTCACATACT   720
CACTGCCTAC  CCTCCATCAG  GGATTAGATT  GAAGGGCAGG  AGAAAAAGAA  GTCAGAGCTG   780
CTGCTTGTTC  TGGGTGGTAT  CACTTTCCTC  CCGTCAGTCC  ACTCTACCTT  GCTCTGCACC   840
ACCTGCCATC  ACCCACTAGG  AGAACCCAGA  TGGAAGCCAC  AGGTGGCTAG  CCACCTCAAT   900
CCAAATCTTA  AAAGGGCTG   GTCCCTGAAG  GAGCTGGAAA  AGTCCATCCT  GTCTATTCCT   960
CTGTTCCCAG  GTGAAGCTAT  TCTTGAGAAA  TCCAAGTGGA  GCTTCCAAGT  AGAACTTCTT  1020
TTTTTTTTTT  TTTTGAGAC   AGAGTCTCGC  TCTGTTGCCC  AGGCTAGAGT  GCAGTGGCGT  1080
GATCTCAGCT  CACTGCAACC  TCCACCTCCT  GGGTTCAAGT  GATTGGCCTG  CCTCAGCCTC  1140
CCTAGTAGCT  GGAATTACAG  GCATGCACCA  CCACGCCTGG  TTAGTTTTTT  TTTAGTAGAG  1200
ACAGGGTTTC  ACCATGTTGC  CCAGCCTGGT  TTTGAACTCC  TGAACTCAGG  CAATCCACCT  1260
GCCTCGGCCT  CCCAAAGTGC  CAAGATTACA  AGTGTGAGCC  ACCGCGCTCG  GCCCAAGGGG  1320
AGCTTCTGAC  AAGCAGGGCC  TGGGATAGGG  GCCTGTCCAG  GCATCCACAT  ATAGAATATT  1380
TACCCAGCAG  GAGTCCCCCT  GCCACTCACA  CAGCATCTCC  AAGATCAGGG  ACCAGTACTT  1440
CCTGAGCTTG  ACAGAGAATG  AATGTGTCAG  ACTGACCTCT  GCCCATTTTG  TAGTTTTCTC  1500
ATCATTTTCT  CACTCAGTCT  TCCCTTTTCA  AGGGCCCACA  CTCTTCCCGA  GGGCTGGGCC  1560
TAGTGAGCGG  GGTCACAGTA  CATATGGTTT  CTGGGACTGA  GAAGGTGGAA  GATGTGTCCA  1620
TAGAGCTTTT  GTTTCCTAAG  CAACGTATTA  CTGCCATGAT  TCCATTCCCT  AGATGATGCT  1680
GGTGATGCAA  GCTGGCTTCT  CTTGGCCAGC  CTACCCTACT  GCTGGGTAGT  GTTTATGCCC  1740
CATGGCCAGA  CACTGAAGAG  GGAGACAGGA  AAAGCACATA  TCCACACCTT  CCACCCTCAG  1800
ACATTCCTGT  AACTTGAGCT  TATCTAAGGG  GGCATTGTCA  TATGTCAGGG  GTTCCCAAAC  1860
TACGGTCTTC  AGAAACACTG  TTTACCCTCC  ATAGAGGTTG  TGTGCATCAG  CCCAGGCAGA  1920
ATCCTGCTTC  ATGAAGGTGT  TTTCCTAATG  CATGTGTGCA  TGGACCTGTC  TCATGCTACA  1980
CTGCAGGGCT  GGTATTCAGC  ACCAATAGTT  ATTGTTGGCT  GCTAAAATAG  CAAACTAGCC  2040
AAAATGGCAG  GTAAATAACC  CCAAGCCCCT  ATCGCCAGTG  TCCTCCCACT  ACTCCAAACC  2100
CCTCTCCCTC  AGACCTGCCC  CCAGTCCAGT  ATCTACCTGC  ACTGTTCAAT  ATGGTAACCA  2160
CTGACCACAT  GTGACTATTT  ACATACAGTT  TATTAAATGC  AATTAAAGT   TCAATTCCTT  2220
ATTGCACTGG  CCACATCTCA  AGTGCTTAGC  TGGCACATGT  GGCTAGTGCC  AGTGCCTACT  2280
GTATTGAGCG  GTACAGACAG  ACATTTCATC  ACTCTAGAAA  CTGGATGGCA  AGTGCTACTC  2340
```

| | | | | | |
|---|---|---|---|---|---|
|AGCACAGCAG|CCGTGAGGAC|CTTTCTTGGG|CTGCTGACTG|TTCTGTCTGT|GACTGTGTCA|2400|
|TGTCAACTGA|CTTTTTGGAG|CAGCATCTGT|GTGTTAGCAG|GACACATCAC|CTATGGCACA|2460|
|TGCCTCAAAA|CTTAACACTC|CTTGGGCCCC|AGGAGCCCAG|AATCAACTGA|CAGCCCTGGT|2520|
|GATTGTCAAG|GACAGGTGAC|TATGTTTATA|TAAGCATGTT|CCTATGACAG|GAATGTCCCC|2580|
|TCCTTCTGCC|ATTGTCTATG|TGAGCATAAA|CAAAAGGATT|TTTTTTTTT|GAGACAAAGT|2640|
|CTCGCTCTTG|TCACCCAGGC|TGGCGTGCAG|TGGCACAGTC|TCAGCTCACT|GCAACCTTCA|2700|
|TCTCCCGGGT|TCAAGTGATT|CTTGTGCTTC|AGCCTCCACA|GTAGCCGGGA|TTACAGGCGC|2760|
|CCGCCACCAG|GCCCGGCTAA|TTTTTTTTT|TGAGACGGAG|TCTCGCACTG|TCGCCCAGGC|2820|
|TGGAGTGCAG|CGGTGCAATC|TCGGCTCGCT|GCAGCTCTGC|CTCCGGNGTT|CATGCCATCT|2880|
|CCTGCCTCAG|CCTCCCGAGT|AGCTTGGGAC|TACAGGCACC|CGCCACTAGG|CCCGGATTAT|2940|
|TTTTTATTT|AGGAGGAACG|GGTTCACGGT|AGCCAGGATG|CTTGATCTCG|ACCGG|2995|

( 2 ) INFORMATION FOR SEQ ID NO:86:

( i ) SEQUENCE CHARACTERISTICS:
        ( A ) LENGTH: 1870 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: A25con.seq ( x i ) SEQUENCE DESCRIPTION: SEQ ID NO:86:

| | | | | | |
|---|---|---|---|---|---|
|GTCATCCTTC|AACAAACACT|TAAAAATGT|TTGAAACCC|CATCAATTCA|GTCAGACTCT|60|
|TTGGGTGGGA|GCAAGATCCA|GGCATCAGTA|TTTTTAATA|TCCCAGATGA|TGGTAATATG|120|
|CAGCCAGGAT|TTAAAGTCAC|TGGTTTAATA|TCTTGGGAAA|AGCAGATCCA|CTCAAGACCT|180|
|CACAGGGTCC|TGACAAAGGC|CACTTTCAGC|TCAGTGGAGT|GGGACACTGG|GGTGGGAAGA|240|
|TGTCCATTTT|TTGGATGTGG|GTCAGTCTCT|TGCACAGGCA|GAGGTATTGC|AGCATGCTGT|300|
|TGTAATGTGT|ATCTTCCTTG|GCAGTGTCTG|TTGAAAGCTG|GTTGCATCAG|TTTGTAATGG|360|
|GGTGTTATGG|CAACAAGGTG|GGCCCAGCCC|CCCCCAGGAA|GTGGATCACT|GAGCACAGCT|420|
|TCTACAGGGC|CATTTGTAGA|GAGGTGGCAG|ATGGGCTTCC|CAGGGGCTGC|CACCCAGGGC|480|
|AGAGCCAGTG|CTGAGGCTCT|GACAACCTCG|GCAGGGTGGG|GGAGAAGGCC|AGACTCAGGG|540|
|TGTTTATGTT|TGTGGGTAAT|GACAGTCAGC|TCTGGGCTCC|AGATGATGCC|TACTCCCTGG|600|
|CCTCTGTGTT|CAGATTAGGA|ACTTGCAACA|TCTTGCTGAG|GACCATGTCA|GGCTCAGCTC|660|
|TAAGTGCTGT|GGCTGAGAAT|TTTCCTTCCT|CTCTGTGTGG|TTAGTGGCAG|CCTCCCTAGC|720|
|AATGGCTGAC|CTCTAGCATA|CTCTGTCAAA|CTACAGGCAG|CTGGACAAG|ACAGGACATG|780|
|GGGCTCACAG|ACAGGTATTC|CACAACCTGG|GCCCTGTCAA|CCCTCCCAGA|AATGCATGGG|840|
|CCATGAACCT|CCTGCTGTGG|GAGGGGCAGT|GCAGAGAAGT|CTCAATAAGC|TTCTCTTGGC|900|
|CCTCTGGGAT|CTCCACCATC|CACAGTGTGT|AGGGCTGAGC|TGCAGGCTGG|GTCTTCAGGT|960|
|GGTGTCCCTG|CACATCTGCT|TTGCAGCGTG|GCGTCTATAG|AGCAAGAGTG|AACGGGAAGG|1020|
|GGCCTCGGGC|CTCCTGTAGC|TCTGCTGGGC|AGGGACGCTG|CGGGGCCTCA|GCTGGGCTTC|1080|
|CTTGGCTAAA|GGGCACAGAG|TGGCGTAGGC|TGCAAGAGGA|CAAGCTAAGC|TGATGAAGGC|1140|

| TCTATCACTC | AAGGGTAGCC | ATGTAAAAAA | AAATCCCTAC | AGGTAAAAGA | AGCATGAATG | 1200 |
| AGACAGGCGG | GGCATAACAA | TGTCTCCCCA | CTGAAGCTGC | AACTCTCTGC | TTCACTGGCT | 1260 |
| TCAGCCTCCT | CTCTGTGAAA | TGGGGGCAAT | GTCCCCTAGG | CCTCTTCCTC | CCTGTCCAGT | 1320 |
| TAGAGCTGAG | GGTCTACAGG | CCAGAGGGAG | GCCTGGCTCT | CAGGGCCTTG | TTCTCTGTNT | 1380 |
| TNGCCTCTNC | GCTGGCNACC | CCAGCCCCAN | TTTCCACGTC | AACCTCCCTT | GTTTTTTAT | 1440 |
| TATACCNCAA | CAGCAGCTCT | TGGCAGCCCA | GTTGGACTAC | CCCCTTCCTG | TTGNCTTCCT | 1500 |
| TAGCAAAGCA | TTTTATGGAA | TGCTTCCTTT | TCATGCTTCA | GGAAACCGGT | GGCCGGGAGG | 1560 |
| AGTTCTTGAT | TTCATTTTCT | TCCCTAGAGA | TATGTGTGCT | TCGGAATACA | CAAATTAAAC | 1620 |
| AAAAGCGAGG | GCTGACTGGG | ACCAGGAGAG | TGAGTGATCC | TGGCTTCCCT | TGATTACAT | 1680 |
| GCTTATTTTC | CTTCTCAAAT | CACTCCAGTA | AGTACAGAAG | TCACTAATCT | ATTGCCTTCT | 1740 |
| ATTATCTGCA | TTATAGTTAA | AAACATCGAC | ATGAACAAAC | AAAAGCCCTT | GCGTAGCCTA | 1800 |
| GAGAAGTCAC | AAAGCTCACA | CCCAGACTCT | CGCCTAAGAG | AGTCTCTCAG | GGCTCACTCA | 1860 |
| GGGACTATTT | | | | | | 1870 |

( 2 ) INFORMATION FOR SEQ ID NO:87:

( i ) SEQUENCE CHARACTERISTICS:
        ( A ) LENGTH: 806 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: A46.seq ( x i ) SEQUENCE DESCRIPTION: SEQ ID NO:87:

| CTACTACTAC | TAACTCGAGA | ATTCTGGATC | CTCCAAACAC | ACTCCACCTT | ACTACCAGAC | 60 |
| AACCTTAGCC | AAACCATTTA | CCCAAATAAA | GTATAGGCGA | TAGAAATTGA | AACCTGGCGC | 120 |
| AATAGATATA | GTACCGCAAG | GGAAAGATGA | AAAATTATAA | CCAAGCATAA | TATAGCGAGG | 180 |
| ACTAACCCCT | ATACCTTCTG | CATAATGAAT | TAACTAGAAA | TAACTTTGCA | AGGAGAGCCA | 240 |
| AAGCTAAGAC | CCCCGAAACC | AGACGAGCTA | CCTAAGAACA | GCTAAAGAG | CACACCCGTC | 300 |
| TATGTAGCAA | AATAGTGGGA | AGATTTATTG | GTAGAGGCGA | CAAACCTACC | GAGCCTGGTG | 360 |
| ATAGCTGGTT | GTCCAAGATA | GAATCTTAGG | TCACTTTAAT | TTGCCACAGA | ACCCTCTAAA | 420 |
| TCCCCTTGTA | AATTTTCTGT | TAGCCCAAAG | AGGAACAGCT | CTTTGGACAC | TAGGNNNNNA | 480 |
| CCTTGTAGAG | AGAGTGAGAG | AATTTAACAC | CCATAGTAGC | CCTAAAAGCA | GCCACCAATT | 540 |
| AAGAAAGCGT | TCAAGCTCAA | CACCCACTAC | CTAAAAAATC | CCAAACATAT | AGCTGAACTC | 600 |
| CTCACACCCA | ATTGGGCCAA | TCTATCACCC | TATAGAAGAG | CTAATGTTAG | TATAAGTAAC | 660 |
| ATGAAAACAT | TCTCCTCCGC | ATAAGCCTGC | GTCAGATTAA | AACACTGAAC | TGACNATTAA | 720 |
| CAGCCCAATA | TCTACAATCA | ACCAACAAGT | CATTATTACC | CTCACTCTCA | ACGAGGATCC | 780 |
| AGAATTCTCG | AGTTAGTAGT | AGTAGT | | | | 806 |

( 2 ) INFORMATION FOR SEQ ID NO:88:

( i ) SEQUENCE CHARACTERISTICS:
        ( A ) LENGTH: 639 base pairs (B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: A66.seq (xi) SEQUENCE DESCRIPTION: SEQ ID NO:88:

| | | | | | | |
|---|---|---|---|---|---|---|
| CTGAAGACTG | TTCCCAGTGG | TCTTAGATAC | AGAGTGGTGG | CCCTTGGTCC | TGTCAGAGTA | 60 |
| GGTTTAAAGA | CCACACAGGT | AGATTTCTCC | CAGAAACAAC | ACCACTTAGA | ATTTTCCTTC | 120 |
| AGGGAGCATA | GCACAGGGGA | GATGTCCACA | CACAGTCATA | CCTGTGTTTG | GAATCCCAGC | 180 |
| TCTGCCTTTT | TGCTTGTGGG | TGGTCGAGTT | GGGAGTGTGC | TTGAGAAATT | ATTCAGCCTC | 240 |
| TTCAACTCTC | AGTTTCTACC | TCTCCTTTCC | AGGCTGAGCT | GAACATCACA | GAGGGGAATA | 300 |
| TCTGTGATTT | TCTTGAGAAA | CTTCACAGCG | AAAGCTGCTG | GCTCTGCCCT | TGGTAGCCAT | 360 |
| TTTTATGGTC | TGGAGGGACA | GTGGCTTCTT | CCTAGAGCCA | CTTTGCAGTG | TTCCCTTGAG | 420 |
| GCCAGCTGTC | CATCCTCGAG | AGCAGTTAGG | AGGTCCATGT | TGAGAGTGTG | CTCAGTCCTT | 480 |
| AGTTGGAAAC | CTGGAAACGC | AGGCCATGAG | GGTGGTGTCC | CACTGGCATA | TGGCAGGTGG | 540 |
| GGCCTTCTGC | CACCCTGGCT | GTGTGTGTGG | CGTCCAGTGC | GAGTGGTAGC | CAGACATCAT | 600 |
| GCCCACCTGC | CCTCGAGCTG | CTTGCCTGCA | GCTGGCTCC | | | 639 |

(2) INFORMATION FOR SEQ ID NO:89:

(i) SEQUENCE CHARACTERISTICS:
(A) LENGTH: 509 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: A42.seq (xi) SEQUENCE DESCRIPTION: SEQ ID NO:89:

| | | | | | | |
|---|---|---|---|---|---|---|
| CTACTACTAC | TAACTCGAGA | ATTCNGGATC | CTCCCCGAAA | CCAGACGAGC | TACCTAAGAA | 60 |
| CAGCTAAAAG | AGCACACCCG | TCTATGTAGC | AAAGTAGTGG | GAAGATTTAT | AGGTAGAGGC | 120 |
| GACAAACCTA | CCGAGCCTGG | TGATAGCTGG | CTGCCCAAGA | TAGAATCTTA | GNNCAACTTT | 180 |
| AAATTTGCCC | ACAGAACCCT | CTAAATCCCC | TTGTAAATTT | ANCTGTTAGT | CCAAAGAGGA | 240 |
| ACAGCTCTTT | GGACACTAGG | AAAAAACCTT | GTAGAGAGAG | TAAAANATTT | AACACCCATA | 300 |
| GTAGGCCTAA | AAGCAGCCAC | CAATTAAGAA | AGCGTTCAAG | CTCAACACCC | ACTACCTAAA | 360 |
| AAATCCCAAA | CATATAACTG | AACTCCTCAC | ACCCAATTGG | ACCAATCTAT | CACCCTATAG | 420 |
| GAGAACTAAT | GTTAGTATAA | GTAACATGAA | AACATTCTCC | TCCGCATAAC | CCTGCGAGGA | 480 |
| TCCAGAATTC | TCGAGTTAGT | AGTAGTAGT | | | | 509 |

(2) INFORMATION FOR SEQ ID NO:90:

(i) SEQUENCE CHARACTERISTICS:
(A) LENGTH: 1834 base pairs (B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (C) INDIVIDUAL ISOLATE: A76con.seq (xi) SEQUENCE DESCRIPTION: SEQ ID NO:90:

| | | | | | | |
|---|---|---|---|---|---|---|
| GGCAGCCAGC | GCAGGGGCTT | CTGCTGAGGG | GGCAGGCGGA | GCTTGAGGAA | ACCNCAGATA | 60 |
| AGTTTTTTTC | TCTTTGAAAG | ATAGAGATTA | ATACAACTAC | TTAAAAATA | TAGTCAATAG | 120 |
| GTTACTAAGA | TATTGCTTAG | CGTTAAGTTT | TTAACGTAAT | TTTAATAGCT | TAAGATTTTA | 180 |
| AGAGAAAATA | TGAAGACTTA | GAAGAGTAGC | ATGAGGAAGG | AAAAGATAAA | AGGGTTTCTA | 240 |
| AAACATGACG | GAGGTTTAGA | TGAAGCTTCT | TCATGGAGTA | AAAATGTATT | TAAAAGAAAA | 300 |
| TTGAGAGAAA | GGACTACAGA | GCCCCGAATT | AATACCCAAT | AGAAGGGCAA | TGCTTTTAGA | 360 |
| TTAAAATGAG | GGGTGACTTA | AACAGCTTAA | AGTTTAGTTT | AAAAGTTGTA | GGGTGATTCA | 420 |
| CATAATTTGN | AGGCGATCCT | TTTCAAAGA | GATTAAACCG | AAGGTGATTA | AAAGACCTTG | 480 |
| TAATCCATGA | CCCAGGGAGA | ATTCCGTCAT | TTAAACCCTA | GTTAACGCAT | TNTCTAAACC | 540 |
| CAGGCGAANC | TGGAAAGATT | AATTGGGAGC | TGGTAGGATG | AAACAATTTG | GAGAAGATAG | 600 |
| AAGTTTGAAG | TGGCAAACTG | GAAGACAGAA | GTACGGGAAG | GCGAAGAAAA | GAATAGAGAA | 660 |
| GATAGGGAAA | TTAGAAGATA | AAAACATACT | TTTAGAAGAA | AAAAGATAAA | TTTAAACCTG | 720 |
| AAAAGTAGGA | AGCAGAAGAA | AAAAGACAAG | CTAGGAAACA | AAAAGCTAAG | GGCAAAATGT | 780 |
| ACAAACTTAG | AAGAAAATTG | GAAGATAGAA | ACAAGATAGA | AAATGAAAAT | ATTGTCAAGA | 840 |
| GTTTCAGATA | GAAAATGAAA | AACAAGCTAA | GACAAGTATT | GGAGAAGTAT | AGAAGATAGA | 900 |
| AAAATATAAA | GCCAAAAATT | GGATAAAATA | GCACTGAAAA | AATGAGGAAA | TTATTGGTAA | 960 |
| CCAATTTATT | TTAAAAGCCC | ATCAATTTAA | TTTCTGGTGG | TGCAGAAGTT | AGAAGGTAAA | 1020 |
| GCTTGAGAAG | ATGAGGGTGT | TTACGTAGAC | CAGAACCAAT | TTAGAAGAAT | ACTTGAAGCT | 1080 |
| AGAAGGGGAA | GTTGGGTTAA | AAATCACATC | AAAAAGCTAC | TAAAAGGACT | GGTGTAATTT | 1140 |
| AAAAAAACTA | AGCAGAAGGC | TTTTGGAAGA | GTTAGAAGAA | TTTGGAGGCC | TTAAATATAG | 1200 |
| TAGCTTAGTT | TGAAAATGTG | AAGGACTTTC | GTACCGGAAG | TAATTCAAGA | TCAAGAGTAA | 1260 |
| TTACCAACTT | AATGTTTTTG | CATTGGACTT | TGAGTTAAGA | TTATTTTTA | AATCCTGAGG | 1320 |
| ACTAGCATTA | ATTGACAGCT | GACCCAGGTG | CTACACAGAA | GTGGATTCAG | TGAATCTAGG | 1380 |
| AAGACAGCAG | CAGACAGGAT | TCCAGGAACC | AGTGTTTGAT | GAAGCTAGGA | CTGAGGAGCA | 1440 |
| AGCGAGCAAG | CAGCAGTTCG | TGGTGAAGGT | AGGAAAAGAG | TCCAGGAGCC | AGTACGATTT | 1500 |
| GGTGAAGGAA | GCTAGGAAGA | AGGAAGGAGC | GCTAACGATT | TGGTGGTGAA | GCTAGGAAAA | 1560 |
| AGGATTCCAG | GAAGGAGCGA | GTGCAATTTG | GTGATGAAGG | TAGCAGGCGG | CTTGGCTTGG | 1620 |
| CAACCACACG | GAGGAGGCGA | GCAGCCGTTG | TGCGTAGAGG | ATCCAAGGCC | ACCATCCAT | 1680 |
| TGTCCCAAGG | CCACAGGGAA | AGCGAGTGGN | TGGTAAANAT | CCGTGAGGTC | GGCAATATGT | 1740 |
| TGTTTTTCTG | GAACTTACTT | ATGGTAACCT | TTTATTTATT | TTCTAATATA | ATGGGGAGT | 1800 |
| TTCGTACTGA | GGTGTAAAGG | GATTTATATG | GGGG | | | 1834 |

(2) INFORMATION FOR SEQ ID NO:91:

( i ) SEQUENCE CHARACTERISTICS:
  ( A ) LENGTH: 1666 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
  ( C ) INDIVIDUAL ISOLATE: E105con.seq ( x i ) SEQUENCE DESCRIPTION: SEQ ID NO:91:

| | | | | | | |
|---|---|---|---|---|---|---|
| CTACTACTAC | TAACTCGAGA | ATTCTGGATC | CTCTGTAGCT | TTTTTTTTTT | ACAGACTNCA | 60 |
| CAGAGGAATG | CAGTTGTCTT | GACTTCAGGT | CTGTCTGTTC | TGTTGGCAAN | TAAATGCAGA | 120 |
| ACTGTTCTNA | TCCCGCTGCT | ATTAGAATGC | ATTGTGAAAC | GACTGGAGTA | TGATTAAAAG | 180 |
| TTGTGTTCCC | CAATGCTTGG | AGTAGTGATT | GTTGAAGGAA | AAAATCCAGC | TGAGTGATAA | 240 |
| AGGCTGAGTG | TCGAGGAAAT | TTCTGCAGTT | TAAGCAGTC | GTATTTGTGA | TTGAAGCTGA | 300 |
| GTACATTTTG | CTGGTGTATT | TTAAGGTAAA | ACGCTTTTG | TTCATTTCTG | GTGGTGAGAG | 360 |
| GGGACTTGAA | GCCTAAGTC | TTTTCCAGAT | GCAACCTTAA | AATCAGTGAC | AAGAACAATT | 420 |
| CCAACCAAGC | AACAGTCTTC | AAGAAATTAA | ACTGGCAAGT | GGAATGTTTA | ACAGTTCAGT | 480 |
| GTCCTTTAGT | GCATTGTTTA | TGTGTGGGTT | TCCTCTCTCC | CCTCCCTTGG | TCTTAATTCC | 540 |
| TTACATGCAG | GAACACTCAG | CAGACACACG | TATGCGAAGG | GCCAGAGAAG | CCAGACCCAG | 600 |
| TAAGAAAAAA | TAGCCTATTT | ACTTTAAATA | AACCAAACAT | TCCATTTTAA | ATGTGGGGAT | 660 |
| TGGGAACCAC | TAGTTCTTTC | AGATGGTATT | CTTCAGACTA | TAGAAGGAGC | TTCCAGTTGA | 720 |
| ATTCACCAGT | GGCCAAAATG | AGGAAAACAG | GTGAACAAGC | TTTTCTGTA | TTTACATACA | 780 |
| AAGTCAGATC | AGTTATGGGG | AGGATCCAGA | ATTCTCGAGT | TAGTAGTAGT | AGTCTACTAC | 840 |
| TACTAACTCG | AGAATTCTGG | ATCCTCTGTA | GCTTTTTTTT | TTTACAGACT | NCACAGAGGA | 900 |
| ATGCAGTTGT | CTTGACTTCA | GGTCTGTCTG | TTCTGTTGGC | AANTAAATGC | AGAACTGTTC | 960 |
| TNATCCCGCT | GCTATTAGAA | TGCATTGTGA | AACGACTGGA | GTATGATTAA | AAGTTGTGTT | 1020 |
| CCCCAATGCT | TGGAGTAGTG | ATTGTTGAAG | GAAAAAATCC | AGCTGAGTGA | TAAAGGCTGA | 1080 |
| GTGTCGAGGA | AATTTCTGCA | GTTTAAGCA | GTCGTATTTG | TGATTGAAGC | TGAGTACATT | 1140 |
| TTGCTGGTGT | ATTTTAAGGT | AAAACGCTTT | TGTTCATTT | CTGGTGGTGA | GAGGGGACTT | 1200 |
| GAAGCCTTAA | GTCTTTTCCA | GATGCAACCT | TAAAATCAGT | GACAAGAACA | ATTCCAACCA | 1260 |
| AGCAACAGTC | TTCAAGAAAT | TAAACTGGCA | AGTGGAATGT | TTAACAGTTC | AGTGTCCTTT | 1320 |
| AGTGCATTGT | TTATGTGTGG | GTTTCCTCTC | TCCCCTCCCT | TGGTCTTAAT | TCCTTACATG | 1380 |
| CAGGAACACT | CAGCAGACAC | ACGTATGCGA | AGGGCCAGAG | AAGCCAGACC | CAGTAAGAAA | 1440 |
| AAATAGCCTA | TTTACTTTAA | ATAAACCAAA | CATTCCATTT | TAAATGTGGG | GATTGGGAAC | 1500 |
| CACTAGTTCT | TTCAGATGGT | ATTCTTCAGA | CTATAGAAGG | AGCTTCCAGT | TGAATTCACC | 1560 |
| AGTGGCCAAA | ATGAGGAAAA | CAGGTGAACA | AGCTTTTTCT | GTATTTACAT | ACAAAGTCAG | 1620 |
| ATCAGTTATG | GGGAGGATCC | AGAATTCTCG | AGTTAGTAGT | AGTAGT | | 1666 |

( 2 ) INFORMATION FOR SEQ ID NO:92:

( i ) SEQUENCE CHARACTERISTICS:
    ( A ) LENGTH: 1033 base pairs
    ( B ) TYPE: nucleic acid
    ( C ) STRANDEDNESS: double ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: G180con.seq ( x i ) SEQUENCE DESCRIPTION: SEQ ID NO:92:

| | | | | | | |
|---|---|---|---|---|---|---|
| GGATCCTCTA | GAGCGGCCGC | CTACTACTAC | TACTCGAGAA | TTCTGGATCC | TCGGCCTGTG | 60 |
| GAGGATAGGG | AAATGGAACA | GTCCTGGCAG | TTCAGGTGGC | TGGGGGCTGG | GACCTTTGGA | 120 |
| CAGGCTGTAT | ATTAAGCAGG | TTTCACGCGA | CGCCTCCTCT | TCTGAGCATT | CCCCATGGCC | 180 |
| TCGCTAGTGC | AGGATGGACA | GGAACTGTAC | TCAGGTCCAG | GTGACAGCTC | ATGCCTGGAT | 240 |
| TTTCCCAAGG | GGGCGGATCC | AACCAGTCCA | CCAGTCCGTT | CTGGCAGCTT | TAAGCTCCTC | 300 |
| TCAGACAGGA | TGACATCCAA | CTTGTTTCAA | GGGCTTTCCA | GTGGGCTGCA | CTTGTTCTGT | 360 |
| CCCACAGGAT | CTATAGGGAA | ACCCCAGCTC | TGGGCAAACA | GACCCCACC | CCCTGACTAA | 420 |
| GGCCTCCAGA | ATCTGGGCCA | GAGGCCAGGG | TGGGGCAAGA | CACTGAGCCA | GGACAGCGGT | 480 |
| TTTCTGGCTT | CCTTAGTTTG | TGTCCACAGA | CATCCTCACT | ATCCTAGGAG | ATGACCCCAG | 540 |
| CAGGAATGGG | GAGCTGAAGC | CTGAAGAGTC | ACTGAAATGA | TTTACATAAT | TTCCTTAATG | 600 |
| CTCACCACGA | TCATGTGAGA | GAGAGAACAT | GACCCGTTTC | ACAGACGCAT | CACTGAAGCT | 660 |
| GTGAGCAGAG | AAACGACTTG | TCTTGCCAGA | CAGTGGCAGA | TACAACACTT | AACCCAAAGT | 720 |
| CTCTGAGTCT | CCTCAGGTGC | CCTTTCATCA | CTCTTCCTGC | TACTTGGCAT | CAACCAGCCG | 780 |
| GGATGAGACA | CTGAAAGGGA | TGCCAGGTCT | TTGTTATGTT | GCATCCAAAT | GCTAGCTAGC | 840 |
| CCCTACCAGC | CCATCTACCA | CACCCGGGCT | GCCTCTCATA | TCTAGTATCT | CAGCCCTCCA | 900 |
| GACCCTCACT | CCTCCTTGAG | ACTCTAGCCC | CCAGTCCCCA | GTTCCTCCCA | GACTTCCCAG | 960 |
| ACTCTTCACA | ATCACCAGTG | TGGGAGGATC | CAGAATTCTC | GAGTAGTAGT | AGTAGTAGTC | 1020 |
| GACCCGGGAA | TTC | | | | | 1033 |

( 2 ) INFORMATION FOR SEQ ID NO:93:

( i ) SEQUENCE CHARACTERISTICS:
        ( A ) LENGTH: 1950 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G310con.seq ( x i ) SEQUENCE DESCRIPTION: SEQ ID NO:93:

| | | | | | | |
|---|---|---|---|---|---|---|
| CTCTGTCATC | CAGGCTGGAT | TGCAGTGGCA | CCATCACAGC | TCACTGCAGC | GTCAACCTCC | 60 |
| TGGGCTCGGG | TGATCCTCCC | ATCTCAGTCT | CCTGGGTAGC | TGGCACTATA | GGCATGTGCC | 120 |
| ACCACGCCAG | GCTAATTTTT | GTATTTTTG | TAGAGATGGG | ATTTCTCCAT | GTTTCCTAGG | 180 |
| CTGGTCTCAA | ACTTCTGGGC | TCAAGCAATC | TGCCTATGTT | GGCCTCCCAA | AGTGCTGGGA | 240 |
| TTACAGGTGT | GTGCCACTGC | ACCCGGCAAC | TTACATTTTT | AAAAGATCTC | TAGCTTTTGT | 300 |
| GTGGGCACAG | ATTAGGTTGT | AATGTTCGAC | CAGAGAAACA | AGTTAGGATG | CTATTGCTCC | 360 |

| | | | | | |
|---|---|---|---|---|---|
| ATGGTGAGTG | ACATGGTTAT | ACAGGGTGAA | TGGTGCAGGG | TGGGCTGGAG | GAGAAGACAG | 420 |
| AATCCTACAG | TGCAGGGCAT | TGTAGTGGGC | ATCTGATCTC | TCTCTTCTCC | CACCTCTATG | 480 |
| CAGCTGCTTC | TCTCTCCTCA | GAATCCAGAC | CCAAATTTTA | CCTTCTGCTG | GGAAAGCCTT | 540 |
| CCTTCCCTAT | TTTTTGTTTG | CAGGTGGCGG | GGGCTCCCTG | GACCTGGGAT | TCCCACGTTC | 600 |
| TTCCTCCTAA | CTTGCTGCCT | CGTGGCCCTA | GACCCCTCTT | GTGTAACACA | GACATCAGTC | 660 |
| AGGCTCTCTC | AGGCTCCTAA | GACCTGGACG | ACAGGCTCAA | GCTCCTATTT | GCTCACGTGC | 720 |
| AAGTGGAAAG | CTTTTGCCAG | GGTGTTTGCA | AGTTCCCTTG | TGCATGACTG | TGCATGACTA | 780 |
| GCACTGACTC | TCTCCTGATA | CAGCATGGTT | AGATCTGTGT | GTGGCTCATC | AGGACATTCA | 840 |
| ACAAGTAATG | CCCCTGTTCT | GCACCCCACA | GAAGGCAGTC | CTTTCCACTG | AGTCCCATTC | 900 |
| ACACAGCCAA | GCTGACCATC | ACCCGGATCT | GCCTGTGGCA | GAAGCAACTT | CAAAGTGAGC | 960 |
| GCTAGTGCTC | CTATTCTTGA | AGTCCTGTGG | TCACGCTACA | GTGATAGAAC | TTCTTCTTCT | 1020 |
| TCACCCCCTT | TCCATTCTGT | CTGCAGCTTT | GTGCCATCTT | GCCAGTTCCC | CCTCTCTCTT | 1080 |
| CACCCAATTG | CAGTTTATTT | CTAATACACA | GAGCAATTTC | TGTAGCCCTT | TTGTAACAAT | 1140 |
| TCATTGCTCA | CCTATGGACC | CAAGATCTCA | GCTTCCTACC | TCCCTCTAGT | GGCTGATGCA | 1200 |
| GGTATTTCCA | AAAAAAAAGT | CCTAGAGCAG | GATCCTGGCT | GGCCACACGG | CTGTCCAGTG | 1260 |
| CTGCTCCTGC | CCACAAGGTT | CTAAGAGGTT | AAGGCTTGAC | ATATCAGAAA | AGGAAAGGAA | 1320 |
| GCCTGTGTGA | CACAGAAGCC | TGGGTTGAGG | GAGGCTACGC | TCTGTGTACT | GTCCCCGGGC | 1380 |
| AGAGGCGGTT | TTCTGGGTCA | CCTGCATGTC | CCAACACCGG | CCTCTGGTGG | TCGGCAGATG | 1440 |
| TTAATCCTAA | AACCCTTCTG | TCCCCACCTC | AGAGGTGAAG | TACCTGTGCA | CTAGCCTTCC | 1500 |
| CCGTCTGGGT | CCCCCAAGGC | CCCCACACTG | GGCGCACAGG | GTACAGGGAG | GAGCCAAGCC | 1560 |
| CTCTGCTCCA | GTTCTGCCTT | CTGCGCAGGA | GCCCTTTGAC | TTCTGGGAGT | CAACCCCAGC | 1620 |
| TCACCCAACA | AGGAGATAGG | GCAGGTGGGA | GACACCCTAA | GCTCAGAAGG | CCTACAGGAG | 1680 |
| ATGGAGAGCA | CCCATCCTCC | ACCTCTACTC | CTTCTCCAGA | CCACTCCACA | CCTCGCAGCT | 1740 |
| TCTTGCTCCT | CACCCTCGCA | TTTGGCCCAG | TGGGCACCAA | GAACAAGCCA | GGGTGACTGG | 1800 |
| CTAAGCTGGG | GCCAAACTCA | CTGACAGAAT | TGGAATTGTG | TCAAAACACC | ACTTTTATGT | 1860 |
| CCTCACCTTT | CAGGCCTGCA | TCAGTGTGAG | CTCTGCAGAG | AAAGGGGCCT | GTCTTACTGA | 1920 |
| ACCCTCAGAT | CCCAGCACGC | TGCTGTCCTA | | | | 1950 |

( 2 ) INFORMATION FOR SEQ ID NO:94:

( i ) SEQUENCE CHARACTERISTICS:
           ( A ) LENGTH: 1328 base pairs
           ( B ) TYPE: nucleic acid
           ( C ) STRANDEDNESS: double
           ( D ) TOPOLOGY: linear ( i i ) MOLECULE TYPE: cDNA to mRNA ( i i i ) HYPOTHETICAL: NO ( i v ) ANTI-SENSE: NO ( v ) ORIGINAL SOURCE:
           ( C ) INDIVIDUAL ISOLATE: G326con.seq ( x i ) SEQUENCE DESCRIPTION: SEQ ID NO:94:

| | | | | | |
|---|---|---|---|---|---|
| GTTTCCAAGA | TGATTGTAGA | ACTAAAATGA | GTTGTAAGCT | CCCCTGGAAG | AAGGGATGTG | 60 |
| GAACCTGTAA | CTAGGTTCCT | GCCCAGCCTG | TGAGAAGAAT | TTGGCAGATC | ATCTCATTGC | 120 |
| CAGTATAGAG | AGGAAGCCAG | AAACCCTCTC | TGCCAAGGCC | TGCAGGGGTT | CTTACCACCT | 180 |

| | | | | | |
|---|---|---|---|---|---|
| GACCCTGCAC | CATAACAAAA | GGACAGAGAG | ACATGGTAGG | GCAGTCCCAT | TAGAAAGACT | 240 |
| GAGTTCCGTA | TTCCCGGGGC | AGGGCAGCAC | CAGGCCGCAC | AACATCCATT | CTGCCTGCTT | 300 |
| ATGGCTATCA | GTAGCATCAC | TAGAGATTCT | TCTGTTTGAG | AAAACTTCTC | TCAAGGATCC | 360 |
| AGAAAATATG | CTCTTTAAAA | TATTTTAAAA | CTGATATAGA | CCCAAAGGAG | AGACCCAGTA | 420 |
| ACAATATTCA | GCTATATTAT | CCATTCTCTC | TTTCTTTCAT | TCAACAAATC | TGTATTGATC | 480 |
| ACAGGCTCTC | TGCTGGGTGT | GGGATGCAGC | TGTGGGCCTG | TGCTGGAGGT | CCTTAGAGGC | 540 |
| CAGTACTCCT | ATCCTGGGCT | TTATCTGCAT | GGATTGCTGC | AGTGTTGGGC | TCCACTGCTG | 600 |
| TGTGAAGCAA | TTGCTCCTGC | TCTTTCTGGG | CATGGGAGAA | GGGTCAGAGC | AGTCGGACAC | 660 |
| AGATTCCCAG | GCAGGAGAAT | GGAACTCCTT | CCGAGGAAGA | AGACGTGTTT | TCCTTCCAGC | 720 |
| ACACACCCAG | GCATGGTGGT | CAGGACCGTG | GACCAGGTCC | CCATCTTGTG | CATGCACCAA | 780 |
| GCCCCAGGAT | CAGGAGCAGA | GCTAGTGAGG | GAGCAAGATG | GATGAGGACA | GCACGGTGCT | 840 |
| GACCACTCTA | GACAGACAGG | AGACAGGAAA | CAGGATCTCA | CTTGCAAAAA | GACTGATCTC | 900 |
| AACTTGATCA | ATTAGGCAGA | TACTTGAGTT | CCAGTATACT | CCAGGACTAT | TCTAGGGGCT | 960 |
| AGGATTCAAC | AGTGAATAAA | ACAGACAAAA | TCCTTTCCCT | TGTACACTTA | TATCTTCTCA | 1020 |
| AAAAGCTCC | TTTCCCTCT | TTCTTATCAG | GGTCTAATAT | AGTTAATAAG | GACTTAAGAC | 1080 |
| TGGAATATCA | CATCTAAATC | CCCAATAATG | AGCCCTCACC | AATCTGCCAG | GTCCAGAGA | 1140 |
| AGCTAAAAAC | AATCAGGGCT | GTTTGCAGCT | AACTGAAATA | AAACTTGATT | CGAACTCATG | 1200 |
| TCAAGCCTGT | TGACAACACA | CACACATGTC | CACGTGTCAC | TGCTGTGCAT | AGAAACCTCT | 1260 |
| GACTCACTAC | CATCTGAAGT | CCAGGCTCCT | TCACAGGTCA | TTCAAGGTCG | ACCTCTGCCC | 1320 |
| CCTCTGAC | | | | | | 1328 |

( 2 ) INFORMATION FOR SEQ ID NO:95:

( i ) SEQUENCE CHARACTERISTICS:
        ( A ) LENGTH: 1093 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G164con.seq ( x i ) SEQUENCE DESCRIPTION: SEQ ID NO:95:

| | | | | | |
|---|---|---|---|---|---|
| GTGCTCAATA | AATATTTTG | GAAAGAATAA | ATCTTCAATC | AATCCTATTC | AGTAGGTTTG | 60 |
| ATGATCACTT | CCAATCTATA | GAAGGAAAA | CTGACTCCTA | GAAAGATTAA | TTAACTTGCC | 120 |
| CAATGGCAGG | TAGCAGTAGA | AGCAGAACTT | AAAACCAGGT | AGCCTGACTT | TAGCATCTTA | 180 |
| ACACTGGGTT | GTTTTGCTTC | TACTACTTGC | ACTGAAGGCA | CTTACCACAA | TTTATAGTTG | 240 |
| TTTTATTTGT | TTGTTGTCTG | ACCCTCCTAA | ATGTGTATGA | TGCTGCTAGA | GCAGGGCTAT | 300 |
| GTCCTGCTCC | CTGCTGTGCC | ACCAATACTT | AGAACAGTGC | CTGGCACATT | GCAGCTGTGT | 360 |
| GAGTATTTGC | TGAGTGAATG | AATAAACAAC | CCAAATGAAC | AGACAAGTGA | GGGATGACTG | 420 |
| TGGAGGAATA | GGGGGTGCCA | GTGTGGCAGT | TTCCCAGGCC | CCAGCTGGAT | CCCAGTGCCC | 480 |
| AGTCCAGCTG | TACCCACGTA | AAGGGATCTG | CCAAGAGGTG | GCTTTTCGCT | GTTGCAGAAG | 540 |
| GCATCTCTTG | GGGCTGATGA | CGGTGAGTCT | CTCATTCTTA | ACAGCAAGAG | TCACCCTGCT | 600 |

| | | | | | | |
|---|---|---|---|---|---|---|
| CCATGAATCT | TCAAATTTGG | GGTCATTTCC | CACCTAAAGG | CAGAGATTTG | GCCTATGTTC | 660 |
| CCAACCACAG | CTGAGAGTCC | AACCTGCCCC | TCGGGTGACA | CACATGGCTC | TGGGTAGGAT | 720 |
| CCGTGTATAC | TGCCTCGATT | CTACTCATTA | CATTATGTCA | GCACCTTTTT | CAGCTTCTGA | 780 |
| GAAACAGGAA | GCATCATGAT | GTGTGGTGGG | GCTTGAAGAA | GATGATAAGA | GACATAATCA | 840 |
| CATTTCTTTG | GTTGGGGCAC | AGAGGGCTGG | GGTTCCTGTT | TGCTCTGACT | CTAAAGTGTC | 900 |
| ACCTTTTCCC | TTAAGCCAGA | ATGTTGGAGG | ATGAGGACTA | TTTAGACAAC | CTGCTTTCAA | 960 |
| GGGGAAAGAA | AAGAGCAGGG | ATCAGAGCCT | TTAAAATTAT | TATTATGAAA | CATCATACAT | 1020 |
| ACAAAAAAAT | TACAATCTCT | ATGTATAGTT | GTTAAAACAT | AACAAAACCC | ATGTGTCCAC | 1080 |
| ACCTGGATCC | TGG | | | | | 1093 |

(2) INFORMATION FOR SEQ ID NO:96:

(i) SEQUENCE CHARACTERISTICS:
        (A) LENGTH: 2104 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G65.seq (xi) SEQUENCE DESCRIPTION: SEQ ID NO:96:

| | | | | | | |
|---|---|---|---|---|---|---|
| GAATTCTGGA | TCCTCGACCG | GGCGACGCCG | CGGGAGGTTC | TGGAAACGCC | CGGAGCTGCG | 60 |
| AGTGTCCAGA | CACTTCCCTC | TGTGACCATG | AAACTCTGGG | TGTCTGCATT | GCTGATGGCC | 120 |
| TGGTTTGGTG | TCCTGAGCTG | TGTGCAGGCC | GAATTCTTCA | CCTCTATTGG | GCACATGACT | 180 |
| GACCTGATTT | ATGCAGAGAA | AGAGCTGGTG | CAGTCTCTGA | AAGAGTACAT | CCTTGTGGAG | 240 |
| GAAGCCAAGC | TTTCCAAGAT | TAAGAGCTGG | GCCAACAAAA | TGGAAGCCTT | GACTAGCAAG | 300 |
| TCAGCTGCTG | ATGCTGAGGG | CTACCTGGCT | CACCCTGTGA | ATGCCTACAA | ACTGGTGAAG | 360 |
| CGGCTAAACA | CAGACTGGCC | TGCGCTGGAG | GACCTTGTCC | TGCAGGACTC | AGCTGCAGGT | 420 |
| TTTATCGCCA | ACCTCTCTGT | GCAGCGGCAG | TTCTTCCCCA | CTGATGAGGA | CGAGATAGGA | 480 |
| GCTGCCAAAG | CCCTGATGAG | ACTTCAGGAC | ACATACAGGC | TGGACCCAGG | CACAATTTCC | 540 |
| AGAGGGAAC | TTCCAGGAAC | CAAGTACCAG | GCAATGCTGA | GTGTGGATGA | CTGCTTTGGG | 600 |
| ATGGGCCGCT | CGGCCTACAA | TGAAGGGGAC | TATTATCATA | CGGTGTTGTG | GATGGAGCAG | 660 |
| GTGCTAAAGC | AGCTTGATGC | CGGGGAGGAG | GCCACCACAA | CCAAGTCACA | GGTGCTGGAC | 720 |
| TACCTCAGCT | ATGCTGTCTT | CCAGTGGGT | GATCTGCACC | GTGCCCTGGA | GCTCACCCGC | 780 |
| CGCCTGCTCT | CCCTTGACCC | AAGCCACGAA | CGAGCTGGAG | GGAATCTGCG | GTACTTTGAG | 840 |
| CAGTTATTGG | AGGAAGAGAG | AGAAAAAACG | TTAACAAATC | AGACAGAAGC | TGAGCTAGCA | 900 |
| ACCCCAGAAG | GCATCTATGA | GAGGCCTGTG | GACTACCTGC | CTGAGAGGGA | TGTTTACGAG | 960 |
| AGCCTCTGTC | GTGGGGAGGG | TGTCAAACTG | ACACCCCGTA | GACAGAAGAG | GCTTTTCTGT | 1020 |
| AGGTACCACC | ATGGCAACAG | GGCCCCACAG | CTGCTCATTG | CCCCCTTCAA | AGAGGAGGAC | 1080 |
| GAGTGGGACA | GCCCGCACAT | CGTCAGGTAC | TACGATGTCA | TGTCTGATGA | GGAAATCGAG | 1140 |
| AGGATCAAGG | AGATCGCAAA | ACCTAAACTT | GCACGAGCCA | CCGTTCGTGA | TCCCAAGACA | 1200 |
| GGAGTCCTCA | CTGTCGCCAG | CTACCGGGTT | TCCAAAAGCT | CCTGGCTAGA | GGAAGATGAT | 1260 |

| | | | | | |
|---|---|---|---|---|---|
|GACCCTGTTG|TGGCCCGAGT|AAATCGTCGG|ATGCAGCATA|TCACAGGGTT|AACAGTAAAG|1320
|ACTGCAGAAT|TGTTACAGGT|TGCAAATTAT|GGAGTGGGAG|GACAGTATGA|ACCGCACTTC|1380
|GACTTCTCTA|GGCGACCTTT|TGACAGCGGC|CTTCCAACAT|TAGGGCAGAG|GGGAATAGTG|1440
|TTAGCGACGT|TTCTTAACTA|CATGAGTGAT|GTAGAAGCTG|GTGGTGCCAC|CGTCTTCCCT|1500
|GATCTGGGGG|CTGCAATTTG|GCCTAAGAAG|GGTACAAAGC|TGTGTTCTGG|TACAACCTCT|1560
|TGCGGAGCGG|GGAAGGTGAC|TACCGAACAA|GACATGCTGC|CTGCCCTGTG|CTTGTGGGCT|1620
|GCAAGTGGGT|CTCCAATAAG|TGGTTCCATG|AACGAGGACA|GGAGTTCTTG|AGACCTTGTG|1680
|GATCAACAGA|AGTTGACTGA|CATCCTTTTC|TGTCCTTCCC|CTTCCTGGTC|CTTCAGCCCA|1740
|TGTCAACGTG|ACAGACACCT|TTGTATGTTC|CTTTGTATGT|TCCTATCAGG|CTGATTTTTG|1800
|GAGAAATGAA|TGTTTGTCTG|GAGCAGAGGG|AGACCATACT|AGGGCGACTC|CTGTGTGACT|1860
|GAAGTCCCAG|CCCTTCCATT|CAGCCTGTGC|CATCCCTGGC|CCCAAGGCTA|GGATCAAAGT|1920
|GGCTGCAGCA|GAGTTAGCTG|TCTAGCGCCT|AGCAAGGTGC|CTTTGTACCT|CAGGTGTTTT|1980
|AGGTGTGAGA|TGTTTCAGTG|AACCAAAGTT|CTGATACCTT|GTTTACATGT|TTGTTTTTAT|2040
|GGCATTTCTA|TCTATTGTGG|CTTTACCAAA|AAATAAAATG|TCCCTACCTG|AAAAAAAAAA|2100
|AAAA| | | | |2104

(2) INFORMATION FOR SEQ ID NO:97:

(i) SEQUENCE CHARACTERISTICS:
        (A) LENGTH: 1534 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Septin-2.seq (xi) SEQUENCE DESCRIPTION: SEQ ID NO:97:

| | | | | | |
|---|---|---|---|---|---|
|CGGGGAGGCC|GGTCCCGCGG|GCGGGGGAAG|GGGCGGTTCC|GCGGCTTCTC|CCGCCGCCGC|60
|CGCCAAGGGG|AGTTTCCAGG|AAGTGGCCAT|ATTGGATCCA|TTCAGCCGCA|GCCCGCCCGG|120
|GCGGAGCGCG|TCCCGCAGCC|GGCTGGTCCC|TGTCTCTGCC|CCTGCGCTCG|TCCCAGCCCA|180
|CCCGCCCGGT|GCGGAGCTCG|CCATGGCGGC|CACCGACCTG|GAGCGCTTCT|CGAATGCAGA|240
|GCCAGAGCCC|CGGAGCCTCT|CCCTGGGCGG|CCATGTGGGT|TTCGACAGCC|TCCCCGACCA|300
|GCTGGTCAGC|AAGTCGGTCA|CTCAGGGCTT|CAGCTTCAAC|ATCCTCTGTG|TGGGGAGAC|360
|CGGCATTGGC|AAATCCACAC|TGATGAACAC|ACTCTTCAAC|ACGACCTTCG|AGACTGAGGA|420
|AGCCAGTCAC|CATGAGGCAT|GCGTGCGCCT|GCGGCCCCAG|ACCTATGACC|TCCAGGAGAG|480
|CAACGTGCAG|CTCAAGCTGA|CCATTGTGGA|TGCCGTGGGC|TTTGGGGATC|AGATCAATAA|540
|GGATGAGAGT|TACAGGCCCA|TAGTTGACTA|CATCGATGCG|CAGTTTGAAA|ATTATCTGCA|600
|GGAGGAGCTG|AAGATCCGCC|GCTCGCTCTT|CGACTACCAT|GACACAAGGT|CCACGGTTTG|660
|GCTCTACTTC|ATCACGCCCA|CAGGGCACTC|CCTGAAGTCT|CTAGATCTAG|TGGCCATGAA|720
|GAAGCTAGAC|AGCAAGGTGA|ACATTATCCC|CATCATCGCC|AAGGCTGACA|CCATCTCCAA|780
|GAGCGAGCTC|CACAAGTTCA|AGATCAAGAT|CATGGGCGAG|TTGGTCAGCA|ACGGGGTCCA|840
|GATCTACCAG|TTCCCCACGG|ATGATGAGGC|TGTTGCAGAG|ATTAACGTAG|TCATGAATGC|900

| | | | | | | |
|---|---|---|---|---|---|---|
| ACATCTGCCC | TTTGCCGTGG | TGGGCAGCAC | CGAGGAGGTG | AAGGTGGGGA | ACAAGCTGGT | 960 |
| CCGAGCACGG | CAGTACCCCT | GGGGAGTGGT | GCAGGTGGAG | AATGAGAATC | ACTGCGACTT | 1020 |
| CGTGAAGCTG | CGGGAGATGT | TGATCCGGGT | GAACATGGAA | GACCTCCGCG | AGCAGACCCA | 1080 |
| CAGCCGGCAC | TACGAGCTCT | ACCGGCGCTG | CAAGTTGGAG | GAGATGGGCT | TTCAGGACAG | 1140 |
| CGATGGTGAC | AGCCAGCCCT | TCAGCCTACA | AGAGACATAC | GAGGCCAAGA | GGAAGGAGTT | 1200 |
| CCTAAGTGAG | CTGCAGAGGA | AGGAGGAAGA | GATGAGGCAG | ATGTTTGTCA | ACAAAGTGAA | 1260 |
| GGAGACAGAG | CTGGAGCTGA | AGGAGAAGGA | AAGGGAGCTC | CATGAGAAGT | TGAGCACCT | 1320 |
| GAAGCGGGTC | CACCAGGAGG | AGAAGCGCAA | GGTGGAGGAA | AAGCGCCGGG | AACTGGAGGA | 1380 |
| GGAGACCAAC | GCCTTCAATC | GCCGGAAGGC | TGGGTGGGAG | GCCTGCAGTC | GCAGGCCTTG | 1440 |
| CACGCCACCT | CGCAGCAGCC | CCTGAGGAAG | GACAAGGACA | AGAAGAAGTA | GGTGGCAGGC | 1500 |
| TGCGCCTGCG | CTGGCTCCTC | TTGCTCCTGT | GGGC | | | 1534 |

( 2 ) INFORMATION FOR SEQ ID NO:98:

( i ) SEQUENCE CHARACTERISTICS:
( A ) LENGTH: 414 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( C ) INDIVIDUAL ISOLATE: G42con.seq ( x i ) SEQUENCE DESCRIPTION: SEQ ID NO:98:

| | | | | | | |
|---|---|---|---|---|---|---|
| CAGGCATAAG | CCACCGTGCC | TGGCCTGGAA | TATTAGTTTT | TATATAACTG | GTGTAAAGGG | 60 |
| TCAAAGAGAT | AATATATGTA | AACACTTAGC | CTGGAACCTG | TCTCAAAGTA | CCTACTCAAA | 120 |
| AAAATGCTAG | CTGTGAAGAT | GGTGATCCTG | TTTAAGGAAG | GGTGACTGCC | TAAAAGAGAG | 180 |
| CAGAAAGTAG | GACTAAAAAG | GAATTATTTC | AATTTGTACC | ATCCATGCTG | TCCACAGGAA | 240 |
| GGCAAAGAGA | GAGACCTACA | AAGTCTCTGT | CCCCAACATG | CACTCTGCCA | AGTTATATAA | 300 |
| CTGTTCTGGT | CTGAGACCCA | TGCTTAGAGA | GGGAGATTAT | CCAGGAACCC | AGTAGTATAA | 360 |
| CTTCTCTTTT | CTTAACGAGG | TCATGAAGGT | AGGAGAAAGC | TCCTCTGGCC | TCAC | 414 |

( 2 ) INFORMATION FOR SEQ ID NO:99:

( i ) SEQUENCE CHARACTERISTICS:
( A ) LENGTH: 606 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( C ) INDIVIDUAL ISOLATE: G105con.seq ( x i ) SEQUENCE DESCRIPTION: SEQ ID NO:99:

| | | | | | | |
|---|---|---|---|---|---|---|
| TGGGAAGATA | GGGATGGGAG | TGGAGGGGCT | GTGGGAAGGA | GAAGGGTCAC | TCAGGGACCT | 60 |
| GGCTGTGCCC | CTTGCATCCT | GACAATGGAT | CCACCACAAC | TCTACCAGTC | TGTATTAGGG | 120 |

| | | | | | | |
|---|---|---|---|---|---|---|
|GAACATGAGC|AAATGGCATC|GTGTCTGTGC|CAGTCACCAA|GCACTGAGGG|GAAGCTCTGG|180|
|AAGTTGCCGC|CTGAACCTGC|CCTCCAGTCT|TGCAAATGCT|GAGCAGGAGC|CACCAGCCTT|240|
|GGACTGTCTG|TGCTTCTTGC|TAGAGCATGT|GGGTCATTCC|AGCCTTTCCC|CAGAACGTCC|300|
|ATTCTCTCCA|CACCTTCTTC|ATTCCAAATG|GGGATCCTTG|CCTTTCTTTT|GGACTCCAGA|360|
|GACATGCATA|AAACCACAAC|ACAGCTTTAG|AAAACAAGGC|ACACCTGTAT|TAGTCTTACA|420|
|CCTAAATTGA|ATGCAGCCTG|CCATAAGGGA|GGAATTACAG|TCCTTCTAGA|GGCCCAAGGT|480|
|ACCTGCAGCT|CCCCCTGACC|AGTCCTGTCA|AAGCCTTGTT|TTTGTCAAAA|TGCCACCTTG|540|
|GACTCTGTCT|GAGAGTTCTG|CTGCCCACCA|AGAGGGATGG|ACAAAGTCTG|TTTATCCAGA|600|
|AACTTG| | | | | |606|

( 2 ) INFORMATION FOR SEQ ID NO:100:

( i ) SEQUENCE CHARACTERISTICS:
        ( A ) LENGTH: 421 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G98con.seq ( x i ) SEQUENCE DESCRIPTION: SEQ ID NO:100:

| | | | | | | |
|---|---|---|---|---|---|---|
|CATAATGGAC|CCCTCTAAGG|ACTTCATGAA|AGCTACGGAC|CTCTCTCCAA|AAAATGCTCA|60|
|CATGTAGTCT|CTAACATTGT|GCATATAATT|TCGAGGGGTT|TGGGATTCTC|TAAGCCGTTA|120|
|ATGCTTCCTT|GAGTTAAAAG|CTTTAGAATT|ATACAAATAA|CCTGCTTATA|AGAAATGGAT|180|
|CAAAACACTA|TTCTCCCTCC|TGTCATAAAG|TAAATGCCAA|AACCACAGGC|CACTTAGCTA|240|
|AGGGGCATCA|GCCTTGTGGA|CAAAAGAGTT|CTGCTTTTCA|TACCACTAGT|GGCTGGTGAG|300|
|AGCTCCTTTC|ACTTTGCAGA|GAGAATGCTG|GTCTTCTTGG|GACTACAGAG|GCAGACACCG|360|
|TGGCACTACT|ACAGATCTAC|AATCTAGCAC|ATGTGCATGT|GTGCATGATG|TCAACCTCTC|420|
|C| | | | | |421|

( 2 ) INFORMATION FOR SEQ ID NO:101:

( i ) SEQUENCE CHARACTERISTICS:
        ( A ) LENGTH: 392 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G73con.seq ( x i ) SEQUENCE DESCRIPTION: SEQ ID NO:101:

| | | | | | | |
|---|---|---|---|---|---|---|
|GTGACTGTGG|AGGGCGAGCT|GAGCCCTGGC|CGCCGCCACA|ATGGGCCGCG|AGTTTGGGAA|60|
|TCTGACGCGG|ATGCGGCATG|TGATCAGCTA|CAGCTTGTCA|CCGTTCGAGC|AGCGCGCCTA|120|
|TCCGCACGTC|TTCACTAAAG|GAATCCCCAA|TGTTCTGCGC|CGCATTCGGG|AGTCTTTCTT|180|

| | | | | | |
|---|---|---|---|---|---|
|TCGCGTGGTG|CCGCAGTTTG|TAGTGTTTTA|TCTTATCTAC|ACATGGGGA|CTGAAGAGTT|240
|CGAGAGATCC|AAGAGGAAGA|ATCCAGCTGC|CTATGAAAAT|GACAAATGAG|CAACGCATCC|300
|GGATGACGGT|TCCCTGTCTC|TGAAAGACCT|TTCTCTGGAA|GAGGAGTCTG|CATTGTAGTG|360
|TCTCAAAGAC|ACAATAAACT|TCCTATGGTC|TG| |392|

( 2 ) INFORMATION FOR SEQ ID NO:102:

( i ) SEQUENCE CHARACTERISTICS:
        ( A ) LENGTH: 2200 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G89con.seq ( x i ) SEQUENCE DESCRIPTION: SEQ ID NO:102:

| | | | | | |
|---|---|---|---|---|---|
|CCACCCAGCC|TCAGCACTCA|TCTGCGCAGC|CATGGAGGCC|CTGGGACCTG|GGGGCGACCG|60
|CGCCTCCCCG|GCCTCGTCCA|CTAGCAGCCT|GGACCTGTGG|CATCTGTCCA|TGCGCGCGGA|120
|CTCGGCCTAC|AGCTCTTTCT|CCGCAGCCTC|CGGCGGCCCC|GAGCCGCGCA|CGCAGTCGCC|180
|GGGGACAGAC|CTCCTTCCTT|ACCTAGACTG|GGACTACGTG|CGTGTGGTTT|GGGGCGGCCC|240
|GGGCCCCGCC|CCGCCCGACG|CTGCCCTTTG|CACATCCCCG|CGGCCCCGGC|CCGCGGTTGC|300
|AGCCCGCAGT|GGGCCGCAGC|CAACAGAGGT|CCCGGGGACC|CCGGGACCAC|TGAACAGGCA|360
|GGCCACCCCG|CTGCTGTACG|CGCTGGCGGC|CGAGGCGGAG|GCCGCGGCGC|AGGCTGTCGA|420
|GCCGCCCAGC|CCGCCGGCCT|CGAGGGCCGC|CTACCGCCAG|CGGCTTCAGG|GCGCGCAGCG|480
|GCGAGTGCTC|CGGGAGACGT|CGTTCCAGCG|CAAGGAGCTC|CGCATGAGCC|TGCCCGCCCG|540
|TCTGCGGCCC|ACTGTCCCAG|CGCGGCCCCC|GGCGACTCAC|CCGCGCTCCG|CCTCGCTCAG|600
|CCACCCGGGC|GGGGAGGGGG|AGCCGGCGCG|CTCCCGGGCT|CCCGCGCCAG|GAACTGCCGG|660
|CCGGGGTCCC|CTCGCCAACC|AGCAGCGGAA|GTGGTGCTTC|TCAGAGCCAG|GAAAGCTGGA|720
|TCGTGTGGGT|CGGGGCGGTG|GGCCGGCGCG|GGAATGCCTG|GGTGAGGCCT|GCTCCAGCTC|780
|TGGCCTCCCT|GGGCCCGAGC|CCTTGGAGTT|CCAGCATCCG|GCGCTGGCTA|AGTTTGAAGA|840
|TCACGAGGTC|GGATGGCTGC|CCGAGACGCA|ACCCCAAGGC|TCCATGAACC|TGGACTCCGG|900
|GTCCTTGAAG|CTCGGTGATG|CCTTCAGGCC|CGCCAGTCGG|AGTCGGAGCG|CTTCAGGCGA|960
|AGTCTTGGGT|TCCTGGGGAG|GATCAGGAGG|GACCATACCC|ATTGTCCAGG|CTGTCCCCAA|1020
|GGAGCAGAAA|CCCCCAGACC|ATTGTTTCAG|ACCAAACTTT|CCAGGTTCTT|GCCTCAGAAA|1080
|GAGGCTGCGG|TGATGTATCC|TGCAGAGTTA|CCCCAGAGCA|GCCCTGCTGA|CAGTGAACAG|1140
|AGGGTCTCAG|AGACCTGCAT|TGTGCCTGCC|TGGCTCCCCT|CCCTTCCTGA|TGAAGTGTTC|1200
|CTAGAAGAGG|CCCCACTGGT|CAGAATGAGA|TCACCACCAG|ACCCCATGC|CTCCCAGGGG|1260
|CCCCCAGCCA|GGTCCTATCA|GTTCAGCTTC|ACCCAGCTCC|TGCCGGCTCC|TCGGGAGGAG|1320
|ACAAGGCTTG|AAAACCCTGC|CACCCACCCT|GTGCTTGACC|AGCCATGTGG|GCAGGGGCTC|1380
|CCTGCACCAA|ACAACAGCAT|CCAGGGCAAG|AAAGTGGAGC|TGGCCGCCCG|CCTCCAAAAG|1440
|ATGCTTCAGG|ACCTTCACAC|GGAGCAGGAG|CGGCTGCAGG|GGGAGGCACA|AGCGTGGGCC|1500
|AGGCGCCAAG|CGGCTCTGGA|GGCTGCAGTG|CGCCAGGCCT|GTGCCCCTCA|GGAGCTGGAG|1560

| | | | | | | |
|---|---|---|---|---|---|---|
| CGGTTCAGCC | GGTTCATGGC | CGACCTAGAG | CGCGTGCTTG | GCCTTCTGCT | GCTGCTGGGC | 1620 |
| AGTCGCCTGG | CGCGCGTGCG | CCGCGCCCTG | GCCCGGGCGG | CCTCAGACAG | CGACCCTGAT | 1680 |
| GAGCAGCGAC | TCCGGCTCCT | GCAGCGGCAG | GAGGAGGACG | CCAAGGAGCT | GAAGGAGCAC | 1740 |
| GTAGCGCGGC | GCGAGCGGGC | CGTGCGGGAG | GTGCTGGTGC | GAGCACTACC | GGTGGAGGAG | 1800 |
| CTGCGCGTCT | ATTGCGCCCT | GCTGGCGGGC | AAGGCCGCCG | TCCTGGCCCA | GCAGCGCAAC | 1860 |
| CTGGACGAGC | GCATCCGCCT | CCTTCAGGAC | CAACTGGACG | CCATCAGGGA | CGACCTTGGC | 1920 |
| CATCATGCCC | CGTCTCCCAG | CCCGGCGCGG | CCCCCAGGGA | CCTGTCCTCC | AGTTCAGCCG | 1980 |
| CCCTTCCCTC | TTCTCCTTAC | ATAAGATACC | ACTGGGTCAG | CCAGGCCTGA | GGCGGGCAGT | 2040 |
| CGAGGGTGGG | AGCTGAAGGG | AAGCCATGTT | CGGCGGTGCC | CGAAACCGGC | GCGCAGTCTG | 2100 |
| TCTTGAACAT | CCTGCTCGGC | ACAAAACTTA | CCCCTGAGAG | CGGCTGGCGC | AAACCTCAGG | 2160 |
| GCTCCTCATT | GGAACAAATT | GCCGTGCTGT | GCATTCACAT | | | 2200 |

( 2 ) INFORMATION FOR SEQ ID NO:103:

( i ) SEQUENCE CHARACTERISTICS:
        ( A ) LENGTH: 371 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G102.seq ( x i ) SEQUENCE DESCRIPTION: SEQ ID NO:103:

| | | | | | | |
|---|---|---|---|---|---|---|
| GGGGGATCCA | GCTCAGAAGC | AGAGTGTCCA | CGCCAGGGAA | TAGTGTGGGG | ATTCAGAGCC | 60 |
| TGATAATGAT | GAGAAGGGGA | CCCACCTGAG | GGTTAAGTCG | GCTAGGGGA | AGTCAGATCA | 120 |
| TAGAGTAGAG | ACGGCATTCT | TGCGAGAAGC | CACCTGGTAT | AAAGTATCAG | ACCGAGAAGA | 180 |
| GTGACCCTCT | CAGTGACACA | GATCTGGGGA | GATTCAGGTC | AGAGTACAGT | GGGCATCCCT | 240 |
| GCAAGAGGCC | ACCTGGTATC | AGAGAAGGGC | GGGGAATGAG | GACATGATCT | AGCACCAGAA | 300 |
| GTCAAAGTGT | ATACAGAATG | GAAAAGCATC | CCATGAGGGA | GTCGGAATGA | AGAGTCAAGA | 360 |
| GCCTACGCAG | G | | | | | 371 |

( 2 ) INFORMATION FOR SEQ ID NO:104:

( i ) SEQUENCE CHARACTERISTICS:
        ( A ) LENGTH: 407 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G57.seq ( x i ) SEQUENCE DESCRIPTION: SEQ ID NO:104:

| | | | | | | |
|---|---|---|---|---|---|---|
| GGCAGAGGAG | GACAGGCACC | TACTGCATCC | AAGCCTTAGG | ATATGAGTCA | TGTTCCAAAG | 60 |
| GTGGGATTGG | GAAGGACAAT | CAGGGCGTGA | TAGTAATATA | TGCTGAGTAG | AGGCACTAGA | 120 |

| | | | | | | |
|---|---|---|---|---|---|---|
| CATGGGAAGC | AACTAATTCC | AACTGAAGAC | CCATAGGTGT | GGGAGAGAGA | GGCTAGAGAG | 180 |
| GTCAGCAGGT | CCTGAACATC | TGCAGAAGGT | GGATTGTCCT | GTTGGCTCAG | GGAGCTTAGG | 240 |
| CTTCAAGCCC | CCTCACTTGC | ATCAGCCCCT | TCCAAGGCCC | TGCACTTCAA | TTTTACCTGG | 300 |
| TTTTTCTTAG | AAAGGGCCCT | CAATATTGTA | AAAGCTTGAA | GTCTCACAAA | TCCCTGGATC | 360 |
| TGCTGCTGAT | GCCCTGTAAC | TTGAATGAAA | CCATTCACCA | TTTAGGG | | 407 |

(2) INFORMATION FOR SEQ ID NO:105:

(i) SEQUENCE CHARACTERISTICS:
        (A) LENGTH: 235 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G108.seq (xi) SEQUENCE DESCRIPTION: SEQ ID NO:105:

| | | | | | | |
|---|---|---|---|---|---|---|
| GTCCTCTGGG | AAGCAGACAC | CAAAACAGAA | TGAAAAGTGC | AGAAGATTTA | TTGGGGGTAA | 60 |
| GAAGAGCTAA | TGCCTATGAA | AGATAAAGGA | GAAAGGAGCA | GAAGTACGGA | GAGAAAAGAC | 120 |
| AGCTTTCAGA | CTGCAGTCCA | GATCTAACTC | TGGGACGCAA | GAGAGGGAAG | GATAATTCTG | 180 |
| TTGAAAGAGC | ATCAGACTGT | GATGCGGCTG | TAAGAGTGTC | TCAACGAGCC | CAGTG | 235 |

(2) INFORMATION FOR SEQ ID NO:106:

(i) SEQUENCE CHARACTERISTICS:
        (A) LENGTH: 397 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G127.seq (xi) SEQUENCE DESCRIPTION: SEQ ID NO:106:

| | | | | | | |
|---|---|---|---|---|---|---|
| GGCAGCTGAT | AAACAAACAG | GGCAAGCACA | TTCAGGCCAG | AGCAAGGGGA | AGCCCCTGAG | 60 |
| TCCCCTCTAT | GTGCTCTCTG | GCAAGATCTA | CTTTCTGAAG | CATTGACTGG | AAATAGAAGT | 120 |
| CTCGCCGGGC | TGGCTGGAGC | CAGAGGCCCC | CACACCTTAT | CCCCTTTGGA | ATCTGCCAGA | 180 |
| GGGCAGGTCT | GAGTATGGAC | TTGGATGATC | AACTTGGTTA | ATATTCAGGC | TATCTTGACA | 240 |
| GTCTCCACAC | CCGTGAGCAA | TGTCCCAGGC | AGCCTGCAGG | CCTGATAGAA | ACTCCACAAA | 300 |
| CCCGCCTATC | ACGGAAGGTT | TTCCCCTTTT | GTCGGGGCCT | ACCCAGACCC | CAGGGGAGGT | 360 |
| GCATCCTTGA | AAGCCGCTAT | GTGAAGTCCC | ACATAGT | | | 397 |

(2) INFORMATION FOR SEQ ID NO:107:

(i) SEQUENCE CHARACTERISTICS:
        (A) LENGTH: 266 base pairs
        (B) TYPE: nucleic acid
        (C) STRANDEDNESS: double ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
            ( C ) INDIVIDUAL ISOLATE: G86.seq ( x i ) SEQUENCE DESCRIPTION: SEQ ID NO:107:

| | | | | | | |
|---|---|---|---|---|---|---|
| CCACCCCTG | TGGCCTTCTT | TAACCATGCT | GGCTAATTCA | GGATCCCTAG | TTCCTTATGA | 60 |
| CTTTCCTTTA | AAACGTCTAC | CAGAAATTGG | GGGAAAAAAA | GTGTTATTAT | AGGATTAATG | 120 |
| TAGGTCTTCC | CCACTATACT | GTGAATATCA | TTGAGAGCTT | GGTCCCTACA | CCTTAAATCC | 180 |
| CCCATCGTCA | ACTATTTTTT | CCCATCTCAG | TGTCCCATGA | TCAAGGAGAC | CCTCCCTGAA | 240 |
| TGTCCAGTTC | CCCAACCCTT | ACCCCC | | | | 266 |

( 2 ) INFORMATION FOR SEQ ID NO:108:

( i ) SEQUENCE CHARACTERISTICS:
            ( A ) LENGTH: 370 base pairs
            ( B ) TYPE: nucleic acid
            ( C ) STRANDEDNESS: double
            ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
            ( C ) INDIVIDUAL ISOLATE: G78.seq ( x i ) SEQUENCE DESCRIPTION: SEQ ID NO:108:

| | | | | | | |
|---|---|---|---|---|---|---|
| GTAGGTGATG | GGATGATGGT | GAAATACAGG | ATCAAGTACT | CAACTCCAAC | CTGATGGCCA | 60 |
| TACCCAGGAC | AAATGCTGCC | CCATAGTTGG | AGATCTGGCC | CATGCCTACA | AGGACAAACA | 120 |
| GCACGACAAA | CATCTCAAAA | TTCTTCGAGA | AGGTCTGCAG | GAAGCTGAAG | CCTGTCTGCA | 180 |
| CGCCCATGGT | CACGAACAGC | ACATTCTTCC | GGCCAAACCT | GGGAAGGAAA | GGAGAGTGAC | 240 |
| AGATAACCAG | CTGGAAAAGG | GCAGCAGGAA | TGGGCTCCAC | CAAGTGGGGC | TTTCTCAAGA | 300 |
| TCCATCCAGT | AAGTGGGTGT | GAACAGTGTT | GCCAGAATAC | TGGCTGCCAG | GGACAGTCTC | 360 |
| GGTCTCACAG | | | | | | 370 |

( 2 ) INFORMATION FOR SEQ ID NO:109:

( i ) SEQUENCE CHARACTERISTICS:
            ( A ) LENGTH: 481 base pairs
            ( B ) TYPE: nucleic acid
            ( C ) STRANDEDNESS: double
            ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
            ( C ) INDIVIDUAL ISOLATE: H993.seq ( x i ) SEQUENCE DESCRIPTION: SEQ ID NO:109:

| | | | | | | |
|---|---|---|---|---|---|---|
| GGGAGAAATA | GCATGGGCAC | TGTGAGACCG | AGACTGTCCC | TGGCAGCCAG | TATTCTGGAA | 60 |
| ACACTGTTCA | CACCCACTTA | CTGGATGGAT | CTTGAGAAAG | CCCCACTTGG | TGGAGCCCAT | 120 |

| | | | | | |
|---|---|---|---|---|---|
| TCCTGCTGCC | CTTTTCCAGC | TGGTTATCTG | TCACTCTCCT | TTTCTTCCCA | GGTTTGGCCG | 180 |
| GAAGAATGTG | CTGTTCGTGG | CCATGGGCAT | GCAGACAGGC | TTCAGCTTCC | TGCAGATCTT | 240 |
| CTCGAAGAAT | TTTGAGATGT | TTGTCGTGCT | GTTTGTCCTT | GTAGGCATGG | CCAGATCTC | 300 |
| CAACTATGTG | GCAGCATTTG | TCCTGGGTAT | GGCCATCAGG | TTGGAGTTGA | GTACTTGATC | 360 |
| CTGTATTTCA | CCATCATCCC | ATCACCTACC | TTTCTGGAGA | CAGCTGTAAT | GTCCCTCAAG | 420 |
| GGGGACAGGG | TTTCTAACAA | AACTAGCCAG | AGCTTCCTGG | TGAACCTTAC | TTACAGGCAG | 480 |
| G | | | | | | 481 |

( 2 ) INFORMATION FOR SEQ ID NO:110:

( i ) SEQUENCE CHARACTERISTICS:
        ( A ) LENGTH: 670 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G38a.seq ( x i ) SEQUENCE DESCRIPTION: SEQ ID NO:110:

| | | | | | |
|---|---|---|---|---|---|
| GGGGCAAGTA | GCCGGTGCGG | GTGGTAGAAC | TGGCAGATAA | AAGGGCCTGT | GGTGAGACTC | 60 |
| CAGGTGTGGT | TGTATAGGGG | GTTGAGGGAG | GTAAGCGCGG | AGGCGGGATC | GAGCAGGGGT | 120 |
| CCTTGTAGCC | GCCTAAGAAG | TGCAGTGGTG | AAGCTGACTC | CTGTGAGGTG | GAGGGGAGGG | 180 |
| GTCTGGAAAC | AGTGGAGATA | CAGCAGCCCT | GGGCAGAGCA | GAGGAGCCAG | GTGAACCCTA | 240 |
| CCTTACAGAA | ATCTTGTACC | CTGGCTGAAG | GACGGGCAGG | GAGGGGTCGT | GAGGAACCCC | 300 |
| CTCGCCGGGA | TCAGGAAGCC | TAGGTCAGTC | CGGGTTACAT | AGCTGACCTG | CTGTGGGACC | 360 |
| TCGGGGACCA | ACACCCTCGG | TTTCTGGTCC | CAGGAGATGG | ACAAGGACGC | AATGTCTGTT | 420 |
| CCTGGCCTTG | GCTCAGGGCC | TAATCTGATC | CGCGGATGGT | CCTTGCCATC | AGGGAAGGGG | 480 |
| GACGCAAGAA | CTCGGCGGGG | GTTTGTGGTG | GGGTCGCAGA | GAGCAAGCCC | TATATCTCCC | 540 |
| TCCGCAGACC | CAGGTGCTCC | CCAAACCCGG | CCCGGAGCCC | GCGAGAACTG | GGGGCGGAGG | 600 |
| GTGTACTTAG | GCGGCCCTGG | GGACCTTGAC | GGGACAGCTC | AGCAGCAGGG | GATGGGGCT | 660 |
| CGGCGGCCGC | | | | | | 670 |

( 2 ) INFORMATION FOR SEQ ID NO:111:

( i ) SEQUENCE CHARACTERISTICS:
        ( A ) LENGTH: 408 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: H90.seq ( x i ) SEQUENCE DESCRIPTION: SEQ ID NO:111:

| | | | | | |
|---|---|---|---|---|---|
| GTCACCAGCA | CCTTGGGCTG | GGTGTCAGAG | AGCTCACAGA | ATGTGGATAA | CCAACCAGGC | 60 |

| | | | | | | |
|---|---|---|---|---|---|---|
|AGATGTTGGT|AACAGCAACC|AGGAGGGCAC|AGCACAAACC|TGAGCAGGTC|TTTTATGTAT|120|
|GTGAAGGTGA|AGGAGTTATG|ATTTAGAAAT|GGCAGTGGGA|AGCAAGGAGA|ATGCTGAGGG|180|
|CCTGCTCAGC|TCTTGTCTTC|CAGGATCATG|GATAGTGCAA|AATGAGTAGC|CTTCATTTGA|240|
|GAGACAGAGC|CATGAGGCTA|GTGGAGTGCT|CAGAAAGAAG|CCAGATCTCT|ATCAAGGAAA|300|
|GGAGATGGAG|AGAACAACCA|GGGATGTACT|GAAAGGGGAG|AGTTGCATGT|CTCCAATGGA|360|
|ATATGTGTTG|CAGAGGACTC|AGTCACAGAG|AAGACAACTC|CAGGAGGG| |408|

( 2 ) INFORMATION FOR SEQ ID NO:112:

( i ) SEQUENCE CHARACTERISTICS:
        ( A ) LENGTH: 254 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G66.seq ( x i ) SEQUENCE DESCRIPTION: SEQ ID NO:112:

| | | | | | | |
|---|---|---|---|---|---|---|
|GGCGATCAAG|AAGGATGCCC|CCCAGGACAG|TGACTCTGCT|GGACTTCTCT|ACAGAAAACA|60|
|GTATATCCCT|CAGTGGCATG|AGAAGATCCA|ATAGGGTCAC|CACACTCCAC|AACTGCAGGG|120|
|GACACTGTTC|ACATTTTAGT|CTATGCAGCC|TCTGGTGGCC|AAAGATTAAT|ATGAGAACAC|180|
|CTTTGCTGTG|TGACCTGAAG|TTCATGGGCA|GTAAATTGTA|GCTATTGTTA|TGCACGACTT|240|
|TGGGCGAACC|AGGG| | | | |254|

( 2 ) INFORMATION FOR SEQ ID NO:113:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: H973.seq ( x i ) SEQUENCE DESCRIPTION: SEQ ID NO:113:

| | | | | | | |
|---|---|---|---|---|---|---|
|CACAGGAGGA|TCACATAGGG|TCACCACACT|CCACAACTCC|AGGAGATGCT|GTTAACATTT|60|
|TAGTCTATGG|ATCCTCTGGT|GGCCTAAGAT|TTAAATGAGA|GCACTTTTGT|TATGTGACCT|120|
|GAAGTTAATG|TCAATAAGTT|ATAGCTATTG|TTATGTACGA|TGTAAGCAGG|GGTCACTGCA|180|
|GGCCAGAAGG|CTGACACAAT|TTGGCCAGGC|TTTGTTCTTC|AAGGAAGGGC|AGGGCTCTGA|240|
|GAAGTGCAGA|CCGTGATGCA|GGTGAAGGCC|AGGAGGCAGG|GACTCCCAGG|GCAGGTCTGG|300|
|AAGGAGCGAG|GCTGGTGACG|GAAGTGGTCA|GCAACCTCAA|GGCGT| |345|

( 2 ) INFORMATION FOR SEQ ID NO:114:

( i ) SEQUENCE CHARACTERISTICS:
        ( A ) LENGTH: 413 base pairs (B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: H505.seq (xi) SEQUENCE DESCRIPTION: SEQ ID NO:114:

| | | | | | | |
|---|---|---|---|---|---|---|
| GGGAGATCTG | CTGCTCTTTT | CAGAGCCAGC | AGGTAGGAAC | ATTTAAGTCT | GCTGAAGCTG | 60 |
| TGCCCACAGC | CGCCCCTTTC | CCCACGTGCT | CTGTCCCAGG | GAGATGGGAG | TTTTATCTAT | 120 |
| AAGCCTCTGA | CTTGGGCTGC | TGCTGTTCTT | TCAGAGGTGC | CCTGCCCAGA | GAGGAGGAAT | 180 |
| CTGGTGAGGC | AGTCTGGCTA | CAGAGGCTTT | GCTGAGCTGC | GGTGAGCTCT | GCCCAGTTCC | 240 |
| AGCTTCCTCG | TGGCATTGTA | TACACTGTGA | GGGGTAAACC | ACGTACTCAA | GCCTCAGTAA | 300 |
| TGGTGGATGT | CCCTTCCCCC | ACCAAGCTTG | AGTGCCCCAG | GTCTACTTCA | GACTGCTGTG | 360 |
| CTGGCAGCAA | GAATTTCAAA | CCAGTGGATC | TTAGCTTGCT | GGGCTTCTTG | GGG | 413 |

(2) INFORMATION FOR SEQ ID NO:115:

(i) SEQUENCE CHARACTERISTICS:
(A) LENGTH: 283 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: H989.seq (xi) SEQUENCE DESCRIPTION: SEQ ID NO:115:

| | | | | | | |
|---|---|---|---|---|---|---|
| GGTGCCTATG | CCACCAGGGC | CCTGGGTTTC | AAGCATAAAA | CGAAGTGGCC | GGTTCACCAG | 60 |
| ACACCGAGCT | AGCTACAAGA | GTTTTTTTTC | ATACCCCAGT | GGCAGTGGAA | CACCAGCGAC | 120 |
| ACAGAATCAT | TTACTCCCCT | GGAAAGGGGC | TGAAGCCAAG | AAACCAAAGG | GGCTGGCTCA | 180 |
| GCGGATCCCA | CTCCCATGGA | GCCCAGCAAG | CTAAGATCCA | CTGGCTTGAA | ATTCTCGCTG | 240 |
| CCAGCACAGC | AGTCTGAAGT | TGACCTGGGA | TGCTCGAGCT | TGG | | 283 |

(2) INFORMATION FOR SEQ ID NO:116:

(i) SEQUENCE CHARACTERISTICS:
(A) LENGTH: 768 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(C) INDIVIDUAL ISOLATE: E118con.seq (xi) SEQUENCE DESCRIPTION: SEQ ID NO:116:

| | | | | | | |
|---|---|---|---|---|---|---|
| TGCCTGGAAT | TATTATATGC | TCATCACTTT | ATGAAGAATA | AAATTTGTCT | TTCCTGCCTT | 60 |

```
AAAGTTACAT  TCGTTCTTCC  GCTCAAATCC  TGATCTGGTC  CATTAAAGAG  TGTTCGCAGA    120

CAAAGTTTCT  GAAAGATTAG  AGAAGAATCC  CCCCCAAGAT  TGCCCCAACA  CTGAACTACA    180

GACAAACACT  ATTTTATTTA  AATAAGGAGA  CAGCTTTCTA  AAAGTATACA  TTCTCTAATA    240

AAAATAGTTT  ATTATTTTGA  ATGATTTAAT  GGTTTTCTAC  ACAATTTACA  TCACAACATG    300

TAAATTTTAG  CAGTAACATC  TGATTCTAAC  AGCACATCAT  GCTATTCCTT  TCATAGAGCC    360

TTCAGAGATT  CAATGCTAAA  CAAATTTCCT  TAGTTGGCAT  CAAGGCACTG  ATCACTTTAG    420

AGGCTTTTAA  GAAATTATTT  AAAGATGCAA  ATGCCTCTGA  GTGAAGTGTA  CTATCCCATC    480

ACTGAAGCCC  ACAGGAACAA  GTCCTACAAT  TTTAAAAAGG  CTCGATGGAA  AAATTTCTCA    540

ATCCTGAAAT  CCCCTAGGGA  AGGGGTCAGG  AGAAAGTGCC  ATGGTTGATA  TTTAAGAACT    600

CCACAGCTCT  TAAAAATAAG  CACTTATCCC  TAACATGCAA  TACTGCAGAT  GCAAGTTAAA    660

CTTATCTGTT  AACAGCTGCC  TGCTGTTTTC  TGCTCCAGA  TGAAATGAAG  CAACTCTTCT    720

GATAACGAAG  AGATACCTGT  CTGAGGCAAA  CGAAACATTG  GCACACAG                 768
```

( 2 ) INFORMATION FOR SEQ ID NO:117:

( i ) SEQUENCE CHARACTERISTICS:
        ( A ) LENGTH: 493 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: E69f.seq ( x i ) SEQUENCE DESCRIPTION: SEQ ID NO:117:

```
GGGTCATTTT  TGCTGTCACC  AGCAACGTTG  CCACGACGAA  CATCCTTGAC  AGACACATTC    60

TTGACATTGA  AGCCCACATT  GTCCCCAGGA  AGAGCTTCAC  TCAAAGCTTC  ATGGTGCATT    120

TCGACAGATC  TCACTTCCGT  TGTAACGTTG  ACTGGAGCAA  AGGTGACCAC  CATACCGGGT    180

TTGAGAACAC  CAGTCTCCAC  TCGGCCAACA  GGAACAGTAC  CAATACCACC  AATTTTGTAG    240

ACATCCTGGA  GAGGCAGGCG  CAAGGGCTTG  TCAGTTGGAC  GAGTTGGTGG  TAGGATGCAG    300

TCCCAGAGCC  TCAAGCAGGG  TTGGGTTCCC  ACTGGCATTG  CCATCCCTTA  CGGGTTGACT    360

TTCCATCCCC  TTGGACCCAA  GGCATTTTTA  GCACTTGGGT  TCCCAGCATG  TTGTCACCAA    420

TCCCAACCAA  GAATTTGGAA  AAATTNTACT  GNGTCGGGGT  TGGTAGCCAA  TTTCTTATGT    480

AGTGTGNTCC  CTA                                                          493
```

( 2 ) INFORMATION FOR SEQ ID NO:118:

( i ) SEQUENCE CHARACTERISTICS:
        ( A ) LENGTH: 483 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: E69r.seq ( x i ) SEQUENCE DESCRIPTION: SEQ ID NO:118:

| | | | | | |
|---|---|---|---|---|---|
| CAGCCAAATT | CTACTGGAGG | TACAAAGAGG | AGTTGGTACC | ATTCCTTCGG | AAACTATTCC | 60 |
| AATCAATAGA | AAAAGAGAGA | ATCCTCCCTA | ACTCATTTCA | TGAGAACAGG | ATCATCCTGA | 120 |
| TACTAAAGCC | GGGCAGAGAC | ACAACAAAAT | NNGGAATTTT | AAGCCAATAT | CCCTGATGAA | 180 |
| CATCAATGCA | AAAATCCTCA | ATAAAATACT | GGCAAACGAA | ATCCAGCAGC | ACATCAAAAA | 240 |
| GCTTATCCAC | CATGGTCAGG | CCGGGTTCAT | CCCTGGGATT | CAAGGCTGGT | TCAACATATG | 300 |
| CAAATCAATA | AATGTNATCC | ATCACATNAA | CAGAACCCAA | CGNCAAAAAC | CACATGATTA | 360 |
| TCTCAATAGA | TTGTAGAAAA | GGCCTCCGAC | AAAAANTCAA | CAACCCTTCA | AGCTAAAANN | 420 |
| TCTCAATAAA | CTATGTTTTG | ATGACATATT | CAAAATTATA | GAGTATTTGA | AACCACGGCA | 480 |
| TTA | | | | | | 483 |

( 2 ) INFORMATION FOR SEQ ID NO:119:

( i ) SEQUENCE CHARACTERISTICS:
    ( A ) LENGTH: 707 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: E36.seq ( x i ) SEQUENCE DESCRIPTION: SEQ ID NO:119:

| | | | | | |
|---|---|---|---|---|---|
| CGAGGACCAA | ACTCAGGACA | CCGAGCTTGT | GGAGACCAGA | CCAGCAGGAG | ATAGAACCTT | 60 |
| CCAGAAGTGG | GCAGCTGTGG | TGGTGCCTTC | TGGAGAAGAG | CAGAGATACA | CATGCCATGT | 120 |
| ACAGCATGAG | GGGCTGCCGA | AGCCCCTCAC | CCTGAGATGG | GAGCCATCTT | CNCAGTCCAC | 180 |
| CATCCCCATC | GTGGGCATTG | TTGCTGGACC | TGGCTGTCCT | AGCAGTTGTG | TCATATCGGA | 240 |
| GCCTGTGGTC | GCCACTGTGA | TGTGTAGGAG | GAAGAAGCTC | AGTGGAATAA | GGAGGGAGCC | 300 |
| AACTGTCAGG | CTGCCGTGCC | AGCGACAGTG | CCCAGGGGCG | CTGATGTGTC | TCTCACAGCT | 360 |
| TGGGAAGCCT | GAGGCAAGCT | GTGCTTGTGA | GGGGCTGAGA | TGCAGGGATT | TCTTGACGCC | 420 |
| TCCCCTTTGT | GACTTCAAGA | GCCTCTGGCA | TCTCTTTCTG | CAAAGGCACC | TGAATGTGTC | 480 |
| TGCGTCCCTG | TTAGCATAAT | GTGAGGAGGT | GGAGAGACAG | CCCACCCTTG | TGTCCACTGT | 540 |
| GACCCCTGTT | CCCATGCTGA | CCTGTGTTTC | CTCCCCGTCN | CTAATTAGAT | GACGAGGCAT | 600 |
| TTGGCTACCT | TAAGAGAGTC | ATAGTTACTC | CCGCCGTTTA | CCCGCGCTTC | ATTGAATTTC | 660 |
| TTCACTTTGA | CATTCAGAGC | ACTGGGCAGA | AATCACATCG | CCTCAAC | | 707 |

( 2 ) INFORMATION FOR SEQ ID NO:120:

( i ) SEQUENCE CHARACTERISTICS:
    ( A ) LENGTH: 324 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO (v i) ORIGINAL SOURCE:
  (C) INDIVIDUAL ISOLATE: A104f.seq (x i) SEQUENCE DESCRIPTION: SEQ ID NO:120:

| | | | | | | |
|---|---|---|---|---|---|---|
| CATGAAGTCA | CTGAGCCTGC | TCCACCTCTT | TCCTCTCCCA | AGAGCTAAAA | GAGAGCAAGG | 60 |
| AGGAAACAAC | AGCAGCTCCA | ACCAGGGCAG | CCTTCCTGAG | AAGATGCAAC | CAATCCTGCT | 120 |
| TCTGCTGGCC | TTCCTCCTGC | TGCCCAGGGC | AGATGCAGGG | GAGATCATCG | GGGACATGA | 180 |
| GGCCAAGCCC | CACTCCCGCC | CCTACATGGG | TTATCTTATG | ATCTGGGATC | AGAAGTCTCT | 240 |
| GAAGAGGTGC | GGTGGCTTCC | TGATACAAGA | CGACTTCGTG | CTGACAGNTG | CTCACTGTTG | 300 |
| GGGAAGCTCC | ATAAATGTCA | CCTA | | | | 324 |

(2) INFORMATION FOR SEQ ID NO:121:

(i) SEQUENCE CHARACTERISTICS:
    (A) LENGTH: 387 base pairs
    (B) TYPE: nucleic acid
    (C) STRANDEDNESS: double
    (D) TOPOLOGY: linear (i i) MOLECULE TYPE: cDNA to mRNA (i i i) HYPOTHETICAL: NO (i v) ANTI-SENSE: NO (v i) ORIGINAL SOURCE:
    (C) INDIVIDUAL ISOLATE: A104r.seq (x i) SEQUENCE DESCRIPTION: SEQ ID NO:121:

| | | | | | | |
|---|---|---|---|---|---|---|
| ACTACTACTA | CTACTAACTC | GAGAATTCTG | GATCCTCGGC | TTAGTTTGCT | TCCTGTAGTT | 60 |
| AGTAGCGTTT | CATGGTTTTC | TTTATCCAGT | GTACAAAGCT | TGAGACTTTG | GTGCAGGCTC | 120 |
| GTGGAGGCAT | GCCATTGTTT | CGTCCATAGG | AGACAATGCC | CTGGGCCACC | TTTGTTACAC | 180 |
| ACAAGGAGGG | CGCTCCAGAG | TCCCCCTTAA | AGGAAGTCTT | TTNAATCTCT | GGGTCCCCCA | 240 |
| CGCACAACTC | AAGGGTACTG | TCGNAATAAT | GGCGTAAGTC | AGATTCGCAC | TTTTCGATCT | 300 |
| NCCTGCACTG | TCATCTTCAC | CTCTAGGTAG | TGTGTGTGAG | TTGTGATGCC | CAGGGGGGN | 360 |
| CCNNCTGNCC | CCAGNCGGGN | CANACTN | | | | 387 |

(2) INFORMATION FOR SEQ ID NO:122:

(i) SEQUENCE CHARACTERISTICS:
    (A) LENGTH: 562 base pairs
    (B) TYPE: nucleic acid
    (C) STRANDEDNESS: double
    (D) TOPOLOGY: linear (i i) MOLECULE TYPE: cDNA to mRNA (i i i) HYPOTHETICAL: NO (i v) ANTI-SENSE: NO (v i) ORIGINAL SOURCE:
    (C) INDIVIDUAL ISOLATE: H622.seq (x i) SEQUENCE DESCRIPTION: SEQ ID NO:122:

| | | | | | | |
|---|---|---|---|---|---|---|
| GGAACGTCTG | AGGTTATCAA | TAAGCTCCTA | GTCCAGACGC | CATGGGTCAT | TTCACAGAGG | 60 |
| AGGACAAGGC | TACTATCACA | AGCCTGTGGG | GCAAGGTGAA | TGTGGAAGAT | GCTGGAGGAG | 120 |
| AAACCCTGGG | AAGGCTCCTG | GTTGTCTACC | CATGGACCAG | AGGTTCTTTG | ACAGATTTGG | 180 |
| CAACCTGTCC | TCTGCCTCTG | CCATCATGGG | TAACCCAAAG | TCAAGGCACA | TGGCAAGAGG | 240 |
| GTGCTGACTT | CCTTGGGAGA | TGCCATAAAG | CACCTGGATG | ATCTCAAGGG | CACCTTTGCC | 300 |

| | | | | | | |
|---|---|---|---|---|---|---|
| CAGCTGAGTG | AACTGCGCTG | TGACAACCTG | CATGTGGATC | CTGAGAACTT | CAAGCTCCTG | 360 |
| GGAAATGTGC | TGGTGGCCGT | TTTGGCAATC | CATTTCGGCA | AAGAATTCAC | CCCTGAGGTG | 420 |
| CAGTCTTCCT | GGCAGAAGAT | GGTGACTGGA | GTGGCCAGTG | CCCTGTCCTC | CAGATACCAC | 480 |
| TGAGCTCACT | GCCCATGATG | CAGAGCTTTC | AAGGATAGGC | TTTATTCTGC | AAGCAATCAA | 540 |
| ATAATAAATC | TATTCTGCTA | AG | | | | 562 |

( 2 ) INFORMATION FOR SEQ ID NO:123:

( i ) SEQUENCE CHARACTERISTICS:
        ( A ) LENGTH: 692 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G61con.seq ( x i ) SEQUENCE DESCRIPTION: SEQ ID NO:123:

| | | | | | | |
|---|---|---|---|---|---|---|
| GTGGGAGGTA | GCCACCTGTT | CTGGGCTGTG | TCTGTCCTGC | TGCCTGCTGG | AGAGGCCAGC | 60 |
| AATGAGTCCT | GGGCCAGCCC | AGATCTCACC | TGTGTGTTGA | ATACTAAACA | AGGAGACAAG | 120 |
| TAAAATAAGT | CCAGCATGAG | TCAGATGCTA | GGTCTTGGCT | TGGGGAAGCA | TGCCCTCAAG | 180 |
| TGCCATAAAC | ACCTAGAGGA | CAAATGGGAG | CAGAGGATCA | AGAGCTTCTG | CCTGCCTGTA | 240 |
| CAGCACCTTT | GGTGCAAAGT | AGGAAGAAGT | CTCACTCTGG | GTGGATAACT | TTCTTAAAGG | 300 |
| CACACCTCCC | TCTAGGCTAA | GGCAGCCCCA | TGCCGCAGGG | TCTAATCTTG | TCAATCAAAA | 360 |
| TACCCACCCA | TCAGTGACAA | TATGAGTGGC | TTCTGCAGCA | TTCAGGGGAA | TTTTGTCAGA | 420 |
| GATAGGGAGG | CCAAGATCCA | AGTGGAGGAA | GCCTGACTAG | CAGAGTCTGT | GGAAGAACTG | 480 |
| CAATGGGGGA | TGAGTCTTCA | GGGTCTTGTG | CCTGAGCAAT | GTGGGTTGTG | GGAGAGGATT | 540 |
| CTGGAGAAGG | TTTTATTTGG | ATGGTAGAGG | ATCCCTCCAT | TTAGCTGCTG | AGTCAAGAGG | 600 |
| AAGAGAGTGG | AGTCCAGGAG | GGTAGTAGGA | GGTCGTTATG | ATGTTATGGA | TAAGAATAGA | 660 |
| TGTGGTCCAA | GGATGGCTTG | AGTCATGGCT | GG | | | 692 |

( 2 ) INFORMATION FOR SEQ ID NO:124:

( i ) SEQUENCE CHARACTERISTICS:
        ( A ) LENGTH: 289 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G45.seq ( x i ) SEQUENCE DESCRIPTION: SEQ ID NO:124:

| | | | | | | |
|---|---|---|---|---|---|---|
| CCCAAGATAG | GCCGGGGCAG | GGAGAAGTAG | GGATGGATGG | GATCCCCACA | GTGTGACATA | 60 |
| GCATGGCTGT | GAATGAGGTG | GGTGGGCGAG | GGTGAGCCCC | AGAAGCCAGG | ACATCTGGAC | 120 |
| TCCAGCTAAG | GGTGTGGAAA | CAGGCTATGA | AGATCGCCAG | GGAGAAGTGA | CTCATAGTTG | 180 |

| TCCCCACCTG | ACTACTCCGT | TGACTACACT | CCTGGTGCTG | GGAAAGGCCT | CCCTGCCATC | 240 |
| CAGTCTTTCT | CTCCTCTCTC | CACTCTGCAG | GAACAACTCC | AGCCTCTAC | | 289 |

( 2 ) INFORMATION FOR SEQ ID NO:125:

( i ) SEQUENCE CHARACTERISTICS:
        ( A ) LENGTH: 1200 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G3con.seq ( x i ) SEQUENCE DESCRIPTION: SEQ ID NO:125:

| ATGTATGTTT | GGCTCTGCTT | TTAACTTTAT | AAATCCAGTG | ACCTCTCTCT | CTGGGACTTG | 60 |
| GTTTCCCCAA | CTAAAATTTG | AAGTAGTTGA | ATGGGGTCTC | AAAGTTTGAC | AGGAACCTTA | 120 |
| AGTAATCATC | TAAGTCAGTA | CCCACCACCT | TCTTCTCCTA | CATATCCCTT | CCAGATGGTC | 180 |
| ATCCAGACTC | AGAGCTCTCT | CTACAGAGAG | GGAAATCTCC | ACTGTTGCAC | ACCCACCTTT | 240 |
| GGAAAGCTCT | GACCACTTGA | GGCCTGATCT | GCCCATCGTG | AAGAAGCCTG | TAACACTCCT | 300 |
| CTGCGTCTAT | CCTGTGTAGC | ATACTGGCTT | CACCATCAAT | CCTGATTCCT | CTCTAAGTGG | 360 |
| GCATTGCCAT | GTGGAAGGCA | AGCCAGGCTC | ACTCACAGAG | TCAAGGCCTG | CTCCCTGTAG | 420 |
| GGTCCAACCA | GACCTGGAAG | AACAGGCCTC | TCCATTTGCT | CTTCAGATGC | CACTTCTAAG | 480 |
| AAAAGCCTAA | TCACAGTTTT | TCCTGGAATT | GCCAGCTGAC | ATCTTGAATC | CTTCCATTCC | 540 |
| ACACAGAATG | CAACCAAGTC | ACACGCTTTT | GAATTATGCT | TTGTAGAGTT | TTGTCATTCA | 600 |
| GAGTCAGCCA | GGACCATACC | GGGTCTTGAT | TCAGTCACAT | GGCATGGTTT | TGTGCCATCT | 660 |
| GTAGCTATAA | TGAGCATGTT | TGCCTAGACA | GCTTTTCTCA | ACTGGGTCCA | GAAGAGAATT | 720 |
| AAGCCCTAAG | GTCCTAAGGC | ATCTATCTGT | GCTAGGTTAA | ATGGTTGGCC | CCAAAGATAG | 780 |
| ACAGGTCCTG | ATTTCTAGAA | CCCGTGACTG | TTACTTTATA | CAGCAAAGGG | AAACTTTGCA | 840 |
| GATGTGATTA | AAGCTAAGGA | CCTTAAGACA | GAGTATCCTG | GGGGTGGTGG | TGGGGTGGGG | 900 |
| GGGGGTCCTA | AATGTAATCA | CGAGTAAGAT | TAAGAGCAAA | TCAATTCTAG | TCATATATTA | 960 |
| AACATCCACA | ATAACCAAGA | TATTTTATC | CCAAGAATGC | AAGATTTCAG | AAAATGAAAA | 1020 |
| ATCTGTTGAT | AAATCCATCA | CTATAATAAA | ACCGAAGGTG | AAAAAAATTC | TGAAAAAATT | 1080 |
| CTAGCAGCTA | TATTTGATAA | AATTCAACAT | CTCCTAGCTT | TAGCAAACTC | ACAGTTTTGC | 1140 |
| AAATAATATT | TTCTTAATGT | TATCTGTTGC | TAAATCAAAA | TTAAACAGTC | ATCTTAACTG | 1200 |

( 2 ) INFORMATION FOR SEQ ID NO:126:

( i ) SEQUENCE CHARACTERISTICS:
        ( A ) LENGTH: 319 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO (v i) ORIGINAL SOURCE:
 (C) INDIVIDUAL ISOLATE: G30.seq (x i) SEQUENCE DESCRIPTION: SEQ ID NO:126:

| | | | | | |
|---|---|---|---|---|---|
| ACGTGGTATG | AAGTGTAAAG | TTCTACTTTT | AATTTTTGC | ATATTTTATT | AGGATAGGAT | 60 |
| GGGCTTTTTC | TGTAGTAATA | ATCCCTAAAT | CTCAGGGGCT | TAATATATAA | AATTGTCTCA | 120 |
| TGCAAAAAAC | CACTGGGTCT | AGGGCAATTG | CTATCTACTG | CCGTCTAATC | TCCCTCTAGT | 180 |
| GGCTTCCATT | GGTAGACCCT | AACAGGAAGC | CAGCTGATAA | GGGAATCTGG | GAAATGTAGT | 240 |
| TTACAGAGTG | GCAGCTACAG | TAGAACAGTA | GAGACTACAA | GGATGAGCTT | GCAGCTGAGA | 300 |
| ATAGAAACGT | GACTGGCAC | | | | | 319 |

(2) INFORMATION FOR SEQ ID NO:127:

(i) SEQUENCE CHARACTERISTICS:
  (A) LENGTH: 383 base pairs
  (B) TYPE: nucleic acid
  (C) STRANDEDNESS: double
  (D) TOPOLOGY: linear (i i) MOLECULE TYPE: cDNA to mRNA (i i i) HYPOTHETICAL: NO (i v) ANTI-SENSE: NO (v i) ORIGINAL SOURCE:
  (C) INDIVIDUAL ISOLATE: G32.seq (x i) SEQUENCE DESCRIPTION: SEQ ID NO:127:

| CAGAACTTGA | ATCTCTTCTG | TTAATGGCAA | CTCCATTATT | CCAATTGCTC | AGGCAAAAAT | 60 |
|---|---|---|---|---|---|---|
| TGGCATTAAC | CTTGATTCTT | TATCTTACAT | CTTATATCTA | ATTCGCCAGT | TTAATACTAT | 120 |
| GGGTTCAATT | TTCAAAACAT | CCGGAATCTG | ACCATGCCTC | ACCATTAAA | CCAGCAGTCC | 180 |
| CCAACCATTT | TGGCACCAGA | GACCGATTTA | GTGGAAGACA | ATTTTTCCAT | GGACGGGTGG | 240 |
| GGTGAGGGGG | ATGGTTTCGG | GATGAAACTG | TTCCACCTCA | GATCATCAGG | CATTAGTCAG | 300 |
| ATTCTCATAA | GGAGCATGCA | ACCTAGATCC | CTCACGTGCA | AATTCACAAT | AGAGTTTGCA | 360 |
| TTCCCGTGAG | AATCTAATGC | CAC | | | | 383 |

(2) INFORMATION FOR SEQ ID NO:128:

(i) SEQUENCE CHARACTERISTICS:
  (A) LENGTH: 407 base pairs
  (B) TYPE: nucleic acid
  (C) STRANDEDNESS: double
  (D) TOPOLOGY: linear (i i) MOLECULE TYPE: cDNA to mRNA (i i i) HYPOTHETICAL: NO (i v) ANTI-SENSE: NO (v i) ORIGINAL SOURCE:
  (C) INDIVIDUAL ISOLATE: G37.seq (x i) SEQUENCE DESCRIPTION: SEQ ID NO:128:

| GGATAATGCA | AAGGAAGACG | CTGCCTGGGA | ATTCACCGTC | TGTGGAAATG | AGTCCCAGAG | 60 |
|---|---|---|---|---|---|---|
| AGGAATAAAG | CAGCCCTCAC | CTTGCTCTCC | CCACCCGAAC | CCACTTTCCC | CACCCGCCTC | 120 |
| GGCCCCCACC | CCAACACCAC | CATCACTCCC | TTCCCTCCCT | CTACTGCAAT | CAGCTATTTT | 180 |
| CCATCATTCT | TACCTCCCTC | TCTTACACCA | TTCTTCATAG | AACAGCCTAT | TGTATTTTTT | 240 |
| AAGAGACTGT | GTTCCTCCTC | CACTTCTGTT | CAATGGCTTC | ATATTCACTT | AAATTAAAAT | 300 |

-continued

| | | | | | |
|---|---|---|---|---|---|
| TCAAACGTTT | ACCACGGCTT | TCAATGACCT | GAATGATGTG | CCTGCTGCCC | TCCTTTCCAA | 360
| TCTCACTTCA | GGACTCCTAC | CCTCTGGCTA | TTAGGAGGCT | GCAGCTG | | 407

( 2 ) INFORMATION FOR SEQ ID NO:129:

( i ) SEQUENCE CHARACTERISTICS:
        ( A ) LENGTH: 428 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G39.seq ( x i ) SEQUENCE DESCRIPTION: SEQ ID NO:129:

| | | | | | |
|---|---|---|---|---|---|
| GGGTGGGGTA | GGGGGAAGAG | GTGGACATCA | AAAAGGACCT | GACTCCAAGA | TGATATGCAA | 60
| TAATTAACCA | TTGGAGGGCA | GAAAGAGACT | AAACACTTTT | TTTTTCTTTT | TAATGAATAA | 120
| TTGCTAATAC | TCTGGAGATG | AAATACTTCT | AACTCCAAAT | CTATTTGTGC | TTTACATTTT | 180
| ACGTTTGGGG | TTAGCTTTGT | AAGGTGACAA | GCCACCTTAG | GTATAAGAAA | CAATGATTTT | 240
| CCCAAATGCT | GACTTTATGA | AAGGCCTATT | ACTCCCCAG | AGTATTTATT | GTTAGAAGTA | 300
| ATGGTTAAAA | TATATGATTG | CCTAGAAAGG | AAGTAAAAAA | TGAAAATCTG | AAACCCGTGG | 360
| TGAAAAGAGT | GAGGCAGCTG | TAACCTATTC | CTCAACTTCT | GAGTGTTAAC | AGGGCCCGTG | 420
| TGGGGTTG | | | | | | 428

( 2 ) INFORMATION FOR SEQ ID NO:130:

( i ) SEQUENCE CHARACTERISTICS:
        ( A ) LENGTH: 435 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G75.seq ( x i ) SEQUENCE DESCRIPTION: SEQ ID NO:130:

| | | | | | |
|---|---|---|---|---|---|
| GAATTCTGGA | TCCTCCCTCA | GTGGGTCCCT | CTCAAGAGGC | CATTTAAAAA | CCTGGACTGA | 60
| TAGAAACAGC | CAGTACTTTG | TGCCTCCTGC | ATCCATGTT | GGAGACAATT | GCCCTAACCA | 120
| CCCAGAGCAT | TGCTCAGCCT | ATAAACCCAT | TTCCAAGGAT | AGGGCCTGAC | TTCTTTGAGG | 180
| ATCATGAGTA | TGATTTCCAG | GTCTTTTCTG | ACCTCATTAA | TGACCTTCCT | GCTATGCACT | 240
| GGTCTCTAAA | CCCCTTGGCC | GTGATTGTGA | TGTGGAAATA | AATAGAAGGT | GCTTTATTCT | 300
| TAAGCAGAGA | TTCAGTGGCA | GAGGGTTTGA | TTTTGGAAAA | GAGAAAGGGC | GCAGGATCAA | 360
| GTGAGAATCT | TGTAGAATTG | TGAGGCCAGA | GGAGCTTTCT | CCTACCTTCA | TGACCTTGTT | 420
| GAGGATCCAG | AATTC | | | | | 435

( 2 ) INFORMATION FOR SEQ ID NO:131:

(i) SEQUENCE CHARACTERISTICS:
    (A) LENGTH: 373 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (v) ORIGINAL SOURCE:
    (C) INDIVIDUAL ISOLATE: H100.seq (xi) SEQUENCE DESCRIPTION: SEQ ID NO:131:

| | | | | | | |
|---|---|---|---|---|---|---|
| CCCCATCCTG | CCCGCTGCTA | CCAGCTACAC | CTCCGTTGCC | CAGGCCCTGG | GATCAAACCC | 60 |
| TGCCCACCAG | CTCCCCTCGT | CCAACCAGCT | GCCACGTCCT | GTAACCAAAA | GTGACCGGGA | 120 |
| TGAATGCCTG | GCTCCCCCTC | CTTTCCAGCC | CTAGCTCAGG | CCCATCGTCC | CCAGCTGATG | 180 |
| TCGCCCTGTC | TGCACGATGC | CTGGGCACCT | ACTCCACACT | CCTCACTGGC | CTCAGGCCCC | 240 |
| ACCAGCCCCT | GCCTCGAGCT | AGCCCCTCCA | CCCGTCATCA | CTCCTGCCAG | ACTCCAGATG | 300 |
| TCCAAGGTGC | TCCTTGGCTC | CCACAAGCTC | TCCTCCAGCA | CCCCATCTTC | CCCTGGTTGC | 360 |
| CCCTCGGTTC | CCC | | | | | 373 |

(2) INFORMATION FOR SEQ ID NO:132:

(i) SEQUENCE CHARACTERISTICS:
    (A) LENGTH: 312 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (v) ORIGINAL SOURCE:
    (C) INDIVIDUAL ISOLATE: H414f.seq (xi) SEQUENCE DESCRIPTION: SEQ ID NO:132:

| | | | | | | |
|---|---|---|---|---|---|---|
| GATCCATATC | TGGGGAAGA | GGATTCTATG | CTTGACTGAA | TATGGGATGT | GAAGGAGAAG | 60 |
| AAGTTGTGGC | CTCAATCTAC | CCAATTGGGA | GACTGGTGCA | TGGGCCATGG | TAGTGCCAAA | 120 |
| ACATAGAGCT | ATTAAGGTAA | GGAATGCAGG | AGGGAAGAGT | AGGCATGGTG | GAGAAGATAG | 180 |
| AGAAATCTAG | TTGTACTTAG | TAAGTTTGAG | GTAGGCTGAA | ATTCAGGTAA | CAGTTTTCTT | 240 |
| AGTAGGCAAT | TGGGGTGAGA | GATTTTGGAA | ATTTACCCTT | TAGATCAATT | TTTGGGGAGG | 300 |
| ATCCAAGAAT | CT | | | | | 312 |

(2) INFORMATION FOR SEQ ID NO:133:

(i) SEQUENCE CHARACTERISTICS:
    (A) LENGTH: 503 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (v) ORIGINAL SOURCE:
    (C) INDIVIDUAL ISOLATE: H631.seq ( x i ) SEQUENCE DESCRIPTION: SEQ ID NO:133:

| | | | | | | |
|---|---|---|---|---|---|---|
| CAGAAATGAG | CAAAGGCAAA | GGGGAATACA | GTGGGTCTGA | GGCTGGCTCA | CTGTCCCATT | 60 |
| CTGAGCAGAA | TGCCACTGTT | CCAGCTCCCA | GGGTGCTGGA | GTTTGACCAC | TTGCCAGATC | 120 |
| CTCAGGAGGG | CCCAGGGTCA | GATACTGGAA | CGCAGCAGGA | AGGAGTCCTG | AAGGATCTGA | 180 |
| GGACTGTGAT | TCCATACCGG | GAGTCTGAAA | CACAAGCAGT | CCCTCTTCCC | CTTCCCAAGA | 240 |
| GGGTAGAAAT | CATTGAATAT | ACCCACATAG | TTACATCACC | CAATCACACT | GGGCCAGGGA | 300 |
| GTGAAATAGC | CACCAGTGAG | AAGAGCGGAG | AGCAAGGGCT | GAGGAAAGTG | AACATGGAAA | 360 |
| AATCTGTCAC | TGTGCTCTGC | ACACTGGATG | AAAATCTAAA | CAGGACTCTG | GACCCCAACC | 420 |
| AGGTTTCTCT | GCACCCCCAA | GTGCTACCTC | TGCCTCATTC | TTCCTCCCCT | GAGCACAACA | 480 |
| GACCCACTGA | CCATCCAACC | TCC | | | | 503 |

( 2 ) INFORMATION FOR SEQ ID NO:134:

( i ) SEQUENCE CHARACTERISTICS:
        ( A ) LENGTH: 398 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G93.seq ( x i ) SEQUENCE DESCRIPTION: SEQ ID NO:134:

| | | | | | | |
|---|---|---|---|---|---|---|
| CCCTCCTATC | TTCTTTCTCA | TCCCTGCCTC | CCTCCCATGC | TGACTCCTGT | GTCCCTCCCT | 60 |
| TCAGTCACTC | TCCTGTCAAG | TGGCTCACCT | CTTGGGCCTC | CCCAAGGATC | CCATTCTGAA | 120 |
| AACCCCACCA | AGGCAATCCA | GTTGACGACC | TTCCTGCTCC | CTCCACAGCG | CAGCCCCCGA | 180 |
| GGATCACAGT | CTCTGTCCCA | GAGGGGCTCT | CTTCCCAGAA | ACTGTCAACA | CATGCCCCCT | 240 |
| TTAGACTCCT | CTCATCCTCA | GCCAGGACTC | TGACTCCCAT | TCCACAAAGG | AGGCAGAAGC | 300 |
| CGTCAGAGGA | CTCCCCGCAT | CTTCCTGGCC | TCCAGACTC | TTCTCTTACC | CCTTCCTTCC | 360 |
| TAGCAGGGCC | ATCTCCTCCC | TGGTACTTGG | AGACCTCC | | | 398 |

( 2 ) INFORMATION FOR SEQ ID NO:135:

( i ) SEQUENCE CHARACTERISTICS:
        ( A ) LENGTH: 629 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: G115a.seq ( x i ) SEQUENCE DESCRIPTION: SEQ ID NO:135:

| | | | | | | |
|---|---|---|---|---|---|---|
| CCTTTTTTTT | TTTTAGGGA | AGCCAATTTG | ATGATGTAGC | TTGTGACTCC | CAGGGTATTG | 60 |
| TCTACCCCAM | CCTGGGGGAA | AACATGGGGA | AGTTTCTGGG | ATCTAAGCTT | CAATCGCAAG | 120 |
| CATCACAGGG | GATTTTGAAA | GTGATGCAGC | ATCGTGAAAT | GAGCATAGGG | GATCGTTTGG | 180 |

| | | | | | | |
|---|---|---|---|---|---|---|
| AGTCGAGCGC | TTGTTATTTG | AAGCTCCTCC | TGTCTATGTG | GTGACTCAAG | GAGGGGAGAA | 240 |
| TTTCCCCTTT | GTGAGCCAGC | TGGACAAGTG | TCAGCACTGC | TGTCTTTGCA | GGCTCTGGCA | 300 |
| CAGAGGCGCA | GGGCCTGGAC | TAAAGGGAGT | CTCCAGGGTT | TGGGGGTCAG | ACCCAGCTTA | 360 |
| ACACACATGA | AAAGGAGTGA | TCTTTCTCTT | AAGCCATTGA | GCCAGGGTCC | CCCTACAGCC | 420 |
| CACAGAGCCC | TTTCCACCAC | CTGGCGCAGC | ATCTGAACCA | AACAGAGGGC | ATGTTTGTTG | 480 |
| CACTGCCTGG | GGGTTCAGCT | CCCATCCATA | CCACAACACA | GGACAAGGCC | CGGGCTTTGC | 540 |
| ACAGCACAGT | CAAGTGAGCA | CACTCTCACG | ATCTGATGCA | GTCCTTCTCC | CACACCCACC | 600 |
| ATCCAATTTT | TTCCGAGGAT | CCAGAATTC | | | | 629 |

(2) INFORMATION FOR SEQ ID NO:136:

(i) SEQUENCE CHARACTERISTICS:
        (A) LENGTH: 696 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G115b.seq (xi) SEQUENCE DESCRIPTION: SEQ ID NO:136:

| | | | | | | |
|---|---|---|---|---|---|---|
| GTGGCACATG | GAAAAAGTGG | TGGTGAGGGG | CAAGGAACAG | GGACAAAAAA | GGAACCTGGG | 60 |
| TCCTTAAGAG | ATCACTTAGT | TGTTTTACCC | AAGACTTGGC | RTACAAAAAA | TATCAGAAAT | 120 |
| GAGTGTCTGC | TGCCAAGTGG | GGTCACTGCA | CGTCCTAGAA | AAAAAGTATG | CCTTCATCTG | 180 |
| CAGTGACACA | CAGCCATGGT | GTTGGGACTG | GCACACTGCA | TCTCTAAGCC | GCCAAGAGCT | 240 |
| TGACCCTGGA | TGGGAAGAAA | ACTGCCCAG | AGATGCTGGA | GCTGGCTTTA | TGAACTGGCT | 300 |
| TTATGCTGGG | GAGGTGGATG | GCAGATCGCA | TCCATCTGGT | AGGTTGAGGT | CCTCTTGGCA | 360 |
| AGCCTACTAC | CATCACCTCC | CAGCAGAAGA | GGACTGCAAA | CTATCCTTAA | AGGGACTCG | 420 |
| GTCCAGTGAG | TCTTACCTTT | TTTTGAGGTC | ATACACCCCT | TCCGGAATCT | GATGGCACAC | 480 |
| ATAGACCCTT | TCCCCAGGAA | AATTCACAAA | CATCCAGAGT | TTCATATGCC | ACTAGGGGAT | 540 |
| TTAAAAGACC | CTGCATCAAC | TGAACTCATA | ACCTGGAGTC | CAATTCTTAT | GAGAGGGTGG | 600 |
| CACATGGAAA | AAGTGGTGGT | GAGGGGCAAG | GAACAGGGAC | AAAAAAGGAA | CCTGGGTCCT | 660 |
| TAAGAGATCA | CTTAGTTGTT | TTACCCAAGA | CTTGGC | | | 696 |

(2) INFORMATION FOR SEQ ID NO:137:

(i) SEQUENCE CHARACTERISTICS:
        (A) LENGTH: 574 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: G115c.seq (xi) SEQUENCE DESCRIPTION: SEQ ID NO:137:

```
GGAGGCCCCA  GACTGCTACT  CATACAGGCA  GCTGTATCTT  GTCTCCAGGA  GAGAGCAGGG       60

ACCCAGKATG  GAGCAGACAT  AGGTCTTCTG  GGGACTCAGC  CCTTTCGGGA  GGGAGTGTGT      120

GCCCTAGGCA  CACCCTTCCC  ATTTGACAAT  CTGATATGAG  GTGGAAACAG  GGTCCTTGGG      180

CCCCTAAGTC  ATGTTGGGAA  TGTTTCCTTC  TCTCAAGCCG  GAAGAGCTGA  GGTTTATCTG      240

AGAAATGCCT  ATGTCTCTTT  TGACACATCG  TAGTCACTAA  CCCCTTGTTC  CTGCTCCAGG      300

AGCCTCTAAA  AAGCCATCTA  GACCAGAAAA  ATTGGTCTTT  TTTTAGTGAT  GGGAGTGGCT      360

TTAATGTCAT  TCTCCCTAT   TTAGTTATGA  GCTGTACCTC  AGTTTTGGTC  ATTAGAAATA     420

TAATTTTAGG  TCAGGTGCAG  CGGCTCATGC  CTATAATCCC  ACACTTTGGG  AGGCTGAGGG     480

TGGGCAGGTT  ACTTGGAGGT  CAGGAGGTTA  AAGACCAGCC  TGGCAACATG  GTGGAAACCC     540

TATCTCCACT  TAAAATACAA  AAATTAGTTG  CATG                                  574
```

( 2 ) INFORMATION FOR SEQ ID NO:138:

( i ) SEQUENCE CHARACTERISTICS:
    ( A ) LENGTH: 252 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: G122.seq ( x i ) SEQUENCE DESCRIPTION: SEQ ID NO:138:

```
GCTCTGACTA  GCCAATGAGT  CTTGCTCTGA  TATGGCACCT  GCAAAATCTC  TTTCTGGGGT      60

CTTCCACTGC  CTAACTTTAG  CCCCAGTAAT  TTACTAGGTT  CTGGCACATG  GCCCATGATC     120

CTGACACCAG  GCCTGCCTTT  GTTTCAGCTT  CACTATTCTA  ATCTTTGCAT  TAATAGCTTG     180

TAATACCCTG  GTGGCTATCA  TTATATAGTG  TATATGTGCA  ATATCAGTAT  GGCTGACCTA     240

GGTCAGTCCT  GT                                                             252
```

( 2 ) INFORMATION FOR SEQ ID NO:139:

( i ) SEQUENCE CHARACTERISTICS:
    ( A ) LENGTH: 278 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: G329f.seq ( x i ) SEQUENCE DESCRIPTION: SEQ ID NO:139:

```
GTTGATCGGT  GATGCCGCAA  AGAATCAAGT  TGCAATGAAC  CCCACCAACA  CAGTTTTTGA      60

TGCCAAACGT  CTGATTGGAC  GCAGATTTGA  TGATGCTGTT  GTCCAGTCTA  ATATGAAACA     120

TTGGCCCTTT  ATGGTGGTGA  ATGATGCTGG  CAGGCCCAAG  GTCCAAGTAG  AATACAAGGG     180

AGAGACCAAA  AGCTTCTATC  CAGAGGAGGT  GTCTTCTATG  GTTCTGACAA  AGATGAAGGA     240

AATTGCAGAA  GTCTACCTTG  GGAAGACTGT  TACCAATG                               278
```

( 2 ) INFORMATION FOR SEQ ID NO:140:

( i ) SEQUENCE CHARACTERISTICS:
        ( A ) LENGTH: 795 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: E67.seq ( x i ) SEQUENCE DESCRIPTION: SEQ ID NO:140:

```
GCGCGGGGTG  GACTCTTTCT  GGATGTTGTA  GTCAGACAGG  GTGCGTCCAT  CTTCCAGCTG        60
TTTCCCAGCA  AAGATCAACC  TCTGCTGGTC  AGGAGGGATG  CCTTCCTTGN  CTTGGGTCTT       120
TGNCTTGACA  TTCTCAATGG  TGTCACTCGG  TTCCACTTCG  AGAGTGATGG  TCTTACCAGC       180
CAGGGTCTTC  ACGAAGGATC  TGCATCCCAC  CTCTAAGACG  GAGCACCAGG  TGCAGGGTGG       240
GGACTCTTTT  CTGGATGTTG  TAGACAGACA  GGGTGCGTCC  ATCTTCCAGG  TGTTTCCCAG       300
GAAAGGTCAA  ACTCTGCTGA  TCAAGAGGAT  GCTCCTTGTC  TGGATCTTTG  CCTTGACATC       360
TCAATGGTGT  CACTCGGCTC  CACCTCGAGA  GTGATGGTCT  TACCAATCAG  GGTCTTCNCG       420
GAAGATCTNC  ATCCCACCTC  TGAGTCGGAG  CACGCAGGTG  CAAGGTGGAC  TCTTTCTGGA       480
TGTTGTAGTC  AGACAGGGTA  CCGACCATCT  TCCACCTGTT  TTCCGGCAAA  GATCAACCTC       540
TGCTGGTCAG  GAGGGATCCC  TTCCTTGTCT  GGAGCTTTG   CCTTGACATT  CTCAATGGTG       600
TCACTCGGCT  CCACTTCGAG  GGTGATGGTC  TTACCANTNA  GGGTCTTCAC  GAAGAACTGC       660
ATACCCCCTC  TGAGANGGAC  CACCAGGTGC  AGGGNAGACT  CTTTCTGGAT  GTTGTAGTCA       720
GANAGGGTGC  GCCCATCTTC  CAGCTGCTTT  CCGGCAAAGA  TCAACCTCTC  CTGGTCAGGA       780
GGAATGCCTT  CCTTG                                                             795
```

( 2 ) INFORMATION FOR SEQ ID NO:141:

( i ) SEQUENCE CHARACTERISTICS:
        ( A ) LENGTH: 565 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: E94.seq ( x i ) SEQUENCE DESCRIPTION: SEQ ID NO:141:

```
GTCACTGTAG  AAGTATTTTA  ATGTGTCAAA  ACTTCCATCT  GCATGTTTCT  TTAATTTGCA        60
GAGGATTGAT  TATTAGCTCT  TTGTGCCAAA  TAACTGTCAC  TCATTTAAA   ATCTTTCCCA       120
AACACAGGTA  CTATTTCTAT  TCTACATAAT  GGGAGAATGT  GCCAGTAGGA  GACTGCCTGG       180
CCAACTCTGA  AAAAAATGCT  TTAACAATAT  GCCCCAGCTA  AAATCACTTT  TCCTTTATTT       240
CCACAAATCA  AATTCAAAAT  CAAAACTCAT  TATGGTATAC  CTTATATAAC  TCGGATCATG       300
TTTATAAAAT  TAGCATTCTT  TGGATAGTAA  AACACCAGTT  AATACTTAAT  TTGTTTACCC       360
```

```
ATGCACAAAA CTACCTCCCG AGATTAGACT AAGTCCCTTT AAGGATTTTA GGTCTCCATT      420

TTGAGNTGTT TTGATTTATA GAAGGATCTG AAAAAAAATC GAGGAGAAGT CGTTTTCCTC      480

CTTTGTAAAC CTTCTGCCCA GAGGCCGGCG ACGNATGCAC CAGCAAGGAC AAGCCCAGTC      540

TTTTCAAGCG ACACCTGTTC GCCTG                                            565
```

( 2 ) INFORMATION FOR SEQ ID NO:142:

( i ) SEQUENCE CHARACTERISTICS:
        ( A ) LENGTH: 420 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: CDC.pep ( x i ) SEQUENCE DESCRIPTION: SEQ ID NO:142:

```
Met Ala Ala Thr Asp Leu Glu Arg Phe Ser Asn Ala Glu Pro Glu Pro
  1               5                  10                  15

Arg Ser Leu Ser Leu Gly Gly His Val Gly Phe Asp Ser Leu Pro Asp
                 20                  25                  30

Gln Leu Val Ser Lys Ser Val Thr Gln Gly Phe Ser Phe Asn Ile Leu
                 35                  40                  45

Cys Val Gly Glu Thr Gly Ile Gly Lys Ser Thr Leu Met Asn Thr Leu
         50                  55                  60

Phe Asn Thr Thr Phe Glu Thr Glu Glu Ala Ser His His Glu Ala Cys
 65                  70                  75                  80

Val Arg Leu Arg Pro Gln Thr Tyr Asp Leu Gln Glu Ser Asn Val Gln
                 85                  90                  95

Leu Lys Leu Thr Ile Val Asp Ala Val Gly Phe Gly Asp Gln Ile Asn
                100                 105                 110

Lys Asp Glu Ser Tyr Arg Pro Ile Val Asp Tyr Ile Asp Ala Gln Phe
                115                 120                 125

Glu Asn Tyr Leu Gln Glu Glu Leu Lys Ile Arg Arg Ser Leu Phe Asp
            130                 135                 140

Tyr His Asp Thr Arg Ser Thr Val Trp Leu Tyr Phe Ile Thr Pro Thr
145                 150                 155                 160

Gly His Ser Leu Lys Ser Leu Asp Leu Val Ala Met Lys Lys Leu Asp
                165                 170                 175

Ser Lys Val Asn Ile Ile Pro Ile Ile Ala Lys Ala Asp Thr Ile Ser
                180                 185                 190

Lys Ser Glu Leu His Lys Phe Lys Ile Lys Ile Met Gly Glu Leu Val
            195                 200                 205

Ser Asn Gly Val Gln Ile Tyr Gln Phe Pro Thr Asp Asp Glu Ala Val
            210                 215                 220

Ala Glu Ile Asn Val Val Met Asn Ala His Leu Pro Phe Ala Val Val
225                 230                 235                 240

Gly Ser Thr Glu Glu Val Lys Val Gly Asn Lys Leu Val Arg Ala Arg
                245                 250                 255

Gln Tyr Pro Trp Gly Val Val Gln Val Glu Asn Glu Asn His Cys Asp
            260                 265                 270
```

```
Phe  Val  Lys  Leu  Arg  Glu  Met  Leu  Ile  Arg  Val  Asn  Met  Glu  Asp  Leu
     275                 280                           285

Arg  Glu  Gln  Thr  His  Ser  Arg  His  Tyr  Glu  Leu  Tyr  Arg  Arg  Cys  Lys
     290                      295                 300

Leu  Glu  Glu  Met  Gly  Phe  Gln  Asp  Ser  Asp  Gly  Asp  Ser  Gln  Pro  Phe
305                      310                 315                           320

Ser  Leu  Gln  Glu  Thr  Tyr  Glu  Ala  Lys  Arg  Lys  Glu  Phe  Leu  Ser  Glu
               325                      330                           335

Leu  Gln  Arg  Lys  Glu  Glu  Glu  Met  Arg  Gln  Met  Phe  Val  Asn  Lys  Val
          340                      345                           350

Lys  Glu  Thr  Glu  Leu  Glu  Leu  Lys  Glu  Lys  Glu  Arg  Glu  Leu  His  Glu
          355                 360                      365

Lys  Phe  Glu  His  Leu  Lys  Arg  Val  His  Gln  Glu  Glu  Lys  Arg  Lys  Val
     370                      375                 380

Glu  Glu  Lys  Arg  Arg  Glu  Leu  Glu  Glu  Glu  Thr  Asn  Ala  Phe  Asn  Arg
385                      390                      395                      400

Arg  Lys  Ala  Gly  Trp  Glu  Ala  Cys  Ser  Arg  Arg  Pro  Cys  Thr  Pro  Pro
                    405                      410                      415

Arg  Ser  Ser  Pro
               420
```

( 2 ) INFORMATION FOR SEQ ID NO:143:

( i ) SEQUENCE CHARACTERISTICS:
( A ) LENGTH: 321 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: Septin- 2.pep ( x i ) SEQUENCE DESCRIPTION: SEQ ID NO:143:

```
Met  Ala  Ala  Thr  Asp  Leu  Glu  Arg  Phe  Ser  Asn  Ala  Glu  Pro  Glu  Pro
1                   5                      10                          15

Arg  Ser  Leu  Ser  Leu  Gly  Gly  His  Val  Gly  Phe  Asp  Ser  Leu  Pro  Asp
               20                 25                      30

Gln  Leu  Val  Ser  Lys  Ser  Val  Thr  Gly  Phe  Ser  Phe  Asn  Ile  Leu
          35                  40                      45

Cys  Val  Gly  Glu  Thr  Gly  Ile  Gly  Lys  Ser  Thr  Leu  Met  Asn  Thr  Leu
     50                      55                      60

Phe  Asn  Thr  Thr  Phe  Glu  Thr  Glu  Glu  Ala  Ser  His  His  Glu  Ala  Cys
65                       70                      75                       80

Val  Arg  Leu  Arg  Pro  Gln  Thr  Tyr  Asp  Leu  Gln  Glu  Ser  Asn  Val  Gln
               85                       90                      95

Leu  Lys  Leu  Thr  Ile  Val  Asp  Ala  Val  Gly  Phe  Gly  Asp  Gln  Ile  Asn
               100                      105                     110

Lys  Asp  Glu  Ser  Tyr  Arg  Pro  Ile  Val  Asp  Tyr  Ile  Asp  Ala  Gln  Phe
          115                      120                     125

Glu  Asn  Tyr  Leu  Gln  Glu  Glu  Leu  Lys  Ile  Arg  Arg  Ser  Leu  Phe  Asp
     130                      135                     140

Tyr  His  Asp  Thr  Arg  Ser  Thr  Val  Trp  Leu  Tyr  Phe  Ile  Thr  Pro  Thr
145                      150                     155                      160
```

```
Gly  His  Ser  Leu  Lys  Ser  Leu  Asp  Leu  Val  Ala  Met  Lys  Lys  Leu  Asp
               165                 170                           175

Ser  Lys  Val  Asn  Ile  Ile  Pro  Ile  Ile  Ala  Lys  Ala  Asp  Thr  Ile  Ser
               180                 185                           190

Lys  Ser  Glu  Leu  His  Lys  Phe  Lys  Ile  Lys  Ile  Met  Gly  Glu  Leu  Val
          195                      200                      205

Ser  Asn  Gly  Val  Gln  Ile  Tyr  Gln  Phe  Pro  Thr  Asp  Asp  Glu  Ala  Val
          210                 215                      220

Ala  Glu  Ile  Asn  Val  Val  Met  Asn  Ala  His  Leu  Pro  Phe  Ala  Val  Val
225                      230                 235                           240

Gly  Ser  Thr  Glu  Glu  Val  Lys  Val  Gly  Asn  Lys  Leu  Val  Arg  Ala  Arg
               245                      250                           255

Gln  Tyr  Pro  Trp  Gly  Val  Val  Gln  Val  Glu  Asn  Glu  Asn  His  Cys  Asp
               260                      265                      270

Phe  Val  Lys  Leu  Arg  Glu  Met  Leu  Ile  Arg  Val  Asn  Met  Glu  Asp  Leu
          275                      280                 285

Arg  Glu  Gln  Thr  His  Ser  Arg  His  Tyr  Glu  Leu  Tyr  Arg  Arg  Cys  Lys
          290                 295                 300

Leu  Glu  Glu  Met  Gly  Phe  Gln  Asp  Ser  Asp  Gly  Asp  Ser  Gln  Pro  Phe
305                      310                      315                      320

Arg
```

( 2 ) INFORMATION FOR SEQ ID NO:144:

( i ) SEQUENCE CHARACTERISTICS:
        ( A ) LENGTH: 645 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: G18.pep ( x i ) SEQUENCE DESCRIPTION: SEQ ID NO:144:

```
Met  Ser  Arg  Ile  Glu  Lys  Met  Ser  Ile  Leu  Gly  Val  Arg  Ser  Phe  Gly
1                   5                     10                           15

Ile  Glu  Asp  Lys  Asp  Lys  Gln  Ile  Ile  Thr  Phe  Phe  Ser  Pro  Leu  Thr
               20                 25                           30

Ile  Leu  Val  Gly  Pro  Asn  Gly  Ala  Gly  Lys  Thr  Thr  Ile  Ile  Glu  Cys
          35                 40                      45

Leu  Lys  Tyr  Ile  Cys  Thr  Gly  Asp  Phe  Pro  Pro  Gly  Thr  Lys  Gly  Asn
     50                      55                 60

Thr  Phe  Val  Asn  Asp  Pro  Lys  Val  Ala  Gln  Glu  Thr  Asp  Val  Arg  Ala
65                      70                 75                           80

Gln  Ile  Arg  Leu  Gln  Phe  Arg  Asp  Val  Asn  Gly  Glu  Leu  Ile  Ala  Val
               85                      90                      95

Gln  Arg  Ser  Met  Val  Cys  Thr  Gln  Lys  Ser  Lys  Lys  Thr  Glu  Phe  Lys
               100                     105                     110

Thr  Leu  Glu  Gly  Val  Ile  Thr  Arg  Thr  Lys  His  Gly  Glu  Lys  Val  Ser
          115                     120                     125

Leu  Ser  Ser  Lys  Cys  Ala  Glu  Ile  Asp  Arg  Glu  Met  Ile  Ser  Ser  Leu
          130                     135                     140

Gly  Val  Ser  Lys  Ala  Val  Leu  Asn  Asn  Val  Ile  Phe  Cys  His  Gln  Glu
```

-continued

```
        145                        150                        155                        160
Asp   Ser   Asn   Trp   Pro   Leu   Ser   Glu   Gly   Lys   Ala   Leu   Lys   Gln   Lys   Phe
                        165                        170                        175
Asp   Glu   Ile   Phe   Ser   Ala   Thr   Arg   Tyr   Ile   Lys   Ala   Leu   Glu   Thr   Leu
                  180                        185                        190
Arg   Gln   Val   Arg   Gln   Thr   Gln   Gly   Gln   Lys   Val   Lys   Glu   Tyr   Gln   Met
            195                        200                        205
Glu   Leu   Lys   Tyr   Leu   Lys   Gln   Tyr   Lys   Glu   Lys   Ala   Cys   Glu   Ile   Arg
      210                        215                        220
Asp   Gln   Ile   Thr   Ser   Lys   Glu   Ala   Gln   Leu   Thr   Ser   Ser   Lys   Glu   Ile
225                        230                        235                        240
Val   Lys   Ser   Tyr   Glu   Asn   Glu   Leu   Asp   Pro   Leu   Lys   Asn   Arg   Leu   Lys
                        245                        250                        255
Glu   Ile   Glu   His   Asn   Leu   Ser   Lys   Ile   Met   Lys   Leu   Asp   Asn   Glu   Ile
                  260                        265                        270
Lys   Ala   Leu   Asp   Ser   Arg   Lys   Lys   Gln   Met   Glu   Lys   Leu   Asp   Asn   Ser   Glu
                  275                        280                        285
Leu   Glu   Glu   Lys   Met   Glu   Lys   Val   Phe   Gln   Gly   Thr   Asp   Glu   Gln   Leu
      290                        295                        300
Asn   Asp   Leu   Tyr   His   Asn   His   Gln   Arg   Thr   Val   Arg   Glu   Lys   Glu   Arg
305                        310                        315                        320
Lys   Leu   Val   Asp   Cys   His   Arg   Glu   Leu   Glu   Lys   Leu   Asn   Lys   Glu   Ser
                        325                        330                        335
Arg   Leu   Leu   Asn   Gln   Glu   Lys   Ser   Glu   Leu   Leu   Val   Glu   Gln   Gly   Arg
                  340                        345                        350
Leu   Gln   Leu   Gln   Ala   Asp   Arg   His   Gln   Glu   His   Ile   Arg   Ala   Arg   Asp
            355                        360                        365
Ser   Leu   Ile   Gln   Ser   Leu   Ala   Thr   Gln   Leu   Glu   Leu   Asp   Gly   Phe   Glu
      370                        375                        380
Arg   Gly   Pro   Phe   Ser   Glu   Arg   Gln   Ile   Lys   Asn   Phe   His   Lys   Leu   Val
385                        390                        395                        400
Arg   Glu   Arg   Gln   Glu   Gly   Glu   Ala   Lys   Thr   Ala   Asn   Gln   Leu   Met   Asn
                        405                        410                        415
Asp   Phe   Ala   Glu   Lys   Glu   Thr   Leu   Lys   Gln   Lys   Gln   Ile   Asp   Glu   Ile
                  420                        425                        430
Arg   Asp   Lys   Lys   Thr   Gly   Leu   Gly   Arg   Ile   Ile   Glu   Leu   Lys   Ser   Glu
            435                        440                        445
Ile   Leu   Ser   Lys   Lys   Gln   Asn   Glu   Leu   Lys   Asn   Val   Lys   Tyr   Glu   Leu
      450                        455                        460
Gln   Gln   Leu   Glu   Gly   Ser   Ser   Asp   Arg   Ile   Leu   Glu   Leu   Asp   Gln   Glu
465                        470                        475                        480
Leu   Ile   Lys   Ala   Glu   Arg   Glu   Leu   Ser   Lys   Ala   Glu   Lys   Asn   Ser   Asn
                        485                        490                        495
Val   Glu   Thr   Leu   Lys   Met   Glu   Val   Ile   Ser   Leu   Gln   Asn   Glu   Lys   Ala
                  500                        505                        510
Asp   Leu   Asp   Arg   Thr   Leu   Arg   Lys   Leu   Asp   Gln   Glu   Met   Glu   Gln   Leu
            515                        520                        525
Asn   His   His   Thr   Thr   Thr   Arg   Thr   Gln   Met   Glu   Met   Leu   Thr   Lys   Asp
      530                        535                        540
Lys   Ala   Asp   Lys   Asp   Glu   Gln   Ile   Arg   Lys   Ile   Lys   Ser   Arg   His   Ser
545                        550                        555                        560
Asp   Glu   Leu   Thr   Ser   Leu   Leu   Gly   Tyr   Phe   Pro   Asn   Lys   Lys   Gln   Leu
                        565                        570                        575
```

-continued

```
Glu Asp Trp Leu His Ser Lys Ser Lys Glu Ile Asn Gln Thr Arg Asp
            580                 585                 590

Arg Leu Ala Lys Leu Lys Ile Val Leu Val Lys Pro His Ser Ile Thr
595                 600                 605

Ser Cys Tyr Asn Ser Leu Lys Cys Phe Arg Asn Leu Ile Pro Leu
    610                 615                 620

Ile Glu Glu Val Leu Leu Leu Ser Ala Ala Asp Leu Glu Ala Val Ile
625                 630                 635                 640

Trp Ala Ser Ile Lys
                645
```

( 2 ) INFORMATION FOR SEQ ID NO:145:

( i ) SEQUENCE CHARACTERISTICS:
     ( A ) LENGTH: 527 amino acids
     ( B ) TYPE: amino acid
     ( C ) STRANDEDNESS: single
     ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
     ( C ) INDIVIDUAL ISOLATE: G65.pep ( x i ) SEQUENCE DESCRIPTION: SEQ ID NO:145:

```
Met Lys Leu Trp Val Ser Ala Leu Leu Met Ala Trp Phe Gly Val Leu
1               5                   10                  15

Ser Cys Val Gln Ala Glu Phe Phe Thr Ser Ile Gly His Met Thr Asp
            20                  25                  30

Leu Ile Tyr Ala Glu Lys Glu Leu Val Gln Ser Leu Lys Glu Tyr Ile
        35                  40                  45

Leu Val Glu Glu Ala Lys Leu Ser Lys Ile Lys Ser Trp Ala Asn Lys
    50                  55                  60

Met Glu Ala Leu Thr Ser Lys Ser Ala Ala Asp Ala Glu Gly Tyr Leu
65                  70                  75                  80

Ala His Pro Val Asn Ala Tyr Lys Leu Val Lys Arg Leu Asn Thr Asp
                85                  90                  95

Trp Pro Ala Leu Glu Asp Leu Val Leu Gln Asp Ser Ala Ala Gly Phe
            100                 105                 110

Ile Ala Asn Leu Ser Val Gln Arg Gln Phe Phe Pro Thr Asp Glu Asp
        115                 120                 125

Glu Ile Gly Ala Ala Lys Ala Leu Met Arg Leu Gln Asp Thr Tyr Arg
    130                 135                 140

Leu Asp Pro Gly Thr Ile Ser Arg Gly Glu Leu Pro Gly Thr Lys Tyr
145                 150                 155                 160

Gln Ala Met Leu Ser Val Asp Asp Cys Phe Gly Met Gly Arg Ser Ala
                165                 170                 175

Tyr Asn Glu Gly Asp Tyr Tyr His Thr Val Leu Trp Met Glu Gln Val
            180                 185                 190

Leu Lys Gln Leu Asp Ala Gly Glu Glu Ala Thr Thr Thr Lys Ser Gln
        195                 200                 205

Val Leu Asp Tyr Leu Ser Tyr Ala Val Phe Gln Leu Gly Asp Leu His
    210                 215                 220

Arg Ala Leu Glu Leu Thr Arg Arg Leu Leu Ser Leu Asp Pro Ser His
225                 230                 235                 240
```

|     |     |     |     |     |     |     |     |     |     |     |     |     |     |     |
| --- | --- | --- | --- | --- | --- | --- | --- | --- | --- | --- | --- | --- | --- | --- |
| Glu | Arg | Ala | Gly | Gly | Asn | Leu | Arg | Tyr | Phe | Glu | Gln | Leu | Leu | Glu | Glu |
|     |     |     |     | 245 |     |     |     |     | 250 |     |     |     |     | 255 |     |
| Glu | Arg | Glu | Lys | Thr | Leu | Thr | Asn | Gln | Thr | Glu | Ala | Glu | Leu | Ala | Thr |
|     |     |     | 260 |     |     |     |     | 265 |     |     |     |     | 270 |     |     |
| Pro | Glu | Gly | Ile | Tyr | Glu | Arg | Pro | Val | Asp | Tyr | Leu | Pro | Glu | Arg | Asp |
|     |     | 275 |     |     |     |     | 280 |     |     |     |     | 285 |     |     |     |
| Val | Tyr | Glu | Ser | Leu | Cys | Arg | Gly | Glu | Gly | Val | Lys | Leu | Thr | Pro | Arg |
|     | 290 |     |     |     |     | 295 |     |     |     |     | 300 |     |     |     |     |
| Arg | Gln | Lys | Arg | Leu | Phe | Cys | Arg | Tyr | His | His | Gly | Asn | Arg | Ala | Pro |
| 305 |     |     |     |     | 310 |     |     |     |     | 315 |     |     |     |     | 320 |
| Gln | Leu | Leu | Ile | Ala | Pro | Phe | Lys | Glu | Glu | Asp | Glu | Trp | Asp | Ser | Pro |
|     |     |     |     | 325 |     |     |     |     | 330 |     |     |     |     | 335 |     |
| His | Ile | Val | Arg | Tyr | Tyr | Asp | Val | Met | Ser | Asp | Glu | Glu | Ile | Glu | Arg |
|     |     |     | 340 |     |     |     |     | 345 |     |     |     |     | 350 |     |     |
| Ile | Lys | Glu | Ile | Ala | Lys | Pro | Lys | Leu | Ala | Arg | Ala | Thr | Val | Arg | Asp |
|     |     | 355 |     |     |     |     | 360 |     |     |     |     | 365 |     |     |     |
| Pro | Lys | Thr | Gly | Val | Leu | Thr | Val | Ala | Ser | Tyr | Arg | Val | Ser | Lys | Ser |
|     | 370 |     |     |     |     | 375 |     |     |     |     | 380 |     |     |     |     |
| Ser | Trp | Leu | Glu | Glu | Asp | Asp | Pro | Val | Val | Ala | Arg | Val | Asn | Arg |     |
| 385 |     |     |     |     | 390 |     |     |     |     | 395 |     |     |     | 400 |     |
| Arg | Met | Gln | His | Ile | Thr | Gly | Leu | Thr | Val | Lys | Thr | Ala | Glu | Leu | Leu |
|     |     |     |     | 405 |     |     |     |     | 410 |     |     |     |     | 415 |     |
| Gln | Val | Ala | Asn | Tyr | Gly | Val | Gly | Gly | Gln | Tyr | Glu | Pro | His | Phe | Asp |
|     |     |     | 420 |     |     |     |     | 425 |     |     |     |     | 430 |     |     |
| Phe | Ser | Arg | Arg | Pro | Phe | Asp | Ser | Gly | Leu | Pro | Thr | Leu | Gly | Gln | Arg |
|     |     | 435 |     |     |     |     | 440 |     |     |     |     | 445 |     |     |     |
| Gly | Ile | Val | Leu | Ala | Thr | Phe | Leu | Asn | Tyr | Met | Ser | Asp | Val | Glu | Ala |
|     | 450 |     |     |     |     | 455 |     |     |     |     | 460 |     |     |     |     |
| Gly | Gly | Ala | Thr | Val | Phe | Pro | Asp | Leu | Gly | Ala | Ala | Ile | Trp | Pro | Lys |
| 465 |     |     |     |     | 470 |     |     |     |     | 475 |     |     |     |     | 480 |
| Lys | Gly | Thr | Lys | Leu | Cys | Ser | Gly | Thr | Thr | Ser | Cys | Gly | Ala | Gly | Lys |
|     |     |     |     | 485 |     |     |     |     | 490 |     |     |     |     | 495 |     |
| Val | Thr | Thr | Glu | Gln | Asp | Met | Leu | Pro | Ala | Leu | Cys | Leu | Trp | Ala | Ala |
|     |     |     | 500 |     |     |     |     | 505 |     |     |     |     | 510 |     |     |
| Ser | Gly | Ser | Pro | Ile | Ser | Gly | Ser | Met | Asn | Glu | Asp | Arg | Ser | Ser |     |
|     |     | 515 |     |     |     |     | 520 |     |     |     |     | 525 |     |     |     |

( 2 ) INFORMATION FOR SEQ ID NO:146:

( i ) SEQUENCE CHARACTERISTICS:
        ( A ) LENGTH: 727 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: TcA - N- terminal fragment ( x i ) SEQUENCE DESCRIPTION: SEQ ID NO:146:

| | | | | | |
|---|---|---|---|---|---|
| GTTGGTGTCA | GCGGGCAACA | GCCCACAGGA | GTGTGCACCT | CCTAGGACAG | AGTTTGTCCT | 60 |
| CTCACTTCTG | GAGAAGATGC | AGACACAGGA | GATCCTGAGG | ATACTGCGAC | TGCCTGAGCT | 120 |
| AGGTGACTTG | GGACAGTTTT | TCCGCAGCCT | CTCGGCCACC | ACCCTCGTGA | GTATGGGTGC | 180 |

-continued

| | | | | | |
|---|---|---|---|---|---|
| CCTGGCTGCC | ATCCTTGCCT | ACTGGTTCAC | TCACCGGCCA | AAGGCCTTGC | AGCCGCCATG | 240 |
| CAACCTCCTG | ATGCAGTCAG | AAGAAGTAGA | GGACAGTGGC | GGGGCACGGC | GATCTGTGAT | 300 |
| TGGGTCTGGC | CCTCAGCTAC | TTACCCACTA | CTATGATGAT | GCCCGGACCA | TGTACCAGGT | 360 |
| GTTCCGCCGT | GGGCTTAGCA | TCTCAGGGAA | TGGGCCCTGT | CTTGGTTTCA | GGAAGCCTAA | 420 |
| GCAGCCTTAC | CAGTGGCTGT | CCTACCAGGA | GGTGGCCGAC | AGGGCTGAAT | TTCTGGGGTC | 480 |
| CGGACTTCTC | CAGCACAATT | GTAAAGCATG | CACTGATCAG | TTTATTGGTG | TTTTTGCACA | 540 |
| AAATCGGCCA | GAGTGGATCA | TTGTGGAGCT | GGCCTGCTAC | ACATATTCCA | TGGTGGTGGT | 600 |
| CCCGCTCTAT | GACACCCTGG | GCCCTGGGGC | TATCCGCTAC | ATCATCAATA | CAGCGGACAT | 660 |
| CAGCACCGTG | ATTGTGGACA | AACCTCAGAA | GGCTGTGCTT | CTGCTAGAGC | ATGTGGAGAG | 720 |
| GAAGGAG | | | | | | 727 |

( 2 ) INFORMATION FOR SEQ ID NO:147:

( i ) SEQUENCE CHARACTERISTICS:
        ( A ) LENGTH: 874 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: TcA - C- terminal fragment ( x i ) SEQUENCE DESCRIPTION: SEQ ID NO:147:

| | | | | | |
|---|---|---|---|---|---|
| GTGTGAGAGG | ACCAAATGTG | TTCAAAGGCT | ACTTGAAAGA | TCCAGACAGG | ACGAAGGAGG | 60 |
| CCCTGGACAG | CGATGGCTGG | CTTCACACTG | GAGACATCGG | AAAATGGCTG | CCGGCAGGAA | 120 |
| CTCTTAAAAT | TATTGATCGG | AAAAAGCATA | TATTTAAACT | TGCTCAGGGA | GAATATGTTG | 180 |
| CACCCGAGAA | GATTGAGAAC | ATCTACATCC | GGAGCCAACC | TGTGGCGCAA | ATCTATGTCC | 240 |
| ATGGGGACAG | CTTAAAGGCC | TTTTTGGTAG | GCATTGTTGT | GCCTGACCCT | GAAGTTATGC | 300 |
| CCTCCTGGGC | CCAGAAGAGA | GGAATTGAAG | GAACATATGC | AGATCTCTGC | ACAAATAAGG | 360 |
| ATCTGAAGAA | AGCCATTTTG | GAAGATATGG | TGAGGTTAGG | AAAAGAAAGT | GGACTCCATT | 420 |
| CTTTTGAGCA | GGTTAAAGCC | ATTCACATCC | ATTCTGACAT | GTTCTCAGTT | CAAAATGGCT | 480 |
| TGCTGACACC | AACACTAAAA | GCTAAGAGAC | CTGAGCTGAG | AGAGTACTTC | AAAAAACAAA | 540 |
| TAGAAGAGCT | TTACTCAATC | TCCATGTGAA | GTTCAAGGAA | AGTTCTTCTC | AGTGTAATGA | 600 |
| ACTGTCTAGC | AATATTATAG | TTATTCTTGA | AAGTAATGAG | TCAAAATGAC | ACAGCTGAAA | 660 |
| ATGAATAAGC | ATCTGATTTT | ATGACTGAGC | CTTTTCCTGT | CCCAAGAGGT | CTTTAACAAT | 720 |
| ATTTTCTCTA | TCATCAATGA | GTATATTTTA | TTTTTATTAT | AAAAATGATA | TTGTGGTGGA | 780 |
| CTGCTAAAAA | TATCACAAAT | GGCAATGTAA | AAATCAAGAC | ATTTTCTCAA | GAACTGTGTA | 840 |
| CCACTAAAAG | TAATATATTG | TCAATGTTCA | CAGG | | | 874 |

( 2 ) INFORMATION FOR SEQ ID NO:148:

( i ) SEQUENCE CHARACTERISTICS:
        ( A ) LENGTH: 1312 amino acids
        ( B ) TYPE: amino acid
        ( D ) TOPOLOGY: linear ( i i ) MOLECULE TYPE: protein (iii) HYPOTHETICAL: NO (vi) ORIGINAL SOURCE:
    (C) INDIVIDUAL ISOLATE: Rad50.pro- translation of SEQ ID NO:54

(xi) SEQUENCE DESCRIPTION: SEQ ID NO:148:

```
Met Ser Arg Ile Glu Lys Met Ser Ile Leu Gly Val Arg Ser Phe Gly
 1               5                  10                  15

Ile Glu Asp Lys Asp Lys Gln Ile Ile Thr Phe Phe Ser Pro Leu Thr
                20                  25                  30

Ile Leu Val Gly Pro Asn Gly Ala Gly Lys Thr Thr Ile Ile Glu Cys
                35                  40                  45

Leu Lys Tyr Ile Cys Thr Gly Asp Phe Pro Pro Gly Thr Lys Gly Asn
        50                  55                  60

Thr Phe Val His Asp Pro Lys Val Ala Gln Glu Thr Asp Val Arg Ala
65                  70                  75                  80

Gln Ile Arg Leu Gln Phe Arg Asp Val Asn Gly Glu Leu Ile Ala Val
                85                  90                  95

Gln Arg Ser Met Val Cys Thr Gln Lys Ser Lys Lys Thr Glu Phe Lys
                100                 105                 110

Thr Leu Glu Gly Val Ile Thr Arg Thr Lys His Gly Glu Lys Val Ser
                115                 120                 125

Leu Ser Ser Lys Cys Ala Glu Ile Asp Arg Glu Met Ile Ser Ser Leu
        130                 135                 140

Gly Val Ser Lys Ala Val Leu Asn Asn Val Ile Phe Cys His Gln Glu
145                 150                 155                 160

Asp Ser Asn Trp Pro Leu Ser Glu Gly Lys Ala Leu Lys Gln Lys Phe
                165                 170                 175

Asp Glu Ile Phe Ser Ala Thr Arg Tyr Ile Lys Ala Leu Glu Thr Leu
                180                 185                 190

Arg Gln Val Arg Gln Thr Gln Gly Gln Lys Val Lys Glu Tyr Gln Met
                195                 200                 205

Glu Leu Lys Tyr Leu Lys Gln Tyr Lys Glu Lys Ala Cys Glu Ile Arg
        210                 215                 220

Asp Gln Ile Thr Ser Lys Glu Ala Gln Leu Thr Ser Ser Lys Glu Ile
225                 230                 235                 240

Val Lys Ser Tyr Glu Asn Glu Leu Asp Pro Leu Lys Asn Arg Leu Lys
                245                 250                 255

Glu Ile Glu His Asn Leu Ser Lys Ile Met Lys Leu Asp Asn Glu Ile
                260                 265                 270

Lys Ala Leu Asp Ser Arg Lys Lys Gln Met Glu Lys Asp Asn Ser Glu
                275                 280                 285

Leu Glu Glu Lys Met Glu Lys Val Phe Gln Gly Thr Asp Glu Gln Leu
        290                 295                 300

Asn Asp Leu Tyr His Asn His Gln Arg Thr Val Arg Glu Lys Glu Arg
305                 310                 315                 320

Lys Leu Val Asp Cys His Arg Glu Leu Glu Lys Leu Asn Lys Glu Ser
                325                 330                 335

Arg Leu Leu Asn Gln Glu Lys Ser Glu Leu Leu Val Glu Gln Gly Arg
                340                 345                 350

Leu Gln Leu Gln Ala Asp Arg His Gln Glu His Ile Arg Ala Arg Asp
                355                 360                 365

Ser Leu Ile Gln Ser Leu Ala Thr Gln Leu Glu Leu Asp Gly Phe Glu
        370                 375                 380

Arg Gly Pro Phe Ser Glu Arg Gln Ile Lys Asn Phe His Lys Leu Val
```

-continued

|     |     |     |     |     |     |     |     |     |     |     |     |     |     |     |     |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |
| Arg | Glu | Arg | Gln | Glu | Gly | Glu | Ala | Lys | Thr | Ala | Asn | Gln | Leu | Met | Asn |
|     |     |     |     | 405 |     |     |     |     | 410 |     |     |     |     | 415 |     |
| Asp | Phe | Ala | Glu | Lys | Glu | Thr | Leu | Lys | Gln | Lys | Gln | Ile | Asp | Glu | Ile |
|     |     |     |     | 420 |     |     |     |     | 425 |     |     |     |     | 430 |     |
| Arg | Asp | Lys | Lys | Thr | Gly | Leu | Gly | Arg | Ile | Ile | Glu | Leu | Lys | Ser | Glu |
|     |     |     |     | 435 |     |     |     |     | 440 |     |     |     |     | 445 |     |
| Ile | Leu | Ser | Lys | Lys | Gln | Asn | Glu | Leu | Lys | Asn | Val | Lys | Tyr | Glu | Leu |
|     |     |     |     | 450 |     |     |     |     | 455 |     |     |     |     | 460 |     |
| Gln | Gln | Leu | Glu | Gly | Ser | Ser | Asp | Arg | Ile | Leu | Glu | Leu | Asp | Gln | Glu |
| 465 |     |     |     |     |     | 470 |     |     |     |     | 475 |     |     |     | 480 |
| Leu | Ile | Lys | Ala | Glu | Arg | Glu | Leu | Ser | Lys | Ala | Glu | Lys | Asn | Ser | Asn |
|     |     |     |     | 485 |     |     |     |     | 490 |     |     |     |     | 495 |     |
| Val | Glu | Thr | Leu | Lys | Met | Glu | Val | Ile | Ser | Leu | Gln | Asn | Glu | Lys | Ala |
|     |     |     |     | 500 |     |     |     |     | 505 |     |     |     |     | 510 |     |
| Asp | Leu | Asp | Arg | Thr | Leu | Arg | Lys | Leu | Asp | Gln | Glu | Met | Glu | Gln | Leu |
|     |     |     |     | 515 |     |     |     |     | 520 |     |     |     |     | 525 |     |
| Asn | His | His | Thr | Thr | Thr | Arg | Thr | Gln | Met | Glu | Met | Leu | Thr | Lys | Asp |
|     |     |     |     | 530 |     |     |     |     | 535 |     |     |     |     | 540 |     |
| Lys | Ala | Asp | Lys | Asp | Glu | Gln | Ile | Arg | Lys | Ile | Lys | Ser | Arg | His | Ser |
| 545 |     |     |     |     |     | 550 |     |     |     |     | 555 |     |     |     | 560 |
| Asp | Glu | Leu | Thr | Ser | Leu | Leu | Gly | Tyr | Phe | Pro | Asn | Lys | Lys | Gln | Leu |
|     |     |     |     | 565 |     |     |     |     | 570 |     |     |     |     | 575 |     |
| Glu | Asp | Trp | Leu | His | Ser | Lys | Ser | Lys | Glu | Ile | Asn | Gln | Thr | Arg | Asp |
|     |     |     |     | 580 |     |     |     |     | 585 |     |     |     |     | 590 |     |
| Arg | Leu | Ala | Lys | Leu | Asn | Lys | Glu | Leu | Ala | Ser | Ser | Glu | Gln | Asn | Lys |
|     |     |     |     | 595 |     |     |     |     | 600 |     |     |     |     | 605 |     |
| Asn | His | Ile | Asn | Asn | Glu | Leu | Lys | Arg | Arg | Glu | Glu | Gln | Leu | Ser | Ser |
|     |     |     |     | 610 |     |     |     |     | 615 |     |     |     |     | 620 |     |
| Tyr | Glu | Asp | Lys | Leu | Phe | Asp | Val | Cys | Gly | Ser | Gln | Asp | Phe | Glu | Ser |
| 625 |     |     |     |     |     | 630 |     |     |     |     | 635 |     |     |     | 640 |
| Asp | Leu | Asp | Arg | Leu | Lys | Glu | Glu | Ile | Glu | Lys | Ser | Ser | Lys | Gln | Arg |
|     |     |     |     | 645 |     |     |     |     | 650 |     |     |     |     | 655 |     |
| Ala | Met | Leu | Ala | Gly | Ala | Thr | Ala | Val | Tyr | Ser | Gln | Phe | Ile | Thr | Gln |
|     |     |     |     | 660 |     |     |     |     | 665 |     |     |     |     | 670 |     |
| Leu | Thr | Asp | Glu | Asn | Gln | Ser | Cys | Cys | Pro | Val | Cys | Gln | Arg | Val | Phe |
|     |     |     |     | 675 |     |     |     |     | 680 |     |     |     |     | 685 |     |
| Gln | Thr | Glu | Ala | Glu | Leu | Gln | Glu | Val | Ile | Ser | Asp | Leu | Gln | Ser | Lys |
|     |     |     |     | 690 |     |     |     |     | 695 |     |     |     |     | 700 |     |
| Leu | Arg | Leu | Ala | Pro | Asp | Lys | Leu | Lys | Ser | Thr | Glu | Ser | Glu | Leu | Lys |
| 705 |     |     |     |     |     | 710 |     |     |     |     | 715 |     |     |     | 720 |
| Lys | Lys | Glu | Lys | Arg | Arg | Asp | Glu | Met | Leu | Gly | Leu | Val | Pro | Met | Arg |
|     |     |     |     | 725 |     |     |     |     | 730 |     |     |     |     | 735 |     |
| Gln | Ser | Ile | Ile | Asp | Leu | Lys | Glu | Lys | Glu | Ile | Pro | Glu | Leu | Arg | Asn |
|     |     |     |     | 740 |     |     |     |     | 745 |     |     |     |     | 750 |     |
| Lys | Leu | Gln | Asn | Val | Asn | Arg | Asp | Ile | Gln | Arg | Leu | Lys | Asn | Asp | Ile |
|     |     |     |     | 755 |     |     |     |     | 760 |     |     |     |     | 765 |     |
| Glu | Glu | Gln | Glu | Thr | Leu | Leu | Gly | Thr | Ile | Met | Pro | Glu | Glu | Glu | Ser |
|     |     |     |     | 770 |     |     |     |     | 775 |     |     |     |     | 780 |     |
| Ala | Lys | Val | Cys | Leu | Thr | Asp | Val | Thr | Ile | Met | Glu | Arg | Phe | Gln | Met |
| 785 |     |     |     |     |     | 790 |     |     |     |     | 795 |     |     |     | 800 |
| Glu | Leu | Lys | Asp | Val | Glu | Arg | Lys | Ile | Ala | Gln | Gln | Ala | Ala | Lys | Leu |
|     |     |     |     | 805 |     |     |     |     | 810 |     |     |     |     | 815 |     |

```
Gln Gly Ile Asp Leu Asp Arg Thr Val Gln Gln Val Asn Gln Glu Lys
            820                 825                 830

Gln Glu Lys Gln His Lys Leu Asp Thr Val Ser Ser Lys Ile Glu Leu
            835                 840                 845

Asn Arg Lys Leu Ile Gln Asp Gln Glu Gln Gln His Leu Lys
850                 855                 860

Ser Thr Thr Asn Glu Leu Lys Ser Glu Lys Leu Gln Ile Ser Thr Asn
865                 870                 875                 880

Leu Gln Arg Arg Gln Gln Leu Glu Glu Gln Thr Val Glu Leu Ser Thr
            885                 890                 895

Glu Val Gln Ser Leu Tyr Arg Glu Ile Lys Asp Ala Lys Glu Gln Val
            900                 905                 910

Ser Pro Leu Glu Thr Thr Leu Glu Lys Phe Gln Gln Glu Lys Glu Glu
            915                 920                 925

Leu Ile Asn Lys Lys Asn Thr Ser Asn Lys Ile Ala Gln Asp Lys Leu
            930                 935                 940

Asn Asp Ile Lys Glu Lys Val Lys Asn Ile His Gly Tyr Met Lys Asp
945                 950                 955                 960

Ile Glu Asn Tyr Ile Gln Asp Gly Lys Asp Tyr Lys Lys Gln Lys
                965                 970                 975

Glu Thr Glu Leu Asn Lys Val Ile Ala Gln Leu Ser Glu Cys Glu Lys
            980                 985                 990

His Lys Glu Lys Ile Asn Glu Asp Met Arg Leu Met Arg Gln Asp Ile
            995                 1000                1005

Asp Thr Gln Lys Ile Gln Glu Arg Trp Leu Gln Asp Asn Leu Thr Leu
    1010                1015                1020

Arg Lys Arg Asn Glu Glu Leu Lys Glu Val Glu Glu Glu Arg Lys Gln
1025                1030                1035                1040

His Leu Lys Glu Met Gly Gln Met Gln Val Leu Gln Met Lys Ser Glu
            1045                1050                1055

His Gln Lys Leu Glu Glu Asn Ile Asp Asn Ile Lys Arg Asn His Asn
            1060                1065                1070

Leu Ala Leu Gly Arg Gln Lys Gly Tyr Glu Glu Glu Ile Ile His Phe
        1075                1080                1085

Lys Lys Glu Leu Arg Glu Pro Gln Phe Arg Asp Ala Glu Glu Lys Tyr
    1090                1095                1100

Arg Glu Met Met Ile Val Met Arg Thr Thr Glu Leu Val Asn Lys Asp
1105                1110                1115                1120

Leu Asp Ile Tyr Tyr Lys Thr Leu Asp Gln Ala Ile Met Lys Phe His
                1125                1130                1135

Ser Met Lys Met Glu Glu Ile Asn Lys Ile Ile Arg Asp Leu Trp Arg
            1140                1145                1150

Ser Thr Tyr Arg Gly Gln Asp Ile Glu Tyr Ile Glu Ile Arg Ser Asp
            1155                1160                1165

Ala Asp Glu Asn Val Ser Ala Ser Asp Lys Arg Arg Asn Tyr Asn Tyr
    1170                1175                1180

Arg Val Val Met Leu Lys Gly Asp Thr Ala Leu Asp Met Arg Gly Arg
1185                1190                1195                1200

Cys Ser Ala Gly Gln Lys Val Leu Ala Ser Leu Ile Ile Arg Leu Ala
            1205                1210                1215

Leu Ala Glu Thr Phe Cys Leu Asn Cys Gly Ile Ile Ala Leu Asp Glu
            1220                1225                1230

Pro Thr Thr Asn Leu Asp Arg Glu Asn Ile Glu Ser Leu Ala His Ala
        1235                1240                1245
```

| Leu | Val | Glu | Ile | Ile | Lys | Ser | Arg | Ser | Gln | Gln | Arg | Asn | Phe | Gln | Leu |
|---|---|---|---|---|---|---|---|---|---|---|---|---|---|---|---|
| | 1250 | | | | | 1255 | | | | | 1260 | | | | |

| Leu | Val | Ile | Thr | His | Asp | Glu | Asp | Phe | Val | Glu | Leu | Leu | Gly | Arg | Ser |
|---|---|---|---|---|---|---|---|---|---|---|---|---|---|---|---|
| 1265 | | | | | 1270 | | | | | 1275 | | | | | 1280 |

| Glu | Tyr | Val | Glu | Lys | Phe | Tyr | Arg | Ile | Lys | Lys | Asn | Ile | Asp | Gln | Cys |
|---|---|---|---|---|---|---|---|---|---|---|---|---|---|---|---|
| | | | | 1285 | | | | | 1290 | | | | | 1295 | |

| Ser | Glu | Ile | Val | Lys | Cys | Ser | Val | Ser | Ser | Leu | Gly | Phe | Asn | Val | His |
|---|---|---|---|---|---|---|---|---|---|---|---|---|---|---|---|
| | | | 1300 | | | | | 1305 | | | | | 1310 | | |

( 2 ) INFORMATION FOR SEQ ID NO:149:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer A116- 2

( x i ) SEQUENCE DESCRIPTION: SEQ ID NO:149:

GGACCAGTAC TTCCTGAGCT TG        22

( 2 ) INFORMATION FOR SEQ ID NO:150:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: A116-1

( x i ) SEQUENCE DESCRIPTION: SEQ ID NO:150:

TTGGTGCTGA ATACCAGCCC TG        22

( 2 ) INFORMATION FOR SEQ ID NO:151:

( i ) SEQUENCE CHARACTERISTICS:
        ( A ) LENGTH: 650 base pairs
        ( B ) TYPE: nucleic acid
        ( C ) STRANDEDNESS: unknown
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: a94g6ds- 116f.seq ( x i ) SEQUENCE DESCRIPTION: SEQ ID NO:151:

GCCACTCACA CAGCATCTCC AAGATCAGGG ACCAGTACTT CCTGAGCTTG ACAGAGAATG        60

AATGTGTCAG ACTGACCTCT GCCCATTTTG TAGTTTTCTC ATCATTTTCT CACTCAGTCT        120

| | | | | | | |
|---|---|---|---|---|---|---|
| TCCCTTTTCA | AGGGCCCACA | CTCTTCCCGA | GGGCTGGGCC | TAGTGAGCGG | GGTCACAGTA | 180 |
| CATATGGTTT | CTGGGACTGA | GAAGGTGGAA | GATGTGTCCA | TAGAGCTTTT | GTTTCCTAAG | 240 |
| CAACGTATTA | CTGCCATGAT | TCCATTCCCT | AGATGATGCT | GGTGATGCAA | GCTGGCTTCT | 300 |
| CTTGGCCAGC | CTACCCTACT | GCTGGGTAGT | GTTTATGCCC | CATGGCCAGA | CACTGAAGAG | 360 |
| GGAGACAGGA | AAAGCACATA | TCCACACCTT | CCACCCTCAG | ACATTCCTGT | AACTTGAGCT | 420 |
| TATCTAAGGG | GGCATTGTCA | TATGTCAGGG | GTTCCCAAAC | TACGGTCTTC | AGAAACACTG | 480 |
| TTTACCCTCC | ATAGAGGTTG | TGTGCATCAG | CCCAGGCAGA | ATCCTGCTTC | ATGAAGGTGT | 540 |
| TTTCCTAATG | CATGTGTGCA | TGGACCTGTC | TCATGCTACA | CTGCAGGGCT | GGTATTCAGC | 600 |
| ACCAATAGTT | ATTGTTGGCT | GCTAAAATAG | CAAACTAGCC | AAAATGGCAG | | 650 |